US008263559B2

(12) United States Patent
Wonderling

(10) Patent No.: US 8,263,559 B2
(45) Date of Patent: Sep. 11, 2012

(54) FELINE GRANULOCYTE MACROPHAGE COLONY STIMULATING FACTOR PROTEINS

(75) Inventor: Ramani S. Wonderling, Mundelein, IL (US)

(73) Assignee: Heska Corporation, Loveland, CO (US)

( * ) Notice: Subject to any disclaimer, the term of this patent is extended or adjusted under 35 U.S.C. 154(b) by 0 days.

(21) Appl. No.: 12/819,964

(22) Filed: Jun. 21, 2010

(65) Prior Publication Data

US 2010/0285529 A1 Nov. 11, 2010

Related U.S. Application Data

(62) Division of application No. 11/486,995, filed on Jul. 14, 2006, now Pat. No. 7,780,959, which is a division of application No. 10/218,654, filed on Aug. 13, 2002, now Pat. No. 7,078,506, which is a division of application No. 09/322,409, filed on May 28, 1999, now Pat. No. 6,471,957.

(60) Provisional application No. 60/087,306, filed on May 29, 1998.

(51) Int. Cl.
*A61K 38/21* (2006.01)
*C07K 14/00* (2006.01)
*C07K 14/52* (2006.01)

(52) U.S. Cl. ............... 514/21.2; 424/85.1; 424/85.2; 435/69.1; 530/350; 530/351; 536/23.5

(58) Field of Classification Search ............... None
See application file for complete search history.

(56) References Cited

U.S. PATENT DOCUMENTS

| 5,831,023 | A  | 11/1998 | Capon et al. |
| 6,713,279 | B1 | 3/2004  | Short |
| 2003/0219752 | A1 | 11/2003 | Short |

FOREIGN PATENT DOCUMENTS

| EP | 0 186 098 A1 | 7/1986 |
| EP | 0 322 870 A2 | 7/1989 |
| EP | 0 414 355 A1 | 2/1991 |
| EP | 0 759 468 A1 | 2/1997 |
| EP | 0 875 251 A1 | 11/1998 |
| WO | WO 94/04680 | 3/1994 |
| WO | WO 99/61618 | 12/1999 |

OTHER PUBLICATIONS

Anderson WF, "Human gene therapy," Nature 392:25-30,1998.
Armitage et al., "Molecular and biological characterization of a murine ligand for CD40," Nature, vol. 357, 1992, pp. 80-82.
Armitage et al., "CD40L: a multi-functional ligand," Seminars in Immunology, vol. 5, 1993, pp. 401-412.
Azuma et al., "Cloning of cDNA for human T-cell replacing factor (interleukin-5) and comparison with the murine homologue," Nucleic Acids Research, vol. 14, No. 22, 1986, pp. 9149-9158.
Brown et al., "A family of small inducible proteins secreted by leukocytes are members of a new superfamily that includes leukocyte and fibroblast-derived inflammatory agents, growth factors, and indicators of various activation processes," Journal of Immunology, vol. 142, No. 2, 1989, pp. 679-687.
Brown et al., "Dangerous liaisons: the role of "danger" signals in the immune response to gene therapy," Blood 100(4):133-1140, 2002.
Cantrell et al., "Cloning, sequence, and expression of a human granulocyte/macrophage colony-stimulating factor," Proc. Natl., Acad. Sci. USA, vol. 82, 1985, pp. 6250-6254.
Daugherty et al., "Isolation and bacterial expression of a murine alpha leukocyte interferon gene," Journal of Interferon Research, vol. 4, 1984, pp. 635-643.
Dion et al., "Sequence and expression of a novel murine interferon alpha gene—homology with enhancer elements in the regulatory region of the gene," Biochemical and Biophysical Research Communications, vol. 138, No. 2, 1986, pp. 826-834.
Drexler, "Expression of FLT3 receptor and response to FLT3 ligand by leukemic cells," Leukemia, vol. 10, 1996, pp. 588-599.
Feng et al., "Aligning amino acid sequences: Comparison of commonly used methods," J. Mol. Evol., vol. 21, 1985, pp. 112-125.
Gauchat et al., "Human CD40-ligand: molecular cloning, cellular distribution and regulation of expression by factors controlling IgE production," FEBS 11964, vol. 315, No. 3, 1993, pp. 259-266.
Gauchat et al., "Human CD40 ligand: molecular cloning, cellular distribution and regulation of IgE synthesis," Res. Immunol., vol. 145(3), Mar.-Apr. 1994, pp. 240-249.
Goeddel et al., "The structure of eight distinct cloned human leukocyte interferon cDNAs," Nature, vol. 290, 1981, pp. 20-26.
Gough et al., "Structure and expression of the mRNA for murine granulocyte-macrophage colony stimulating factor," The EMBO Journal, vol. 4, No. 3, 1985, pp. 645-653.
Graf et al., "Cloning of TRAP, a ligand for CD40 on human T cells," Eur. J. Immunol., vol. 22, 1992, pp. 3191-3194.

(Continued)

Primary Examiner — Robert Landsman
Assistant Examiner — Ian Dang
(74) Attorney, Agent, or Firm — Sheridan Ross P.C.

(57) ABSTRACT

The present invention relates to canine interleukin-4, canine or feline Flt-3 ligand, canine or feline CD40, canine or feline CD154, canine interleukin-5, canine interleukin-13, feline interferon alpha, and/or feline GM-CSF proteins; to canine interleukin-4, canine or feline Flt-3 ligand, canine or feline CD40, canine or feline CD154, canine interleukin-5, canine interleukin-13, feline interferon alpha, and/or feline GM-CSF nucleic acid molecules, including those that encode canine interleukin-4, canine or feline Flt-3 ligand, canine or feline CD40, canine or feline CD154, canine interleukin-5, canine interleukin-13, feline interferon alpha, and/or feline GM-CSF proteins, respectively; to antibodies raised against such proteins; and to inhibitory compounds that regulate such proteins. The present invention also includes methods to identify and obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to regulate an immune response in an animal.

18 Claims, No Drawings

OTHER PUBLICATIONS

Grimaldi et al., "Genomic structure and chromosomal mapping of the murine CD40 gene," *Journal of Immunology*, vol. 149, No. 12, 1992, pp. 3921-3926.

Hannum et al., "Ligand for FLT3/FLK2 receptor tyrosine kinase regulates growth of haematopoietic stem cells and is encoded by variant RNAs," *Nature*, vol. 368, 1994, pp. 643-648.

Heussler et al., "Cloning of a full-length cDNA encoding bovine interleukin 4 by the polymerase chain reaction," *Gene*, vol. 114, 1992, pp. 273-278.

Himmler et al., "Structure and expression in *Escherichia coli* of canine interferon-alpha genes," *Journal of Interferon Research*, vol. 7, 1987, pp. 173-183.

Hirano et al., "Cloning, expression and biological function of the bovine CD40 homologue: role in B-lymphocyte growth and differentiation in cattle," *Immunology*, vol. 90, 1997, pp. 294-300.

Hollenbaugh et al., "The human T cell antigen gp39, a member of the TNF gene family, is a ligand for the CD40 receptor: expression of a soluble form of gp39 with B cell co-stimulatory activity," *The EMBO Journal*, vol. 11, No. 12, 1992, pp. 4313-4321.

Inumaru et al.,"cDNA cloning of porcine granulocyte-macrophage colony-stimulating factor," *Immunology and Cell Biology*, vol. 73, 1995, pp. 474-476.

Johnson et al., "A structural basis for sequence comparisons. An evaluation of scoring methodologies," *J. Mol. Biol.*, vol. 233, 1993, pp. 716-738.

Juengst, 2003, "What next for human gene therapy?", BMJ, vol. 326, pp. 1410-1411.

Kelley et al., "Characterization of a mouse interferon gene locus I. Isolation of a cluster of four alpha interferon genes," *Nucleic Acids Research*, vol. 13, No. 3, 1985, pp. 805-823.

Khatlani et al J., "Cloning of a Full Length cDNA Encoding Canine Interleukin-4," Vet. Med. Sci. 61(8):967-969, 1999.

Lakkis et al., "Cloning of rat interleukin-13 (IL-13) cDNA and analysis of IL-13 gene expression in experimental glomerulonephritis," *Biochemical and Biophysical Research Communications*, vol. 197, No. 2, 1993, pp. 612-618.

Leong et al., "Cloning and expression of the cDNA for bovine granulocyte-macrophage colony-stimulating factor," *Veterinary Immunology and Immunopathology*, vol. 21, 1989, pp. 261-278.

Lyman et al., "Cloning of the human homologue of the murine flt3 ligand: a growth factor for early hematopoietic progenitor cells," *Blood*, vol. 83, No. 10, 1994, pp. 2795-2801.

Lyman et al., "Molecular cloning of a ligand for the flt3/flk-2 tyrosine kinase receptor: a proliferative factor for primitive hematopoietic cells," *Cell*, vol. 75, 1993, pp. 1157-1167.

Lyman et al., "Identification of soluble and membrane-bound isoforms of the murine flt3 ligand generated by alternative splicing of mRNAs," *Oncogene*, vol. 10, 1995, pp. 149-157.

Lyman et al., "Structural analysis of human and murine flt3 ligand genomic loci," *Oncogene*, vol. 11, 1995, pp. 1165-1172.

McClanahan et al., "Biochemical and genetic characterization of multiple splice variants of the Flt3 ligand," *Blood*, vol. 88, No. 9, 1996, pp. 3371-3382.

McInnes et al., "Cloning and expression of a cDNA encoding ovine granulocyte-macrophage colony-stimulating factor," *Gene*, vol. 105, 1991, pp. 275-279.

McKenzie et al., "Interleukin-13, a T-cell-derived cytokine that regulates human monocyte and B-cell function," *Proc. Natl. Acad. Sci. USA*, vol. 90, 1993, pp. 3735-3739.

Mertens et al., "Cloning of two members of the Tnf-superfamily in cattle: CD40 ligand and tumor necrosis factor alpha," *Immunogenetics*, vol. 42, 1995, pp. 430-431.

Minty et al., "Interleukin-13 is a new human lymphokine regulating inflammatory and immune responses," *Nature*, vol. 362, 1993, pp. 248-250.

Nagata et al., "The structure of one of the eight or more distinct chromosomal genes for human interferon-alpha," *Nature*, vol. 287, 1980, pp. 401-408.

Nakamura et al., "Molecular Cloning of Feline Interferon cDNA by Direct Expression," *Biosci. Biotech. Biochem.*, vol. 56, No. 2, 1992, pp. 211-214.

Nash et al., "Molecular cloning and in vivo evaluation of canine granulocyte-macrophage colony-stimulating factor," *Blood*, vol. 78, No. 4, 1991, pp. 930-937.

Navarro et al., "Isolation and characterization of a functional murine interferon alpha gene which is not expressed in fibroblasts upon virus induction," *J. Gen. Virol.* vol. 70, 1989, pp. 1381-1389.

Ngo, in the Protein Folding Problem and Tertiary Structure Prediction, Merz et al. (eds.), Birkhauser Boston: Boston, MA, pp. 433 and 492-495, 1994.

O'Brien et al., "Cloning and sequencing of the cDNA for ovine granulocyte-macrophage colony-stimulating factor (GM-CSF," *Immunology and Cell Biology*, vol. 69, 1991, pp. 51-55.

Osorio et al., "Immunization of dogs and cats with a DNA vaccine against rabies virus," *Vaccine*, vol. 17, 1999, pp. 1109-1116.

Padrid et al., "Sequence and structural analysis of feline interleukin-5 cDNA," *AJVR*, vol. 59, No. 10, 1998, pp. 1263-1269.

Patterson et al., "The Passive Transfer of Immediate Type Hypersensitivity From Man to Other Primates," *Journal of Clinical Investigation*, vol. 44, No. 1, 1965, pp. 140-148.

PTO sequence search report conducted on Aug. 2005 for US 2003/0219752, 2003, pp. 1-8.

PTO sequence search report conducted on Aug. 2005 for US 6713279, 2004, pp. 109.

Raomagnani, S., "Immulogic influences on allergy and the $T_H$ and the $1\_2\_T_H$ balance," J. Allergy Clin. Immunol 113:395-400, 2004.

Rosenberg, et al., "Gene Therapist, Heal Thyself," 2000, Science, vol. 287, p. 1751.

Rudinger, in Peptide Hormones, Parsons (ed.), University Park Press: Baltimore, MD, pp. 1-7, 1976.

Seow et al., "Cloning and sequencing an ovine interleukin-4-encoding cDNA," *Gene*, vol. 124, 1993, pp. 291-293.

Sideras et al., "IgG1 induction factor: a single molecular entity with multiple biological functions," *Adv. Exp. Med. Biol.*, vol. 213, 1987, pp. 227-236.

Stamenkovic et al., "A B-lymphocyte activation molecule related to the nerve growth factor receptor and induced by cytokines in carcinomas," *The EMBO Journal*, vol. 8, No. 5, 1989, pp. 1403-1410.

Torres et al., "Differential increase of an alternatively polyadenylated mRNA species of murine CD40 upon B lymphocyte activation," *Journal of Immunology*, vol. 148, No. 2, 1992, pp. 620-626.

Touchette, "Gene therapy: Not ready for prime time," Nat. Med., 1996, vol. 2(1), pp. 7-8.

Ueda, et al., "Homogeneous production of feline interferon in silkworm by replacing single amino acid code in signal peptide region in recombinant baculovirus and characterization of the product," 1993, Journal of Veterinary Medical Science, vol. 55, No. 2, pp. 251-258, XP001001462.

Van Der Kaaij, et al., 1999, "Molecular Cloning and Sequencing of the cDNA for dog interleukin-4," "Immunogenetics," vol. 49, pp. 142-143.

Verma, et al., "Gene Therapy-promises, problems and prospects," 1997, Nature, vol. 389, pp. 239-242.

Wong et al., "Human GM-CSF: molecular cloning of the complementary DNA and purification of the natural and recombinant proteins," *Science*, vol. 228, 1985, pp. 810-815.

Lerner et al., GenBank Accession No. AAB42052 (U39634.1), Feb. 6, 1997.

Lerner et al., GenBank Accession No. U39634, Feb. 6, 1997.

Venta et al., GenBank Accession No. L77382, Apr. 11, 1996, 1 page.

Venta et al., GenBank Accession No. L77383, Apr. 9, 1996, 1 page.

Zhou et al., GenBank Accession No. L12991, Jun. 12, 1993, 1 page.

FELINE GRANULOCYTE MACROPHAGE COLONY STIMULATING FACTOR PROTEINS

CROSS-REFERENCE TO RELATED APPLICATIONS

This application is a divisional of U.S. patent application Ser. No. 11/486,995, filed Jul. 14, 2006, entitled "FELINE GRANULOCYTE MACROPHAGE COLONY STIMULATING FACTOR NUCLEIC ACID MOLECULES" now U.S. Pat. No. 7,780,959, which issued on Aug. 24, 2010; which is a divisional of U.S. patent application Ser. No. 10/218,654, filed Aug. 13,2002, entitled "CANINE IL-4 NUCLEIC ACID MOLECULES AND USES THEREOF", now U.S. Pat. No. 7,078,506, which issued on Jul. 18, 2006; which is a divisional of U.S. patent application Ser. No. 09/322,409, filed May 28, 1999, entitled "CANINE IL-4 IMMUNOREGULATORY PROTEINS AND USES THEREOF", now U.S. Pat. No. 6,471,957, which issued on Oct. 29,2002; which claims priority to U.S. Provisional Patent Application Ser. No. 60/087,306, filed May 29,1998, entitled "CANINE INTERLEUKIN-4 AND FLT-3 LIGAND PROTEINS, NUCLEIC ACID MOLECULES AND USES THEREOF", all of which are incorporated herein by reference in their entirety.

FIELD OF THE INVENTION

The present invention relates to canine interleukin-4, canine or feline Flt-3 ligand, canine or feline CD40, canine or feline CD154, canine interleukin-5, canine interleukin-13, feline interferon alpha, or feline GM-CSF nucleic acid molecules, proteins encoded by such nucleic acid molecules, antibodies raised against such proteins and/or inhibitors of such proteins or nucleic acid molecules. The present invention also includes therapeutic compositions comprising such nucleic acid molecules, proteins, antibodies and/or inhibitors, as well as their use to regulate an immune response in an animal.

Incorporated by reference herein in its entirety is the Sequence Listing submitted with the instant application, entitled IM-2-C1_seq_listing_ST.25.txt, created Jun. 17, 2010, size of 195 KB.

BACKGROUND OF THE INVENTION

Regulating immune responses in animals is important in disease management. Immune responses can be regulated by modifying the activity of immunoregulatory molecules and immune cells.

Several immunoregulatory molecules have been found in humans and other mammal species. Interleukin-4, produced by activated type 2 helper cells ($T_H2$ cells), has a number of functions. These functions include promotion of naive T cells and B cells to differentiate and proliferate. IL-4 promotes $T_H2$ differentiation and inhibits $T_H1$ development. FMS-like tyrosine kinase 3, (Flt-3 ligand) stimulates the expansion and mobilization of hematopoetic precursor cell stimulating activity. CD40 is a type I transmembrane protein expressed on antigen presenting cells, such as B lymphocytes, and other types of cells such as endothelial cells, epithelial cells, and fibroblasts. CD40 ligand (also known as CD154) is a type II transmembrane protein that is preferentially expressed on activated T lymphocytes. The CD40-CD154 interaction regulates diverse pathways of the immune system, including B cell proliferation, immunoglobulin production and class switching by B cells, activation and clonal expansion of T cells, activity of antigen presenting cells, growth and differentiation of epithelial cells, and regulation of inflammatory responses at mucosal and cutaneous sites. Interleukin-5 is produced by activated type 2 helper cells ($T_H2$), mast cells, and eosinophils. Its main functions include promotion of growth and differentiation of eosinophils and generation of cytotoxic T cells from thymocytes. Interleukin-13 is produced by $T_H1$ and $T_H2$ cells, and promotes growth and differentiation of B cells, up-regulation of MHC class II and CD23 expression on monocytes/macrophages and B cells; and inhibition of production of inflammatory cytokines such as IL-1α, IL-1β, IL-6, IL-8, IL-10, IL-12, among others. Interferon alpha is an antiviral protein that has three major functions: it inhibits viral replication by activating cellular genes that destroy mRNA and inhibit protein translation, it induces MHC class I expression in non virally-infected cells, increasing resistance to NK cells, and can activate NK cells. GM-CSF, (granulocyte-macrophage colony-stimulating factor) stimulates the production of granulocytes and macrophages.

Prior investigators have disclosed sequences encoding feline IL-4 (Lerner et al., GENBANK® Accession No. U39634); porcine IL-4 (Zhou et al., GENBANK® Accession No. L12991); bovine IL-4 (Heussler, V. T., et al., *Gene.* vol. 114, pp. 273-278, 1992); ovine IL-4 (Seow, H.-F., et al., *Gene*, vol. 124, pp. 291-293, 1993); human IL-4 (Yokota, T., et al., *Proc. Natl. Acad. Sci. U.S.A.*, vol. 83(16), pp. 5894-5898, 1986); and murine IL-4 (Sideras, P., et al., *Adv. Exp. Med. Biol.*, vol. 213, pp. 227-236, 1987). Prior investigators have disclosed sequences encoding murine Flt-3 ligand (McClanahan et al., GENBANK® Accession No. U44024); and human Flt-3 ligand (Lyman et al., *Blood*, vol. 83, pp. 2795-2801, 1994). Prior investigators have disclosed sequences encoding human CD40 (Stamenkovic et al., *EMBO J.*, vol. 8:1403-1410, 1989, GENBANK® Accession No. (X60592), bovine CD40 (Hirano et al., *Immunology*, vol. 90, pp. 294-300, 1997, GENBANK® Accession No. U57745), and murine CD40 (Grimaldi et al., *J. Immunol.*, vol. 143, pp. 3921-3926. 1992; Tones and Clark, *J. Immunol.*, vol. 148, pp. 620-626, 1992, GENBANK® Accession No. M83312). Prior investigators have disclosed sequences encoding human CD154 (Graf et al., *Eur. J. Immunol.*, vol. 22, pp. 3191-3194, 1992; Hollenbaugh, et al., *EMBO J.*, vol. 11:4313-4321, 1992; Gauchat et al., *FEBS lett.*, vol., 315, pp. 259-266, 1993; GENBANK® Accession Nos L07414, X68550, Z15017, X67878, respectively); bovine CD154 (Mertens et al., *Immunogenetics*, vol. 42, pp. 430-431, GENBANK® Accession No. Z48468); and murine CD154 (Armitage et al., *Nature*, vol. 357, pp. 80-82; 1992, GENBANK® Accession No. X65453). Prior investigators have disclosed sequences encoding feline interleukin-5 (Padrid et al., *Am. J. Vet. Res.*, vol. 59, pp. 1263-1269, 1998, GENBANK® Accession No. AF025436) and human interleukin-5 (Azuma et al., *Nucleic Acids Res.*, vol. 14, pp. 9149-9158, 1986, GENBANK° Accession No. X04688). Prior investigators have disclosed sequences encoding human interleukin-13 (McKenzie et al., *Proc. Natl. Acad. Sci. USA*, vol. 90, pp. 3735-3739, 1993; Minty et al., *Nature*, vol. 362, pp. 248-250, 1993, GENBANK® Accession Nos L06801 and X69079, respectively); murine interleukin-13 (Brown et al., *J. Immunol.*, vol. 142, pp. 679-687, 1989, GENBANK® Accession No M23504); and rat interleukin-13 (Lakkis et al., *Biochem. Biophys. Res. eCommun.*, Vol. 197, pp. 612-618, 1993, GENBANK® Accession No. L26913). Prior investigators have disclosed sequences encoding feline interferon (Nakamura, N., Sudo, T., Matsuda, S., Yanai, A., *Biosci. Biotechnol. Biochem.* (1992) Vol: 56 pp 211-214, GEN- BANK® accession # E02521). Prior investigators have also disclosed sequences encoding feline GM-CSF (direct submission to GENBANK®, Accession No. AF053007)

There remains a need for compounds and methods to regulate an immune response by manipulation of the function of canine interleukin-4, canine or feline Flt-3 ligand, canine or feline CD40, canine or feline CD154, canine interleukin-5, canine interleukin-13, feline interferon alpha, or feline GM-CSF.

SUMMARY OF THE INVENTION

The present invention relates to canine interleukin-4, canine or feline Flt-3 ligand, canine or feline CD40, canine or feline CD154, canine interleukin-5, canine interleukin-13, feline interferon alpha, or feline GM-CSF nucleic acid molecules, proteins encoded by such nucleic acid molecules, antibodies raised against such proteins and/or inhibitors of such proteins or nucleic acid molecules. Identification of the nucleic acid molecules of the present invention is unexpected because initial attempts to obtain nucleic acid molecules using PCR were unsuccessful. After numerous attempts, the inventors discovered specific primers that were useful for isolating such nucleic acid molecules.

One embodiment of the present invention is an isolated nucleic acid molecule selected from the group consisting of: (a) an isolated nucleic acid molecule comprising a nucleic acid sequence selected from the group consisting of SEQ ID NO:1, SEQ ID NO:3, SEQ ID NO:4, SEQ ID NO:5, SEQ ID NO:19, and/or SEQ ID NO:21 or a homolog thereof, wherein said homolog has an at least about 50 contiguous nucleotide region identical in sequence to a 50 contiguous nucleotide region of a nucleic acid sequence selected from the group consisting of SEQ ID NO:1, SEQ ID NO:3, SEQ ID NO:4, SEQ ID NO:5, SEQ ID NO:19, and/or SEQ ID NO:21; (b) an isolated nucleic acid molecule comprising a nucleic acid sequence selected from the group consisting of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37 or a homolog thereof, wherein said homolog has an at least 40 contiguous nucleotide region identical in sequence to a 40 contiguous nucleotide region of a nucleic acid molecule having a nucleic acid sequence selected from the group consisting of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37; (c) an isolated nucleic acid molecule comprising a nucleic acid sequence selected from the group consisting of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50, and/or a homolog thereof, wherein said homolog has an at least 30 contiguous nucleotide region identical in sequence to a 30 contiguous nucleotide region of a nucleic acid molecule having a nucleic acid sequence selected from the group consisting of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50; (d) an isolated nucleic acid molecule comprising a nucleic acid sequence selected from the group consisting of SEQ ID NO:51, SEQ ID NO:52, SEQ ID NO:54, SEQ ID NO:55, SEQ ID NO:56, SEQ ID NO:57, and/or SEQ ID NO:59, and/or a homolog thereof, wherein said homolog has an at least 40 contiguous nucleotide region identical in sequence to a 40 contiguous nucleotide region of a nucleic acid sequence selected from the group consisting of SEQ ID NO:51, SEQ ID NO:52, SEQ ID NO:54, SEQ ID NO:55, SEQ ID NO:56, SEQ ID NO:57, and/or SEQ ID NO:59; (e) an isolated nucleic acid molecule comprising a nucleic acid sequence selected from the group consisting of SEQ ID NO:60 and/or SEQ ID NO:62, and/or a homolog thereof, wherein said homolog has an at least 30 contiguous nucleotide region identical in sequence to a 30 contiguous nucleotide region of a nucleic acid molecule having a nucleic acid sequence selected from the group consisting of SEQ ID NO:60 and/or SEQ ID NO:62; (f) an isolated nucleic acid molecule comprising a nucleic acid sequence selected from the group consisting of SEQ ID NO:63, SEQ ID NO:64, SEQ ID NO:66, SEQ ID NO:67, SEQ ID NO:68, SEQ ID NO:69 and/or SEQ ID NO:71, and/or a homolog thereof, wherein said homolog has an at least 45 contiguous nucleotide region identical in sequence to a 45 nucleotide region of a nucleic acid molecule having a nucleic acid sequence selected from the group consisting of SEQ ID NO:63, SEQ ID NO:64, SEQ ID NO:66, SEQ ID NO:67, SEQ ID NO:68, SEQ ID NO:69 and/or SEQ ID NO:71; (g) an isolated nucleic acid molecule comprising a nucleic acid sequence selected from the group consisting of SEQ ID NO:72, SEQ ID NO:74, SEQ ID NO:75, SEQ ID NO:76, SEQ ID NO:77, and/or SEQ ID NO:79, and/or a homolog thereof, wherein said homolog has an at least 35 contiguous nucleotide region identical in sequence to a 35 contiguous nucleotide region of a nucleic acid molecule having a nucleic acid sequence selected from the group consisting of SEQ ID NO:72, SEQ ID NO:74, SEQ ID NO:75, SEQ ID NO:76, SEQ ID NO:77, and/or SEQ ID NO:79; (h) an isolated nucleic acid molecule comprising a nucleic acid sequence selected from the group consisting of SEQ ID NO:80, SEQ ID NO:82, SEQ ID NO:83, SEQ ID NO:84, SEQ ID NO:85, and/or SEQ ID NO:87, and/or a homolog thereof, wherein said homolog has an at least 45 contiguous nucleotide region identical in sequence to a 45 contiguous nucleotide region of a nucleic acid molecule having a nucleic acid sequence selected from the group consisting of SEQ ID NO:80, SEQ ID NO:82, SEQ ID NO:83, SEQ ID NO:84, SEQ ID NO:85, and/or SEQ ID NO:87; (i) an isolated nucleic acid molecule comprising a nucleic acid sequence selected from the group consisting of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106, and/or a homolog thereof, wherein said homolog has an at least 15 contiguous nucleotide region identical to a 15 contiguous nucleotide region of a nucleic acid molecule having a nucleic acid sequence selected from the group consisting of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106; (j) an isolated nucleic acid molecule having a nucleic acid sequence selected from the group consisting of SEQ ID NO:107, SEQ ID NO:109, SEQ ID NO:110, SEQ ID NO:112, SEQ ID NO:113, SEQ ID NO:115, SEQ ID NO:116, SEQ ID NO:118; and/or (k) an isolated nucleic acid molecule having a nucleic acid sequence selected from the group consisting of SEQ ID NO:119, SEQ ID NO:121, SEQ ID NO:122, SEQ ID NO:123, SEQ ID NO:124, SEQ ID NO:126. Another embodiment of the present invention is an isolated nucleic acid molecule selected from the group consisting of: (a) a nucleic acid molecule having a nucleic acid sequence that is at least about 92 percent identical to a nucleic acid sequence selected from the group consisting of SEQ ID NO:1, SEQ ID NO:3, SEQ ID NO:4, SEQ ID NO:5, SEQ ID NO:19, and/or SEQ ID NO:21; (b) a nucleic acid molecule having a nucleic acid sequence that is at least about 75 percent identical to a nucleic acid sequence selected from the group consisting of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37; (c) a nucleic acid molecule having a nucleic acid sequence that is at least about 75 percent identical to a nucleic acid sequence selected from the group consisting of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50; (d) a nucleic acid molecule having a nucleic acid sequence that is at least about 70 percent identical to a nucleic acid sequence selected from the group consisting of SEQ ID NO:51, SEQ ID NO:52, SEQ ID NO:54, SEQ ID NO:55, SEQ ID NO:56, SEQ ID NO:57, and/or SEQ ID NO:59; (e) a nucleic acid molecule having a nucleic acid sequence that is at least about 70 percent identical to a nucleic acid sequence selected from the group consisting of SEQ ID NO:60 and/or SEQ ID NO:62; (f) a nucleic acid molecule having a nucleic acid sequence that is at least about 85 percent identical to a nucleic acid sequence selected from the group consisting of SEQ ID NO:63, SEQ ID NO:64, SEQ ID NO:66, SEQ ID NO:67, SEQ ID NO:68, SEQ ID NO:69, and/or SEQ ID NO:71; (g) a nucleic acid molecule having a nucleic acid sequence that is at least about 91 percent identical to a nucleic acid sequence selected from the group consisting of SEQ ID NO:72, SEQ ID NO:74, SEQ ID NO:75, SEQ ID NO:76, SEQ ID NO:77, and/or SEQ ID NO:79; (h) a nucleic acid molecule having a nucleic acid sequence that is at least about 90 percent identical to a nucleic acid sequence selected from the group consisting of SEQ ID NO:80, SEQ ID NO:82, SEQ ID NO:83, SEQ ID NO:84, SEQ ID NO:85, and/or SEQ ID NO:87; (i) a nucleic acid molecule having a nucleic acid sequence that is at least about 65 percent identical to a nucleic acid sequence selected from the group consisting of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106; (j) a nucleic acid molecule having a nucleic acid sequence that is selected from the group consisting of SEQ ID NO:107, SEQ ID NO:109, SEQ ID NO:110, SEQ ID NO:112, SEQ ID NO:113, SEQ ID NO:115, SEQ ID NO:116, and/or SEQ ID NO:118; and/or (k) a nucleic acid molecule having a nucleic acid sequence that is selected from the group consisting of SEQ ID NO:119, SEQ ID NO:121, SEQ ID NO:122, SEQ ID NO:123, SEQ ID NO:124, and/or SEQ ID NO:126.

Yet another embodiment of the present invention is an isolated nucleic acid molecule selected from the group consisting of: (a) a nucleic acid molecule having a nucleic acid sequence encoding an IL-4 protein selected from the group consisting of (i) a protein having an amino acid sequence that is at least about 85 percent identical to an amino acid sequence selected from the group consisting of SEQ ID NO:2 and/or SEQ ID NO:20 and/or (ii) a protein comprising a fragment of at least 20 amino acids of an amino acid sequence selected from the group consisting of SEQ ID NO:2 and/or SEQ ID NO:20; (b) a nucleic acid molecule having a nucleic acid sequence encoding a Flt-3 ligand protein selected from the group consisting of (i) a protein having an amino acid sequence that is at least about 75 percent identical to an amino acid sequence selected from the group consisting of SEQ ID NO:7, SEQ ID NO:23, SEQ ID NO:26, SEQ ID NO:31, and/or SEQ ID NO:34 and/or (ii) a protein comprising a fragment of at least 25 amino acids of an amino acid sequence selected from the group consisting of SEQ ID NO:7, SEQ ID NO:23, SEQ ID NO:26, SEQ ID NO:31, and/or SEQ ID NO:34; (c) a nucleic acid molecule having a nucleic acid sequence encoding a Flt-3 ligand protein selected from the group consisting of (i) a protein having an amino acid sequence that is at least about 75 percent identical to an amino acid sequence selected from the group consisting of SEQ ID NO:44 and/or SEQ ID NO:49 and/or (ii) a protein comprising a fragment of at least 25 amino acids of an amino acid sequence selected from the group is consisting of SEQ ID NO:44 and/or SEQ ID NO:49;

(d) a nucleic acid molecule having a nucleic acid sequence encoding a CD40 protein selected from the group consisting of (i) a protein having an amino acid sequence that is at least about 70 percent identical to an amino acid sequence selected from the group consisting of SEQ ID NO:53 and/or SEQ ID NO:58 and/or (ii) a protein comprising a fragment of at least 30 amino acids of an amino acid sequence selected from the group consisting of SEQ ID NO:53 and/or SEQ ID NO:58; (e) a nucleic acid molecule having a nucleic acid sequence encoding a CD40 protein selected from the group consisting of (i) a protein having an amino acid sequence that is at least about 60 percent identical to an amino acid sequence comprising SEQ ID NO:61 and/or (ii) a protein comprising a fragment of at least 20 amino acids of an amino acid sequence comprising SEQ ID NO:61; (f) a nucleic acid molecule having a nucleic acid sequence encoding a CD154 protein selected from the group consisting of (i) a protein having an amino acid sequence that is at least about 80 percent identical to an amino acid sequence selected from the group consisting of SEQ ID NO:65 and/or SEQ ID NO:70, and/or (ii) a protein comprising a fragment of at least 35 amino acids of an amino acid sequence selected from the group consisting of SEQ ID NO:65 and/or SEQ ID NO:70; (g) a nucleic acid molecule having a nucleic acid sequence encoding a CD154 protein selected from the group consisting of (i) a protein having an amino acid sequence that is at least about 85 percent identical to an amino acid sequence selected from the group consisting of SEQ ID NO:73 and/or SEQ ID NO:78, and/or (ii) a protein comprising a fragment of at least 50 amino acids of an amino acid sequence selected from the group consisting of SEQ ID NO:73 and/or SEQ ID NO:78; (h) a nucleic acid molecule having a nucleic acid sequence encoding an IL-5 protein selected from the group consisting of (i) a protein having an amino acid sequence that is at least about 85 percent identical to an amino acid sequence selected from the group consisting of SEQ ID NO:81 and/or SEQ ID NO:86 and/or (ii) a protein comprising a fragment of at least 20 amino acids of an amino acid sequence selected from the group consisting of SEQ ID NO:81 and/or SEQ ID NO:86; (i) a nucleic acid molecule having a nucleic acid sequence encoding an IL-13 protein selected from the group consisting of (i) a protein having an amino acid sequence that is at least about 70 percent identical to an amino acid sequence selected from the group consisting of SEQ ID NO:92, SEQ ID NO:97, SEQ ID NO:100, and/or SEQ ID NO:105 and/or (ii) a protein comprising a fragment of at least 15 amino acids of an amino acid sequence selected from the group consisting of SEQ ID NO:92, SEQ ID NO:97, SEQ ID NO:100, and/or SEQ ID NO:105; (j) a nucleic acid molecule having a nucleic acid sequence encoding an interferon alpha protein having an amino acid sequence that is selected from the group consisting of amino acid sequence SEQ ID NO:108, SEQ ID NO:111, SEQ ID NO:114, and/or SEQ ID NO:117; (k) a nucleic acid molecule having a nucleic acid sequence encoding a GMCSF protein having an amino acid sequence that is selected from the group consisting of amino acid sequence SEQ ID NO:120, SEQ ID NO:125, and/or (l) a nucleic acid molecule comprising a complement of any of said nucleic acid molecules as set forth in (a), (b), (c), (d), (e), (f), (g), (h), (i), (j), and/or (k), wherein said IL-4 protein elicits an immune response against an IL-4 protein selected from the group consisting of SEQ ID NO:2 and/or SEQ ID NO:20 and/or is a protein with interleukin-4 activity, said Flt-3 ligand protein elicits an immune response against a Flt-3 ligand protein selected from the group consisting of SEQ ID NO:7, SEQ ID NO:23, SEQ ID NO:26, SEQ ID NO:31, SEQ ID NO:34, SEQ ID NO:44, and/or SEQ ID NO:49 and/or is a protein with Flt-3 ligand activity, said CD40 protein elicits an immune response against a CD40 protein selected from the group consisting of SEQ ID NO:53, SEQ ID NO:58, and/or SEQ ID NO:61 and/or is a protein with CD40 activity, said CD154 protein elicits an immune response against a CD154 protein selected from the group consisting of SEQ ID NO:65, SEQ ID NO:70, SEQ ID NO:73, and/or SEQ ID NO:78 and/or is a protein with CD154 activity, said IL-5 protein elicits an immune response against a IL-5 protein selected from the group consisting of SEQ ID NO:81 and/or SEQ ID NO:86 and/or is a protein with IL-5 activity, said IL-13 protein elicits an immune response against an IL-13 protein selected from the group consisting of SEQ ID NO:92, SEQ ID NO:97, SEQ ID NO:100, and/or SEQ ID NO:105 and/or is a protein with IL-13 activity, said interferon alpha protein elicits an immune response against an interferon alpha protein selected from the group consisting of SEQ ID NO:108, SEQ ID NO:111, SEQ ID NO:114, and/or SEQ ID NO:117 and/or is a protein with interferon alpha activity, and/or said GMCSF protein elicits an immune response against a GMCSF protein selected from the group consisting of SEQ ID NO:120 and/or SEQ ID NO:125 and/or is a protein with GM-CSF activity.

The present invention also includes methods to produce any of the proteins of the present invention using nucleic acid molecules of the present invention and recombinantly using such nucleic acid molecules.

The present invention also includes an isolated protein selected from the group consisting of: (a) (i) an isolated protein of at least about 20 amino acids in length, wherein said protein is encoded by a nucleic acid molecule, wherein said nucleic acid molecule has an at least 60 contiguous nucleotide region identical in sequence to a 60 contiguous nucleotide region of a nucleic acid sequence selected from the group consisting of SEQ ID NO:1, SEQ ID NO:4, and/or SEQ ID NO:19; and/or (ii) an isolated protein of at least about 20 amino acids in length, wherein said protein has an at least 20 contiguous amino acid region identical in sequence to a 20 contiguous amino acid region selected from the group consisting of SEQ ID NO:2 and/or SEQ ID NO:20, wherein said isolated protein elicits an immune response against a canine IL-4 protein and/or has IL-4 activity; (b) (i) an isolated protein of at least about 20 amino acids in length, wherein said protein is encoded by a nucleic acid molecule, wherein said nucleic acid molecule has an at least 60 contiguous nucleotide region identical in sequence to a 60 contiguous nucleotide region of a nucleic acid sequence selected from the group consisting of SEQ ID NO:6, SEQ ID NO:9, SEQ ID NO:22, SEQ ID NO:25, SEQ ID NO:28, SEQ ID NO:30, SEQ ID NO:33, and/or SEQ ID NO:36; and/or (ii) an isolated protein of at least about 20 amino acids in length, wherein said protein has an at least 20 contiguous amino acid region identical in sequence to a 20 contiguous amino acid region selected from the group consisting of SEQ ID NO:7, SEQ ID NO:23, SEQ ID NO:26, SEQ ID NO:31, and/or SEQ ID NO:34, wherein said isolated protein is capable of eliciting an immune response against a canine Flt-3 ligand protein and/or has Flt-3 activity; (c) (i) an isolated protein of at least about 20 amino acids in length, wherein said protein is encoded by a nucleic acid molecule, wherein said nucleic acid molecule has an at least 60 contiguous nucleotide region identical in sequence to a 60 contiguous nucleotide region of a nucleic acid sequence selected from the group consisting of SEQ ID NO:41, SEQ ID NO:42, SEQ ID NO:43, SEQ ID NO:46, and/or SEQ ID NO:48; and/or (ii) an isolated protein of at least about 20 amino acids in length, wherein said protein has an at least 20 contiguous amino acid region identical in sequence to a 20 contiguous amino acid region selected from the group consisting of SEQ ID NO:44 and/or SEQ ID NO:49, wherein said isolated protein is capable of eliciting an immune response against a feline Flt-3 ligand protein and/or has Flt-3 activity; (d) (i) an isolated protein of at least about 30 amino acids in length, wherein said protein is encoded by a nucleic acid molecule, wherein said nucleic acid molecule has an at least 90 contiguous nucleotide region identical in sequence to a 90 contiguous nucleotide region of a nucleic acid sequence selected from the group consisting of SEQ ID NO:51, SEQ ID NO:52, SEQ ID NO:55, and/or SEQ ID NO:57; and/or (ii) an isolated protein of at least about 30 amino acids in length, wherein said protein has an at least 30 contiguous amino acid region identical in sequence to a 30 contiguous amino acid region selected from the group consisting of SEQ ID NO:53, SEQ ID NO:58, wherein said isolated protein is capable of eliciting an immune response against a canine CD40 protein and/or has CD40 activity; (e) (i) an isolated protein of at least about 20 amino acids in length, wherein said protein is encoded by a nucleic acid molecule, wherein said nucleic acid molecule has an at least 60 contiguous nucleotide region identical in sequence to a 60 contiguous nucleotide region of a nucleic acid sequence comprising Seq id no:60; and/or (ii) an isolated protein of at least about 20 amino acids in length, wherein said protein has an at least 20 contiguous amino acid region identical in sequence to a 20 contiguous amino acid region comprising the amino acid sequence SEQ ID NO:61, wherein said isolated protein is capable of eliciting an immune response against a feline CD40 protein and/or has CD40 activity; (f) (i) an isolated protein of at least about 35 amino acids in length, wherein said protein is encoded by a nucleic acid molecule, wherein said nucleic acid molecule has an at least 105 contiguous nucleotide region identical in sequence to a 105 contiguous nucleotide region of a nucleic acid sequence selected from the group consisting of SEQ ID NO:63, SEQ ID NO:64, SEQ ID NO:67, and/or SEQ ID NO:69; and/or (ii) an isolated protein of at least about 35 amino acids in length, wherein said protein has an at least 35 contiguous amino acid region identical in sequence to a 35 contiguous amino acid region selected from the group consisting of SEQ ID NO:65 and/or SEQ ID NO:70, wherein said isolated protein is capable of eliciting an immune response against a canine CD154 protein and/or has CD154 activity; (g) (i) an isolated protein of at least about 50 amino acids in length, wherein said protein is encoded by a nucleic acid molecule, wherein said nucleic acid molecule has an at least 150 contiguous nucleotide region identical in sequence to a 150 contiguous nucleotide region of a nucleic acid sequence selected from the group consisting of SEQ ID NO:72, SEQ ID NO:75, and/or SEQ ID NO:77; and/or (ii) an isolated protein of at least about 50 amino acids in length, wherein said protein has an at least 50 contiguous amino acid region identical in sequence to a 50 contiguous amino acid region selected from the group consisting of SEQ ID NO:73 and/or SEQ ID NO:78, wherein said isolated protein is capable of eliciting an immune response against a feline CD154 protein and/or has CD154 activity; (h) (i) an isolated protein of at least about 20 amino acids in length, wherein said protein is encoded by a nucleic acid molecule, wherein said nucleic acid molecule has an at least 60 contiguous nucleotide region identical in sequence to a 60 contiguous nucleotide region of a nucleic acid sequence selected from the group consisting of SEQ ID NO:80, SEQ ID NO:83, and/or SEQ ID NO:85; and/or (ii) an isolated protein of at least about 20 amino acids in length, wherein said protein has an at least 20 contiguous amino acid region identical in sequence to a 20 contiguous amino acid region selected from the group consisting of SEQ ID NO:81 and/or SEQ ID NO:86, wherein said isolated protein is capable of eliciting an immune response against a canine IL-5 protein and/or has IL-5 activity; (i) (i) an isolated protein of at least about 15 amino acids in length, wherein said protein is encoded by a nucleic acid molecule, wherein said nucleic acid molecule has an at least 45 contiguous nucleotide region identical in sequence to a 45 contiguous nucleotide region of a nucleic acid sequence selected from the group consisting of SEQ ID NO:88, SEQ ID NO:89, SEQ ID NO:90, SEQ ID NO:91, SEQ ID NO:94, SEQ ID NO:96, SEQ ID NO:99, SEQ ID NO:102, and/or SEQ ID NO:104; and/or (ii) an isolated protein of at least about 15 amino acids in length, wherein said protein has an at least 15 contiguous amino acid region identical in sequence to a 15 contiguous amino acid region selected from the group consisting of SEQ ID NO:92, SEQ ID NO:97, SEQ ID NO:100, and/or SEQ ID NO:105, wherein said isolated protein is capable of eliciting an immune response against a canine IL-13 protein and/or has IL-13 activity; (j) (i) an isolated protein encoded by a nucleic acid molecule selected from the group consisting of SEQ ID NO:107, SEQ ID NO:110, SEQ ID NO:113, and/or SEQ ID NO:116, and/or (ii) an isolated protein selected from the group consisting of SEQ ID NO:108, SEQ ID NO:111, SEQ ID NO:114, and/or SEQ ID NO:117, wherein said isolated protein is capable of eliciting an immune response against a feline interferon alpha protein and/or has interferon alpha activity; (k) (i) an isolated protein encoded by a nucleic acid molecule selected from the group consisting of SEQ ID NO:119, SEQ ID NO:122, and/or SEQ ID NO:124, and/or (ii) an isolated protein selected from the group consisting of SEQ ID NO:120 and/or SEQ ID NO:125, wherein said isolated protein is capable of eliciting an immune response against a feline GM-CSF and/or has GM-CSF activity.

The present invention also includes an isolated protein selected from the group consisting of: (a) a protein having an amino acid sequence that is at least about 85 percent identical to an amino acid sequence selected from the group consisting of SEQ ID NO:2 and/or SEQ ID NO:20; (b) a protein having an amino acid sequence that is at least about 75 percent identical to an amino acid sequence selected from the group consisting of SEQ ID NO:7, SEQ ID NO:23, SEQ ID NO:26, SEQ ID NO:31, and/or SEQ ID NO:34; (c) a protein having an amino acid sequence that is at least about 75 percent identical to an amino acid sequence selected from the group consisting of SEQ ID NO:44 and/or SEQ ID NO:49; (d) a protein having an amino acid sequence that is at least about 70 percent identical to an amino acid sequence selected from the group consisting of SEQ ID NO:53 and/or SEQ ID NO:58; (e) a protein having an amino acid sequence that is at least about 60 percent identical to an amino acid sequence comprising SEQ ID NO:61; (f) a protein having an amino acid sequence that is at least about 80 percent identical to an amino acid sequence selected from the group consisting of SEQ ID NO:65 and/or SEQ ID NO:70; (g) a protein having an amino acid sequence that is at least about 85 percent identical to the amino acid sequence SEQ ID NO:73 and/or SEQ ID NO:78; (h) a protein having an amino acid sequence that is at least about 85 percent identical to an amino acid sequence selected from the group consisting of SEQ ID NO:81 and/or SEQ ID NO:86; (i) a protein having an amino acid sequence that is at least about 70 percent identical to an amino acid sequence selected from the group consisting of SEQ ID NO:92, SEQ ID NO:97, SEQ ID NO:100, and/or SEQ ID NO:105; (j) a protein having an amino acid sequence selected from the group consisting of SEQ ID NO:108, SEQ ID NO:111, SEQ ID NO:114, and/or SEQ ID NO:117; and/or (k) a protein having an amino acid sequence selected from the group consisting of SEQ ID NO:120, and/or SEQ ID NO:125.

The present invention also includes isolated antibodies that selectively bind to a protein of the present invention.

One aspect of the present invention is a therapeutic composition that, when administered to an animal, regulates an immune response in said animal, said therapeutic composition comprising a therapeutic compound selected from the group consisting of: an immunoregulatory protein of the present invention; a mimetope of any of said immunoregulatory proteins; and a multimeric form of any of said immunoregulatory proteins; an isolated nucleic acid molecule of the present invention; an antibody that selectively binds to any of said immunoregulatory proteins; and/or an inhibitor of a immunoregulatory protein activity identified by its ability to inhibit the activity of any of said immunoregulatory proteins. Yet another aspect of the present invention is a method to regulate an immune response in an animal comprising administering to the animal a therapeutic composition of the present invention.

The present invention also includes a method to produce an immunoregulatory protein, said method comprising culturing a cell capable of expressing said protein, said protein being encoded by a nucleic acid molecule of the present invention.

One embodiment of the present invention is a method to identify a compound capable of regulating an immune response in an animal, said method comprising: (a) contacting an isolated canine IL-4 protein of the present invention with a putative inhibitory compound under conditions in which, in the absence of said compound, said protein has T cell proliferation stimulating activity; and determining if said putative inhibitory compound inhibits said activity; (b) contacting an isolated canine Flt-3 ligand protein of the present invention with a putative inhibitory compound under conditions in which, in the absence of said compound, said protein has dendritic precursor cell proliferation stimulating activity; and determining if said putative inhibitory compound inhibits said activity; (c) contacting an isolated feline Flt-3 ligand protein of the present invention with a putative inhibitory compound under conditions in which, in the absence of said compound, said protein has dendritic precursor cell proliferation stimulating activity; and determining if said putative inhibitory compound inhibits said activity; (d) contacting an isolated canine CD40 protein of the present invention with a putative inhibitory compound under conditions in which, in the absence of said compound, said protein has CD40 ligand binding activity; and determining if said putative inhibitory compound inhibits said activity; (e) contacting an isolated feline CD40 protein of the present invention with a putative inhibitory compound under conditions in which, in the absence of said compound, said protein has CD40 ligand binding activity; and determining if said putative inhibitory compound inhibits said activity; (f) contacting an isolated canine CD154 protein of the present invention with a putative inhibitory compound under conditions in which, in the absence of said compound, said protein has B cell proliferation activity; and determining if said putative inhibitory compound inhibits said activity; (g) contacting an isolated feline CD154 protein of the present invention with a putative inhibitory compound under conditions in which, in the absence of said compound, said protein has B cell proliferation activity; and determining if said putative inhibitory compound inhibits said activity; (h) contacting an isolated canine IL-5 protein of the present invention with a putative inhibitory compound under conditions in which, in the absence of said compound, said protein has TF-1 cell proliferation activity; and determining if said putative inhibitory compound inhibits said activity; (i) contacting an isolated canine IL-13 protein of the present invention with a putative inhibitory compound under conditions in which, in the absence of said compound, said protein has TF-1 cell proliferation activity; and determining if said putative inhibitory compound inhibits said activity; (j) contacting an isolated feline IFNα protein of the present invention with a putative inhibitory compound under conditions in which, in the absence of said compound, said protein has inhibition of proliferation of GM-CSF stimulated TF-1 cell activity; and determining if said putative inhibitory compound inhibits said activity; or (k) contacting an isolated feline GMCSF protein of the present invention with a putative inhibitory compound under conditions in which, in the absence of said compound, said protein has TF-1 cell proliferation activity; and determining if said putative inhibitory compound inhibits said activity.

DETAILED DESCRIPTION OF THE INVENTION

The present invention provides for isolated canine interleukin-4, canine or feline Flt-3 ligand, canine or feline CD40, canine or feline CD154, canine interleukin-5, canine interleukin-13, feline interferon alpha, or feline GM-CSF proteins, isolated canine interleukin-4, canine or feline Flt-3 ligand, canine or feline CD40, canine or feline CD154, canine interleukin-5, canine interleukin-13, feline interferon alpha, or feline GM-CSF nucleic acid molecules, antibodies directed against canine interleukin-4, canine or feline Flt-3 ligand, canine or feline CD40, canine or feline CD154, canine interleukin-5, canine interleukin-13, feline interferon alpha, or feline GM-CSF proteins, and compounds derived therefrom that regulate the immune response of an animal (e.g. inhibitors, antibodies and peptides).

Canine IL-4 protein can refer to a canine IL-4 protein, including homologs thereof. Canine Flt-3 ligand protein can refer to a canine Flt-3 ligand, including homologs thereof, and feline Flt-3 ligand can refer to feline Flt-3 ligand, including homologs thereof. Canine CD40 can refer to a canine CD40, including homologs thereof; feline CD40 can refer to a feline CD40, including homologs thereof. Canine CD154 can refer to a canine CD154, including homologs thereof; feline CD154 can refer to a feline CD154, including homologs thereof. Canine IL-5 can refer to canine IL-5, including homologs thereof; canine IL-13 can refer to canine IL-13, including homologs thereof. Feline IFNα can refer to a feline IFNα, including homologs thereof, and feline GM-CSF can refer to a feline GM-CSF, including homologs thereof. As used herein, the phrase "regulate an immune response" refers to modulating the activity of cells or molecules involved in an immune response. The term "regulate" can refer to increasing or decreasing an immune response. Regulation of an immune response can be determined using methods known in the art as well as methods disclosed herein. The term, "immunoregulatory protein" refers to a protein that can modulate the activity of cells or of molecules involved in an immune response. An immunoregulatory protein of the present invention refers to a canine IL-4, a canine and/or feline CD40, a canine and/or feline Flt3 ligand, a canine and/or feline CD154, a canine IL-5, a canine IL-13, a feline IFNα, and/or a feline GM-CSF protein as described herein. As used herein, the terms isolated canine interleukin-4, canine or feline Flt-3 ligand, canine or feline CD40, canine or feline CD154, canine interleukin-5, canine interleukin-13, feline interferon alpha, or feline GM-CSF proteins and/or isolated canine interleukin-4, canine or feline Flt-3 ligand, canine or feline CD40, canine or feline CD154, canine interleukin-5, canine interleukin-13, feline interferon alpha, or feline GM-CSF nucleic acid molecules refer to canine interleukin-4, canine or feline Flt-3 ligand, canine or feline CD40, canine or feline CD154, canine interleukin-5, canine interleukin-13, feline interferon alpha, or feline GM-CSF proteins and/or canine interleukin-4, canine or feline Flt-3 ligand, canine or feline CD40, canine or feline CD154, canine interleukin-5, canine interleukin-13, feline interferon alpha, or feline GM-CSF nucleic acid molecules derived from mammals and, as such, can be obtained from their natural source, or can be produced using, for example, recombinant nucleic acid technology or chemical synthesis. Also included in the present invention is the use of these proteins, nucleic acid molecules, antibodies, and/or compounds derived therefrom as therapeutic compositions to regulate the immune response of an animal as well as in other applications, such as those disclosed below.

One embodiment of the present invention is an isolated protein that includes a canine IL-4 protein, a canine and/or feline Flt-3 ligand protein, a canine and/or feline CD40 protein, a canine and/or feline CD154 protein, a canine interleukin-5 protein, a canine interleukin-13 protein, a feline interferon alpha protein, and/or a feline GM-CSF protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and/or "biologically pure" do not necessarily reflect the extent to which the protein has been purified. An isolated protein of the present invention can be obtained from its natural source, can be produced using recombinant DNA technology, or can be produced by chemical synthesis. Nucleic acid molecules of the present invention of known length isolated from *Canis familiaris* are denoted as follows: IL-4 is denoted as nCaIL-$4_x$, for example, nCaIL-$4_{549}$, wherein "#" refers to the number of nucleotides in that molecule; and in a similar fashion, Flt-3 ligand nucleic acid molecules are referred to as nCaFlt3$L_x$; CD40, nCaCD$40_x$; CD154, nCaCD$154_x$; IL-5, nCaIL-$5_x$; and IL-13, nCaIL-$13_x$. In a similar fashion, Flt-3 ligand nucleic acid molecules of the present invention of known length isolated from *Felis catus* are denoted as nFeFlt3$L_x$, CD40, nFeCD$40_x$; CD154, nFeCD$154_x$; IFNα, nFeIFNα$_x$; and GM-CSF (also denoted GMCSF), nFeGM-CSF$_x$. Similarly, proteins of the present invention of known length isolated from *Felis catus* are denoted as PFeFlt$31_x$, PFeCD$40_x$, PFeCD$154_x$, PFeIFNα$_x$, and/or PFeGM-CSF$_x$; and proteins of the present invention of known length isolated from *Canis familiaris* are denoted PCaIL-$4_x$, PCaFlt3$L_x$, PCaCD$40_x$, PCaCD$154_x$, PCaIL-$5_x$, and/or PCaIL-$13_x$.

As used herein, an isolated canine interleukin-4, canine or feline Flt-3 ligand, canine or feline CD40, canine or feline CD154, canine interleukin-5, canine interleukin-13, feline interferon alpha, and/or feline GM-CSF ligand protein of the present invention (i.e., an canine interleukin-4, canine or feline Flt-3 ligand, canine or feline CD40, canine or feline CD154, canine interleukin-5, canine interleukin-13, feline interferon alpha, or feline GM-CSF protein, respectively) can be a full-length protein or any homolog of such a protein. An isolated IL-4 protein of the present invention, including a homolog, can be identified in a straight-forward manner by the protein's ability to elicit an immune response against, (or to) an IL-4 protein, bind to an IL-4 receptor, stimulate B cell differentiation or activation or stimulate production of immunoglobulin by a B cell. An isolated Flt-3 ligand protein of the present invention, including a homolog, can be identified in a straight-forward manner by the protein's ability to elicit an immune response against a Flt-3 ligand protein, bind to Flt-3 receptor or stimulate Flt-3 receptor-bearing hematopoietic stem cells, early hematopoietic progenitor cells or immature lymphocytes. An isolated CD40 protein of the present invention, including a homolog, can be identified in a straight-forward manner by the protein's ability to elicit an immune response against a CD40 protein, bind to CD154 or stimulate CD154-bearing B cells, T cells, and/or epithelial cells. An isolated CD154 protein of the present invention, including a homolog, can be identified in a straight-forward manner by the protein's ability to elicit an immune response to a CD154 protein, bind to CD40 or stimulate CD40-bearing B cells, T cells, and/or epithelial cells. An isolated IL-5 protein of the present invention, including a homolog, can be identified in a straight-forward manner by the protein's ability to elicit an immune response to an IL-5 protein, bind to an IL-5 receptor, and/or stimulate eosinophils and/or cause thymocytes to produce cytotoxic T cells. An isolated IL-13 protein of the present invention, including a homolog, can be identified in a straight-forward manner by the protein's ability to elicit an immune response to an IL-13 protein, bind to an IL-13 receptor, and/or stimulate B cells, up-regulate expression of MHC class II and/or CD23 on monocytes, macrophages and/or B cells; and/or inhibition of proinflammatory cytokines. An isolated interferon alpha protein of the present invention, including a homolog, can be identified in a straight-forward manner by the protein's ability to elicit an immune response to an interferon alpha protein, bind to an interferon-alpha receptor, and/or activate NK cells and/or inhibit viral replication. An isolated GM-CSF protein of the present invention, including a homolog, can be identified in a straight-forward manner by the protein's ability to elicit an immune response to a GM-CSF protein, bind to a GM-CSF receptor, and/or activate granulocytes and/or macrophages. Examples of protein homologs of the present invention include immunoregulatory proteins of the present invention in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the protein homolog includes at least one epitope capable of eliciting an immune response against the parent protein, of binding to an antibody directed against the parent protein and/or of binding to the parent's receptor, where the term parent refers to the longer and/or full-length protein that the homolog is derived from. That is, when the homolog is administered to an animal as an immunogen, using techniques known to those skilled in the art, the animal will produce an immune response against at least one epitope of an immunoregulatory protein of the present invention, depending upon which protein is administered to an animal. The ability of a protein to effect an immune response can be measured using techniques known to those skilled in the art. As used herein, the term "epitope" refers to the smallest portion of a protein capable of selectively binding to the antigen binding site of an antibody. It is well accepted by those skilled in the art that the minimal size of a protein epitope capable of selectively binding to the antigen binding site of an antibody is about five or six to seven amino acids.

Homologs of immunoregulatory proteins of the present invention can be the result of natural allelic variation, including natural mutation. Protein homologs of the present invention can also be produced using techniques known in the art including, but not limited to, direct modifications to the protein and/or modifications to the gene encoding the protein using, for example, classic or recombinant DNA techniques to effect random or targeted mutagenesis.

Immunoregulatory proteins of the present invention include variants of a full-length protein of a protein of the present invention. Such variants include proteins that are less than full-length. As used herein, variants of the present invention refer to nucleic acid molecules that are naturally-occurring as defined below, and may result from alternative RNA splicing, alternative termination of an amino acid sequence or DNA recombination. Examples of variants include allelic variants as defined below. It is to be noted that a variant is an example of a homolog of the present invention.

Immunoregulatory proteins of the present invention are encoded by nucleic acid molecules of the present invention. As used herein, an IL-4 nucleic acid molecule includes nucleic acid sequences related to a natural canine IL-4 gene. As used herein, a Flt-3 ligand nucleic acid molecule includes nucleic acid sequences related to a natural canine Flt-3 ligand gene. As used herein, a CD40 nucleic acid molecule includes nucleic acid sequences related to a natural CD40 gene. As used herein, a CD154 nucleic acid molecule includes nucleic acid sequences related to a natural CD154 gene. As used herein, an IL-5 nucleic acid molecule includes nucleic acid sequences related to a natural IL-5 gene. As used herein, an IL-13 nucleic acid molecule includes nucleic acid sequences related to a natural IL-13 gene. As used herein, an IFNα nucleic acid molecule includes nucleic acid sequences related to a natural IFNα gene. As used herein, a GM-CSF nucleic acid molecule includes nucleic acid sequences related to a natural GM-CSF gene. As used herein, a canine IL-4, a canine and/or feline CD40, a canine and/or feline Flt3 ligand, a canine and/or feline CD154, a canine IL-5, a canine IL-13, a feline IFNα, and/or a feline GM-CSF gene refers to the natural genomic elements that encode an canine IL-4, a canine and/or feline CD40, a canine and/or feline Flt3 ligand, a canine and/or feline CD154, a canine IL-5, a canine IL-13, a feline IFNα, and/or a feline GM-CSF protein, respectively, and includes all regions such as regulatory regions that control production of the protein encoded by the gene (such as, but not limited to, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that region that is translated into a full-length, i.e., a complete, protein as would be initially translated in its natural milieu, prior to any post-translational modifications.

In one embodiment, an IL-4 gene of the present invention includes the nucleic acid sequence SEQ ID NO:1, as well as the complement of SEQ ID NO:1. Nucleic acid sequence SEQ ID NO:1 represents the deduced sequence of the coding strand of a cDNA (complementary DNA) denoted herein as nucleic acid molecule nCaIL-4$_{549}$, the production of which is disclosed in the Examples. Nucleic acid molecule nCaIL-4$_{549}$ comprises an apparently full-length coding region of canine IL-4. The complement of SEQ ID NO:1 (represented herein by SEQ ID NO:3) refers to the nucleic acid sequence of the strand fully complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is fully complementary to (i.e., can form a double helix with) the strand for which the sequence is cited. It should be noted that since nucleic acid sequencing technology is not entirely error-free, SEQ ID NO:1 (as well as other nucleic acid and protein sequences presented herein) represents an apparent nucleic acid sequence of the nucleic acid molecule encoding an immunoregulatory protein of the present invention.

In another embodiment, a Flt-3 ligand gene of the present invention includes the nucleic acid sequence SEQ ID NO:6, as well as the complement represented by SEQ ID NO:8. Nucleic acid sequence SEQ ID NO:6 represents the deduced sequence of the coding strand of a cDNA denoted herein as nucleic acid molecule nCaFlt3L$_{1013}$, the production of which is disclosed in the Examples. Nucleic acid molecule nCaFlt3L$_{1013}$ comprises an apparently full-length coding region of canine Flt-3 ligand.

In another embodiment, a Flt-3 ligand gene of the present invention includes the nucleic acid sequence SEQ ID NO:43, as well as the complement represented by SEQ ID NO:45. Nucleic acid sequence SEQ ID NO:43 represents the deduced sequence of the coding strand of a cDNA denoted herein as nucleic acid molecule nFeFlt3L$_{942}$, the production of which is disclosed in the Examples. Nucleic acid molecule nFeFlt3L$_{942}$ comprises an apparently full-length coding region of feline Flt-3 ligand.

In another embodiment, a CD40 gene of the present invention includes the nucleic acid sequence SEQ ID NO:52, as well as the complement represented by SEQ ID NO:54. Nucleic acid sequence SEQ ID NO:52 represents the deduced sequence of the coding strand of a cDNA denoted herein as nucleic acid molecule nCaCD40$_{1425}$, the production of which is disclosed in the Examples. Nucleic acid molecule nCaCD40$_{1425}$ comprises an apparently full-length coding region of canine CD40.

In another embodiment, a CD40 gene of the present invention includes the nucleic acid sequence SEQ ID NO:60, as well as the complement represented by SEQ ID NO:62. Nucleic acid sequence SEQ ID NO:60 represents the deduced sequence of the coding strand of a cDNA denoted herein as nucleic acid molecule nFeCD40$_{336}$, the production of which is disclosed in the Examples. Nucleic acid molecule nFeCD40$_{336}$ comprises an apparent portion of the coding region of feline CD40.

In another embodiment, a CD154 gene of the present invention includes the nucleic acid sequence SEQ ID NO:64, as well as the complement represented by SEQ ID NO:66. Nucleic acid sequence SEQ ID NO:64 represents the deduced sequence of the coding strand of a cDNA denoted herein as nucleic acid molecule nCaCD154$_{1878}$, the production of which is disclosed in the Examples. Nucleic acid molecule nCaCD154$_{1878}$ comprises an apparently full-length coding region of canine CD154.

In another embodiment, a CD154 gene of the present invention includes the nucleic acid sequence SEQ ID NO:72, as well as the complement represented by SEQ ID NO:74.

Nucleic acid sequence SEQ ID NO:72 represents the deduced sequence of the coding strand of a cDNA denoted herein as nucleic acid molecule nFeCD154$_{885}$, the production of which is disclosed in the Examples. Nucleic acid molecule nFeCD154$_{885}$ comprises an apparently full-length coding region of feline CD154.

In another embodiment, an IL-5 gene of the present invention includes the nucleic acid sequence SEQ ID NO:80, as well as the complement represented by SEQ ID NO:82. Nucleic acid sequence SEQ ID NO:80 represents the deduced sequence of the coding strand of a cDNA denoted herein as nucleic acid molecule nCaIL-5$_{610}$, the production of which is disclosed in the Examples. Nucleic acid molecule nCaIL-5$_{610}$ comprises an apparently full-length coding region of canine IL-5.

In another embodiment, an IL-13 gene of the present invention includes the nucleic acid sequence SEQ ID NO:91, as well as the complement represented by SEQ ID NO:93. Nucleic acid sequence SEQ ID NO:91 represents the deduced sequence of the coding strand of a cDNA denoted herein as nucleic acid molecule nCaIL-13$_{1302}$, the production of which is disclosed in the Examples. Nucleic acid molecule nCaIL-13$_{1302}$ comprises an apparently full-length coding region of canine IL-13.

In another embodiment, an IFNα gene of the present invention includes the nucleic acid sequence SEQ ID NO:107, as well as the complement represented by SEQ ID NO:109. Nucleic acid sequence SEQ ID NO:107 represents the deduced sequence of the coding strand of a cDNA denoted herein as nucleic acid molecule nFeIFNα$_{567a}$, the production of which is disclosed in the Examples. Nucleic acid molecule nFeIFNα$_{567a}$ comprises an apparently full-length coding region of feline IFNα.

In another embodiment, a GM-CSF gene of the present invention includes the nucleic acid sequence SEQ ID NO:119, as well as the complement represented by SEQ ID NO:121. Nucleic acid sequence SEQ ID NO:119 represents the deduced sequence of the coding strand of a cDNA denoted herein as nucleic acid molecule nFeGM-CSF$_{444}$, the production of which is disclosed in the Examples. Nucleic acid molecule nFeGM-CSF$_{444}$ comprises an apparently full-length coding region of feline GM-CSF.

Additional immunoregulatory nucleic acid molecules and proteins of the present invention having specific sequence identifiers are described in Table 1.

TABLE 1

Sequence identification numbers (SEQ ID NOs) and their corresponding nucleic acid molecules or proteins.

| SEQ ID NO: | DESCRIPTION |
|---|---|
| 1 | nCaIL-4$_{549}$ coding strand |
| 2 | PCaIL-4$_{132}$ |
| 3 | nCaIL-4$_{549}$ complementary strand |
| 4 | nCaIL-4$_{396}$ coding strand |
| 5 | nCaIL-4$_{396}$ complementary strand |
| 6 | nCaFlt3L$_{1013}$ coding strand |
| 7 | PCaFlt3L$_{294}$ |
| 8 | nCaFlt3L$_{1013}$ complementary strand |
| 9 | nCaFlt3L$_{882}$ coding strand |
| 10 | nCaFlt3L$_{882}$ complementary strand |
| 19 | nCaIL-4$_{324}$ coding strand |
| 20 | PCaIL-4$_{108}$ |
| 21 | nCaIL-4$_{324}$ complementary strand |
| 22 | nCaFlt3L$_{804}$ coding strand |
| 23 | PCaFlt3L$_{268}$ |
| 24 | nCaFlt3L$_{804}$ complementary strand |
| 25 | nCaFlt3L$_{985}$ coding strand |

TABLE 1-continued

Sequence identification numbers (SEQ ID NOs) and their corresponding nucleic acid molecules or proteins.

| SEQ ID NO: | DESCRIPTION |
|---|---|
| 26 | PCaFlt3L$_{276}$ |
| 27 | nCaFlt3L$_{985}$ complementary strand |
| 28 | nCaFlt3L$_{828}$ coding strand |
| 29 | nCaFlt3L$_{828}$ complementary strand |
| 30 | nCaFlt3L$_{750}$ coding strand |
| 31 | PCaFlt3L$_{250}$ |
| 32 | nCaFlt3L$_{750}$ complementary strand |
| 33 | nCaFlt3L$_{1019}$ coding strand |
| 34 | PCaFlt3L$_{31}$ |
| 35 | nCaFlt3L$_{1019}$ complementary strand |
| 36 | nCaFlt3L$_{93}$ coding strand |
| 37 | nCaFlt3L$_{93}$ complementary strand |
| 41 | nFeFlt3L$_{395}$ coding strand |
| 42 | nFeFlt3L$_{793}$ coding strand |
| 43 | nFeFlt3L$_{942}$ coding strand |
| 44 | PFeFlt3L$_{291}$ |
| 45 | nFeFlt3L$_{942}$ complementary strand |
| 46 | nFeFlt3L$_{873}$ coding strand |
| 47 | nFeFlt3L$_{873}$ complementary strand |
| 48 | nFeFlt3L$_{795}$ coding strand |
| 49 | PFeFlt3L$_{265}$ |
| 50 | nFeFlt3L$_{795}$ complementary strand |
| 51 | nCaCD40$_{321}$ coding strand |
| 52 | nCaCD40$_{1425}$ coding strand |
| 53 | PCaCD40$_{274}$ |
| 54 | nCaCD40$_{1425}$ complementary strand |
| 55 | nCaCD40$_{822}$ coding strand |
| 56 | nCaCD40$_{822}$ complementary strand |
| 57 | nCaCD40$_{765}$ coding strand |
| 58 | PCaCD40$_{255}$ |
| 59 | nCaCD40$_{765}$ complementary strand |
| 60 | nFeCD40$_{336}$ coding strand |
| 61 | PFeCD40$_{112}$ |
| 62 | nFeCD40$_{336}$ complementary strand |
| 63 | nCaCD154$_{390}$ coding strand |
| 64 | nCaCD154$_{1878}$ coding strand |
| 65 | PCaCD154$_{260}$ |
| 66 | nCaCD154$_{1878}$ complementary strand |
| 67 | nCaCD154$_{780}$ coding strand |
| 68 | nCaCD154$_{780}$ complementary strand |
| 69 | nCaCD154$_{633}$ coding strand |
| 70 | PCaCD154$_{211}$ |
| 71 | nCaCD154$_{633}$ complementary strand |
| 72 | nFeCD154$_{885}$ coding strand |
| 73 | PFeCD154$_{260}$ |
| 74 | nFeCD154$_{885}$ complementary strand |
| 75 | nFeCD154$_{780}$ coding strand |
| 76 | nFeCD154$_{780}$ complementary strand |
| 77 | nFeCD154$_{633}$ coding strand |
| 78 | PFeCD154$_{211}$ |
| 79 | nFeCD154$_{633}$ complementary strand |
| 80 | nCaIL-5$_{610}$ coding strand |
| 81 | PCaIL-5$_{134}$ |
| 82 | nCaIL-5$_{610}$ complementary strand |
| 83 | nCaIL-5$_{402}$ coding strand |
| 84 | nIL-5$_{402}$ complementary strand |
| 85 | nCaIL-5$_{345}$ coding strand |
| 86 | PCaIL-5$_{115}$ |
| 87 | nCaIL-5$_{345}$ complementary strand |
| 88 | nCaIL-13$_{166}$ coding strand |
| 89 | nCaIL-13$_{272}$ coding strand |
| 90 | nCaIL-13$_{278}$ coding strand |
| 91 | nCaIL-13$_{1302}$ coding strand |
| 92 | PCaIL-13$_{131}$ |
| 93 | nCaIL-13$_{1302}$ complementary strand |
| 94 | nCaIL-13$_{393}$ coding strand |
| 95 | nCaIL-13$_{393}$ complementary strand |
| 96 | nCaIL-13$_{333}$ coding strand |
| 97 | PaIL-13$_{111}$ |
| 98 | nCaIL-13$_{333}$ complementary strand |
| 99 | nCaIL-13$_{1269}$ coding strand |
| 100 | PCaIL-13$_{130}$ |
| 101 | nCaIL-13$_{1269}$ complementary strand |
| 102 | nCaIL-13$_{390}$ coding strand |
| 103 | nCaIL-13$_{390}$ complementary strand |
| 104 | nCaIL-13$_{330}$ coding strand |
| 105 | PCaIL-13$_{110}$ |
| 106 | nCaIL-13$_{330}$ complementary strand |
| 107 | nFeIFNα$_{567a}$ coding strand |
| 108 | PFeIFNα$_{189a}$ |
| 109 | nFeIFNα$_{567a}$ complementary strand |
| 110 | nFeIFNα$_{567b}$ coding strand |
| 111 | PFeIFNα$_{189b}$ |
| 112 | nFeIFNα$_{567b}$ complementary strand |
| 113 | nFeIFNα$_{498a}$ coding strand |
| 114 | PFeIFNα$_{166a}$ |
| 115 | nFeIFNα$_{498a}$ complementary strand |
| 116 | nFeFeIFNα$_{498b}$ coding strand |
| 117 | PFeIFNα$_{166b}$ |
| 118 | nFeIFNα$_{498b}$ complementary strand |
| 119 | nFeGMCSF$_{444}$ coding strand |
| 120 | PFeGMCSF$_{144}$ |
| 121 | nFeGMCSF$_{444}$ complementary strand |
| 122 | nFeGMCSF$_{432}$ coding strand |
| 123 | nFeGMCSF$_{432}$ complementary strand |
| 124 | nFeGMCSF$_{381}$ coding strand |
| 125 | PFeGMCSF$_{127}$ |
| 126 | nFeGMCSF$_{381}$ complementary strand |

In another embodiment, an IL-4 gene or nucleic acid molecule can be an allelic variant that includes a similar but not identical sequence to SEQ ID NO:1, SEQ ID NO:3, SEQ ID NO:4, SEQ ID NO:5, SEQ ID NO:19, SEQ ID NO:21, and/or any other IL-4 nucleic acid sequence cited herein. In another embodiment, a Flt-3 ligand gene or nucleic acid molecule can be an allelic variant that includes a similar but not identical sequence to SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID to NO:36, SEQ ID NO:37, SEQ ID NO:41, SEQ ID NO:42, SEQ ID NO:43, SEQ ID NO:45, SEQ ID NO:46, SEQ ID NO:47, SEQ ID NO:48, SEQ ID NO:50 and/or any other Flt-3 ligand nucleic acid sequence cited herein. In another embodiment, a CD40 gene or nucleic acid molecule can be an allelic variant that includes a similar but not identical sequence to SEQ ID NO:51, SEQ ID NO:52, SEQ ID NO:54, SEQ ID NO:55, SEQ ID NO:56, SEQ ID NO:57, SEQ ID NO:59, SEQ ID NO:60, SEQ ID NO:62 and/or any other CD40 nucleic acid sequence cited herein. In another embodiment, a CD154 gene or nucleic acid molecule can be an allelic variant that includes a similar but not identical sequence to SEQ ID NO:63, SEQ ID NO:64, SEQ ID NO:66, SEQ ID NO:67, SEQ ID NO:68, SEQ ID NO:69, SEQ ID NO:71, SEQ ID NO:72, SEQ ID NO:74, SEQ ID NO:75, SEQ ID NO:76, SEQ ID NO:77, SEQ ID NO:79 and/or any other CD154 nucleic acid sequence cited herein. In another embodiment, an IL-5 gene or nucleic acid molecule can be an allelic variant that includes a similar but not identical sequence to SEQ ID NO:80, SEQ ID NO:82, SEQ ID NO:83, SEQ ID NO:84, SEQ ID NO:85, SEQ ID NO:87 and/or any other IL-5 nucleic acid sequence cited herein. In another embodiment, an IL-13 gene or nucleic acid molecule can be an allelic variant that includes a similar but not identical sequence to SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, SEQ ID NO:106 and/or any other IL-13 nucleic acid sequence cited herein. In another embodiment, an IFNα gene or nucleic acid molecule can be an allelic variant that includes a similar but not identical sequence to SEQ ID NO:107, SEQ ID NO:109, SEQ ID NO:110, SEQ ID NO:112, SEQ ID NO:113, SEQ ID NO:115, SEQ ID NO:116, and/or SEQ ID NO:118 and/or any other IFNα nucleic acid sequence cited herein. In another embodiment, a GM-CSF gene or nucleic acid molecule can be an allelic variant that includes a similar but not identical sequence to SEQ ID NO:119, SEQ ID NO:121, SEQ ID NO:122, SEQ ID NO:123, SEQ ID NO:124, and/or SEQ ID NO:126 and/or any other GM-CSF nucleic acid cited herein. An allelic variant of a canine interleukin-4, canine or feline Flt-3 ligand, canine or feline CD40, canine or feline CD154, canine interleukin-5, canine interleukin-13, feline interferon alpha, or feline GM-CSF gene, including the particular SEQ ID NO's cited herein, is a gene that occurs at essentially the same locus (or loci) in the genome as the gene including the particular SEQ ID NO's cited herein, but which, due to natural variations caused by, for example, mutation or recombination, has a similar but not identical sequence. Also included in the term allelic variant are allelic variants of cDNAs derived from such genes. Because natural selection typically selects against alterations that affect function, allelic variants usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to be found within a given animal, since the respective genomes are diploid, and sexual reproduction will result in the reassortment of alleles.

The minimal size of an canine interleukin-4, canine or feline Flt-3 ligand, canine or feline CD40, canine or feline CD154, canine interleukin-5, canine interleukin-13, feline interferon alpha, or feline GM-CSF protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267-284, each of which is incorporated herein by this reference. As explained in detail in the cited references, the determination of hybridization conditions involves the manipulation of a set of variables including the ionic strength (M, in moles/liter), the hybridization temperature (° C.), the concentration of nucleic acid helix destabilizing agents, such as formamide, the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° C. + 16.6 \log M + 0.41(\% G+C) - 500/n - 0.61(\% \text{ formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$, or $T_d$ for nucleic acid molecules of different sizes. For example, $T_m$, decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions, by altering, for example, the salt concentration, the formamide concentration or the temperature, so that only nucleic acid hybrids with greater than a specified % base pair mismatch will hybridize. Stringent hybridization conditions are commonly understood by those skilled in the art to be those experimental conditions that will allow about 30% base pair mismatch, i.e., about 70% identity. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene or specified nucleic acid molecule under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

Preferred portions, or fragments, of a canine interleukin-4, canine or feline Flt-3 ligand, canine or feline CD40, canine or feline CD154, canine interleukin-5, canine interleukin-13, feline interferon alpha, or feline GM-CSF, protein of the present invention include at least 15 amino acids, at least 20 amino acids, at least 25 amino acids, at least 30 amino acids, at least 35 amino acids, at least 40 amino acids, at least 45 amino acids, at least 50 amino acids, at least 60 amino acids, at least 75 amino acids or at least 100 amino acids. An IL-4, IL-5, and/or IL-13 protein of the present invention can include at least a portion of an IL-4, IL-5, and/or IL-13 protein that is capable of binding to an IL-4, IL-5, and/or IL-13 receptor, respectively. IL-4, IL-5, and IL-13 receptors are known to those of skill in the art, and are described in Janeway et al., in *Immunobiology, the Immune System in Health and Disease*, Garland Publishing, Inc., NY, 1996 (which is incorporated herein by this reference in its entirety). The IL-4, IL-5, and/or IL-13 receptor-binding portion of an IL-4, IL-5, and/or IL-13 protein, respectively, can be determined by incubating the protein with an isolated IL-4, IL-5, and/or IL-13 receptor, as appropriate, or a cell having an IL-4, IL-5, and/or IL-13 receptor on its surface, as appropriate. IL-4, IL-5, and/or IL-13 protein binding to purified IL-4, IL-5, and/or IL-13 receptor, respectively, can be determined using methods known in the art including BIACORE® screening, confocal immunofluorescent microscopy, immunoprecipitation, gel chromatography, determination of inhibition of binding of antibodies that bind specifically to the IL-4, IL-5, and/or IL-13 binding domain of an IL-4, IL-5, and/or IL-13 receptor, ELISA using an IL-4, IL-5, and/or IL-13 receptor, respectively, labeled with a detectable tag such as an enzyme or chemiluminescent tag or yeast-2 hybrid technology. A Flt-3 ligand protein of the present invention can include at least a portion of a Flt-3 ligand protein that is capable of binding to Flt-3 receptor or stimulating Flt-3 receptor-bearing hematopoietic stem cells, early hematopoietic progenitor cells or immature lymphocytes. Flt-3 receptors are known to those of skill in the art, and are described in Drexler, *Leukemia*, vol. 10, pp. 588-599, 1996 (which is incorporated herein in its entirety by this reference). The Flt-3 receptor-binding portion of a Flt-3 ligand protein can be determined by incubating the protein with isolated Flt-3 receptor or a cell having a Flt-3 receptor on its surface. Flt-3 ligand protein binding to purified Flt-3 receptor can be determined using methods known in the art including BIACORE® screening, confocal immunofluorescent microscopy, immunoprecipitation, gel chromatography, determination of inhibition of binding of antibodies that bind specifically to the Flt-3 ligand binding domain of a Flt-3 receptor, ELISA using a Flt-3 receptor labeled with a detectable tag such as an enzyme or chemiluminescent tag or yeast-2 hybrid technology. A CD40 and/or CD154 protein of the present invention can include at least a portion of a CD40 and/or CD154 protein that is capable of binding to a CD40 and/or CD154 receptor, respectively, or stimulating CD40 and/or CD154 receptor-bearing hematopoietic stem cells, early hematopoietic progenitor cells or immature lymphocytes. The CD40 and/or CD154 receptor-binding portion of a CD40 and/or CD154 protein can be determined by incubating the protein with isolated CD40 and/or CD154 receptor, as appropriate, or a cell having a CD40 and/or CD154 receptor on its surface, as appropriate. CD40 and/or CD154 protein binding to CD154 and/or CD40, respectively, can be determined using methods known in the art including BIACORE® screening, confocal immunofluorescent microscopy, immunoprecipitation, gel chromatography, determination of inhibition of binding of antibodies that bind specifically to the CD40 and/or CD154 binding domain of CD40 and/or CD154, as appropriate, ELISA using a CD40 and/or CD154 labeled with a detectable tag such as an enzyme or chemiluminescent tag or yeast-2 hybrid technology.

The present invention also includes mimetopes of canine interleukin-4, canine or feline Flt-3 ligand, canine or feline CD40, canine or feline CD154, canine interleukin-5, canine interleukin-13, feline interferon alpha, or feline GM-CSF proteins of the present invention. As used herein, a mimetope of an immunoregulatory protein of the present invention refers to any compound that is able to mimic the activity of such a canine interleukin-4, canine or feline Flt-3 ligand, canine or feline CD40, canine or feline CD154, canine interleukin-5, canine interleukin-13, feline interferon alpha, or feline GM-CSF protein, respectively, often because the mimetope has a structure that mimics the particular protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and/or synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of an immunoregulatory protein of the present invention is a fusion protein that includes either a canine interleukin-4, canine or feline Flt-3 ligand, canine or feline CD40, canine or feline CD154, canine interleukin-5, canine interleukin-13, feline interferon alpha, or feline GM-CSF protein-containing domain, each attached to one or more fusion segments. Suitable fusion segments for use with the present invention include, but are not limited to, segments that can: link two or more immunoregulatory proteins of the present invention, to form multimeric forms of an immunoregulatory protein of the present invention; enhance a protein's stability; act as an immunopotentiator to enhance an immune response against an canine interleukin-4, canine or feline Flt-3 ligand, canine or feline CD40, canine or feline CD154, canine interleukin-5, canine interleukin-13, feline interferon alpha, or feline GM-CSF protein; and/or assist in purification of an canine interleukin-4, canine or feline Flt-3 ligand, canine or feline CD40, canine or feline CD154, canine interleukin-5, canine interleukin-13, feline interferon alpha, or feline GM-CSF protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the IL-4-containing domain, or the Flt-3 ligand-containing domain, or the CD40-containing domain, or the CD154-containing domain, or the IL-5-containing domain, or the IL-13-containing domain, or the IFNα-containing domain, or GM-CSF-containing domain, of a protein and can be susceptible to cleavage in order to enable straight-forward recovery of either canine interleukin-4, canine or feline Flt-3 ligand, canine or feline CD40, canine or feline CD154, canine interleukin-5, canine interleukin-13, feline interferon alpha, or feline GM-CSF protein, respectively. Fusion proteins are preferably produced by culturing a recombinant cell transformed with a fusion nucleic acid molecule that encodes a protein including the fusion segment attached to either the carboxyl and/or amino terminal end of an canine interleukin-4-, canine or feline Flt-3 ligand-, canine or feline CD40-, canine or feline CD154-, canine interleukin-5-, canine interleukin-13-, feline interferon alpha-, or feline GM-CSF-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of -galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

A suitable fusion segment that links one IL-4 protein to another IL-4 protein, or one Flt-3 ligand protein to another Flt-3 ligand protein, or one CD40 protein to another CD40 protein, or one CD154 protein to another CD154 protein, or one IL-5 protein to another IL-5 protein to another IL-5 protein, or one IL-13 protein to another IL-13 protein, or one IFNα protein to another IFNα protein, or one GM-CSF protein to another GM-CSF protein, includes any amino acid sequence that enables such proteins to be linked while maintaining the biological function of either the canine interleukin-4, canine or feline Flt-3 ligand, canine or feline CD40, canine or feline CD154, canine interleukin-5, canine interleukin-13, feline interferon alpha, or feline GM-CSF, proteins, respectively. Selection of a suitable linker is dependent upon how many proteins are to be linked to form one multimeric molecule and from where on either the canine interleukin-4, canine or feline Flt-3 ligand, canine or feline CD40, canine or feline CD154, canine interleukin-5, canine interleukin-13, feline interferon alpha, or feline GM-CSF molecule the linker extends. Preferably, a linker fusion segment of the present invention comprises a peptide of from about 6 amino acid residues to about 40 residues, more preferably from about 6 residues to about 30 residues in length.

In another embodiment, an canine interleukin-4, canine or feline Flt-3 ligand, canine or feline CD40, canine or feline CD154, canine interleukin-5, canine interleukin-13, feline interferon alpha, or feline GM-CSF protein of the present invention also includes at least one additional protein segment that is capable of targeting either canine interleukin-4, canine or feline Flt-3 ligand, canine or feline CD40, canine or feline CD154, canine interleukin-5, canine interleukin-13, feline interferon alpha, or feline GM-CSF protein, respectively, to a desired cell or receptive molecule. Such a multivalent targeting protein can be produced by culturing a cell transformed with a nucleic acid molecule comprising two or more nucleic acid domains joined together in such a manner that the resulting nucleic acid molecule is expressed as a multivalent targeting protein containing a canine interleukin-4, canine or feline Flt-3 ligand, canine or feline CD40, canine or feline CD154, canine interleukin-5, canine interleukin-13, feline interferon alpha, or feline GM-CSF protein or portion thereof and/or at least one targeting compound capable of delivering the canine interleukin-4, canine or feline Flt-3 ligand, canine or feline CD40, canine or feline CD154, canine interleukin-5, canine interleukin-13, feline interferon alpha, or feline GM-CSF protein, respectively, to a desired site in an animal.

Examples of multivalent targeting proteins include, but are not limited to, a canine interleukin-4, canine or feline Flt-3 ligand, canine or feline CD40, canine or feline CD154, canine interleukin-5, canine interleukin-13, feline interferon alpha, or feline GM-CSF protein of the present invention attached to one or more compounds that can bind to a receptive molecule on the surface of a cell located in an area of an animal where regulation of an immune response is desired. One of skill in the art can select appropriate targeting fusion segments depending upon the cell or receptive molecule being targeted.

Another example of a multivalent protein of the present invention includes, but is not limited to, a canine interleukin-4, canine or feline Flt-3 ligand, canine or feline CD40, canine or feline CD154, canine interleukin-5, canine interleukin-13, feline interferon alpha, or feline GM-CSF protein of the present invention attached to one or more proteins that are potentially antigenic in mammals. Thus, immunogenicity of the potentially antigenic protein could be enhanced by administering to a mammal together with an immunoregulatory protein of the present invention.

A naturally-occurring variant of a canine interleukin-4, canine or feline Flt-3 ligand, canine or feline CD40, canine or feline CD154, canine interleukin-5, canine interleukin-13, feline interferon alpha, or feline GM-CSF protein of the present invention is preferably isolated from (including isolation of the natural protein or production of the protein by recombinant or synthetic techniques) from mammals, including but not limited to dogs (i.e., canids), cats (i.e., felids), horses (i.e., equids), humans, cattle, chinchillas, ferrets, goats, mice, minks, rabbits, raccoons, rats, sheep, squirrels, swine, chickens, ostriches, quail and/or turkeys as well as other furry animals, pets, zoo animals, work animals and/or food animals. Particularly preferred animals from which to isolate canine interleukin-4, canine or feline Flt-3 ligand, canine or feline CD40, canine or feline CD154, canine interleukin-5, canine interleukin-13, feline interferon alpha, or feline GM-CSF proteins are dogs, cats, horses and/or humans.

A preferred isolated protein of the present invention is a protein encoded by at least one of the following nucleic acid molecules: $nCaIL-4_{549}$, $nCaIL-4_{396}$, $nCaIL-4_{324}$, $nCaFlt3L_{1013}$, $nCaFlt3L_{882}$, $nCaFlt3L_{804}$, $nCaFlt3L_{828}$, $nCaFlt3L_{985}$, $nCaFlt3L_{1019}$, $nCaFlt3L_{93}$, $nCaFlt3L_{750}$, $nFeFlt3L_{395}$, $nFeFlt3L_{793}$, $nFeFlt3L_{942}$, $nFeFlt3L_{873}$, $nFeFlt3L_{795}$, $nCaCD40_{321}$, $nCaCD40_{1425}$, $nCaCD40_{822}$, $nCaCD40_{765}$, $nFeCD40_{336}$, $nCaCD154_{390}$, $nCaCD1541_{878}$, $nCaCD154_{780}$, $nCaCD154_{633}$, $nFeCD154_{885}$, $nFeCD154_{780}$, $nFeCD154_{633}$, $nCaIL-5_{610}$, $nCaIL-5_{402}$, $nCaIL-5_{345}$, $nCaIL-13_{166}$, $nCaIL-13_{272}$, $nCaIL-13_{278}$, $nCaIL-13_{1302}$, $nCaIL-13_{393}$, $nCaIL-13_{333}$, $nCaIL-13_{1269}$, $nCaIL-13_{390}$, $nCaIL-13_{330}$, $nFeIFN\alpha_{567a}$, $nFeIFN\alpha_{567b}$, $nFeIFN\alpha_{498a}$, $nFeIFN\alpha4_{98b}$, $nFeGMCSF_{444}$, $nFeGMCSF_{432}$, $nFeGMCSF_{381}$ and/or allelic variants of any of these nucleic acid molecules. Also preferred is an isolated protein that is encoded by a nucleic acid molecule the having nucleic acid sequence SEQ ID NO:1, SEQ ID NO:4, SEQ ID NO:19, SEQ ID NO:6, SEQ ID NO:9, SEQ ID NO:22, SEQ ID NO:25, SEQ ID NO:28, SEQ ID NO:30, SEQ ID NO:33, SEQ ID NO:36, SEQ ID NO:41, SEQ ID NO:42, SEQ ID NO:43, SEQ ID NO:46, SEQ ID NO:48, SEQ ID NO:51, SEQ ID NO:52, SEQ ID NO:55, SEQ ID NO:57, SEQ ID NO:60, SEQ ID NO:63, SEQ ID NO:64, SEQ ID NO:67, SEQ ID NO:69, SEQ ID NO:72, SEQ ID NO:75, SEQ ID NO:77, SEQ ID NO:80, SEQ ID NO:83, SEQ ID NO:85, SEQ ID NO:88, SEQ ID NO:89, SEQ ID NO:90, SEQ ID NO:91, SEQ ID NO:94, SEQ ID NO:96, SEQ ID NO:99, SEQ ID NO:102, SEQ ID NO:104, SEQ ID NO:107, SEQ ID NO:110, SEQ ID NO:113, SEQ ID NO:116, SEQ ID NO:119, SEQ ID NO:122, SEQ ID NO:124; and/or an allelic variant of such a nucleic acid molecule.

Translation of SEQ ID NO:1, the coding strand of $nCaIL-4_{549}$, yields a protein of about 132 amino acids, denoted herein as $PCaIL-4_{132}$, the amino acid sequence of which is presented in SEQ ID NO:2, assuming an open reading frame having an initiation codon spanning from nucleotide 43 through nucleotide 45 of SEQ ID NO:1 and a stop codon spanning from nucleotide 439 through nucleotide 441 of SEQ ID NO:1.

Translation of SEQ ID NO:6, the coding strand of nCaFlt3L$_{1013}$, yields a protein of about 294 amino acids, denoted herein as PCaFlt3L$_{294}$, the amino acid sequence of which is presented in SEQ ID NO:7, assuming an open reading frame having an initiation codon spanning from nucleotide 35 through nucleotide 37 of SEQ ID NO:6 and a stop codon spanning from nucleotide 917 through nucleotide 919 of SEQ ID NO:6.

Translation of SEQ ID NO:43, the coding strand for nFeFlt3L$_{942}$, yields a protein of about 291 amino acids, denoted herein as PFeFlt3L$_{291}$, the amino acid sequence of which is presented in SEQ ID NO:44, assuming an open reading frame having an initiation codon spanning from nucleotide 31 through nucleotide 33 of SEQ ID NO:43 and a stop codon spanning from nucleotide 904 through nucleotide 906 of SEQ ID NO:43.

Translation of SEQ ID NO:52, the coding strand for nCaCD40$_{1425}$, yields a protein of about 274 amino acids, denoted herein as PCaCD40$_{274}$, the amino acid sequence of which is presented in SEQ ID NO:53, assuming an open reading frame having an initiation codon spanning from nucleotide 196 through nucleotide 198 of SEQ ID NO:52 and a stop codon spanning from about nucleotide 1018 through nucleotide 1020 of SEQ ID NO:52.

Translation of SEQ ID NO:60, the coding strand for nFeCD40$_{336}$, yields a protein of about 112 amino acids, denoted herein as PFeCD40$_{112}$, the amino acid sequence of which is presented in SEQ ID NO:61, assuming an open reading frame having an initiation codon spanning from nucleotide 1 through nucleotide 3 of SEQ ID NO:60.

Translation of SEQ ID NO:64, the coding strand for nCaCD154$_{1878}$, yields a protein of about 260 amino acids, denoted herein as PCaCD154$_{260}$, the amino acid sequence of which is presented in SEQ ID NO:65, assuming an open reading frame having an initiation codon spanning from nucleotide 284 through nucleotide 286 of SEQ ID NO:64 and a stop codon spanning from nucleotide 1064 through nucleotide 1066 of SEQ ID NO:64.

Translation of SEQ ID NO:72, the coding strand for nFeCD154$_{885}$, yields a protein of about 260 amino acids, denoted herein as PFeCD154$_{260}$, the amino acid sequence of which is presented in SEQ ID NO:73, assuming an open reading frame having an initiation codon spanning from nucleotide 29 through nucleotide 31 of SEQ ID NO:72, and a stop codon spanning from nucleotide 809 through nucleotide 811 of SEQ ID NO:72.

Translation of SEQ ID NO:80, the coding strand for nCaIL-5$_{610}$, yields a protein of about 134 amino acids, denoted herein as PCaIL-5$_{134}$, the amino acid sequence of which is presented in SEQ ID NO:81, assuming an open reading frame having an initiation codon spanning from nucleotide 29 through nucleotide 31 of SEQ ID NO:80, and a stop codon spanning from nucleotide 431 through nucleotide 433 of SEQ ID NO:80.

Translation of SEQ ID NO:91, the coding strand for nCaIL-13$_{1302}$, yields a protein of about 131 amino acids, denoted herein as PCaIL-13$_{131}$, the amino acid sequence of which is presented in SEQ ID NO:92, assuming an open reading frame having an initiation codon spanning from nucleotide 52 through nucleotide 54 of SEQ ID NO:91 and a stop codon spanning from nucleotide 445 through nucleotide 447 of SEQ ID NO:91.

Translation of SEQ ID NO:107, the coding strand for nFeIFNα$_{567a}$, yields a protein of about 189 amino acids, denoted herein as PFeIFNα$_{180a}$, the amino acid sequence of which is presented in SEQ ID NO:108, assuming an open reading frame having an initiation codon spanning from nucleotide 1 through nucleotide 3 and a last codon prior to a stop codon spanning from nucleotide 565 through nucleotide 567 of SEQ ID NO:107.

Translation of SEQ ID NO:119, the coding strand for nFeGMCSF$_{444}$, yields a protein of about 144 amino acids, denoted herein as PFeGMCSF$_{144}$, the amino acid sequence of which is presented in SEQ ID NO:120, assuming an open reading frame having an initiation codon spanning from nucleotide 10 through nucleotide 12 of SEQ ID NO:119 and a stop codon spanning from nucleotide 442 through nucleotide 444 of SEQ ID NO:119.

Preferred IL-4 proteins of the present invention include proteins that are at least about 85%, preferably at least about 90%, and even more preferably at least about 95% identical to PCaIL-4$_{132}$, PCaIL-4$_{108}$, or fragments thereof. Preferred Flt-3 ligand proteins of the present invention include proteins that are at least about 75%, even more preferably at least about 80%, even more preferably at least about 85%, even more preferably at least about 90%, and even more preferably at least about 95% identical to PCaFlt3L$_{294}$, PCaFlt3L$_{268}$, PCaFlt3L$_{276}$, PCaFlt3L$_{250}$, PCaFlt3L$_{31}$, and/or fragments thereof. Additional preferred Flt-3 ligand proteins of the present invention includes proteins that are at least about 75%, even more preferably at least about 80%, even more preferably at least about 85%, even more preferably at least about 90%, and even more preferably at least about 95% identical to PfeFlt3L$_{291}$, PFeFlt3L$_{265}$ and/or fragments thereof. Preferred CD40 proteins of the present invention includes proteins that are at least about 70%, preferably at least about 75%, even more preferably at least about 80%, is even more preferably at least about 85%, even more preferably at least about 90%, and even more preferably at least about 95% identical to PCaCD40$_{274}$, PCaCD40$_{255}$ and/or fragments thereof. Additional preferred CD40 proteins of the present invention includes proteins that are at least about 60%, at least about 65%, preferably at least about 70%, preferably at least about 75%, even more preferably at least about 80%, even more preferably at least about 85%, even more preferably at least about 90%, and even more preferably at least about 95% identical to PFeCD40$_{112}$ and/or fragments thereof. Preferred CD154 proteins of the present invention includes proteins that are at least about 80% identical, preferably at least about 85% identical, even more preferably at least about 90%, and even more preferably at least about 95% identical to PCaCD154$_{260}$, PCaCD154$_{211}$ and/or fragments thereof. Additional preferred CD154 proteins of the present invention includes proteins that are at least about 85% identical, even more preferably at least about 90%, and even more preferably at least about 95% identical to PFeCD154$_{260}$, PFeCD154$_{211}$ and/or fragments thereof. Preferred IL-5 proteins of the present invention includes proteins that are at least about 85% identical, even more preferably at least about 90%, and even more preferably at least about 95% identical to PCaIL-5$_{134}$, PCaIL-5$_{115}$ and/or fragments thereof. Preferred IL-13 proteins of the present invention includes proteins that are at least about 70% identical, preferably at least about 75% identical, more preferably at least about 80% identical, more preferably at least about 85% identical, even more preferably at least about 90%, and even more preferably at least about 95% identical to PCaIL-13$_{131}$, PCaIL-13$_{111}$, PCaIL-13$_{130}$, PCaIL-13$_{110}$, and/or fragments thereof. Preferred IFNα proteins of the present invention include PFeIFNα$_{189a}$, PFeIFNα$_{189b}$, PFeIFNα$_{166a}$, and/or PFeIFNα$_{166b}$. Preferred GM-CSF proteins of the present invention include PFeG-MCSF$_{144}$, and/or PFeGMCSF$_{127}$.

More preferred are IL-4 proteins comprising PCaIL-4$_{132}$, PCaIL-4$_{108}$, and/or proteins encoded by allelic variants of a nucleic acid molecule encoding proteins PCaIL-4$_{132}$ and/or PCaIL-4$_{108}$. More preferred are Flt-3 ligand proteins comprising PCaFlt3L$_{294}$, PCaFlt3L$_{268}$, PCaFlt3L$_{276}$, PCaFlt3L$_{250}$, PCaFlt3L$_{31}$, PFeFlt3L$_{291}$, PFeFlt3L$_{265}$ and/or proteins encoded by allelic variants of a nucleic acid molecule encoding proteins PCaFlt3L$_{294}$, PCaFlt3L$_{268}$, PCaFlt3L$_{276}$, PCaFlt3L$_{250}$, PCaFlt3L$_{31}$, PFeFlt3L$_{291}$, and/or PFeFlt3L$_{265}$. More preferred are CD40 proteins comprising PCaCD40$_{274}$, PCaCD40$_{255}$, and/or PFeCD40$_{112}$ and/or proteins encoded by allelic variants of a nucleic acid molecule encoding proteins PCaCD40$_{274}$, PCaCD40$_{255}$, and/or PFeCD40$_{112}$. More preferred are CD154 proteins comprising PCaCD154$_{260}$, PCaCD154$_{211}$, PFeCD154$_{260}$, PFeCD154$_{21}$ and/or proteins encoded by allelic variants of a nucleic acid molecule encoding one of proteins PCaCD154$_{260}$, PCaCD154$_{211}$, PFeCD154$_{260}$, PFeCD154$_{211}$. More preferred are IL-5 proteins comprising PCaIL-5$_{134}$, PCaIL-5$_{115}$ and/or proteins encoded by allelic variants of a nucleic acid molecule encoding one of the proteins PCaIL-5$_{134}$ and/or PCaIL-5$_{115}$. More preferred are IL-13 proteins comprising PCaIL-13$_{131}$, PCaIL-13$_{111}$, PCaIL-13$_{130}$, PCaIL-13$_{110}$, and/or proteins encoded by allelic variants of anucleic acid molecule encoding one of the proteins PCaIL-13$_{131}$, PCaIL-13$_{111}$, PCaIL-13$_{130}$, PCaIL-13$_{110}$.

Also preferred are IL-4 proteins of the present invention having amino acid sequences that are at least about 85%, preferably at least about 90%, and even more preferably at least about 95% identical to SEQ ID NO:2, SEQ ID NO:20 and/or fragments thereof. Also preferred are Flt-3 ligand proteins of the present invention having amino acid sequences that are at least about 75%, even more preferably at least about 80%, even more preferably at least about 85%, even more preferably at least about 90%, and even more preferably at least about 95% identical to SEQ ID NO:7, SEQ ID NO:23, SEQ ID NO:26, SEQ ID NO:31, and/or SEQ ID NO:34 and/or fragments thereof. Additional preferred Flt-3 ligand proteins of the present invention includes proteins that are at least about 75%, even more preferably at least about 80%, even more preferably at least about 85%, even more preferably at least about 90%, and/or even more preferably at least about 95% identical to SEQ ID NO:44, SEQ ID NO:49 and/or fragments thereof. Preferred CD40 proteins of the present invention includes proteins that are at least about 70%, preferably at least about 75%, even more preferably at least about 80%, even more preferably at least about 85%, even more preferably at least about 90%, and/or even more preferably at least about 95% identical to SEQ ID NO:53, SEQ ID NO:58 and/or fragments thereof. Additional preferred CD40 proteins of the present invention includes proteins that are at least about 60%, at least about 65%, preferably at least about 70%, preferably at least about 75%, even more preferably at least about 80%, even more preferably at least about 85%, even more preferably at least about 90%, and even more preferably at least about 95% identical to SEQ ID NO:61 and/or fragments thereof. Preferred CD154 proteins of the present invention includes proteins that are at least about 80% identical, preferably at least about 85% identical, even more preferably at least about 90%, and even more preferably at least about 95% identical to SEQ ID NO:65, SEQ ID NO:70 and/or fragments thereof. Additional preferred CD154 proteins of the present invention includes proteins that are at least about 85% identical, even more preferably at least about 90%, and even more preferably at least about 95% identical to SEQ ID NO:73, SEQ ID NO:78 and/or fragments thereof. Preferred IL-5 proteins of the present invention includes proteins that are at least about 85% identical, even more preferably at least about 90%, and even more preferably at least about 95% identical to SEQ ID NO:81, SEQ ID NO:86 and/or fragments thereof. Preferred IL-13 proteins of the present invention includes proteins that are at least about 70% identical, preferably at least about 75% identical, more preferably at least about 80% identical, more preferably at least about 85% identical, even more preferably at least about 90%, and even more preferably at least about 95% identical to SEQ ID NO:92, SEQ ID NO:97, SEQ ID NO:100, SEQ ID NO:105, and/or fragments thereof. Preferred IFNα proteins of the present invention include SEQ ID NO:108, SEQ ID NO:111, SEQ ID NO:114, SEQ ID NO:117. Preferred GM-CSF proteins of the present invention include SEQ ID NO:120, SEQ ID NO:125.

More preferred are IL-4 proteins comprising the amino acid sequence SEQ ID NO:2, SEQ ID NO:20; and/or IL-4 proteins encoded by allelic variants of nucleic acid molecules encoding IL-4 proteins having the amino acid sequence SEQ ID NO:2, SEQ ID NO:20. More preferred are Flt-3 ligand proteins comprising SEQ ID NO:7, SEQ ID NO:23, SEQ ID NO:26, SEQ ID NO:31, and/or SEQ ID NO:34, SEQ ID NO:44, SEQ ID NO:49 and/or proteins encoded by allelic variants of a nucleic acid molecule encoding proteins SEQ ID NO:7, SEQ ID NO:23, SEQ ID NO:26, SEQ ID NO:31, SEQ ID NO:34, SEQ ID NO:44, and/or SEQ ID NO:49. More preferred are CD40 proteins comprising SEQ ID NO:53, SEQ ID NO:58, SEQ ID NO:61 and/or proteins encoded by allelic variants of a nucleic acid molecule encoding proteins SEQ ID NO:53, SEQ ID NO:58, and/or SEQ ID NO:61. More preferred are CD154 proteins comprising SEQ ID NO:65, SEQ ID NO:70, SEQ ID NO:73, SEQ ID NO:78 and/or proteins encoded by allelic variants of a nucleic acid molecule encoding one of proteins SEQ ID NO:65, SEQ ID NO:70, SEQ ID NO:73, and/or SEQ ID NO:78. More preferred are IL-5 proteins comprising SEQ ID NO:81, SEQ ID NO:86 and/or proteins encoded by allelic variants of a nucleic acid molecule encoding one of the proteins SEQ ID NO:81, and/or SEQ ID NO:86. More preferred are IL-13 proteins comprising SEQ ID NO:92, SEQ ID NO:97, SEQ ID NO:100, SEQ ID NO:105, and/or proteins encoded by allelic variants of anucleic acid molecule encoding one of the proteins SEQ ID NO:92, SEQ ID NO:97, SEQ ID NO:100, and/or SEQ ID NO:105.

Percent identities between amino acid or nucleic acid sequences can be determined using standard methods known to those of skill in the art. It is known in the art that methods to determine the percentage identity and the number of gaps are substantially similar when different methods for determining sequence similarity are used and when the degree of similarity is greater than 30% amino acid identity, as described by Johnson et al., *J. Mol. Biol.*, vol. 233, pages 716-738, 1993, and Feng et al., *J. Mol. Evol.*, vol. 21, pages 112-125, 1985, which are incorporated by reference herein in their entirety. Preferred methods to determine percentage identities between amino acid sequences and between nucleic acid sequences include comparisons using various computer programs such as GCG® program (available from Genetics Computer Group, Madison, Wis.), DNASIS® program (available from Hitachi Software, San Bruno, Calif.) or the MACVECTOR® program (available from the Eastman Kodak Company, New Haven, Conn.). Preferred settings for sequence comparisons using the DNASIS® computer program or the GAP GCG® program are disclosed herein in the Examples section.

Additional preferred IL-4 proteins of the present invention include proteins encoded by nucleic acid molecules comprising at least a portion of $nCaIL-4_{549}$, $nCaIL-4_{396}$, and/or $nCaIL-4_{324}$, as well as IL-4 proteins encoded by allelic variants of such nucleic acid molecules. Additional preferred Flt-3 ligand proteins of the present invention include proteins encoded by nucleic acid molecules comprising at least a portion of $nCaFlt3L_{1013}$, $nCaFlt3L_{882}$, $nCaFlt3L_{804}$, $nCaFlt3L_{828}$, $nCaFlt3L_{985}$, $nCaFlt3L_{1019}$, $nCaFlt3L_{93}$, $nCaFlt3L_{750}$, $nFeFlt3L_{395}$, $nFeFlt3L_{793}$, $nFeFlt3L_{942}$, $nFeFlt3L_{873}$, and/or $nFeFlt3L_{795}$ as well as Flt-3 ligand proteins encoded by allelic variants of such nucleic acid molecules. Additional preferred CD40 proteins of the present invention include proteins encoded by nucleic acid molecules encoding at least a portion of $nCaCD40_{321}$, $nCaCD40_{1425}$, $nCaCD40_{822}$, $nCaCD40_{765}$, and/or $nFeCD40_{336}$ as well as CD40 proteins encoded by allelic variants of such nucleic acid molecules. Additional preferred CD154 proteins of the present invention include proteins encoded by nucleic acid molecules encoding at least a portion of $nCaCD154_{390}$, $nCaCD1541_{878}$, $nCaCD154_{780}$, $nCaCD154_{633}$, $nFeCD154_{885}$, $nFeCD154_{780}$, and/or $nFeCD154_{633}$ as well as CD154 proteins encoded by allelic variants of such nucleic acid molecules. Additional preferred IL-5 proteins of the present invention include proteins encoded by nucleic acid molecules encoding at least a portion of $nCaIL-5_{610}$, $nCaIL-5_{402}$, and/or $nCaIL-5_{345}$ as well as IL-5 proteins encoded by allelic variants of such nucleic acid molecules. Additional preferred IL-13 proteins of the present invention include proteins encoded by nucleic acid molecules encoding at least a portion of $nCaIL-5_{610}$, $nCaIL-5_{402}$, and/or $nCaIL-5_{345}$ as well as IL-13 proteins encoded by allelic variants of such nucleic acid molecules.

Also preferred are IL-4 proteins encoded by nucleic acid molecules having nucleic acid sequences comprising at least a portion of SEQ ID NO:1, SEQ ID NO:4, and/or SEQ ID NO:19, as well as allelic variants of these nucleic acid molecules. Also preferred are Flt-3 ligand proteins encoded by nucleic acid molecules having nucleic acid sequences comprising at least a portion of SEQ ID NO:6, SEQ ID NO:9, SEQ ID NO:22, SEQ ID NO:25, SEQ ID NO:28, SEQ ID NO:30, SEQ ID NO:33, SEQ ID NO:36, SEQ ID NO:41, SEQ ID NO:42, SEQ ID NO:43, SEQ ID NO:46, and/or SEQ ID NO:48, as well as allelic variants of these nucleic acid molecules. Also preferred are CD40 proteins encoded by nucleic acid molecules having nucleic acid sequences comprising at least a portion of SEQ ID NO:51, SEQ ID NO:52, SEQ ID NO:55, SEQ ID NO:57, and/or SEQ ID NO:60, as well as allelic variants of these nucleic acid molecules. Also preferred are CD154 proteins encoded by nucleic acid molecules having nucleic acid sequences comprising at least a portion of SEQ ID NO:63, SEQ ID NO:64, SEQ ID NO:67, SEQ ID NO:69, SEQ ID NO:72, SEQ ID NO:75, and/or SEQ ID NO:77, as well as allelic variants of these nucleic acid molecules. Also preferred are IL-5 proteins encoded by nucleic acid molecules having nucleic acid sequences comprising at least a portion of SEQ ID NO:80, SEQ ID NO:83, and/or SEQ ID NO:85, as well as allelic variants of these nucleic acid molecules. Also preferred are IL-13 proteins encoded by nucleic acid molecules having nucleic acid sequences comprising at least a portion of SEQ ID NO:88, SEQ ID NO:89, SEQ ID NO:90, SEQ ID NO:91, SEQ ID NO:94, SEQ ID NO:96, SEQ ID NO:99, SEQ ID NO:102, and/or SEQ ID NO:104, as well as allelic variants of these nucleic acid molecules.

Another embodiment of the present invention is a canine interleukin-4, canine or feline Flt-3 ligand, canine or feline CD40, canine or feline CD154, canine interleukin-5, canine interleukin-13, feline interferon alpha, or feline GM-CSF nucleic acid molecule that includes one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a canine interleukin-4, canine or feline Flt-3 ligand, canine or feline CD40, canine or feline CD154, canine interleukin-5, canine interleukin-13, feline interferon alpha, or feline GM-CSF nucleic acid molecule of the present invention is from about 12 to about 18 nucleotides in length.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. An isolated canine interleukin-4, canine or feline Flt-3 ligand, canine or feline CD40, canine or feline CD154, canine interleukin-5, canine interleukin-13, feline interferon alpha, or feline GM-CSF nucleic acid molecule of the present invention can be isolated from its natural source or produced using recombinant DNA technology (e.g., polymerase chain reaction (PCR) amplification or cloning) or chemical synthesis. Isolated canine interleukin-4, canine or feline Flt-3 ligand, canine or feline CD40, canine or feline CD154, canine interleukin-5, canine interleukin-13, feline interferon alpha, and/or feline GM-CSF, nucleic acid molecules can include, for example, natural allelic variants and/or nucleic acid molecules modified by nucleotide insertions, deletions, substitutions, and/or inversions in a manner such that the modifications do not substantially interfere with the nucleic acid molecule's ability to encode an canine interleukin-4, canine or feline Flt-3 ligand, canine or feline CD40, canine or feline CD154, canine interleukin-5, canine interleukin-13, feline interferon alpha, and/or feline GM-CSF protein of the present invention.

A canine interleukin-4, canine or feline Flt-3 ligand, canine or feline CD40, canine or feline CD154, canine interleukin-5, canine interleukin-13, feline interferon alpha, and/or feline GM-CSF ligand nucleic acid molecule homolog can be produced using a number of methods known to those skilled in the art, see, for example, Sambrook et al., 1989, *Molecular Cloning: A Laboratory Manual*, Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologs can be selected by hybridization with either a canine interleukin-4, canine or feline Flt-3 ligand, canine or feline CD40, canine or feline CD154, canine interleukin-5, canine interleukin-13, feline interferon alpha, or feline GM-CSF nucleic acid molecule or by screening the function of a protein encoded by the nucleic acid molecule (e.g., ability to elicit an immune response against at least one epitope of a canine interleukin-4, canine or feline Flt-3 ligand, canine or feline CD40, canine or feline CD154, canine interleukin-5, canine interleukin-13, feline interferon alpha, or feline GM-CSF protein, respectively).

An isolated nucleic acid molecule of the present invention can include a nucleic acid sequence that encodes at least one canine interleukin-4, canine or feline Flt-3 ligand, canine or feline CD40, canine or feline CD154, canine interleukin-5, canine interleukin-13, feline interferon alpha, or feline GM-CSF protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a canine interleukin-4, canine or feline Flt-3 ligand, canine or feline CD40, canine or feline CD154, canine interleukin-5, canine interleukin-13, feline interferon alpha, or feline GM-CSF ligand protein.

A preferred nucleic acid molecule of the present invention, when administered to an animal, is capable of regulating an immune response in an animal. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode an immunoregulatory protein (e.g., a cell-bound or soluble protein of the present invention), the nucleic acid molecule being delivered to the animal, for example, by direct injection (i.e, as a genetic vaccine) or in a vehicle such as a recombinant virus vaccine or a recombinant cell vaccine.

One embodiment of the present invention is an IL-4 nucleic acid molecule comprising all or part (i.e., a fragment of the IL-4 nucleic acid molecule) of nucleic acid molecules nCaIL-$4_{549}$, nCaIL-$4_{396}$, and/or nCaIL-$4_{324}$, or allelic variants of these nucleic acid molecules. One embodiment of the present invention is a Flt-3 ligand nucleic acid molecule comprising all or part (i.e., a fragment of the Flt-3 ligand nucleic acid molecule) of nucleic acid molecules nCaFlt3L$_{1013}$, nCaFlt3L$_{882}$, nCaFlt3L$_{804}$, nCaFlt3L$_{828}$, nCaFlt3L$_{985}$, nCaFlt3L$_{1019}$, nCaFlt3L$_{93}$, nCaFlt3L$_{750}$, nFeFlt3L$_{395}$, nFeFlt3L$_{793}$, nFeFlt3L$_{942}$, nFeFlt3L$_{873}$, and/or nFeFlt3L$_{795}$ and/or allelic variants of these nucleic acid molecules. One embodiment of the present invention is a CD40 nucleic acid molecule comprising all or part (i.e. a fragment of the CD40 nucleic acid molecule) of nucleic acid molecules nCaCD40$_{321}$, nCaCD40$_{1425}$, nCaCD40$_{822}$, nCaCD40$_{765}$, and/or nFeCD40$_{336}$ and/or allelic variants of these nucleic acid molecules. One embodiment of the present invention is a CD154 nucleic acid molecule comprising all or part of nucleic acid molecules nCaCD154$_{390}$, nCaCD1541$_{878}$, nCaCD154$_{780}$, nCaCD154$_{633}$, nFeCD154$_{885}$, nFeCD154$_{780}$, and/or nFeCD154$_{633}$, and/or allelic variants of these nucleic acid molecules. One embodiment of the present invention is an IL-5 nucleic acid molecule comprising all or part of nucleic acid molecules nCaIL-$5_{610}$, nCaIL-$5_{402}$, and/or nCaIL-$5_{345}$, and/or allelic variants of these nucleic acid molecules. One embodiment of the present invention is an IL-13 nucleic acid molecule comprising all or part of nucleic acid molecules nCaIL-13$_{166}$, nCaIL-13$_{272}$, nCaIL-13$_{278}$, nCaIL-13$_{1302}$, nCaIL-13$_{393}$, nCaIL-13$_{333}$, nCaIL-13$_{1269}$, nCaIL-13$_{390}$, and/or nCaIL-13$_{330}$, and/or allelic variants of these nucleic acid molecules. Another preferred nucleic acid molecule of the present invention includes at least a portion of (i.e., a fragment of the nucleic acid molecule) nucleic acid sequence SEQ ID NO:1, SEQ ID NO:3, SEQ ID NO:4, SEQ ID NO:5, SEQ ID NO:19, SEQ ID NO:21, SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, SEQ ID NO:37, SEQ ID NO:41, SEQ ID NO:42, SEQ ID NO:43, SEQ ID NO:45, SEQ ID NO:46, SEQ ID NO:47, SEQ ID NO:48, SEQ ID NO:50, SEQ ID NO:51, SEQ ID NO:52, SEQ ID NO:54, SEQ ID NO:55, SEQ ID NO:56, SEQ ID NO:57, SEQ ID NO:59, SEQ ID NO:60, SEQ ID NO:62, SEQ ID NO:63, SEQ ID NO:64, SEQ ID NO:66, SEQ ID NO:67, SEQ ID NO:68, SEQ ID NO:69, SEQ ID NO:71, SEQ ID NO:72, SEQ ID NO:74, SEQ ID NO:75, SEQ ID NO:76, SEQ ID NO:77, SEQ ID NO:79, SEQ ID NO:80, SEQ ID SEQ ID NO:83, SEQ ID NO:84, SEQ ID NO:85, SEQ ID NO:87, SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, SEQ ID NO:106, SEQ ID NO:107, SEQ ID NO:109, SEQ ID NO:110, SEQ ID NO:112, SEQ ID NO:113, SEQ ID NO:115, SEQ ID NO:116, SEQ ID NO:118, SEQ ID NO:119, SEQ ID NO:121, SEQ ID NO:122, SEQ ID NO:123, SEQ ID NO:124, and/or SEQ ID NO:126, as well as allelic variants of nucleic acid molecules having these nucleic acid sequences. Such nucleic acid molecules can include nucleotides in addition to those included in the SEQ ID NOs, such as, but not limited to, a full-length gene, a full-length coding region, a nucleic acid molecule encoding a fusion protein, and/or a nucleic acid molecule encoding a multivalent therapeutic compound.

One embodiment of an isolated nucleic acid molecule of the present invention is a is nucleic acid molecule that can be any of the following: (a) an isolated nucleic acid molecule comprising a nucleic acid sequence selected from the group consisting of SEQ ID NO:1, SEQ ID NO:3, SEQ ID NO:4, SEQ ID NO:5, SEQ ID NO:19, and/or SEQ ID NO:21 and/or a homolog thereof, wherein said homolog has an at least 50 contiguous nucleotide region identical in sequence to a 50 contiguous nucleotide region of a nucleic acid sequence selected from the group consisting of SEQ ID NO:1, SEQ ID NO:3, SEQ ID NO:4, SEQ ID NO:5, SEQ ID NO:19, and/or SEQ ID NO:21; (b) an isolated nucleic acid molecule comprising a nucleic acid sequence selected from the group consisting of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37, and/or a homolog thereof, wherein said homolog has an at least 40 contiguous nucleotide region identical in sequence to a 40 contiguous nucleotide region of a nucleic acid molecule having a nucleic acid sequence selected from the group consisting of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37; (c) an isolated nucleic acid molecule comprising a nucleic acid sequence selected from the group consisting of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50, and/or a homolog thereof, wherein said homolog has an at least 30 contiguous nucleotide region identical in sequence to a 30 contiguous nucleotide region of a nucleic acid molecule having a nucleic acid sequence selected from the group consisting of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50; (d) an isolated nucleic acid molecule comprising a nucleic acid sequence selected from the group consisting of SEQ ID NO:51, SEQ ID NO:52, SEQ ID NO:54, SEQ ID NO:55, SEQ ID NO:56, SEQ ID NO:57, and/or SEQ ID NO:59, and/or a homolog thereof, wherein said homolog has an at least 40 contiguous nucleotide region identical in sequence to a 40 contiguous nucleotide region of a nucleic acid molecule having a nucleic acid sequence selected from the group consisting of SEQ ID NO:51, SEQ ID NO:52, SEQ ID NO:54, SEQ ID NO:55, SEQ ID NO:56, SEQ ID NO:57, and/or SEQ ID NO:59; (e) an isolated nucleic acid molecule comprising a nucleic acid sequence selected from the group consisting of SEQ ID NO:60 and/or SEQ ID NO:62, and/or a homolog thereof, wherein said homolog has an at least 30 contiguous nucleotide region identical in sequence to a 30 contiguous nucleotide region of a nucleic acid molecule having a nucleic acid sequence selected from the group consisting of SEQ ID NO:60 and/or SEQ ID NO:62; (f) an isolated nucleic acid molecule comprising a nucleic acid sequence selected from the group consisting of SEQ ID NO:63, SEQ ID NO:64, SEQ ID NO:66, SEQ ID NO:67, SEQ ID NO:68, SEQ ID NO:69 and/or SEQ ID NO:71, and/or a homolog thereof, wherein said homolog has an at least 45 contiguous nucleotide region identical in sequence to a 45 contiguous nucleotide region of a nucleic acid molecule having a nucleic acid sequence selected from the group consisting of SEQ ID NO:63, SEQ ID NO:64, SEQ ID NO:66, SEQ ID NO:67, SEQ ID NO:68, SEQ ID NO:69 and/or SEQ ID NO:71; (g) an isolated nucleic acid molecule comprising a nucleic acid sequence selected from the group consisting of SEQ ID NO:72, SEQ ID NO:74, SEQ ID NO:75, SEQ ID NO:76, SEQ ID NO:77, and/or SEQ ID NO:79, and/or a homolog thereof, wherein said homolog has an at least 35 contiguous nucleotide region identical in sequence to a 35 contiguous nucleotide region of a nucleic acid molecule having a nucleic acid sequence selected from the group consisting of SEQ ID NO:72, SEQ ID NO:74, SEQ ID NO:75, SEQ ID NO:76, SEQ ID NO:77, and/or SEQ ID NO:79; (h) an isolated nucleic acid molecule comprising a nucleic acid sequence selected from the group consisting of SEQ ID NO:80, SEQ ID NO:82, SEQ ID NO:83, SEQ ID NO:84, SEQ ID NO:85, and/or SEQ ID NO:87, and/or a homolog thereof, wherein said homolog has an at least 45 contiguous nucleotide region identical in sequence to a 45 contiguous nucleotide region of a nucleic acid molecule having a nucleic acid sequence selected from the group consisting of SEQ ID NO:80, SEQ ID NO:82, SEQ ID NO:83, SEQ ID NO:84, SEQ ID NO:85, and/or SEQ ID NO:87; (i) an isolated nucleic acid molecule comprising a nucleic acid sequence selected from the group consisting of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106, and/or a homolog thereof, wherein said homolog has an at least 15 contiguous nucleotide region identical in sequence to a 15 contiguous nucleotide region of a nucleic acid molecule having a nucleic acid sequence selected from the group consisting of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106; (j) an isolated nucleic acid molecule having a nucleic acid sequence selected from the group consisting of SEQ ID NO:107, SEQ ID NO:109, SEQ ID NO:110, SEQ ID NO:112, SEQ ID NO:113, SEQ ID NO:115, SEQ ID NO:116, and/or SEQ ID NO:118; and/or (k) an isolated nucleic acid molecule having a nucleic acid sequence selected from the group consisting of SEQ ID NO:119, SEQ ID NO:121, SEQ ID NO:122, SEQ ID NO:123, SEQ ID NO:124, and/or SEQ ID NO:126. The phrase, a homolog having an at least "x" contiguous nucleotide region identical in sequence to an "x" contiguous nucleotide region of a nucleic acid molecule selected from the group consisting of SEQ ID NO:"y", refers to an "x"-nucleotide in length nucleic acid molecule that is identical in sequence to an "x"-nucleotide portion of SEQ ID NO:"y", as well as to nucleic acid molecules that are longer in length than "x". The additional length may be in the form of nucleotides that extend from either the 5' or the 3' end(s) of the contiguous identical "x"-nucleotide portion. The 5' and/or 3' extensions can include one or more extensions that have no identity to an immunoregulatory molecule of the present invention, as well as extensions that show similarity or identity to cited nucleic acids sequences or portions thereof.

In another embodiment, an isolated nucleic acid molecule of the present invention can be any of the following: (a) a nucleic acid molecule having a nucleic acid sequence encoding an IL-4 protein selected from the group consisting of (i) a protein having an amino acid sequence that is at least about 85 percent identical to an amino acid sequence selected from the group consisting of SEQ ID NO:2 and/or SEQ ID NO:20 and/or (ii) a protein comprising a fragment of at least 20 amino acids of an amino acid sequence selected from the group consisting of SEQ ID NO:2 and/or SEQ ID NO:20; (b) a nucleic acid molecule having a nucleic acid sequence encoding a Flt-3 ligand protein selected from the group consisting of (i) a protein having an amino acid sequence that is at least about 75 percent identical to an amino acid sequence selected from the group consisting of SEQ ID NO:7, SEQ ID NO:23, SEQ ID NO:26, SEQ ID NO:31, and/or SEQ ID NO:34, and/or (ii) a protein comprising a fragment of at least 25 amino acids of an amino acid sequence selected from the group consisting of SEQ ID NO:7, SEQ ID NO:23, SEQ ID NO:26, SEQ ID NO:31, and/or SEQ ID NO:34; (c) a nucleic acid molecule having a nucleic acid sequence encoding a Flt-3 ligand protein selected from the group consisting of (i) a protein having an amino acid sequence that is at least about 75 percent identical to an amino acid sequence selected from the group consisting of SEQ ID NO:44 and/or SEQ ID NO:49 and/or (ii) a protein comprising a fragment of at least 25 amino acids of an amino acid sequence selected from the group consisting of SEQ ID NO:44 and/or SEQ ID NO:49; (d) a nucleic acid molecule having a nucleic acid sequence encoding a CD40 protein selected from the group consisting of (i) a protein having an amino acid sequence that is at least about 70 percent identical to an amino acid sequence selected from the group consisting of SEQ ID NO:53 and/or SEQ ID NO:58 and/or (ii) a protein comprising a fragment of at least 30 amino acids of an amino acid sequence selected from the group consisting of SEQ ID NO:53 and/or SEQ ID NO:58; (e) a nucleic acid molecule having a nucleic acid sequence encoding a CD40 protein selected from the group consisting of (i) a protein having an amino acid sequence that is at least about 60 percent identical to an amino acid sequence comprising SEQ ID NO:61 and/or (ii) a protein comprising a fragment of at least 20 amino acids of an amino acid sequence comprising SEQ ID NO:61; (f) a nucleic acid molecule having a nucleic acid sequence encoding a CD154 protein selected from the group consisting of (i) a protein having an amino acid sequence that is at least about 80 percent identical to an amino acid sequence selected from the group consisting of SEQ ID NO:65 and/or SEQ ID NO:70, and/or (ii) a protein comprising a fragment of at least 35 amino acids of an amino acid sequence selected from the group consisting of SEQ ID NO:65 and/or SEQ ID NO:70; (g) a nucleic acid molecule having a nucleic acid sequence encoding a CD154 protein selected from the group consisting of (i) a protein having an amino acid sequence that is at least about 85 percent identical to an amino acid sequence selected from the group consisting of SEQ ID NO:73 and/or SEQ ID NO:78, and/or (ii) a protein comprising a fragment of at least 50 amino acids of an amino acid sequence selected from the group consisting of SEQ ID NO:73 and/or SEQ ID NO:78; (h) a nucleic acid molecule having a nucleic acid sequence encoding an IL-5 protein selected from the group consisting of (i) a protein having an amino acid sequence that is at least about 85 percent identical to an amino acid sequence selected from the group consisting of SEQ ID NO:81 and/or SEQ ID NO:86 and/or (ii) a protein comprising a fragment of at least 20 amino acids of an amino acid sequence selected from the group consisting of SEQ ID NO:81 and/or SEQ ID NO:86; (i) a nucleic acid molecule having a nucleic acid sequence encoding an IL-13 protein selected from the group consisting of (i) a protein having an amino acid sequence that is at least about 70 percent identical to an amino acid sequence selected from the group consisting of SEQ ID NO:92, SEQ ID NO:97, SEQ ID NO:100, and/or SEQ ID NO:105 and/or (ii) a protein comprising a fragment of at least 15 amino acids of an amino acid sequence selected from the group consisting of SEQ ID NO:92, SEQ ID NO:97, SEQ ID NO:100, and/or SEQ ID NO:105; (j) a nucleic acid molecule having a nucleic acid sequence encoding an interferon alpha protein having an amino acid sequence that is selected from the group consisting of amino acid sequence SEQ ID NO:108, SEQ ID NO:111, SEQ ID NO:114, and/or SEQ ID NO:117; (k) a nucleic acid molecule having a nucleic acid sequence encoding a GMCSF protein having an amino acid sequence that is selected from the group consisting of amino acid sequence SEQ ID NO:120, SEQ ID NO:125, and/or (l) a nucleic acid molecule comprising a complement of any of the before-mentioned nucleic acid sequences; wherein said IL-4 protein elicits an immune response against an IL-4 protein selected from the group consisting of SEQ ID NO:2 and/or SEQ ID NO:20 and/or is a protein with interleukin-4 activity, said Flt-3 ligand protein elicits an immune response against a Flt-3 ligand protein selected from the group consisting of SEQ ID NO:7, SEQ ID NO:23, SEQ ID NO:26, SEQ ID NO:31, SEQ ID NO:34, SEQ ID NO:44, and/or SEQ ID NO:49 and/or is a protein with Flt-3 ligand activity, said CD40 protein elicits an immune response against a CD40 protein selected from the group consisting of SEQ ID NO:53, SEQ ID NO:58, and/or SEQ ID NO:61 and/or is a protein with CD40 activity, said CD154 protein elicits an immune response against a CD154 protein selected from the group consisting of SEQ ID NO:65, SEQ ID NO:70, SEQ ID NO:73, and/or SEQ ID NO:78 and/or is a protein with CD154 activity, said IL-5 protein elicits an immune response against a IL-5 protein selected from the group consisting of SEQ ID NO:81 and/or SEQ ID NO:86 and/or is a protein with IL-5 activity, said IL-13 protein elicits an immune response against an IL-13 protein selected from the group consisting of SEQ ID NO:92, SEQ ID NO:97, SEQ ID NO:100, and/or SEQ ID NO:105 and/or is a protein with IL-13 activity, said interferon alpha protein elicits an immune response against an interferon alpha protein selected from the group consisting of SEQ ID NO:108, SEQ ID NO:111, SEQ ID NO:114, and/or SEQ ID NO:117 and/or is a protein with interferon alpha activity, and said GMCSF protein elicits an immune response against a GMCSF protein selected from the group consisting of SEQ ID NO:120 and/or SEQ ID NO:125 and/or is a protein with GM-CSF activity.

In one embodiment, an IL-4 nucleic acid molecule of the present invention encodes a protein that is at least about 85%, preferably at least about 90%, preferably at least about 92%, and even more preferably at least about 95% identical to PCaIL-4$_{132}$ and/or PCaIL-4$_{108}$. In one embodiment, a Flt-3 ligand nucleic acid molecule of the present invention encodes a protein that is at least about 75%, even more preferably at least about 80%, even more preferably at least about 85%, even more preferably at least about 90%, and even more preferably at least about 95% identical to PCaFlt3L$_{294}$, PCaFlt3L$_{268}$, PCaFlt3L$_{276}$, PCaFlt3L$_{250}$, and/or PCaFlt3L$_{31}$. In one embodiment, a Flt-3 ligand nucleic acid molecule of the present invention encodes a protein that is at least about 75%, more preferably at least about 80%, even more preferably at least about 85%, even more preferably at least about 90%, and even more preferably at least about 95% identical to PFeFlt3L$_{291}$, and/or PFeFlt3L$_{265}$. In one embodiment, a CD40 nucleic acid molecule of the present invention encodes a protein that is at least about PCaCD40$_{274}$, and/or PCaCD40$_{255}$. In one embodiment, a CD40 nucleic acid molecule of the present invention encodes a protein that is at least about 60%, preferably at least about 65%, preferably at least about 70%, preferably at least about 75%, even more preferably at least about 80%, even more preferably at least about 85%, even more preferably at least about 90%, and even more preferably at least about 95% identical to PFeCD40$_{112}$. In one embodiment, a CD154 nucleic acid molecule of the present invention encodes a protein that is at least about 80%, at least about 85%, more preferably at least about 90%, and even more preferably at least about 95% identical to PCaCD154$_{260}$, and/or PCaCD154$_{211}$. In one embodiment, a CD154 nucleic acid molecule of the present invention encodes a protein that is at least about 85%, more preferably at least about 90%, and even more preferably at least about 95% identical to PFeCD154$_{260}$, PFeCD154$_{211}$. In one embodiment, an IL-5 nucleic acid molecule of the present invention encodes a protein that is at least about 85%, more preferably at least about 90%, and even more preferably at least about 95% identical to PCaIL-5$_{134}$, and/or PCaIL-5$_{115}$. In one embodiment, an IL-13 nucleic acid molecule of the present invention encodes a protein that is at least about 70%, at least about 75%, at least about 80%, preferably at least about 85%, more preferably at least about 90%, and even more preferably at least about 95% identical to PCaIL-13$_{131}$, PCaIL-13$_{111}$, PCaIL-13$_{130}$, PCaIL-13$_{110}$. Even more preferred is a nucleic acid molecule encoding PCaIL-4$_{132}$, PCaIL-4$_{108}$, PCaFlt3L$_{294}$, PCaFlt3L$_{268}$, PCaFlt3L$_{276}$, PCaFlt3L$_{250}$, PCaFlt3L$_{31}$, PFeFlt3L$_{291}$, PFeFlt3L$_{265}$, PCaCD40$_{274}$, PCaCD40$_{255}$, PFeCD40$_{112}$, PCaCD154$_{260}$, PCaCD154$_{211}$, PFeCD154$_{260}$, PFeCD154$_{211}$, PCaIL-5$_{134}$, PCaIL-5$_{115}$, PCaIL-13$_{131}$, PCaIL-13$_{111}$, PCaIL-13$_{130}$, PCaIL-13$_{110}$ and/or an allelic variant of such a nucleic acid molecule.

In another embodiment, an IL-4 nucleic acid molecule of the present invention encodes a protein having an amino acid sequence that is at least about 85%, preferably at least about 90%, and even more preferably at least about 95% identical to SEQ ID NO:2, SEQ ID NO:20. The present invention also includes an IL-4 nucleic acid molecule encoding a protein having at least a portion of SEQ ID NO:2, and/or SEQ ID NO:20, as well as allelic variants of an IL-4 nucleic acid molecule encoding a protein having these sequences, including nucleic acid molecules that have been modified to accommodate codon usage properties of the cells in which such nucleic acid molecules are to be expressed.

In another embodiment, a Flt-3 ligand nucleic acid molecule of the present invention encodes a protein having an amino acid sequence that is at least about 75%, even more preferably at least about 80%, even more preferably at least about 85%, even more preferably at least about 90%, and even more preferably at least about 95% identical to SEQ ID NO:7, SEQ ID NO:23, SEQ ID NO:26, SEQ ID NO:31, and/or SEQ ID NO:34. The present invention also includes a Flt-3 ligand nucleic acid molecule encoding a protein having at least a portion of SEQ ID NO:7, SEQ ID NO:23, SEQ ID NO:26, SEQ ID NO:31, and/or SEQ ID NO:34, as well as allelic variants of a Flt-3 ligand nucleic acid molecule encoding a protein having these sequences, including nucleic acid molecules that have been modified to accommodate codon usage properties of the cells in which such nucleic acid molecules are to be expressed.

In another embodiment, a Flt-3 ligand nucleic acid molecule of the present invention encodes a protein having an amino acid sequence that is at least about 75%, more preferably at least about 80%, even more preferably at least about 85%, even more preferably at least about 90%, and even more preferably at least about 95% identical to SEQ ID NO:44, and/or SEQ ID NO:49. The present invention also includes a Flt-3 ligand nucleic acid molecule encoding a protein having at least a portion of SEQ ID NO:44, and/or SEQ ID NO:49, as well as allelic variants of a Flt-3 ligand nucleic acid molecule encoding a protein having these sequences, including nucleic acid molecules that have been modified to accommodate codon usage properties of the cells in which such nucleic acid molecules are to be expressed.

In another embodiment, a CD40 nucleic acid molecule of the present invention encodes a protein having an amino acid sequence that is at least about 70%, preferably at least about 75%, even more preferably at least about 80%, even more preferably at least about 85%, even more preferably at least about 90%, and even more preferably at least about 95% identical to SEQ ID NO:53 and/or SEQ ID NO:58. The present invention also includes a CD40 nucleic acid molecule encoding a protein having at least a portion of SEQ ID NO:53 and/or SEQ ID NO:58, as well as allelic variants of a CD40 nucleic acid molecule encoding a protein having these sequences, including nucleic acid molecules that have been modified to accommodate codon usage properties of the cells in which such nucleic acid molecules are to be expressed.

In another embodiment, a CD40 nucleic acid molecule of the present invention encodes a protein having an amino acid sequence that is at least about 60%, preferably at least about 65%, preferably at least about 70%, preferably at least about 75%, even more preferably at least about 80%, even more preferably at least about 85%, even more preferably at least about 90%, and even more preferably at least about 95% identical to SEQ ID NO:60. The present invention also includes a CD40 nucleic acid molecule encoding a protein having at least a portion of SEQ ID NO:60, as well as allelic variants of a CD40 nucleic acid molecule encoding a protein having these sequences, including nucleic acid molecules that have been modified to accommodate codon usage properties of the cells in which such nucleic acid molecules are to be expressed.

In another embodiment, a CD154 nucleic acid molecule of the present invention encodes a protein having an amino acid sequence that is at least about at least about 80%, at least about 85%, more preferably at least about 90%, and even more preferably at least about 95% identical to SEQ ID NO:63, SEQ ID NO:64, SEQ ID NO:67, and/or SEQ ID NO:69. The present invention also includes a CD154 nucleic acid molecule encoding a protein having at least a portion of SEQ ID NO:63, SEQ ID NO:64, SEQ ID NO:67, and/or SEQ ID NO:69, as well as allelic variants of a CD154 nucleic acid molecule encoding a protein having these sequences, including nucleic acid molecules that have been modified to accommodate codon usage properties of the cells in which such nucleic acid molecules are to be expressed.

In another embodiment, a CD154 nucleic acid molecule of the present invention encodes a protein having an amino acid sequence that is at least about at least about 85%, more preferably at least about 90%, and even more preferably at least about 95% identical to SEQ ID NO:72, SEQ ID NO:75, and/or SEQ ID NO:77. The present invention also includes a CD154 nucleic acid molecule encoding a protein having at least a portion of SEQ ID NO:72, SEQ ID NO:75, and/or SEQ ID NO:77, as well as allelic variants of a CD154 nucleic acid molecule encoding a protein having these sequences, including nucleic acid molecules that have been modified to accommodate codon usage properties of the cells in which such nucleic acid molecules are to be expressed.

In another embodiment, an IL-5 nucleic acid molecule of the present invention encodes a protein having an amino acid sequence that is at least about at least about 85%, at least about 85%, more preferably at least about 90%, and even more preferably at least about 95% identical to SEQ ID NO:80, SEQ ID NO:83, and/or SEQ ID NO:85. The present invention also includes an IL-5 nucleic acid molecule encoding a protein having at least a portion of SEQ ID NO:80, SEQ ID NO:83, and/or SEQ ID NO:85, as well as allelic variants of an IL-5 nucleic acid molecule encoding a protein having these sequences, including nucleic acid molecules that have been modified to accommodate codon usage properties of the cells in which such nucleic acid molecules are to be expressed.

In another embodiment, an IL-13 nucleic acid molecule of the present invention encodes a protein having an amino acid sequence that is at least about at least about 70%, at least about 75%, at least about 80%, preferably at least about 85%, more preferably at least about 90%, and even more preferably at least about 95% identical to SEQ ID NO:88, SEQ ID NO:89, SEQ ID NO:90, SEQ ID NO:91, SEQ ID NO:94, SEQ ID NO:96, SEQ ID NO:99, SEQ ID NO:102, and/or SEQ ID NO:104. The present invention also includes an IL-13 nucleic acid molecule encoding a protein having at least a portion of SEQ ID NO:88, SEQ ID NO:89, SEQ ID NO:90, SEQ ID NO:91, SEQ ID NO:94, SEQ ID NO:96, SEQ ID NO:99, SEQ ID NO:102, and/or SEQ ID NO:104, as well as allelic variants of an IL-13 nucleic acid molecule encoding a protein having these sequences, including nucleic acid molecules that have been modified to accommodate codon usage properties of the cells in which such nucleic acid molecules are to be expressed.

In one embodiment, an IL-4 nucleic acid molecule of the present invention is at least about 90%, and preferably at least about 95% identical to nCaIL-4$_{549}$. Even more preferred is a nucleic acid molecule comprising nCaIL-4$_{549}$, nCaIL-4$_{396}$, nCaIL-4$_{324}$, and/or an allelic variant of such a nucleic acid molecule. In another embodiment, a Flt-3 ligand nucleic acid molecule of the present invention is at least about 75%, more preferably at least about 80%, more preferably at least about 85%, more preferably at least about 90% and even more preferably at least about 95% identical to nCaFlt3L$_{1013}$. Even more preferred is a nucleic acid molecule comprising nCaFlt3L$_{1013}$, nCaFlt3L$_{882}$, nCaFlt3L$_{804}$, nCaFlt3L$_{828}$, nCaFlt3L$_{985}$, nCaFlt3L$_{1019}$, nCaFlt3L$_{93}$, and/or nCaFlt3L$_{750}$, and/or an allelic variant of such a nucleic acid molecule. In one embodiment, a Flt-3 ligand nucleic acid molecule of the present invention is at least about 75%, more preferably at least about 80%, more preferably at least about 85%, more preferably at least about 90% and even more preferably at least about 95% identical to nFeFlt3L$_{942}$. Even more preferred is a nucleic acid molecule comprising nFeFlt3L$_{395}$, nFeFlt3L$_{793}$, nFeFlt3L$_{942}$, nFeFlt3L$_{873}$, and/or nFeFlt3L$_{795}$, and/or an allelic variant of such a nucleic acid molecule. In one embodiment, a CD40 nucleic acid molecule of the present invention is at least about 70%, at least about 75%, more preferably at least about 80%, more preferably at least about 85%, more preferably at least about 90% and even more preferably at least about 95% identical to nCaCD40$_{321}$, nCaCD40$_{1425}$, nCaCD40$_{822}$, and/or nCaCD40$_{765}$, and/or an allelic variant of such a nucleic acid molecule. In one embodiment, a CD40 nucleic acid molecule of the present invention is at least about 70%, at least about 75%, more preferably at least about 80%, more preferably at least about 85%, more preferably at least about 90% and even more preferably at least about 95% identical to nFeCD40$_{336}$, and/or an allelic variant of such a nucleic acid molecule. In one embodiment, a CD154 nucleic acid molecule of the present invention is at least about 85%, preferably at least about 85%, more preferably at least about 90% and even more preferably at least about 95% identical to nCaCD154$_{390}$, nCaCD1541$_{878}$, nCaCD154$_{780}$, and/or nCaCD154$_{633}$, and/or an allelic variant of such a nucleic acid molecule. In one embodiment, a CD154 nucleic acid molecule of the present invention is at least about 91%, and preferably about 95% identical to nFeCD154$_{885}$, nFeCD154$_{780}$, and/or nFeCD154$_{633}$, and/or an allelic variant of such a nucleic acid molecule. In one embodiment, an IL-5 molecule of the present invention is at least about 90% and preferably at least about 95% identical to nCaIL-5$_{610}$, nCaIL-5$_{402}$, and/or nCaIL-5$_{345}$, and/or an allelic variant of such a nucleic acid molecule. In another embodiment, an IL-13 molecule of the present invention is at least about 65%, at least about 70%, preferably at least about 75%, more preferably at least about 80%, more preferably at least about 85%, more preferably at least about 90% and even more preferably at least about 95% identical to nCaIL-13$_{166}$, nCaIL-13$_{272}$, nCaIL-13$_{278}$, nCaIL-13$_{1302}$, nCaIL-13$_{393}$, nCaIL-13$_{333}$, nCaIL-13$_{1269}$, nCaIL-13$_{390}$, and/or nCaIL-13$_{330}$, and/or an allelic variant of such a nucleic acid molecule.

In another embodiment, an IL-4 nucleic acid molecule of the present invention comprises a nucleic acid sequence that is at least about 90%, and preferably at least about 95% identical to SEQ ID NO:1, SEQ ID NO:3, SEQ ID NO:4, SEQ ID NO:5, SEQ ID NO:19, and/or SEQ ID NO:21. The present invention also includes an IL-4 nucleic acid molecule comprising at least a portion of SEQ ID NO:1, SEQ ID NO:3, SEQ ID NO:4, SEQ ID NO:5, SEQ ID NO:19, and/or SEQ ID NO:21, as well as allelic variants of such IL-4 nucleic acid molecules, including nucleic acid molecules that have been modified to accommodate codon usage properties of the cells in which such nucleic acid molecules are to be expressed.

In another embodiment, a Flt-3 ligand nucleic acid molecule of the present invention comprises a nucleic acid sequence that is at least about 75%, preferably at least about 80%, more preferably at least about 85%, more preferably at least about 90% and even more preferably at least about 95% identical to SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37. The present invention also includes a Flt-3 ligand-nucleic acid molecule comprising at least a portion of SEQ ID NO:6, SEQ ID NO:8, SEQ ID NO:9, SEQ ID NO:10, SEQ ID NO:22, SEQ ID NO:24, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, and/or SEQ ID NO:37, as well as allelic variants of such Flt-3 ligand nucleic acid molecules, including nucleic acid molecules that have been modified to accommodate codon usage properties of the cells in which such nucleic acid molecules are to be expressed.

In one embodiment, a Flt-3 ligand nucleic acid molecule of the present invention comprises a nucleic acid sequence that is at least about 75%, more preferably at least about 80%, more preferably at least about 85%, more preferably at least about 90% and even more preferably at least about 95% identical to SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50. The present invention also includes a Flt-3 ligand-nucleic acid molecule comprising at least a portion of SEQ ID NO:41, SEQ ID NO:42, SEQ ID NO:43, SEQ ID NO:45, SEQ ID NO:46, SEQ ID NO:47, SEQ ID NO:48, and/or SEQ ID NO:50, as well as allelic variants of such Flt-3 ligand nucleic acid molecules, including to nucleic acid molecules that have been modified to accommodate codon usage properties of the cells in which such nucleic acid molecules are to be expressed.

In one embodiment, a CD40 nucleic acid molecule of the present invention comprises a nucleic acid sequence that is at least about 70%, at least about 75%, more preferably at least about 80%, more preferably at least about 85%, more preferably at least about 90% and even more preferably at least about 95% identical to SEQ ID NO:51, SEQ ID NO:52, SEQ ID NO:54, SEQ ID NO:55, SEQ ID NO:56, SEQ ID NO:57, and/or SEQ ID NO:59. The present invention also includes a CD40 nucleic acid molecule comprising at least a portion of SEQ ID NO:51, SEQ ID NO:52, SEQ ID NO:54, SEQ ID NO:55, SEQ ID NO:56, SEQ ID NO:57, and/or SEQ ID NO:59, as well as allelic variants of such CD40 nucleic acid molecules, including nucleic acid molecules that have been modified to accommodate codon usage properties of the cells in which such nucleic acid molecules are to be expressed.

In one embodiment, a CD40 nucleic acid molecule of the present invention comprises a nucleic acid sequence that is at least about 70%, at least about 75%, more preferably at least about 80%, more preferably at least about 85%, more preferably at least about 90% and even more preferably at least about 95% identical to SEQ ID NO:60 and/or SEQ ID NO:62. The present invention also includes a CD40 nucleic acid molecule comprising at least a portion of SEQ ID NO:60 and/or SEQ ID NO:62, as well as allelic variants of such CD40 nucleic acid molecules, including nucleic acid molecules that have been modified to accommodate codon usage properties of the cells in which such nucleic acid molecules are to be expressed.

In one embodiment, a CD154 nucleic acid molecule of the present invention comprises a nucleic acid sequence that is at least about 85%, preferably at least about 85%, more preferably at least about 90% and even more preferably at least about 95% identical to SEQ ID NO:63, SEQ ID NO:64, SEQ ID NO:66, SEQ ID NO:67, SEQ ID NO:68, SEQ ID NO:69, and/or SEQ ID NO:71. The present invention also includes a CD154 nucleic acid molecule comprising at least a portion of SEQ ID NO:63, SEQ ID NO:64, SEQ ID NO:66, SEQ ID NO:67, SEQ ID NO:68, SEQ ID NO:69, and/or SEQ ID NO:71, as well as allelic variants of such CD154 nucleic acid molecules, including nucleic acid molecules that have been modified to accommodate codon usage properties of the cells in which such nucleic acid molecules are to be expressed.

In one embodiment, a CD154 nucleic acid molecule of the present invention comprises a nucleic acid sequence that is at least about 91%, and preferably about 95% identical to SEQ ID NO:72, SEQ ID NO:74, SEQ ID NO:75, SEQ ID NO:76, SEQ ID NO:77, and/or SEQ ID NO:79. The present invention also includes a CD154 nucleic acid molecule comprising at least a portion of SEQ ID NO:72, SEQ ID NO:74, SEQ ID NO:75, SEQ ID NO:76, SEQ ID NO:77, and/or SEQ ID NO:79, as well as allelic variants of such CD154 nucleic acid molecules, including nucleic acid molecules that have been modified to accommodate codon usage properties of the cells in which such nucleic acid molecules are to be expressed.

In one embodiment, an IL-5 nucleic acid molecule of the present invention comprises a nucleic acid sequence that is at least about 90% and preferably at least about 95% identical to SEQ ID NO:80, SEQ ID NO:82, SEQ ID NO:83, SEQ ID NO:84, SEQ ID NO:85, and/or SEQ ID NO:87. The present invention also includes an IL-5 nucleic acid molecule comprising at least a portion of SEQ ID NO:80, SEQ ID NO:82, SEQ ID NO:83, SEQ ID NO:84, SEQ ID NO:85, and/or SEQ ID NO:87, as well as allelic variants of such IL-5 nucleic acid molecules, including nucleic acid molecules that have been modified to accommodate codon usage properties of the cells in which such nucleic acid molecules are to be expressed.

In one embodiment, an IL-13 nucleic acid molecule of the present invention comprises a nucleic acid sequence that is at least about 65%, at least about 70%, preferably at least about 75%, more preferably at least about 80%, more preferably at least about 85%, more preferably at least about 90% and even more preferably at least about 95% identical to SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106. The present invention also includes an IL-13 nucleic acid molecule comprising at least a portion of SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:98, SEQ ID NO:99, SEQ ID NO:101, SEQ ID NO:102, SEQ ID NO:103, SEQ ID NO:104, and/or SEQ ID NO:106, as well as allelic variants of such IL-13 nucleic acid molecules, including nucleic acid molecules that have been modified to accommodate codon usage properties of the cells in which such nucleic acid molecules are to be expressed.

In one embodiment, an IFNα nucleic acid molecule of the present invention is identical to SEQ ID NO:107, SEQ ID NO:109, SEQ ID NO:110, SEQ ID NO:112, SEQ ID NO:113, SEQ ID NO:115, SEQ ID NO:116, and/or SEQ ID NO:118.

In another embodiment, a GM-CSF nucleic acid molecule of the present invention is identical to SEQ ID NO:119, SEQ ID NO:121, SEQ ID NO:122, SEQ ID NO:123, SEQ ID NO:124, and/or SEQ ID NO:126.

Knowing the nucleic acid sequences of certain immunoregulatory nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and/or (c) obtain other immunoregulatory nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include mammalian cDNA libraries as well as genomic DNA libraries. Similarly, preferred DNA sources from which to amplify nucleic acid molecules include mammalian cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising canine interleukin-4, canine or feline Flt-3 ligand, canine or feline CD40, canine or feline CD154, canine interleukin-5, canine interleukin-13, feline interferon alpha, or feline GM-CSF nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of about 100 nucleotides. The present invention includes oligonucleotides that can be used as, for example, probes to identify nucleic acid molecules, primers to produce nucleic acid molecules, or therapeutic reagents to inhibit canine interleukin-4, canine or feline Flt-3 ligand, canine or feline CD40, canine or feline CD154, canine interleukin-5, canine interleukin-13, feline interferon alpha, or feline GM-CSF protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating immunoregulatory nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein, more preferably in vivo.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth and/or other endoparasite, insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with mammals, such as dog, cat, horse or human transcription control sequences.

Suitable and preferred nucleic acid molecules to include in recombinant vectors of the present invention are as disclosed herein. Preferred nucleic acid molecules to include in recombinant vectors, and particularly in recombinant molecules, include nCaIL-4$_{549}$, nCaIL-4$_{396}$, nCaIL-4$_{324}$, nCaFlt3L$_{1013}$, nCaFlt3L$_{882}$, nCaFlt3L$_{804}$, nCaFlt3L$_{828}$, nCaFlt3L$_{985}$, nCaFlt3L$_{1019}$, nCaFlt3L$_{93}$, nCaFlt3L$_{750}$, nFeFlt3L$_{395}$, nFeFlt3L$_{793}$, nFeFlt3L$_{942}$, nFeFlt3L$_{873}$, nFeFlt3L$_{795}$, nCaCD40$_{321}$, nCaCD40$_{1425}$, nCaCD40$_{822}$, nCaCD40$_{765}$, nFeCD40L$_{336}$, nCaCD154$_{390}$, nCaCD1541$_{878}$, nCaCD154$_{780}$, nCaCD154$_{633}$, nFeCD154$_{885}$, nFeCD154$_{780}$, nFeCD154$_{633}$, nCaIL-5$_{610}$, nCaIL-5$_{402}$, nCaIL-5$_{345}$, nCaIL-13$_{166}$, nCaIL-13$_{272}$, nCaIL-13$_{278}$, nCaIL-13$_{1302}$, nCaIL-13$_{393}$, nCaIL-13$_{333}$, nCaIL-13$_{1269}$, nCaIL-13$_{390}$, nCaIL-13$_{330}$, nFeIFNα$_{567a}$, nFeIFNα$_{567b}$, nFeIFNα$_{498a}$, nFeIFNα4$_{98b}$, nFeGMCSF$_{444}$, nFeGMCSF$_{432}$, and/or nFeGMCSF$_{381}$.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include immunoregulatory nucleic acid molecules of the present invention disclosed herein. Particularly preferred nucleic acid molecules with which to transform a cell include nCaIL-4$_{549}$, nCaIL-4$_{396}$, nCaIL-4$_{324}$, nCaFlt3L$_{1013}$, nCaFlt3L$_{882}$, nCaFlt3L$_{804}$, nCaFlt3L$_{828}$, nCaFlt3L$_{985}$, nCaFlt3L$_{1019}$, nCaFlt3L$_{93}$, nCaFlt3L$_{750}$, nFeFlt3L$_{395}$, nFeFlt3L$_{793}$, nFeFlt3L$_{942}$, nFeFlt3L$_{873}$, nFeFlt3L$_{795}$, nCaCD40$_{321}$, nCaCD40$_{1425}$, nCaCD40$_{822}$, nCaCD40$_{765}$, nFeCD40$_{336}$, nCaCD154$_{390}$, nCaCD1541$_{878}$, nCaCD154$_{780}$, nCaCD154$_{633}$, nFeCD154$_{885}$, nFeCD154$_{780}$, nFeCD154$_{633}$, nCaIL-5$_{610}$, nCaIL-5$_{402}$, nCaIL-5$_{345}$, nCaIL-13$_{166}$, nCaIL-13$_{272}$, nCaIL-13$_{278}$, nCaIL-13$_{1302}$, nCaIL-13$_{393}$, nCaIL-13$_{333}$, nCaIL-13$_{1269}$, nCaIL-13$_{390}$, nCaIL-13$_{330}$, nFeIFNα$_{567a}$, nFeIFNα$_{567b}$, nFeIFNα$_{498}$, nFeIFNα4$_{98b}$, nFeGMCSF$_{444}$, nFeGMCSF$_{432}$, and/or nFeGMCSF$_{381}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing immunoregulatory proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include *Salmonella, Escherichia, Bacillus, Listeria, Saccharomyces, Spodoptera, Mycobacteria, Trichoplusia*, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, chinese hamster ovary (CHO) cells, Ltk cells and Vero cells. Particularly preferred host cells are *Escherichia coli*, including *E. coli* K-12 derivatives; *Salmonella typhi; Salmonella typhimurium*, including attenuated strains such as UK-1 $_\triangle$3987 and SR-11 $_\triangle$4072; *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including any of canine interleukin-4, canine or feline Flt-3 ligand, canine or feline CD40, canine or feline CD154, canine interleukin-5, canine interleukin-13, feline interferon alpha, or feline GM-CSF nucleic acid molecule encoding one or more proteins of the present invention and/or one or more other nucleic acid molecules encoding other therapeutic compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated immunoregulatory proteins of the present invention can be produced in a variety of ways, including production and/or recovery of natural proteins, production and/or recovery of recombinant proteins, and/or chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce an immunoregulatory protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and/or differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to an immunoregulatory protein of the present invention and/or a mimetope thereof (e.g., anti-IL-4 antibodies, anti-Flt-3 ligand antibodies, anti-CD40 antibodies, anti-CD154 antibodies, anti-IL-5 antibodies, anti-IL-13 antibodies, anti-IFNα antibodies, and/or anti-GM-CSF antibodies). As used herein, the term "selectively binds to" an immunoregulatory protein of the present invention, refers to the ability of antibodies of the present invention to preferentially bind to specified proteins and/or mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by this reference herein in its entirety. An anti-IL-4 antibody of the present invention preferably selectively binds to an IL-4 protein in such a way as to inhibit the function of that protein. An anti-Flt-3 ligand antibody of the present invention preferably selectively binds to a Flt-3 ligand-protein in such a way as to inhibit the function of that protein. An anti-CD40 antibody of the present invention preferably selectively binds to a CD40 protein in such a way as to inhibit the function of that protein. An anti-CD154 antibody of the present invention preferably selectively binds to a CD154 protein in such a way as to inhibit the function of that protein. An anti-IL-5 antibody of the present invention preferably selectively binds to an IL-5 protein in such a way as to inhibit the function of that protein. An anti-IL-13 antibody of the present invention preferably selectively binds to an IL-13 protein in such a way as to inhibit the function of that protein. An anti-IFNα antibody of the present invention preferably selectively binds to an IFNα protein in such a way as to inhibit the function of that protein. An anti-GM-CSF antibody of the present invention preferably selectively binds to a GM-CSF protein in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and/or genetically-engineered antibodies, including single chain antibodies or chimeric antibodies that can bind to one or more epitopes.

A preferred method to produce antibodies of the present invention includes (a) administering to an animal an effective amount of a protein, peptide and/or mimetope thereof of the present invention to produce the antibodies and (b) recovering the antibodies. In another method, antibodies of the present invention are produced recombinantly using techniques as heretofore disclosed to produce any of the immunoregulatory proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as reagents in assays to detect an immunoregulatory protein of the present invention, (b) as reagents in assays to modulate cellular activity through an immunoregulatory protein of the present invention (e.g., mimicking ligand binding to a canine interleukin-4, canine or feline Flt-3 ligand, canine or feline CD40, canine or feline CD154, canine interleukin-5, canine interleukin-13, feline interferon alpha, or feline GM-CSF protein, as appropriate), and/or (c) as tools to screen expression libraries and/or to recover desired proteins of the present invention from a mixture of proteins and other contaminants. Furthermore, antibodies of the present invention can be used to target compounds (e.g., nucleic acid molecules, drugs or proteins) to antigen presenting cells. Targeting can be accomplished by conjugating (i.e., stably joining) such antibodies to the compounds using techniques known to those skilled in the art. Suitable compounds are known to those skilled in the art.

One embodiment of the present invention is a therapeutic composition that, when administered to an animal in an effective manner, is capable of regulating an immune response in an animal. Therapeutic compositions of the present invention can include at least one of the following therapeutic compounds: an isolated IL-4, Flt-3 ligand, CD40, CD154, IL-5, IL-13, IFNα, and/or GM-CSF protein of the present invention and/or a mimetope thereof; an isolated IL-4, Flt-3 ligand, CD40, CD154, IL-5, IL-13, IFNα, and/or GM-CSF nucleic acid molecule of the present invention; an isolated antibody that selectively binds to an IL-4, Flt-3 ligand, CD40, CD154, IL-5, IL-13, IFNα, and/or GM-CSF protein of the present invention; an inhibitor of canine IL-4, Flt-3 ligand, CD40, CD154, IL-5, IL-13, IFNα, and/or GM-CSF function identified by its ability to bind to an IL-4, Flt-3 ligand, CD40, CD154, IL-5, IL-13, IFNα, and/or GM-CSF protein, respectively, of the present invention; such an inhibitor can inhibit binding of the respective immunoregulatory protein with its respective receptor, or inhibit the activity the respective protein. Methods to perform such assays to measure binding and/or activity of an immunoregulatory protein of the present invention are known to those of skill in the art, and are described, for example, in Janeway et al., ibid. As used herein, a therapeutic compound refers to a compound that, when administered to an animal in an effective manner, is able to treat, ameliorate, and/or prevent a disease. Examples of proteins, nucleic acid molecules, antibodies and/or inhibitors of the present invention are disclosed herein.

The present invention also includes a therapeutic composition comprising at least one IL-4-, Flt-3 ligand-, CD40-, CD154-, IL-5-, IL-13-, IFNα-, and/or GM-CSF-based compound of the present invention in combination with at least one additional therapeutic compound. Examples of such compounds are disclosed herein.

Therapeutic compositions of the present invention can be administered to any animal susceptible to such therapy, preferably to mammals, and more preferably to dogs, cats, humans, ferrets, horses, cattle, sheep and/or other pets, economic food animals and/or zoo animals. Preferred animals include dogs, cats, horses and/or humans.

A therapeutic composition of the present invention is administered to an animal in an effective manner such that the composition is capable of regulating an immune response in that animal. Therapeutic compositions of the present invention can be administered to animals prior to onset of a disease (i.e., as a preventative vaccine) and/or can be administered to animals after onset of a disease in order to treat the disease (i.e., as a therapeutic vaccine). Preferred diseases to prevent and/or treat include autoimmune diseases, allergic reactions, infectious diseases, tumor development, inflammatory diseases and/or graft rejection. In one embodiment, a therapeutic composition of the present invention is administered with an antigen to enhance an immune response against that antigen.

Therapeutic compositions of the present invention can be formulated in an excipient that the animal to be treated can tolerate. Examples of such excipients include water, saline, Ringer's solution, dextrose solution, Hank's solution, and/or other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and/or Tris buffer, while examples of preservatives include thimerosal, o-cresol, formalin and/or benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and/or compounds that induce the production of cytokines and/or chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 5 (IL-5), interleukin 6

(IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and *Leishmania* elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's TITERMAX® adjuvant (Vaxcel, Inc. Norcross, Ga.), Ribi adjuvants (Ribi ImmunoChem Research, Inc., Hamilton, Mont.); and saponins and their derivatives (e.g., QuilA (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to regulate an immune response in an animal. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to and/or after onset of disease. Acceptable protocols to administer therapeutic compositions in an effective manner include individual dose size, number of doses, frequency of dose administration, and/or mode of administration. Determination of such protocols can be accomplished by those skilled in the art. A suitable single dose is a dose that is capable of regulating the immune response in an animal when administered one or more times over a suitable time period. For example, a preferred single dose of a protein, mimetope or antibody therapeutic composition is from about 1 microgram (µg) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 µg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, intraoccular, oral, transdermal and/or intramuscular routes.

According to one embodiment, a nucleic acid molecule of the present invention can be administered to an animal in a fashion to enable expression of that nucleic acid molecule into a therapeutic protein or therapeutic RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465-1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome (i.e., a viral vector). Preferred viral vectors include those based on alphaviruses, poxviruses, adenoviruses, herpesviruses, picornaviruses, and/or retroviruses, with those based on alphaviruses (such as sindbis or Semliki forest virus), species-specific herpesviruses and/or poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intranasal and/or oral routes of administration being preferred. A preferred single dose of a genetic vaccine ranges from about 1 nanogram (ng) to about 600 µg, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and/or retroviruses. Preferred recombinant virus vaccines are those based on alphaviruses (such as Sindbis virus), raccoon poxviruses, species-specific herpesviruses and/or species-specific poxviruses. An example of methods to produce and use alphavirus recombinant virus vaccines are disclosed in U.S. Pat. No. 5,766,602 by Xiong et al., issued Jun. 16, 1998, which is incorporated by this reference herein in its entirety.

When administered to an animal, a recombinant virus vaccine of the present invention infects cells within the immunized animal and directs the production of a therapeutic protein or RNA nucleic acid molecule that is capable of protecting the animal from disease caused by a parasitic helminth as disclosed herein. For example, a recombinant virus vaccine comprising an immunoregulatory nucleic acid molecule of the present invention is administered according to a protocol that results in the regulation of an immune response in an animal. A preferred single dose of a recombinant virus vaccine of the present invention is from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intranasal, intraoccular and/or oral administration routes being preferred.

A recombinant cell vaccine of the present invention includes recombinant cells of the present invention that express at least one protein of the present invention. Preferred recombinant cells for this embodiment include *Salmonella, E. coli, Listeria, Mycobacterium, S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to regulate the immune response in an animal can be tested in a variety of ways including, but not limited to, detection of cellular immunity within the treated animal, determining lymphocyte or dendritic cell activity, detection of immunoglobulin levels, determining hematopoietic stem cell or hematopoietic early progenitor cell development, determining dendritic cell development or challenge of the treated animal with an infectious agent to determine whether the treated animal is resistant to disease. In one embodiment, therapeutic compositions can be tested in animal models such as mice. Such techniques are known to those skilled in the art.

One embodiment of the present invention is an inhibitory compound. Preferably, such an inhibitory compound is derived from an IL-4, Flt-3 ligand, CD40, CD154, IL-5, IL-13, IFNα, and/or GM-CSF protein of the present invention. Examples of inhibitory compounds include an antibody of the present invention, that is administered to an animal in an effective manner (i.e., is administered in an amount so as to be present in the animal at a titer that is sufficient, upon interaction of that antibody with a native IL-4, Flt-3 ligand, CD40, CD154, IL-5, IL-13, IFNα, and/or GM-CSF protein, to decrease the activity of such proteins in an animal, at least temporarily). Oligonucleotide nucleic acid molecules of the present invention can also be administered in an effective manner, thereby reducing expression of either an IL-4, Flt-3 ligand, CD40, CD154, IL-5, IL-13, IFNα, and/or GM-CSF protein, in order to interfere with the protein activity targeted in accordance with the present invention. Peptides of an IL-4, Flt-3 ligand, CD40, CD154, IL-5, IL-13, IFNα, and/or GM-CSF protein of the present invention can also be administered in an effective manner, thereby reducing binding of IL-4, Flt-3 ligand, CD40, CD154, IL-5, IL-13, IFNα, and/or GM-CSF proteins to the appropriate receptor, in order to interfere with the protein activity targeted in accordance with the present invention. An inhibitory compound of an IL-4, Flt-3 ligand, CD40, CD154, IL-5, IL-13, IFNα, and/or GM-CSF function can be identified using IL-4, Flt-3 ligand, CD40, CD154, IL-5, IL-13, IFNα, and/or GM-CSF proteins of the present invention, respectively.

One embodiment of the present invention is a method to identify a compound 20 capable of inhibiting IL-4 function. Such a method includes the steps of: (a) contacting (e.g., combining, mixing) an isolated IL-4 protein of the present invention, with a putative inhibitory compound under conditions in which, in the absence of the compound, the IL-4 protein binds to IL-4 receptor or stimulates T cells in a T cell proliferation assay, and (b) determining if the putative inhibitory compound inhibits the binding of IL-4 protein to IL-4 receptor or the stimulation of T cells in a T cell proliferation assay. Another embodiment of the present invention is a method to identify a compound capable of inhibiting Flt-3 ligand function. Such a method includes the steps of: (a) contacting an isolated Flt-3 ligand protein of the present invention, with a putative inhibitory compound under conditions in which, in the absence of the compound, the Flt-3 ligand protein binds to Flt-3 receptor or stimulates dendritic precursor cells in a proliferation assay, and (b) determining if the putative inhibitory compound inhibits the binding of Flt-3 ligand protein to Flt-3 receptor or the stimulation of dendritic precursor cells in a proliferation assay. Another embodiment of the present invention is a method to identify a compound capable of inhibiting CD40 function. Such a method includes the steps of (a) contacting an isolated CD40 protein of the present invention, with a putative inhibitory compound under conditions in which, in the absence of the compound, the CD40 protein binds to a CD40 binding partner (e.g., CD154) and (b) determining if the putative inhibitory compound inhibits the binding of CD40 protein to the CD40 binding partner. A CD40 binding partner is a molecule that selectively binds to CD40 protein. Likewise, a binding partner for any other immunoregulatory protein of the present invention includes molecules that selectively bind to that particular immunoregulatory protein. Another embodiment of the present invention is a method to identify a compound capable of inhibiting CD154 function. Such a method includes the steps of (a) contacting an isolated CD154 protein of the present invention, with a putative inhibitory compound under conditions in which, in the absence of the compound, the CD154 protein binds to a CD154 binding partner (e.g., CD40) and (b) determining if the putative inhibitory compound inhibits the binding of CD154 protein to the CD154 binding partner. Yet another embodiment of the present invention is a method to identify a compound capable of inhibiting IL-5 function. Such a method includes the steps of: (a) contacting an isolated IL-5 protein of the present invention, with a putative inhibitory compound under conditions in which, in the absence of the compound, the IL-5 protein binds to IL-5 receptor or stimulates T cells in a T cell proliferation assay, and (b) determining if the putative inhibitory compound inhibits the binding of IL-5 protein to IL-5 receptor or the stimulation of T cells in a T cell proliferation assay. Another embodiment of the present invention is a method to identify a compound capable of inhibiting IL-13 function. Such a method includes the steps of: (a) contacting an isolated IL-13 protein of the present invention, with a putative inhibitory compound under conditions in which, in the absence of the compound, the IL-13 protein binds to IL-13 receptor or stimulates T cells in a T cell proliferation assay, and (b) determining if the putative inhibitory compound inhibits the binding of IL-13 protein to IL-13 receptor or the stimulation of T cells in a T cell proliferation assay. Another embodiment of the present invention is a method to identify a compound capable of inhibiting IFNα function. Such a method includes the steps of: (a) contacting an isolated IFNα protein of the present invention, with a putative inhibitory compound under conditions in which, in the absence of the compound, the IFNα protein binds to IFNα receptor or inhibits proliferation of GM-CSF stimulated TF-1 cells, and (b) determining if the putative inhibitory compound inhibits the binding of IFNα protein to IFNα receptor or inhibits proliferation of GM-CSF stimulated TF-1 cells. Another embodiment of the present invention is a method to identify a compound capable of inhibiting GM-CSF function. Such a method includes the steps of: (a) contacting an isolated GM-CSF protein of the present invention, with a putative inhibitory compound under conditions in which, in the absence of said compound, the GM-CSF protein binds to GM-CSF receptor or stimulates T cells in a T cell proliferation assay, and (b) determining if the putative inhibitory compound inhibits the binding of GM-CSF protein to GM-CSF receptor or the stimulation of T cells in a T cell proliferation assay.

Putative inhibitory compounds to screen include small organic molecules, antibodies (including mimetopes thereof), and/or ligand analogs. Such compounds are also screened to identify those that are substantially not toxic in host animals.

Preferred IL-4, Flt-3 ligand, CD40, CD154, IL-5, IL-13, IFNα, and/or GM-CSF, proteins to inhibit are those produced by dogs, cats, horses or humans, even more preferred IL-4, Flt-3 ligand, CD40, CD154, IL-5, IL-13, IFNα, and/or GM-CSF proteins to inhibit are those produced by domestic dogs or cats. A particularly preferred inhibitor of the present invention is capable of regulating an immune response in an animal. It is also within the scope of the present invention to use inhibitors of the present invention to target diseases involving undesired immune activity in animals. Compositions comprising inhibitors of IL-4, Flt-3 ligand, CD40, CD154, IL-5, IL-13, IFNα, and/or GM-CSF function can be administered to animals in an effective manner to regulate the immune response in the animals, and preferably to prevent autoimmune disease, allergy, infectious disease, inflammation or prevent graft rejection in animals, or to treat animals with such diseases. Effective amounts and/or dosing regimens can be determined using techniques known to those skilled in the art.

It is also within the scope of the present invention to use isolated proteins, mimetopes, nucleic acid molecules and/or antibodies of the present invention as diagnostic reagents. Methods to use such diagnostic reagents are well known to those skilled in the art, see, for example, Janeway, et al., ibid., and/or PCT Publication No. WO 98/23964, published Jun. 4, 1998.

The following examples are provided for the purposes of illustration and are not intended to limit the scope of the present invention.

EXAMPLES

It is to be noted that the examples include a number of molecular biology, microbiology, immunology and biochemistry techniques considered to be familiar to those skilled in the art. Disclosure of such techniques can be found, for example, in Sambrook et al., ibid. and Ausubel, et al., 1993, *Current Protocols in Molecular Biology*, Greene/Wiley Interscience, New York, N.Y., and related references. Ausubel, et al, ibid. is incorporated by reference herein in its entirety.

Example 1

This example describes the isolation and sequencing of canine interleukin-4 (IL-4) nucleic acid molecules of the present invention. This example also describes expression of recombinant canine IL-4 in *E. coli* and mammalian cells; development of monoclonal and polyclonal antibodies to *E. coli* expressed canine IL-4; and bioactivity of mammalian-expressed canine IL-4.

A. Isolation and Sequencing of a Canine IL-4 Nucleic Acid Molecule

Initial attempts to isolate a canine IL-4 nucleic acid molecule using various primers corresponding to putative conserved regions of IL-4 nucleic acid molecules failed. Forward and reverse primers were then designed using a sequence tag site (IL-4-sts) described by Venta et al. in GENBANK®. The forward primer was designated as IL-4-stsA, having the nucleic acid sequence 5' CTATTAATGG GTCTCACCTC CCAA CT 3', designated herein as SEQ ID NO:11. The reverse primer was designated as prIL-4-stsB, having the nucleic acid sequence 5' TCAACTCGGT GCACAGAGTC TTGG 3', designated herein as SEQ ID NO:12. The primers were used to amplify PCR products from a *C. familiaris* mitogen activated PBMC cDNA library that was constructed in the UNI-ZAP® XR vector (available from Stratagene Cloning Systems, La Jolla, Calif.), using Stratagene's ZAP-cDNA® Synthesis Kit and the manufacturer's protocol. The mRNA was isolated from *C. familiaris* peripheral blood mononuclear cells about 4 hours after they were activated by a polyclonal activating agent in culture. Four PCR products were produced that had the expected size range. The PCR products were cloned and sequenced using standard techniques. A portion of one of the four products was found to be somewhat homologous with an IL-4 nucleic acid sequence reported in GENBANK®.

To identify a cDNA encoding a full-length canine IL-4 protein, the PCR product showing some homology with the IL-4 sequence reported in GENBANK® was used to generate an about 549 base pair DNA fragment as follows. The PCR product was labeled with $^{32}P$ and used as a probe to screen the canine PBMC cDNA library. Hybridization was done at about 6×SSC, 5× Denhardt's solution, 0.5% SDS, 100 µg/ml of ssDNA and 100 µg/ml of tRNA, at about 68° C., for about 36 hr. (the compositions of SSC and Denhardt's are described in Sambrook et al., ibid.). The filters were washed 3 times, for about 30 minutes per wash, at about 55° C. in about 2×SSC, 0.2% SDS, followed by a final wash of about 30 minutes in the same buffer except using about 1×SSC. Positive clones were isolated and the cDNA inserts were sequenced for both strands using vector flanking primers and gene-specific internal primers. Sequence analysis was performed using the GAP program of GCG (available from the University of Wisconsin) using the alignment settings of: gap weight set at 50, length weight set at 3, and average match set at 10 for nucleic acid sequence comparisons; and gap weight set at 12, length weight set at 4, and average match set at 2.912 for amino acid sequence comparisons.

A cDNA nucleic acid molecule was isolated, referred to herein as nCaIL-4$_{549}$, the coding strand of which was shown to have a nucleic acid sequence denoted herein as SEQ ID NO:1. The complement of SEQ ID NO:1 is represented herein by SEQ ID NO:3. Translation of SEQ ID NO:1 suggests that nucleic acid molecule nCaIL-4$_{549}$ encodes a full-length IL-4 protein of about 132 amino acids, denoted herein as PCaIL-4$_{132}$, the amino acid sequence of which is presented in SEQ ID NO:2, assuming an open reading frame having an initiation codon spanning from nucleotide 43 through nucleotide 45 of SEQ ID NO:1 and a stop codon spanning from nucleotide 439 through nucleotide 441 of SEQ ID NO:1. The coding region encoding PCaIL-4$_{132}$ is presented herein as nCaIL-4$_{396}$, which has the nucleotide sequence SEQ ID NO:4 (the coding strand) and SEQ ID NO:5 (the complementary strand). A putative signal sequence coding region extends from nucleotide 43 through nucleotide 114 of SEQ ID NO:1. The proposed mature protein (i.e., canine IL-4 protein from which the signal sequence has been cleaved), denoted herein as PCaIL-4$_{108}$, contains about 108 amino acids, extending from residue 25 through residue 132 of SEQ ID NO:2; PCaIL-4$_{108}$ amino acid sequence is represented herein as SEQ ID NO:20. The nucleic acid molecule encoding PCaIL-4$_{108}$ is denoted herein as nCaIL-4$_{324}$, extending from nucleotide 115 through nucleotide 438 of SEQ ID NO:1. nCaIL-4$_{324}$ has a coding sequence denoted SEQ ID NO:19 and a complementary sequence denoted SEQ ID NO:21.

Comparison of nucleic acid sequence SEQ ID NO:1 with nucleic acid sequences reported in GENBANK® indicates that SEQ ID NO:1 showed the most homology, i.e., about 89.3% identity, with a feline IL-4 gene. Comparison of amino acid sequence SEQ ID NO:2 with amino acid sequences reported in GENBANK® indicates that SEQ ID NO:2 showed the most homology, i.e., about 82.6% identity, with a feline IL-4 protein. Sequence analysis was performed using the GCG GAP program as described above.

B. Expression of Recombinant Canine IL-4 in *E. coli* and Mammalian Cells i. *E. coli* Expression A recombinant molecule capable of expressing the mature form of canine IL-4, denoted herein as pGEX-nCaIL-4$_{327}$, was produced as follows. A 340-nucleotide fragment was PCR amplified from nucleic acid molecule nCaIL-4$_{549}$ (having coding strand SEQ ID NO:1) using the following primer sequences: positive strand 5' TGAATTCGGA CATAACTTCA ATATTAC 3' (SEQ ID NO:38) (EcoRI site in bold) and 5' TCTCGAGATT CAGCTTCATG CCTGTA 3' (SEQ ID NO39) (XhoI site in bold). The resulting 340-base pair fragment was digested with EcoRI and XhoI restriction enzymes (available from New England Biolabs, Beverly, Mass.), according to the manufacturer's directions, and gel-purified using standard techniques. The digested 340-base pair fragment, now 327 base pairs, was then ligated into pGEX-6P-1 (available from Amersham Pharmacia, Piscataway, N.J.), which had been previously digested with EcoRI and XhoI and gel purified, to produce recombinant molecule pGEX-nCaIL-4$_{327}$. Recombinant molecules of pGEX produce the protein of interest as a glutathione s-transferase (GST) fusion protein. The recombinant molecule pGEX-nCaIL-4$_{327}$ was transformed into DH5alpha cells (available from Life Technologies, Gaithersburg, Md.), a recombination deficient strain of *E. coli*, to produce recombinant cell DH5-pGEX-nCaIL-4$_{327}$. The recombinant cells were screened for presence of insert by PCR and confirmed by enzyme restriction analysis and nucleic acid sequencing, using standard techniques. Several clonal recombinant molecules were transformed into BL21 cells (available from Amersham Pharmacia, Piscataway, N.J.), a protease deficient strain of *E. coli*, to produce recombinant cell BL21-pGEX-nCaIL-4$_{327}$. These recombinant cells were screened, and the clone with the highest level of protein yield was selected for scaling up for larger-scale protein production. The resultant recombinant protein is referred to herein as *E. coli*PCaIL-4$_{109}$.

To produce and purify *E. coli*PCaIL-4$_{109}$, bacterial cultures of recombinant cell BL21:pGEX-nCaIL-4$_{327}$ were grown in shake flasks at 37° C. and induced with 0.1 mM IPTG (isopropyl-β-D-thiogalactopyranoside), (available from Sigma Chemical Company, St. Louis, Mo.) when OD$_{600nm}$ reached about 0.8 units. Growth was allowed to continue for about 4 hours; then bacteria were harvested by centrifugation at 4000×g (times gravity) for 20 minutes. The bacterial pellet was washed and resuspended in phosphate buffered saline (PBS) (for recipe, see Sambrook et al, ibid.), then lysed by exposure to gaseous nitrogen pressure in a Parr pressure vessel (available from Parr Instrument Co., Moline, Ill.), according to the manufacturer's instructions. Cell debris was removed by centrifugation at 10,000×g for 20 minutes. The IL-4-GST fusion protein *E. coli*PCaIL-4$_{109}$ was purified from the supernatant by allowing incubation with glutathione-conjugated resin, removing unbound proteins and then removing the GST tag with PRESCISSION™ protease; all reagents were available from Amersham Pharmacia and all were used according to the manufacturer's directions.

Concentration and purity of *E. coli*PCaIL-4$_{109}$ were estimated by BCA Protein Assay kit (available from Pierce, Rockford, Ill.) and SDS-PAGE followed by Coomassie staining, respectively. The purified material exhibited a single band of approximately 14 kilodaltons (kD) by Coomassie stained SDS-PAGE.

ii. CHO Cell Expression

A recombinant molecule denoted herein as pCMV-nCaIL-4$_{399}$, capable of expressing a full length form of canine IL-4 (including signal sequence) was produced as follows. A 422-nucleotide fragment was PCR amplified from nucleic acid molecule nCaIL-4$_{549}$ using the following primers: 5' CCCAAGCTTA TGGGTCTCACC TCCCAAC (HindIII site in bold), denoted SEQ ID NO:40, and 3' CCTCGAGATT CAGCTTTCAA TGCCTGTA (XhoI site in bold), denoted SEQ ID NO:127. The 422-base pair PCR product was digested with the restriction endonucleases HindIII and XhoI, both available from New England Biolabs. The resulting 399-base pair product encoding full-length canine IL-4 was gel purified using standard techniques and ligated into the cytomegalovirus (CMV) immediate-early transcription control region of the pCMV-Int A plasmid vector that had been digested with HindIII and XhoI (available from New England Biolabs), and gel purified, to produce the recombinant molecule pCMV-nCaIL-4$_{399}$. The pCMV-Int A plasmid vector was generated as referenced by J. E. Osorio et al., 1999, *Vaccine* 17, 1109-1116. Briefly, vector pRc/RSV, (available from Invitrogen Corp., San Diego, Calif.) was cleaved with restriction enzyme PvuII (available from New England Biolabs), and the 2963-base pair PvuII fragment was gel purified. The fragment was self-ligated to form the vector pRc/RSV (Pvu), which contains a Rous Sarcoma Virus (RSV) long terminal repeat, a multiple cloning site, a bovine growth hormone polyadenylation sequence, a bacterial origin of replication, and an ampicillin resistance gene. Vector pRc/RSV (Pvu) was restriction enzyme digested using HindIII and NruI. A HindIII/SspI fragment containing the HCMV intermediate early promoter and first intron (i.e. intron A) was ligated into the digested pRc/RSV (Pvu) vector to produce the vector pCMV-Int A.

Stable expression of CaIL-4 in mammalian cells was carried out by transfecting the recombinant molecule pCMV-nCaIL-4$_{399}$ into Chinese Hamster Ovary cells, (CHO, available from ATCC) as follows. Six-well polystyrene tissue culture plates (available from Corning Costar, Acton, Mass.) were seeded with approximately $5 \times 10^5$ cells/well in 2 milliliter (ml) cell culture media, consisting of Minimal Essential Media (MEM) supplemented with 100 mM L-glutamine, 100 mM gentamicin, and 10% fetal bovine serum (FBS), (all available from Life Technologies). Cells were grown to about 80% confluence (for about 18 hours) before transfection. The recombinant molecules to be transfected were purified using the Plasmid Midi Kit (available from Qiagen, Valencia, Calif.) and used according to the manufacturer's instructions. The recombinant molecule pCMV-nCaIL-4$_{399}$ was linearized using the restriction enzyme PvuI (available from New England Biolabs). The plasmid pcDNA3, (available from Invitrogen), which contains the neomycin resistance gene, was linearized using the restriction enzyme EcoRI. Approximately 2 µg of pCMV-nCaIL-4$_{399}$ was mixed with about 2 ng of linearized pcDNA3 in about 100 µl OPTIMEM™ media, available from Life Technologies. About 10 µl Lipofectamine, (available from Life Technologies) was mixed with 100 µl OPTIMEM. The nucleic acid molecule-containing mixture was then added to the Lipofectamine mixture and incubated at room temperature for about 45 minutes. After incubation, about 0.8 ml OPTIMEM was added, and the mixture was overlaid onto the CHO cells which had been previously rinsed with OPTIMEM. Cells were incubated for about 5 hours at 37° C. 5% CO$_2$, 95% relative humidity. Approximately 1 ml of cell culture media as described previously, with 20% FBS, was added and the cells were incubated overnight. The media was changed at 24 hours, and at 72 hours post transfection, the cells were split 1:4 and put into fresh cell culture media containing about 500 µg/ml geneticin (G418, available from Life Technologies). The media was changed every 3-5 days. After several weeks, G418 resistant colonies were trypsinized using sterile filter papers, 5-6 mm in diameter that were soaked in trypsin, which were then placed over individual wells of 24 well plates that contained separated widely spaced colonies of CHO cells. After 3 days, the papers were removed. The resulting recombinant cells are referred to herein as CHO-pCMV-nCaIL-4$_{399}$. The recombinant cells were then expanded and tested for the presence of nIL-4$_{399}$ RNA by RT-PCR and tested for the presence of PCaIL-4$_{133}$ protein by Western blot analysis. Westerns were developed with rabbit anti-$E.$ $coli$PCaIL-4$_{109}$ serum and 607.1 monoclonal antibody, a monoclonal antibody that selectively binds to $E.$ $coli$PCaIL-4$_{109}$ protein. See Example 1C for a description of how these antibodies were produced.

C. Monoclonal and Polyclonal Antibodies to Recombinant Canine IL-4 (i.e., Anti-Canine IL-4 Antibodies)

The following describes the development of monoclonal and polyclonal antibodies that selectively bind to $E.$ $coli$PCaIL-4$_{109}$.

Female Balb/C mice, 6-8 weeks old, were injected subcutaneously, at about 4 sites, with a total of 25 µg $E.$ $coli$PCaIL-4$_{109}$ (produced as described in Example 1Bi) in Freund's Complete Adjuvant (day 0). Fourteen days later, the mice received an intraperitoneal boost of 25 µg $E.$ $coli$PCaIL-4$_{109}$ in Freund's Incomplete Adjuvant (day 14). Fourteen days later, serum was tested for antibody titer to $E.$ $coli$PCaIL-4$_{109}$ by ELISA (day 28). Three days prior to fusion, mice were boosted intravenously with 20 µg $E.$ $coli$PCaIL-4$_{109}$ in PBS (day 35). Splenocytes were harvested from mice demonstrating the highest serum titer by ELISA and depleted of CD4+ and CD8+ cells. This depletion was achieved by incubation of the splenocytes with biotinylated rat anti-mouse CD4 and anti-mouse CD8 monoclonal antibodies, available from PharMingen, San Diego, Calif. Antibody-labeled cells were then removed by incubation with M-280 streptavidin coated magnetic beads, available from Dynal, Oslo, Norway. Depleted splenocytes were fused to SP2/0 cells (available from ATCC) using 50% polyethylene glycol in unsupplemented Iscove's Modified Dulbecco's Media (IMDM), following established protocols; see, for example, Harlow E., and Lane D., eds., 1995, $Antibodies.$ $A$ $Laboratory$ $Manual$, Monoclonal Antibodies, Cold Spring Harbor Laboratories; Harlow et al, ibid., is incorporated by reference herein in its entirety. Fused cells were plated in 96-well plates using IMDM cell culture media, (available from Life Technologies, Inc., Rockville, Md.), which was supplemented with 10% fetal bovine serum, 2 mM L-glutamine, 1 mM sodium pyruvate, 1×nonessential amino acids, 1×MEM amino acids, 0.05 mg/ml gentamicin, and 0.5 mM β-mercaptoethanol (all reagents available from Life Technologies). Additionally, 100 µM hypoxanthine, 0.4 µM aminopterin, and 16 µM thymidine, all available from Sigma Chemical Corporation, St Louis, Mo., were added.

After about 7 days, wells positive for hybridoma growth were screened by ELISA to $E.$ $coli$PCaIL-4$_{109}$. Immulon II 96-well plates (available from VWR, Denver, Colo.) were coated, overnight, with 100 ng/ml $E.$ $coli$PCaIL-4$_{109}$ in 0.1 M carbonate/bicarbonate buffer, Ph 9.6. After blocking the wells with 20% FBS in Tris buffered saline (TBS), culture supernatants were allowed to bind. Presence of anti-$E.$ $coli$PCaIL-4$_{109}$ mouse antibody was detected with polyclonal goat anti-mouse IgG conjugated to horseradish peroxidase, (available from KPL, Gaithersburg, Md.), and color developed with 3,3',5,5'-tetramethylbenzidine dihydrochloride (TMB), available from Pierce, Rockford, Ill. Specificity of the ELISA reactivity was verified by Western blot analysis to $E.$ $Coli$ PCaIL-4$_{109}$, developed with polyclonal goat anti-mouse IgG conjugated to alkaline phosphatase and nitro-blue tetrazolium/5-bromo-4-chloro-3'-indolyphosphate p-toluidine salt substrate (NBT/BCIP, available from Sigma). Western blots exhibited a single band of approximately 14 kD. Immunoglobulin isotype of the monoclonal antibodies was determined using IsoStrips, available from Boehringer Mannheim, Indianapolis, Ind. Twenty-three monoclonal antibodies were generated to $E.$ $coli$PCaIL-4$_{109}$, 22 of which were of the IgM isotype and one of which was IgG1, and is referred to herein as 607.1.

Polyclonal rabbit serum was produced by repeated immunization (over a 10 month period) of a male, New Zealand White rabbit 12-16 months old. Initial immunization was 50 ug $E.$ $coli$PCaIL-4$_{109}$ (prepared as described in Example 1bi) in Freund's Complete Adjuvant, at several sites subcutaneously and intradermally. One month later, and at one month intervals thereafter, the rabbit was boosted intradermally with 50 ug $E.$ $coli$PCaIL-4$_{109}$ in Freund's Incomplete Adjuvant. Serum was collected bi-weekly and titers monitored by ELISA and Western blot to $E.$ $coli$PCaIL-4$_{109}$. Serum that selectively bound to $E.$ $coli$PCaIL-4$_{109}$ protein is referred to as anti-$E.$ $coli$PCaIL-4$_{109}$ serum.

D. Bioactivity of Mammalian-Expressed Canine IL-4

The following describes a bioassay to detect the expression of canine IL-4 protein expressed in the supernatants from CHO-pCMV-nCaIL-4$_{399}$ recombinant cells by screening for production of CD23.

About 100 µl Ramos cells, available from ATCC, at a concentration of about $3.5 \times 10^3$ cells/ml were seeded into 96-well flat bottom plates, available from Becton Dickinson, Franklin Lakes, N.J.). These cells were grown in RPMI media supplemented with 100 mM L-glutamine, gentamicin, and 10% FBS (called TCM). The Ramos cells were then treated in 5% CO$_2$ for 37° C. for approximately 48 h. with one of the following:

Group Treatment
1 TCM
2 CHO-pCMV (a transfectant cell line containing the empty pCMV vector) supernatant (1:4 final dilution in TCM)
3 CHO-pCMV-nCaIL-$4_{399}$ supernatant (1:20 final dilution in TCM)

Triplicate samples for each treatment group were pooled for staining to look for increased expression of CD23 (one of the reported effects of IL-4). Briefly, $1 \times 10^5$ cells from each treatment group were incubated in phosphate buffered saline (PBS) containing 30% FBS for 15-30 min on ice. The cells were collected and incubated with the following:

| Condition | Primary Incubation | Secondary Incubation |
|---|---|---|
| A | PBS | Goat anti mouse PE |
| B | Mouse anti human CD23 | Goat anti mouse PE |

Mouse anti-human CD23 monoclonal antibody, available from Pharmingen, was used at about 10 µg/ml. Goat (Fab'2) anti mouse IgG PE, available from Southern Biotechnologies was used at about 2.5 µg/ml. These reagents were diluted in PBS with 5% FBS. Primary incubations were performed for 30-60 minutes on ice, and secondary incubations were performed for 20-30 min on ice. Three washes of PBS/5% FBS were performed in between each incubation. Cells were then analyzed on a flow cytometer (e.g., MoFlow Desk Top System, available from Cytomation, Ft. Collins, Colo.) with the fluorescein gate set at $10^1$. The results are shown below in Table 2.

TABLE 2

Induction of CD23 on Ramos cells post-treatment with supernatants from CHO-pCMV-nCaIL-$4_{399}$

| Treatment | Condition | % positive |
|---|---|---|
| 1 | A | 0 |
|   | B | 1 |
| 2 | A | 8 |
|   | B | 1 |
| 3 | A | 3 |
|   | B | 99 |

Table 2 shows that the canine Il-4 expressed by the CHO transfectant CHO-pCMV-nCaIL-$4_{399}$ is biologically active, demonstrated by its ability to induce expression of CD23 in Ramos cells.

Example 2

This example describes the isolation and sequencing of certain canine Flt-3 ligand and feline Flt-3 nucleic acid molecules and proteins of the present invention. The example also describes expression of a canine Flt-3 ligand protein of the present invention in CHO cells, as well as detection of the expressed canine Flt-3 ligand protein.

A. Canine Flt-3 Ligand Nucleic Acid Molecules and Proteins.

i. This example describes the isolation and sequencing of certain canine Flt-3 ligand nucleic acid molecules and proteins of the present invention.

A canine Flt-3 ligand nucleic acid molecule was produced as follows. A pair of primers was initially used to amplify DNA from the C. familiaris mitogen activated PBMC cDNA library described above in Example 1. A forward primer referred to as FLT3F1, having the nucleic acid sequence 5' CTGGCGCCAG CCTGGAGCCC 3', designated herein as SEQ ID NO:13 was used in combination with a reverse primer referred to herein as FLT3B1, having the nucleic acid sequence 5' GGGAGATGTT GGTCTGGACG 3', referred to herein as SEQ ID NO:14 to amplify Flt-3 ligand DNA from the cDNA library by polymerase chain reaction (PCR). The primers were designed using conserved regions of IL-4 cDNA sequences from other species in the public databases corresponding to the positions shown below:

| Database | Accession number | Nucleotides | Animal |
|---|---|---|---|
| gb | U04806 | 102-121 | human |
| gb | L23636 | 41-60 | mouse |
| gb | U04806 | 77-458 | human |
| gb | L23636 | 419-400 | mouse |

A 360-base pair (bp) PCR product was generated in the above reaction that was purified, radiolabeled and used as a probe to screen the cDNA library. Hybridization was performed in 6×SSC, 5× Denhardt's solution, 0.5% SDS, 100 µg/ml ssDNA and 100 µg/ml of tRNA, at 68° C., for about 36 hr. The filters were washed 3 times, for about 30 minutes per wash, at 55° C. in 2×SSC, 0.1% SDS, followed by a final wash in 0.25×SSC, for about 30 minutes, at 55'C. Several positive phage clones were identified and shown to produce PCR products when used as templates in combination with the FLT3F1 and FLT3B1 primers. The DNA inserts in the phage clones were sequenced using standard techniques and failed to yield any clones containing DNA inserts having a portion homologous to published Flt-3 ligand sequences. The 360-bp PCR fragment generated above was then cloned into the vector pcDNA 2.1 (available from Invitrogen Corp., San Diego, Calif.). Several independent colonies were generated and the sequences of their inserts determined. One clone was identified that which contained insert sequence having a portion that was somewhat homologous to published human or murine Flt-3 ligand sequence.

Two canine Flt-3 ligand-specific primers were then designed using the nucleic acid sequence obtained using the 360-bp PCR product described above.

| Primer | Sequence | SEQ ID NO |
|---|---|---|
| DFLB1 | 5' GACCAGGCGCCAGAACGC 3' | SEQ ID NO: 15 |
| DFLF1 | 5' CGGTCACCATCCGCAAGC 3' | SEQ ID NO: 16 |

The 5' region of a Flt-3 ligand nucleic acid molecule was PCR amplified from the cDNA library using the DFLB1 primer in combination with the 5' T3 vector primer from the UNI-ZAP® XR vector (available from Stratagene). The 3' region of a Flt-3 ligand nucleic acid molecule was PCR amplified from the cDNA library using the DFLF1 in combination with the 3' T7 primer from the UNI-ZAP® XR vector (available from Stratagene). A 855-bp PCR product was obtained representing the 5' region of a Flt-3 ligand nucleic acid molecule. A 265-bp PCR product was obtained representing the 3' region of a Flt-3 ligand nucleic acid molecule. Both the 855-bp PCR product and 265-bp PCR product were cloned and sequenced using standard methods. Additional canine Flt-3 ligand-specific primers were designed using the nucleic acid sequence obtained from the sequence of the 855-bp PCR product and 265-bp PCR products.

| Primer | Sequence | SEQ ID NO |
|---|---|---|
| DFLB2 | 5' TGGCAAGGCAGTGGCCTC 3' | SEQ ID NO: 17 |
| DFLF2 | 5' GCCGAGATGATAGTGCTGGC 3' | SEQ ID NO: 18 |

A 546-bp PCR product was generated using the primer DFLF2 in combination with the primer DFLB2 to amplify a PCR product from the cDNA library. The 546-bp PCR product was then purified, radiolabelled and used as a probe to screen the cDNA library. Hybridization was performed in 6×SSC, 5× Denhardt's solution, 0.5% SDS, 100 µg/ml of ssDNA and 100 µg/ml of tRNA, at 68° C., for about 36 hr. The filters were washed in 1.25×SSC, for about 30 minutes, at 55° C. Four cDNA clones encoding full-length canine Flt-3 ligand were isolated. Nucleic acid sequence was obtained using standard techniques.

A Flt-3 ligand clone was isolated, referred to herein as nCaFlt3L$_{1013}$, the coding strand of which was shown to have a nucleic acid sequence denoted herein as SEQ ID NO:6. The complement of SEQ ID NO:6 is represented herein by SEQ ID NO:8. Translation of SEQ ID NO:6 suggests that nucleic acid molecule nCaFlt3L$_{1013}$ encodes a full-length Flt-3 ligand protein of about 294 amino acids, denoted herein as PCaFlt3L$_{294}$, the amino acid sequence of which is presented in SEQ ID NO:7, assuming an open reading frame having an initiation codon spanning from nucleotide 35 through nucleotide 37 of SEQ ID NO:6 and a stop codon spanning from nucleotide 917 through nucleotide 919 of SEQ ID NO:6. The coding region encoding PCaFlt3L$_{294}$ is presented herein as nCaFlt3L$_{882}$, which has the nucleotide sequence SEQ ID NO:9 (the coding strand) and SEQ ID NO:10 (the complementary strand). A putative signal sequence coding region extends from nucleotide 35 through nucleotide 112 of SEQ ID NO:6. The proposed mature protein (i.e., canine Flt-3 ligand protein from which the signal sequence has been cleaved), denoted herein as PCaFlt3L$_{268}$ (SEQ ID NO:23), contains about 268 amino acids, extending from residue 27 through residue 294 of SEQ ID NO:7. The nucleic acid molecule encoding PCaFlt3L$_{268}$ is denoted herein as nCaFlt3L$_{804}$, extending from nucleotide 113 through nucleotide 916 of SEQ ID NO:6. nCaFlt3L$_{804}$ has a coding sequence denoted SEQ ID NO:22 and a complementary sequence denoted SEQ ID NO:24.

Below is a description of the identification of alternatively spliced *Canis* Flt3 ligand transcripts. Besides cDNA clones such as nucleic acid molecule nCaFlt3L$_{1013}$ encoding the full-length canine Flt3 ligand protein, two splice variants of canine Flt3 ligand cDNA clones were also isolated, using the same hybridization conditions as mentioned previously in this Example. One such variant (Clone 1), denoted herein as nCaFlt3L$_{985}$, has a coding strand the nucleic acid sequence of which is represented as SEQ ID NO:25. The complement of SEQ ID NO:25 is represented herein by SEQ ID NO:27. Translation of SEQ ID NO:25 suggests that nucleic acid molecule nCaFlt3L$_{985}$ encodes a Flt-3 ligand protein of 276 amino acids, denoted herein as PCaFlt3L$_{276}$, the amino acid sequence of which is represented by SEQ ID NO:26, assuming an open reading frame having an initiation codon spanning from nucleotide 74 through nucleotide 76 of SEQ ID NO:25 and a stop codon spanning from nucleotide 902 through nucleotide 904 of SEQ ID NO:25. The coding region encoding PCaFlt3L$_{276}$ is represented herein as nCaFlt3L$_{828}$, which has the nucleotide sequence SEQ ID NO:28 (the coding strand) and SEQ ID NO:29 (the complementary strand). Alignment of nucleic acid molecules nCaFlt3L$_{882}$ and nCaFlt3L$_{828}$ indicates that the nucleic acid molecules are identical except for a deletion in nCaFlt3L$_{828}$, which spans from nucleotide 343 through nucleotide 396 of nCaFlt3L$_{882}$. Accordingly, nCaFlt3L$_{828}$ encodes 18 fewer amino acids than nCaFlt3L$_{882}$. The deletion in PCaFlt3L$_{276}$, which spans from residue 115 through residue 132 of PCaFlt3L$_{294}$, occurs between helix III and helix IV of the canine Flt3 ligand protein inferred from alignment with the human and mouse Flt3 ligand protein (Lyman et al., *Cell*, vol. 75, pp. 1157-1167, 1993; Hannum et al., *Nature*, vol. 368, pp. 643-648, 1994; Lyamn et al., *Blood*, vol. 83, pp. 2795-2801, 1994). In addition, the alignment shows that there are 39 more nucleotides in the 5' untranslated region of nucleic acid molecule nCaFlt3L$_{985}$ (nucleotides 1 to 39) than nucleic acid molecule nCaFlt3L$_{1013}$ and there are 2 more nucleotides in the 3' untranslated region of nucleic acid molecule nCaFlt3L$_{985}$ (nucleotides 922 to 923) than nucleic acid molecule nCaFlt3L$_{1013}$. The remaining sequences between nCaFlt3L$_{985}$ and nCaFlt3L$_{1013}$ are identical. A putative mature form of nCaFlt3L$_{985}$ (without the signal sequence) is predicted. The putative signal sequence coding region extends from nucleotide 74 to nucleotide 151 of SEQ ID NO:25. The proposed mature protein, denoted herein as PCaFlt3L$_{250}$, represented by SEQ ID NO:31, contains about 250 amino acids, extending from residue 27 through residue 276 of SEQ ID NO:26. The nucleic acid molecule encoding PCaFlt3L$_{250}$, extending from nucleotide 152 through nucleotide 901 of SEQ ID NO:6, denoted herein as nCaFlt3L$_{750}$, is represented by SEQ ID NO:30 (the coding strand) and SEQ ID NO:32 (the complement strand).

A second variant (Clone 19) is represented by nucleic acid molecule nCaFlt3L$_{1019}$, the coding strand of which is denoted herein as SEQ ID NO:33. The complement of SEQ ID NO:33 is denoted herein as SEQ ID NO:35. Translation of SEQ ID NO:33 suggests that nCaFlt3L$_{1019}$ encodes a Flt-3 ligand protein of 31 amino acids, PCaFlt3L$_{31}$, denoted SEQ ID NO:34, assuming an initiation codon spanning from nucleotide 74 through nucleotide 76 and a stop codon spanning nucleotide 167 through nucleotide 169 of SEQ ID NO:33. The coding region encoding PCaFlt3L$_{31}$ is represented herein as nCaFlt3L$_{93}$, which has the nucleotide sequence SEQ ID NO:36 (the coding strand) and SEQ ID NO:37 (the complementary strand). Alignment of nucleic acid molecules nCaFlt3L$_{985}$ and nCaFlt3L$_{1019}$ indicates the presence of an insertion of 91 nucleotides in nCaFl3L$_{1019}$. The insertion spans nucleotide 107 through nucleotide 198 of nCaFlt3L$_{1019}$. A stop codon is found in this insertion in frame with the predicted initiation codon, which span nucleotide 74 through nucleotide 76 of SEQ ID NO:6. Since this insertion (with an in-frame stop codon) occurs in or close to the signal peptide, it is likely that nucleic acid molecule nCaFlt3L$_{1019}$ encodes a nonfunctional Flt-3 ligand protein.

Comparison of nucleic acid sequence SEQ ID NO:6 with nucleic acid sequences reported in GENBANK® indicates that SEQ ID NO:6 showed the most homology, i.e., about 69.8% identity, with a human Flt-3 ligand gene. Comparison of amino acid sequence SEQ ID NO:7 with amino acid sequences reported in GENBANK® indicates that SEQ ID NO:7 showed the most homology, i.e. about 71% identity, with a human Flt-3 ligand protein. Sequence analysis was performed with DNASIS® using the alignment settings of:

gap penalty set at 5; number of top diagonals set at 5; fixed gap penalty set at 10; K-tuple set at 2; window size set at 5 and floating gap penalty set at 10.

ii. This example describes the production of a recombinant molecule encoding a full length canine Flt-3 ligand protein and expression of that protein by a recombinant cell of the present invention.

A recombinant molecule, denoted herein as pCMV-nCaFlt3L$_{882}$ and capable of expressing a full length form of Flt-3 ligand, was produced as follows. Nucleic acid molecule nCaFlt3L$_{882}$ was digested with the restriction endonucleases EcoRI and XbaI, gel purified and ligated into pCMV-Int A (prepared by methods described in Example 1) to produce recombinant molecule pCMV-nCaFlt3L$_{882}$. Insert size and identity were confirmed by restriction digestion, PCR, and sequencing analyses.

Stable transfectants expressing the recombinant molecule pCMV-nCaFlt3L$_{882}$ were established in Chinese Hamster Ovary cells (CHO, available from ATCC) as follows. Briefly, six-well polystyrene tissue culture plates were seeded with approximately 4×10$^5$ cells per well in 2 ml of MEM (available from Life Technologies, Gaithersburg, Md.) supplemented with 100 mM L-glutamine, gentamicin, and 10% FBS (TCM). Cells were grown to about 80% confluence (about 18 hr). The recombinant molecule to be transfected was prepared using the Qiagen Endotoxin-Free Plasmid Maxi Kit as per the manufacturer's instructions. The recombinant molecule was linearized with the restriction enzyme PvuI, extracted with phenol, and precipitated with isopropanol. The plasmid pcDNA 3, available from Invitrogen, which contains the neomycin resistance gene, was linearized with the restriction enzyme EcoRI. Approximately 1 µg of recombinant plasmid DNA and 100 ng of pcDNA3 were mixed with about 100 µl OptiMEM medium, available from Life Technologies. About 10 µl Lipofectamine (available from Life Technologies) was mixed with 100 µl OptiMEM. The DNA-containing mixture was then added to the Lipofectamine mixture and incubated at room temperature for about 30 min. After incubation, about 800 µl of OptiMEM was added, and the entire mixture was overlaid onto the CHO cells that had been rinsed with Opti-MEM. Cells were incubated for 6 hours at 37° C., 5% CO$_2$, 95% relative humidity. Approximately 1 ml of TCM with 20% FBS was added, and the cells were incubated overnight. The media was changed after about 24 hr. About 72 hr post transfection, the cells were split 1:4 and put into selection TCM containing 500 µg/ml Geneticin (G418), available from Life Technologies. The medium was changed every 3-5 days. After several weeks, G418-resistant colonies were trypsinized, and the cells were plated into 24 well plates. The resulting recombinant cells are referred to herein as CHO-pCMV-nCaFlt3L$_{882}$. The recombinant cells were then expanded for testing.

iii. The following describes the detection of expression of a canine Flt-3 ligand protein of the present invention by CHO-pCMV-nCaFlt3L$_{882}$, a recombinant cell of the present invention.

Recombinant cells CHO-pCMV-nCaFlt3L$_{882}$, produced as described in Example 2, part (B) (ii) above, were tested for surface expression of canine Flt-3 ligand using a cross-reactive goat anti-human Flt-3 ligand polyclonal antibody as follows. Briefly, 1×10$^5$ CHO-pCMV-nCaFlt3L$_{882}$ cells or CHO-pCMV cells (i.e., cells transfected with an empty vector as described in Example 1) were incubated in phosphate buffered saline (PBS) containing 30% fetal bovine serum (FBS) for about 30 min on ice. The cells were then spun down and treated with the following:

| Condition | Primary Incubation | Secondary Incubation |
|---|---|---|
| 1 | PBS | Rabbit (Fab'2) anti sheep (H + L) FITC |
| 2 | Goat anti-human Flt3 ligand | Rabbit (Fab'2) anti sheep (H + L) FITC |

Goat anti-human Flt3 ligand, available from R and D Systems, Minneapolis, Minn. was used at about 20 µg/ml. Rabbit (Fab'2) anti sheep (H+L) FITC, available from Southern Biotechnology Associates, Inc., was used at about 10 µg/ml. These reagents were diluted in PBS/5% FBS. All incubations were in 50 µl for about 1 hr on ice with 2 washes of PBS/5% FBS in between each incubation. Cells were then analyzed on a flow cytometer (e.g., MoFlow Desk Top System, available from Cytomation, Ft. Collins, Colo.) with the fluorescein gate set at 10$^1$. The results are shown below in Table 3.

TABLE 3

Expression of canine Flt3 ligand on CHO transfectants.

| | % positive | |
|---|---|---|
| Cells | Condition 1 | Condition 2 |
| CHO-pCMV | 1 | 1 |
| CHO-pCMV nCaFlt3L$_{882}$ | 2 | 48 |
| CHO-pCMV nCaFlt3L$_{882}$ | 1 | 20 |

Table 3 shows that canine Flt3 ligand is expressed on the surface of the CHO transfectants.

B. Feline Flt-3 Ligand Nucleic Acid Molecules and Proteins.

This example describes the production of certain feline Flt-3 ligand nucleic acid molecules and proteins of the present invention.

A nucleic acid molecule encoding a feline Flt 3 ligand was isolated from a feline PBMC cDNA library as follows. A *Felis catus* mitogen activated PBMC cDNA library was constructed in the UNI-ZAP-R XR™ vector, available from Stratagene, La Jolla, Calif., using Stratagene's ZAP-cDNA-R™ Synthesis Kit and the manufacturer's protocol using mRNA isolated from *F. catus* peripheral blood mononuclear cells about 4 hours after they were activated by a polyclonal activating agent in culture. PCR amplification to isolate a feline Flt 3 ligand nucleic acid molecule was conducted according to the following set of steps: one initial denaturation step at 95° C. for 3 minutes; then 35 cycles of the following: 94° C. for 30 seconds, 53.8° C. for 30 seconds, and 72° C. for 105 seconds; then one final extension step at 72° C. for 8 minutes. A 395-nucleotide cDNA fragment containing the 5' end of feline Flt3 ligand coding region, denoted nFeFlt3L$_{395}$, was amplified from the feline PMBC cDNA library using the following primers: vector primer T3 having nucleic acid sequence 5' AATTAACCCT CACTAAAGGG 3' (SEQ ID NO:142) (available from Stratagene) and the antisense primer having SEQ ID NO:14, described in Example 2A. The nucleic acid sequence of the coding strand of nFeFlt3L$_{395}$ is denoted SEQ ID NO:41. A 793-nucleotide cDNA fragment containing the 3' end of feline Flt3 ligand coding region, denoted nFeFlt3L$_{793}$, was isolated using sense primer 2 having the nucleic acid sequence 5' CACAGYC-CCA TCTCCTCC 3' (where Y was either T or C) denoted herein as SEQ ID NO:151, in conjunction with vector primer T7 having the nucleic acid sequence 5' GTAATACGAC TCACTATAGG GC 3' (SEQ ID NO:152). The nucleic acid sequence of the coding strand of nFeFlt3L$_{793}$ is denoted SEQ ID NO:42. Nucleic acid molecules nFeFlt3L$_{395}$ and nFeFlt3L$_{793}$ overlap by 246 nucleotides and form a composite sequence encoding a Flt3 ligand protein that is similar in length to that of PCaFlt3L$_{294}$. This composite feline Flt3 ligand cDNA is referred to herein as nFeFlt3L$_{942}$, the coding strand of which was shown to have nucleic acid sequence SEQ ID NO:43. The reverse complement of SEQ ID NO:43 is referred to herein as SEQ ID NO:45. Translation of SEQ ID NO:43 suggests that nucleic acid molecule nFeFlt3L$_{942}$ encodes a Flt3 ligand protein of 291 amino acids, denoted herein as PFeFlt3L$_{291}$, the amino acid sequence of which is presented in SEQ ID NO:44, assuming an open reading frame having an initiation codon spanning from nucleotide 31 through nucleotide 33 of SEQ ID NO:43 and a stop codon spanning from nucleotide 904 through nucleotide 906 of SEQ ID NO:43. The coding region encoding PFeFlt3L$_{291}$, not including the termination codon, is presented herein as nFeFlt3L$_{873}$, which has the nucleotide sequence SEQ ID NO:46 (the coding strand) and SEQ ID NO:47 (the complementary strand). A putative signal sequence coding region extends from nucleotide 31 to nucleotide 108 of SEQ ID NO:43. The proposed mature protein, denoted herein as PFeFlt3L$_{265}$, denoted SEQ ID NO:49, contains about 265 amino acids, extending from residue 27 though residue 291 of SEQ ID NO:44. The nucleic acid molecule encoding PFeFlt3L$_{265}$ is denoted herein as nFeFlt3L$_{795}$, (SEQ ID NO:48) extending from nucleotide 109 through nucleotide 903 of SEQ ID NO:43. SEQ ID NO:48 has a complementary strand denoted SEQ ID NO:50.

Sequence alignment indicates that nucleic acid sequence SEQ ID NO:43 shares the highest (67.8%) identity with the nucleic acid sequence of human Flt-3 ligand (GENBANK® accession numbers U04806 and U03858). Amino acid sequence SEQ ID NO:44 shares the highest (70.2%) identity with human Flt-3 ligand protein (GENBANK® accession numbers U04806 and U03858).

Example 3

This example describes the isolation and sequencing of certain canine CD40 and feline CD40 nucleic acid molecules and proteins of the present invention.

A. Canine CD40 Nucleic Acid Molecules and Proteins

This example describes the production of certain canine CD40 nucleic acid molecules and proteins of the present invention.

A canine CD40 nucleic acid molecule of the present invention was produced by PCR amplification as follows. A 321-nucleotide canine CD40 nucleic acid molecule, denoted nCaCD40$_{321}$, was amplified from a canine PBMC cDNA library, prepared as described in Example 1, using two degenerate oligonucleotide primers designed in accordance with conserved regions of human, bovine, rabbit, and mouse CD40 gene sequences available in GENBANK®: sense primer, 5' TGCCCRSTCG GCTTCTTCTC C3', denoted herein as SEQ ID NO:128; and antisense primer, 5' CGACTCTCTT TRCCRTCCTC CTG 3', denoted herein as SEQ ID NO:129, where R was either A or G and S was either G or C. PCR conditions were as follows: one initial denaturation step at 95° C. for 3 minutes; then 35 cycles of the following: 94° C. for 30 seconds, then 53° C. for 30 seconds, then 72° C. for 105 seconds; followed by one final extension at 72° C. for 5 minutes. The resulting PCR product, i.e., nCaCD40$_{321}$, with a coding strand represented by SEQ ID NO:51, was radiolabeled using standard techniques and used to screen the canine PBMC cDNA library, under the following hybridization conditions: hybridized in 6×SSC, 5× Denhardt's solution, 0.5% SDS, 100 µg/ml single stranded DNA, 100 µg/ml tRNA for 36 hours at 68° C., followed by a wash of 0.1% SDS, 1×SSC at 55° C. for 60 minutes. A clone (Clone 18B) containing a 1425-nucleotide canine CD40 nucleic acid molecule, denoted nCaCD40$_{1425}$, was obtained. The nucleic acid sequence of the coding strand of nCaCD40$_{1425}$ is represented as SEQ ID NO:52. The reverse complement of SEQ ID NO:52 is referred to herein as SEQ ID NO:54. Translation of SEQ ID NO:52 suggests that nucleic acid molecule nCaCD40$_{1425}$ encodes a canine CD40 protein of 274 amino acids, denoted herein as PCaCD40$_{274}$, the amino acid sequence of which is presented in SEQ ID NO:53, assuming an open reading frame having an initiation codon spanning from nucleotide 196 through nucleotide 198 of SEQ ID NO:52 and a stop codon spanning from nucleotide 1018 through nucleotide 1020 of SEQ ID NO:52. The coding region encoding PCaCD40$_{274}$, not including the termination codon, is presented herein as nCaCD40$_{822}$, which has the nucleotide sequence SEQ ID NO:55 (the coding strand) and SEQ ID NO:56 (the complementary strand).

A putative signal sequence coding region extends from nucleotide 196 through nucleotide 252 of SEQ ID NO:52. The proposed mature protein, denoted herein as PCaCD40$_{255}$, represented by SEQ ID NO:58, contains about 255 amino acids, extending from residue 20 through residue 274 of SEQ ID NO:53. The nucleotide sequence encoding PCaCD40$_{255}$, which extends from nucleotide 253 through nucleotide 1017 of SEQ ID NO:52, is denoted herein as nucleic acid molecule nCaCD40$_{765}$, represented by SEQ ID NO:57 (the coding strand) and SEQ ID NO:59 (the complement strand).

Sequence analysis was performed with DNAsis™ using the alignment settings of: gap penalty set at 5; number of top diagonals set at 5; fixed gap penalty set at 10; k-tuple set at 2; window size set at 5 and floating gap penalty set at 10. At the amino acid level, PCaCD40$_{274}$ shares 65.3%, 50.1%, and 42.3% identity with the CD40 proteins of human, bovine, and mouse, respectively (Stamenkovic et al., *EMBO J.*, vol. 8:1403-1410, 1989; Hirano et al., *Immunology*, vol. 90, pp. 294-300, 1997; Grimaldi et al., *J. Immunol.*, vol. 143, pp. 3921-3926; Torres and Clark, *J. Immuno.*, vol. 148, pp. 620-626). At the nucleotide level, nCaCD40$_{1425}$ shares 69.3%, 69.4%, and 40.4% identity with the cDNA sequences of human, bovine, and mouse CD40, respectively.

B. Feline CD40 Nucleic Acid Molecules and Proteins

This example describes the isolation and sequencing of certain nucleic acid molecules of the present invention that encode certain feline CD40 proteins of the present invention.

A 336-nucleotide feline CD40 nucleic acid molecule, denoted nFeCD40$_{336}$, was amplified from a feline PBMC cDNA library, prepared as described in Example 2, using PCR conditions and primers as described in Example 3A, i.e., a sense primer having SEQ ID NO:128; and an antisense primer having SEQ ID NO:129. The resulting PCR product, i.e., nFeCD40$_{336}$, was shown to have a coding strand the nucleic acid sequence of which is represented as SEQ ID NO:60. The reverse complement of SEQ ID NO:60 is referred to herein as SEQ ID NO:62. Translation of SEQ ID NO:60 suggests that nucleic acid molecule nFeCD40$_{336}$ encodes a partial CD40 protein of 112 amino acids, denoted herein as PFeCD40$_{112}$, the amino acid sequence of which is presented in SEQ ID NO:61, assuming an open reading frame spanning from nucleotide 1 through nucleotide 336 of SEQ ID NO:60.

Comparison of nucleic acid sequence SEQ ID NO:60 with nucleic acid molecules reported in GENBANK® indicates that SEQ ID NO:60 showed the most homology, i.e. 67.2% identity, with a human CD40 gene. Comparison of amino acid sequence SEQ ID NO:61 with amino acid sequences reported in GENBANK® indicates that SEQ ID NO:61 showed the most homology, i.e. about 54.4% identity, with a human CD40 protein. Sequence analysis was performed using the GCG GAP program as described above.

Example 4

This example describes the isolation and sequencing of certain canine CD154 (canine CD40 ligand) and feline CD154 (feline CD40 ligand) nucleic acid molecules and proteins of the present invention.

A. Canine CD154 (CD40 Ligand) Nucleic Acid Molecules and Proteins

The following describes the isolation and sequencing of certain cDNA nucleic acid molecules encoding certain canine CD154 (CD40 ligand) proteins of the present invention.

A canine CD154 nucleic acid molecule of the present invention was produced by PCR amplification as follows. A 390-nucleotide canine CD40 nucleic acid molecule, denoted $nCaCD154_{390}$, was amplified from a canine PBMC cDNA library, prepared as described in Example 1, using two degenerate oligonucleotide primers designed in accordance with human CD154 gene sequences available in GENBANK®: sense primer, 5' CCTCAAATTG CGGCACATGT C3', denoted herein as SEQ ID NO:130; and antisense primer, 5' CTGTTCAGAG TTTGAGTAAG CC 3', denoted herein as SEQ ID NO:131. PCR conditions used for canine CD154 cDNA amplification were standard conditions for PCR amplification (Sambrook, et al., ibid.). The resulting PCR product, i.e., $nCaCD154_{390}$, with a coding strand represented by SEQ ID NO:63, was radiolabeled using standard techniques and used to screen the canine PBMC cDNA library, under the hybridization conditions described in Example 3. A clone containing a 1878-nucleotide canine CD154 nucleic acid molecule, denoted $nCaCD154_{1878}$, was obtained. The nucleic acid sequence of the coding strand of $nCaCD154_{1878}$ is represented as SEQ ID NO:64. The reverse complement of SEQ ID NO:64 is referred to herein as SEQ ID NO:66. Translation of SEQ ID NO:64 suggests that nucleic acid molecule $nCaCD154_{1878}$ encodes a CD154 protein of 260 amino acids, denoted herein as $PCaCD154_{260}$, the amino acid sequence of which is presented in SEQ ID NO:65, assuming an open reading frame having an initiation codon spanning from nucleotide 284 through nucleotide 286 of SEQ ID NO:64 and a stop codon spanning from nucleotide 1064 through nucleotide 1066 of SEQ ID NO:64. The coding region encoding $PCaCD154_{260}$, not including the termination codon, is presented herein as $nCaCD154_{780}$, which has the nucleotide sequence SEQ ID NO:67 (the coding strand) and SEQ ID NO:68 (the complementary strand).

A putative signal/membrane anchor sequence coding region extends from nucleotide 284 through nucleotide 430 of SEQ ID NO:64. The proposed soluble CD154 protein, denoted herein as $PCaCD154_{211}$, represented by SEQ ID NO:70, contains about 211 amino acids, extending from residue 50 though residue 260 of SEQ ID NO:65. The nucleotide sequence encoding $PCaCD154_{211}$, which extends from nucleotide 431 through nucleotide 1063 of SEQ ID NO:64, is denoted herein as nucleic acid molecule $nCaCD154_{633}$, represented by SEQ ID NO:69 (the coding strand) and SEQ ID NO:71 (the complement strand).

Sequence analysis was performed with DNASIS® using the alignment settings of: gap penalty set at 5; number of top diagonals set at 5; fixed gap penalty set at 10; k-tuple set at 2; window size set at 5 and floating gap penalty set at 10. At the amino acid level, $PCaCD154_{260}$ shares 78.0%, 77.6%, and 67.6% identity with the CD154 proteins of human, bovine, and mouse, respectively (Graf et al., *Eur. J. Immunol.*, vol. 22, pp. 3191-3194, 1992; Hollenbaugh, et al., *EMBO J.*, vol. 11:4313-4321, 1992; Gauchat et al., *FEBS lett*, vol., 315, pp. 259-266, 1993; Mertens et al., *Immunogenetics*, vol. 42, pp. 430-431; Armitage et al., *Nature*, vol. 357, pp. 80-82; 1992). At the nucleotide level, $nCaCD154_{1878}$ shares 81.1%, 81.5%, and 74.4% identity with the sequences of human, bovine, and mouse CD154 cDNAs, respectively.

B. Feline CD154 (CD40 Ligand) Nucleic Acid Molecules and Proteins

This example describes the isolation and sequencing of certain nucleic acid molecules encoding certain feline CD154 (CD40 ligand) proteins of the present invention.

A feline CD154 nucleic acid molecule was isolated by PCR amplification from a feline PBMC cDNA library, prepared as described in Example 2, using Amplitaq DNA polymerase (available from PE Applied Biosystems Inc, Foster City, Calif.) under the following PCR protocol: one initial denaturation step at 95° C. for 5 minutes; then 40 cycles of the following: 94° C. for 45 seconds, then 48° C. for 45 seconds, then 72° C. for 120 seconds; followed by a final extension at 72° C. for 7 minutes. The forward and reverse primers used were based on human CD154 cDNA sequences outside the open reading frame in the 5' and 3' untranslated regions, respectively, so that the open reading frame in the PCR product contained only feline sequences. The sequence of the forward primer was 5'GAAGATACCA TTTCAACTTT AACACAGC 3' SEQ ID NO:132, and that of the reverse primer was 5' TGCTGTATTG TGAAGACTCC CAGC 3' SEQ ID NO:133. PCR products were cloned into the TA cloning vector (available from Invitrogen Corporation, Carlsbad, Calif.), and the resulting clones were sequenced using an ABI PRISM® Model 377 Automatic DNA Sequencer (available from PE Applied Biosystems Inc.). DNA sequencing reactions were performed using PRISM™ dRhodamine Terminator Cycle Sequencing Ready Reaction kits (available from PE Applied Biosystems Inc.).

The PCR product was sequenced and found to contain 885 nucleotides, and is denoted as $nFeCD154_{885}$. The nucleotide sequence of the coding strand of $nFeCD154_{885}$ is represented herein as SEQ ID NO:72, and its complement is denoted SEQ ID NO:74. Translation of the open reading frame in SEQ ID NO:72 suggests that $nFeCD154_{885}$ encodes a protein containing 260 amino acids, referred to herein as $PFeCD154_{260}$, the amino acid sequence of which is presented as SEQ ID NO:73, assuming an open reading frame in which the first codon spans from nucleotide 29 through nucleotide 31 of SEQ ID NO:72, and the stop codon spans from nucleotide 809 through nucleotide 811 of SEQ ID NO:72. The encoded protein has a predicted molecular weight of 28.6 kDa for the precursor protein and 27.2 kDa for the mature protein. The coding region encoding $PFeCD154_{260}$, not including the termination codon, is presented herein as $nFeCD154_{780}$, which has the nucleotide sequence SEQ ID NO:75 (the coding strand) and SEQ ID NO:76 (the complementary strand)

A putative signal/membrane anchor sequence coding region extends from nucleotide 29 through nucleotide 175 of SEQ ID NO:72. The proposed soluble feline CD154 protein, denoted herein as $PFeCD154_{211}$, represented by SEQ ID NO:78, contains about 211 amino acids, extending from residue 50 though residue 260 of SEQ ID NO:$_{73}$. The nucleotide sequence encoding $PFeCD154_{211}$, denoted herein as $nFeCD154_{633}$ which extends from nucleotide 176 through nucleotide 808 of SEQ ID NO:72, is represented herein by SEQ ID NO:77 (the coding strand) and SEQ ID NO: 79 (the complementary strand).

Comparison of feline CD154 nucleotide and amino acid sequences with those of other species published in GEN-BANK® reveals that the feline CD154 nucleotide sequence SEQ ID NO:75 is 86%, 88% and 75% identical to the human, bovine and murine CD154 gene sequences, respectively (GENBANK® accession number L07414, Z48469 and X56453 respectively). At the amino acid sequence level, SEQ ID NO:73 is 81%, 82%, and 67% identical to the human, bovine and murine CD154 amino acid sequences, respectively. Hydrophobicity analysis of feline CD154 proteins results in a pattern similar to those of human, bovine and murine CD154 proteins. A putative N-glycosylation site was identified at position 239 in $PFeCD154_{260}$ that is conserved in the human, bovine and murine amino acid sequences. Five cysteine residues are present in the feline CD154 protein sequence SEQ ID NO:73. Four of the five residues, located at positions 72, 84, 177 and 217 of $PFeCD154_{260}$, are conserved in all four species and are likely involved in disulfide bond formation. The cysteine residue located at position 193 of $PFeCD154_{260}$ is present in all but the murine sequence.

Example 5

This example describes the isolation and sequencing of certain canine IL-5 nucleic acid molecules and proteins of the present invention. This example also describes expression of canine IL-5 in a *Pichia* expression system.

A. Isolation and Sequencing of Canine IL-5 Nucleic Acid Molecules and Proteins

A canine IL-5 cDNA nucleic acid molecule encoding a canine IL-5 protein was isolated by PCR amplification from a canine PBMC cDNA library (prepared as described in Example 1) using PCR conditions as described in Example 4B and the following primers. Degenerate oligonucleotide primers were designed in accordance with conserved regions of human and cat IL-5 gene sequences available in GEN-BANK®: sense primer, 5' ATGCACTTTC TTTGCC 3', denoted herein as SEQ ID NO:134; antisense primer 1, 5' CTGGAGGAAA AKACTTCRAT GATTCTGATA TCT-GAAATAT AT 3', denoted herein as SEQ ID NO:135; and antisense primer 2, 5' CTGACYCTTK STTGGSCCTC ATTCTCA 3', denoted herein as SEQ ID NO:136, where K was G or T, R was either A or G, S was either G or C, and Y was either T or C.

An about 610-nucleotide canine IL-5 nucleic acid molecule, denoted $nCaIL-5_{610}$, was obtained using primers having SEQ ID NO:134 and SEQ ID NO:135, respectively. The sequence of the coding strand of $nCaIL-5_{610}$ is represented herein as SEQ ID NO:80. The reverse complement of SEQ ID NO:80 is referred to herein as SEQ ID NO:82. Translation of SEQ ID NO:80 suggests that nucleic acid molecule $nCaIL-5_{610}$ encodes an IL-5 protein of 134 amino acids, denoted herein as $PCaIL-5_{134}$, the amino acid sequence of which is presented in SEQ ID NO:81, assuming an open reading frame having an initiation codon spanning from nucleotide 29 through nucleotide 31 of SEQ ID NO:80 and a stop codon spanning from nucleotide 431 through nucleotide 433 of SEQ ID NO:80. The coding region encoding $PCaIL-13_{134}$, not including the termination codon, is presented herein as $nCaIL-5_{402}$, which has the nucleotide sequence SEQ ID NO:83 (the coding strand) and SEQ ID NO:84 (the complementary strand).

An about 488-nucleotide fragment, denoted herein as $nCaIL-5_{488}$, isolated by PCR with primers having SEQ ID NO:134 and SEQ ID NO:136, respectively, corresponds to nucleotide 1 through nucleotide 488 of $nCaIL-5_{610}$.

A putative signal sequence coding region extends from nucleotide 29 through nucleotide 85 of SEQ ID NO:80. The proposed mature protein, denoted herein as $PCaIL-5_{115}$, represented by SEQ ID NO:86, contains about 115 amino acids, extending from residue 20 though residue 134 of SEQ ID NO:81. The nucleotide sequence encoding $PCaIL-5_{115}$, which extends from nucleotide 86 through nucleotide 430 of SEQ ID NO:80, is denoted herein as nucleic acid molecule $nCaIL-5_{345}$, represented by SEQ ID NO:85 (coding strand) and SEQ ID NO:87 (the complement strand).

Sequence analysis was performed with DNASIS® using the alignment settings of: gap penalty set at 5; number of top diagonals set at 5; fixed gap penalty set at 10; k-tuple set at 2; window size set at 5 and floating gap penalty set at 10. At the amino acid level, $PCaIL-5_{134}$ shared 82.8% and 57.4% identity with feline and human IL-5 proteins, respectively (Padrid et al., *Am. J. Vet. Res.*, vol. 59, pp. 1263-1269, 1998; Azuma et al., *Nucleic Acids Res.*, vol. 14, pp. 9149-9158, 1986). At the nucleotide level, $nCaIL-5_{610}$ shared 81.7% and 75% identity with the cDNA sequences of the feline and human IL-5, respectively.

B. Expression of Canine IL-5 in *Pichia*

This example describes the expression in *Pichia* of a canine IL-5 cDNA fragment, namely a canine IL-5 nucleic acid molecule denoted $nCaIL-5_{348}$, the coding strand of which consists of nucleotides 86-433 of SEQ ID NO:80, and as such, encodes a predicted mature canine IL-5 protein having SEQ ID NO:86. Nucleic acid molecule $nCaIL-5_{348}$, was PCR amplified from $nCaIL-5_{610}$ using sense primer 5' GGGCTC-GAGA AAAGATTTGC TGTAGAAAAT CCCATG 3' denoted herein as SEQ ID NO:137, with nucleotides 16-36 corresponding to nucleotides 86-106 of SEQ ID NO:80; and antisense primer 5' CCCGCGGCCG CTCAACTTTC CGGTGTCCAC TC 3', denoted herein as SEQ ID NO:138, with nucleotides 12-32 corresponding to the reverse complement of nucleotides 413-433 of SEQ ID NO:80. To facilitate cloning, an XhoI site (shown in bold) was added to the sense primer and a NotI site (shown in bold) was added to the antisense primer. The PCR-amplified fragment was digested with restriction endonucleases XhoI and NotI, gel purified and ligated into pPICZαA plasmid vector, available from Invitrogen, that had been digested by Xho I and Not I and gel purified, to produce recombinant molecule pPICZαA-$nCaIL-5_{348}$. The insert in the recombinant molecule was verified by DNA sequencing. The recombinant molecule was used to transform *Pichia pastoris* strain X-33 by electroporation to produce recombinant cell *Pichia*-pPICZαA-nCaIL-$5_{348}$. Recombinant cell *Pichia*-pPICZαA-$nCaIL-5_{348}$ was cultured using techniques known to those skilled in the art and IL-5 expression was induced with methanol. The supernatant was recovered and submitted to SDS-PAGE. Silver staining of the resultant gel indicated a band of about 18 kDa only seen in the supernatant of *Pichia* transformed with recombinant molecule pPICZαA-$nCaIL-5_{348}$.

Example 6

This example describes the isolation and sequencing of certain canine IL-13 nucleic acid molecules and proteins of the present invention. This example also describes expression of canine IL-13 in *E. coli*.

A. Isolation and Sequencing of Canine IL-13 Nucleic Acid Molecules and Proteins

A canine IL-13 cDNA nucleic acid molecule encoding a canine IL-13 protein was isolated by PCR amplification from a canine PBMC cDNA library (prepared as described in Example 1) using the following primers and PCR conditions:

Degenerate oligonucleotide primers were designed in accordance with conserved regions of human and cat IL-5 gene sequences available in GENBANK®: sense primer, 5' GTC-MTKGCTC TYRCTTGCCT TGG 3', denoted herein as SEQ ID NO:139; antisense primer 1, 5' AAASTGGGCY ACYTC-GATTT TGG 3', denoted herein as SEQ ID NO:140; antisense primer 2, 5' GTGATGTTGM YCAGCTCCTC 3', denoted herein as SEQ ID NO:141, where M was either A or C, K was G or T, R was either A or G, S was either G or C, and Y was either T or C. PCR conditions used were as follows: One initial denaturation step at 95° C. for 3 minutes; then 38 cycles of the following: 94° C. for 30 seconds, 51.8° C. for 45 seconds, then 72° C. for 105 seconds; then a final extension at 72° C. for 5 minutes.

An about 272-nucleotide canine IL-13 nucleic acid molecule, denoted nCaIL-13$_{272}$ and having a coding strand represented by SEQ ID NO:89, was PCR amplified using primers having nucleic acid sequences of SEQ ID NO:139 and SEQ ID NO:140, respectively. An about 166-nucleotide canine IL-13 nucleic acid molecule, is denoted nCaIL-13$_{166}$ and having a coding strand represented by SEQ ID NO:88, was isolated using primers having nucleic acid sequences of SEQ ID NO:142 (see Example 2B) and SEQ ID NO:141, respectively. Nucleic acid molecules nCaIL-13$_{272}$ and nCaIL-13$_{272}$ form a overlapping composite fragment of 383 nucleotides, denoted nCaIL-13$_{383}$. Two canine IL-13 specific primers (i.e., sense primer, 5' ATGGCGCTCT GGT-TGACTGT 3', denoted herein as SEQ ID NO:143; and antisense primer, 5' GGCTTTTGAG AGCACAGTGC 3', denoted herein as SEQ ID NO:144) were derived from nCaIL-13$_{383}$ and were used to isolate a 278-nucleotide fragment, denoted nCaIL-13$_{278}$ and having a coding strand represented by SEQ ID NO:90. Nucleic acid molecule nCaIL-13$_{278}$ was radiolabeled and used to screen the canine PBMC cDNA library under the following hybridization conditions: hybridization took place in 6×SSC, 5× Denhardt's solution, 0.5% SDS, 100 μg/ml single stranded DNA, 100 μg/ml tRNA, for 36 hours at 60° C.; the final wash solution was 0.1% SDS, 0.125×SSC at 60° C. for 30 minutes. Two clones were selected, namely clone 80 and clone 78.

Sequence analysis of Clone 80 indicated that the clone includes an about 1302-nucleotide canine IL-13 nucleic acid molecule referred to herein as nCaIL-13$_{1302}$, the coding strand of which was shown to have nucleic acid sequence SEQ ID NO:91. The reverse complement of SEQ ID NO:91 is referred to herein as SEQ ID NO:93. Translation of SEQ ID NO:91 suggests that nucleic acid molecule n nCaIL-13$_{1302}$ encodes an IL-13 protein of 131 amino acids, denoted herein as PCaIL-13$_{131}$, the amino acid sequence of which is presented in SEQ ID NO:92, assuming an open reading frame having an initiation codon spanning from nucleotide 52 through nucleotide 54 of SEQ ID NO:91 and a stop codon spanning from nucleotide 445 through nucleotide 447 of SEQ ID NO:91. The coding region encoding PCaIL-13$_{131}$, not including the termination codon, is presented herein as nCaIL-13$_{393}$, which has the nucleotide sequence SEQ ID NO:94 (the coding strand) and SEQ ID NO:95 (the complementary strand).

A putative signal sequence coding region extends from nucleotide 52 to nucleotide 111 of SEQ ID NO:91. The proposed mature protein, denoted herein as PCaIL-13$_{111}$, represented by SEQ ID NO:97, contains 111 amino acids, extending from residue 21 through residue 131 of SEQ ID NO:91. The nucleotide sequence encoding PCaIL-13$_{111}$, which extends from nucleotide 112 through nucleotide 444 of SEQ ID NO:91, is denoted herein as nucleic acid molecule nCaIL-13$_{333}$, represented by SEQ ID NO:96 (coding strand) and SEQ ID NO:98 (the complement strand).

Sequence analysis of Clone 78 indicated that the clone includes an about 1269-nucleotide canine IL-13 nucleic acid molecule referred to herein as nCaIL-13$_{1269}$, the coding strand of which was shown to have nucleic acid sequence SEQ ID NO:99. The reverse complement of SEQ ID NO:99 is referred to herein as SEQ ID NO:101. Translation of SEQ ID NO:99 suggests that nucleic acid molecule nCaIL-13$_{1269}$ encodes an IL-13 protein of 130 amino acids, denoted herein as PCaIL-13$_{130}$, the amino acid sequence of which is presented in SEQ ID NO:100, assuming an open reading frame having an initiation codon spanning from nucleotide 57 through nucleotide 59 of SEQ ID NO:99 and a stop codon spanning from nucleotide 447 through nucleotide 449 of SEQ ID NO:99. The coding region encoding PCaIL-13$_{130}$, not including the termination codon, is represented herein as nCaIL-13$_{390}$, which has the nucleotide sequence SEQ ID NO:102 (the coding strand) and SEQ ID NO:103 (the complementary strand). PCaIL-13$_{130}$ is missing one amino acid compared to PCaIL-13$_{133}$, namely amino acid position Q97 of PCaIL-13$_{133}$.

A putative signal sequence coding region extends from nucleotide 57 to nucleotide 116 of SEQ ID NO:99. The proposed mature protein, denoted herein as PCaIL-13$_{110}$, represented by SEQ ID NO:105, contains 110 amino acids, extending from residue 21 though residue 130 of SEQ ID NO:100. The nucleotide sequence encoding PCaIL-13$_{110}$, which extends from nucleotide 117 through nucleotide 446 of SEQ ID NO:99, is denoted herein as nucleic acid molecule nCaIL-13$_{330}$, represented by SEQ ID NO:104 (coding strand) and SEQ ID NO:106 (the complement strand).

Sequence analysis was performed with DNAsis™ using the alignment settings of: gap penalty set at 5; number of top diagonals set at 5; fixed gap penalty set at 10; k-tuple set at 2; window size set at 5 and floating gap penalty set at 10. At the amino acid level, PCaIL-13$_{131}$ shared 61.7%, 39.6%, 36.6% identity with the IL-13 proteins of human, mouse, and rat (Brown et al., *J. Immunol.*, vol. 142, pp. 679-687, 1989; Lakkis et al., *Biochem. Biophys. Res. Commun.*, Vol. 197, pp. 612-618, 1993; McKenzie et al., *Proc. Natl Acad. Sci. USA*, vol. 90, pp. 3735-3739, 1993; Minty et al., *Nature*, vol. 362, pp. 248-250, 1993), respectively. At the nucleotide level, nCaIL-13$_{1302}$ shared 56.0%, 57.1%, and 45.9% identity with the sequences of human, rat, and mouse IL-13 cDNAs, respectively.

B. Expression of Canine IL-13 in *E. coli*

This example describes the expression in *E. coli* of a canine IL-13 cDNA fragment, namely a canine IL-13 nucleic acid molecule denoted nCaIL-13$_{336}$, the coding strand of which consists of nucleotides 112-447 of SEQ ID NO:91, and as such, encodes a predicted mature canine IL-13 protein having SEQ ID NO:97. Nucleic acid molecule nCaIL-13$_{336}$ was PCR amplified from nCaIL-13$_{1302}$ using sense primer 5' CCCCATATGA GCCCTGTGAC TCCCTCCCC 3' denoted herein as SEQ ID:145, with nucleotides 10-29 corresponding to nucleotides 112-1131 of SEQ ID NO:91; and antisense primer 5' GGGGAATTCT CATCTGAAAT TTCCATGGCG 3', denoted herein as SEQ ID NO:146, with nucleotides 10-30 corresponding to the reverse complement of nucleotides 427-447 of SEQ ID NO:91. To facilitate cloning, an NdeI site (shown in bold) was added to the sense primer and an EcoRI site (shown in bold) was added to the antisense primer. The resulting PCR fragment was digested with restriction endonucleases NdeI and EcoRI, gel purified and ligated into λcro plasmid vector, the production of which is described in U.S. Pat. No. 5,569,603 by Tripp et al., issued Oct. 29, 1996, that had been digested by NdeI and EcoRI and gel purified to produce recombinant molecule pλcro-nCaIL-13$_{336}$. The insert in the recombinant molecule was verified by DNA sequencing. Recombinant molecule pλcro-nCaIL-13$_{336}$ was used to transform *E. coli* strain HCE101 (BL21), thereby producing BL21-pλcro-nCaIL-13$_{336}$. PCaIL-13$_{111}$ was produced under conditions as described in U.S. Pat. No. 5,569, 603, ibid., protein expression being induced by switching the fermentation temperature from 32° C. to 42° C. SDS-PAGE and Commassie blue staining analysis indicated that a band of about 11 kD was only produced by induced BL21-pλcro-nCaIL-13$_{336}$ recombinant cells. The 11-kD band showed a positive reaction with a rabbit polyclonal antibody against human IL-13 (available from PeproTech Inc, Rocky Hill, N.J.), indicating expression of canine IL-13 in *E. coli*.

Example 7

This example describes the isolation and sequencing of feline interferon alpha nucleic acid molecules and proteins of the present invention.

Feline IFN-alpha nucleic acid molecules were PCR amplified from a feline cDNA library as follows. Total RNA was isolated from cat (kitten) mesenteric lymph node cells stimulated with PMA (phorbol myristate acetate) for 48 hours using TRI REAGENT® (available from Molecular Research Center, Cincinnati, Ohio). cDNA was made from the RNA using the cDNA synthesis kit containing READY TO GO-YOU PRIME FIRST-STRAND BEADS™ (available from Amersham Pharmacia Biotech, Piscataway, N.J.). An aliquot of this cDNA was used as a template to isolate a feline IFN-alpha nucleic acid molecule by PCR amplification using Amplitaq DNA POLYMERASE™ (available from PE Applied Biosystems Inc, Foster City, Calif.) and the following primers and conditions. The sequence of the forward primer was 5'ATGGCGCTGC CCTCTTCCTT CTTG 3' (SEQ ID NO:143), and that of the reverse primer was 5' TCATTTCTCG CTCCTTAATC TTTTCTGC 3' (SEQ ID NO:148). The following PCR protocol was used: one initial denaturation step at 95° C. for 5 minutes; then 43 cycles of the following: 94° C. for 45 seconds, then 47° C. for 45 seconds, then 72° C. for 120 seconds; followed by a final extension at 72° C. for 7 minutes. PCR products were cloned into the TA cloning vector (available from Invitrogen Corporation) and the clones were sequenced using an ABI PRISM® Model 377 Automatic DNA Sequencer (available from PE Applied Biosystems Inc.). DNA sequencing reactions were performed using PRISM™ dRhodamine Terminator Cycle Sequencing Ready Reaction kits (available from PE Applied Biosystems Inc.).

Two PCR products were generated and sequenced. Both contained 570 nucleotides (including the termination codons), and are distinguished as Clone #2 and Clone #3 as there were differences in the sequences of the clones.

Clone #2 includes a feline IFN-alpha nucleic acid molecule that is represented herein as nFeIFNα$_{567a}$, the coding strand of which was shown to have a nucleic acid sequence denoted herein as SEQ ID NO:107. The complement of SEQ ID NO:107 is represented herein by SEQ ID NO:109. Translation of SEQ ID NO:107 suggests that nFeIFNα$_{567a}$ encodes a protein containing 189 amino acids, referred to herein as PFeIFNα$_{189a}$, with an amino acid sequence denoted SEQ ID NO:108. The open reading frame of SEQ ID NO:107 is assumed to be the following: the first codon spans from nucleotide 1 through nucleotide 3 and the last codon before the stop codon spans from nucleotide 565 to nucleotide 567 of SEQ ID NO:107. The encoded protein has a predicted molecular weight of 21 kDa. The putative signal peptide cleavage site occurs between amino acid positions 23 and 24, based on homology with the human and canine interferon-alpha proteins. The proposed mature protein (i.e. feline IFNα protein from which the signal sequence has been cleaved), denoted herein as PFeIFNα$_{166a}$, contains about 166 amino acids, extending from residue 24 to residue 166 of SEQ ID NO:108; the amino acid sequence is denoted herein as SEQ ID NO:114. The nucleic acid molecule encoding PFeIFNα$_{166a}$ is denoted herein as nFeIFNα$_{498a}$, which is represented by SEQ ID NO:113, with a complementary sequence represented by SEQ ID NO:115. A putative N-glycosylation site and an interferon alpha-beta-delta family signature motif are present at amino acid positions 102 and 145, respectively, of PfeIFNα$_{189a}$.

Clone #3 includes a feline IFN-alpha nucleic acid molecule that is represented herein as nFeIFNα$_{567b}$, the coding strand of which was shown to have a nucleic acid sequence denoted herein as SEQ ID NO:110. The complement of SEQ ID NO:110 is represented herein by SEQ ID NO:112. Translation of SEQ ID NO:110 suggests that nFeIFNα$_{567b}$ encodes a protein containing 189 amino acids, referred to herein as PFeIFNα$_{189b}$, with an amino acid sequence denoted SEQ ID NO:111. The open reading frame of SEQ ID NO:110 is assumed to be the following: the first codon spans from nucleotide 1 through nucleotide 3 and the last codon before the stop codon spans from nucleotide 565 through nucleotide 567 of SEQ ID NO:110. The encoded protein has a predicted molecular weight of 21 kDa. The putative signal peptide cleavage site occurs between amino acid positions 23 and 24, based on homology with the human and canine interferon-alpha proteins. The proposed mature protein (i.e. feline IFNα protein from which the signal sequence has been cleaved), denoted herein as PFeIFNα$_{166b}$, contains about 166 amino acids, extending from residue 24 to residue 166 of SEQ ID NO:111; the amino acid sequence is denoted herein as SEQ ID NO:117. The nucleic acid molecule encoding PFeIFNα$_{166b}$ is denoted herein as nFeIFNα$_{498b}$, which is represented by SEQ ID NO:116, with a complementary sequence represented by SEQ ID NO:118. A putative N-glycosylation site and an interferon alpha-beta-delta family signature motif are present at amino acid positions 102 and 145, respectively, of PFeIFNα$_{189b}$.

The differences between the proteins encoded by SEQ ID NO:107 and SEQ ID NO:110 are detailed as follows: The amino acid residues at position 56 in SEQ ID NO:108 (i.e., the protein encoded by SEQ ID NO:107) and at position 56 in SEQ ID NO:111 (i.e., the protein encoded by SEQ ID NO:110) are both arginines, although the corresponding codons in SEQ ID NO:107 and SEQ ID NO:110 are AGA and AGG, respectively. The amino acid residues at position 74 in SEQ ID NO:108 and at position 74 in SEQ ID NO:111 are both alanines, although the corresponding codons in SEQ ID NO:107 and SEQ ID NO:110 are GCC and GCT, respectively. The amino acid residue at position 86 in SEQ ID NO:108 is lysine, encoded by AAG in SEQ ID NO:107, whereas the amino acid residue at position 86 in SEQ ID NO:111 is glutamic acid, encoded by GAG in SEQ ID NO:110. The amino acid residue at position 125 in SEQ ID NO:108 is methionine, encoded by CTG in SEQ ID NO:107, whereas the amino acid residue at position 125 in SEQ ID NO:111 is valine, encoded by GTG in SEQ ID NO:110. The amino acid residue at position 141 in SEQ ID NO:108 is isovaline, encoded by ATC in SEQ ID NO:107, whereas the amino acid residue at position 141 in SEQ ID NO:111 is leucine, encoded by CTC in SEQ ID NO:110.

Feline IFN-alpha proteins of the present invention PFeIFNα$_{189a}$ and PfeIFNα$_{189b}$ are five amino acids shorter than the GENBANK® entry for feline IFN-alpha, accession # E02521. In addition, there are 3 non-conservative and 2 conservative changes at the amino acid level between this GEN-BANK® entry and SEQ ID NO:108 (PFeIFNα$_{189a}$) as well as 4 non-conservative and 3 conservative changes at the amino acid level between this GENBANK® entry and SEQ ID NO:111 (PfeIFNα$_{189b}$). The lengths of SEQ ID NO:108 and SEQ ID NO:111, when compared with those of IFN-alpha proteins of other species, are two amino acids longer than published canine interferon-alpha subtype 1, 2 and 3 sequences, two amino acids longer than published human interferon-alpha type 1, B, D, F, and J sequences, three amino acids longer than the published human interferon-alpha sequence type A sequence and two amino acids longer than published murine interferon-alpha type B, 8, 7, 11, and 19 sequences.

Example 8

This example describes the isolation and sequencing of feline granulocyte-macrophage colony-stimulating factor (GMCSF) nucleic acid molecules and proteins of the present invention. This example also describes expression of a feline GMCSF protein of the present invention.

Nucleic acid molecules encoding feline GMCSF were isolated as follows. A cDNA library was prepared from feline PBMCs stimulated with Con A for 12 hours, as previously described in Example 2. An aliquot of this library was used as a template to amplify feline GMCSF nucleic acid molecules by PCR using Amplitaq DNA Polymerase™ (PE Applied Biosystems Inc, Foster City, Calif.) and the following primers and conditions. The sequence of the forward primer was 5'CAGGGATCCA CCATGTGGCT GCAGAACCTG CTTTTCC 3' (SEQ ID NO:149), and that of the reverse primer was 5' TTACTTCTGG TCTGGTCCCC AGCAGT-CAAA GGGGTTGTTA AACAGAAAAT 3' (SEQ ID NO:150). The following PCR protocol was used: one initial denaturation step at 95° C. for 5 minutes; then 35 cycles of the following: 94° C. for 30 seconds, then 50° C. for 30 seconds, then 72° C. for 90 seconds; followed by a final extension at 72° C. for 7 minutes. PCR products were cloned into the CMV-Intron A vector and the clones were sequenced as described in Example 7.

A PCR product was isolated, referred to herein as nFeG-MCSF$_{444}$, the coding strand of which is represented herein as SEQ ID NO:119, and its complement is denoted SEQ ID NO:121. Translation of the open reading frame in SEQ ID NO:119 suggests that nucleic acid molecule nFeGMCSF$_{444}$ encodes a protein containing 144 amino acids, referred to herein as PFeGMCSF$_{144}$, with an amino acid sequence denoted SEQ ID NO:120, assuming an open reading frame in which the first codon spans from nucleotide 10 through nucleotide 12 of SEQ ID NO:119, and the stop codon spans from nucleotide 442 through nucleotide 444 of SEQ ID NO:121. The encoded protein has a predicted molecular weight of 16 kDa. The coding region encoding PFeGMCSF$_{144}$ is presented herein as nFeGMCSF$_{432}$ which has the nucleotide sequence SEQ ID NO:122 (the coding strand) and SEQ ID NO:123 (the complementary strand). A putative signal peptide cleavage site is between amino acid positions 17 and 18, based on homology with human, mouse and ovine GMCSF proteins. The nucleic acid molecule encoding the proposed mature protein is denoted as nFeGMCSF$_{381}$ and has a nucleotide sequence represented herein as SEQ ID NO:124 and a complementary sequence represented herein as SEQ ID NO:126. The amino acid sequence of the putative mature protein, referred to herein as PFeGMCSF$_{127}$, has an amino acid sequence represented herein as SEQ ID NO:125. The number of amino acids in the feline GMCSF protein is the same compared to human, porcine, ovine and canine GMCSF proteins. The feline GMCSF protein is one amino acid longer than bovine GMCSF and three amino acid longer than murine GMCSF.

The deduced amino acid sequence of the full-length feline GMCSF protein of the present invention has four non-conservative changes and one conservative change compared to a GENBANK® entry for feline GMCSF (accession # AF053007). Amino acids asparagine, methionine, threonine, and lysine at positions 10, 36, 56 and 126 of the GENBANK® entry have been changed to glycine, isoluecine, alanine and asparagine, respectively, in PfeGMCSF$_{144}$. PFeGMCSF$_{144}$, containing the above-noted amino acid substitutions, appears to have GMCSF activity, as demonstrated by an experiment in which supernatant collected from Chinese Hamster Ovary (CHO) cells that were transiently transfected with a recombinant molecule encoding a feline GMCSF protein of the present invention was able to induce proliferation of TF-1 cells.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein comprising an amino acid sequence at least 95% identical to SEQ ID NO:125, wherein the protein comprises at least one amino acid selected from the group consisting of:
   (a) an isoleucine at the position corresponding to position 19 of SEQ ID NO:125;
   (b) an alanine at the position corresponding to position 39 of SEQ ID NO:125; and
   (c) an asparagine at the position corresponding to position 109 of SEQ ID NO:125;
   wherein the isolated protein is able to stimulate the proliferation of granulocytes or macrophages.

2. The isolated protein of claim 1, wherein the protein comprises an isoleucine at the position corresponding to position 19 of SEQ ID NO:125, an alanine at the position corresponding to position 39 of SEQ ID NO:125, and an asparagine at the position corresponding to position 109 of SEQ ID NO:125.

3. The isolated protein of claim 1, wherein the amino acid sequence is at least 95% identical to SEQ ID NO:120, wherein the protein comprises at least one amino acid selected from the group consisting of:
   (a) a glycine at the position corresponding to position 10 of SEQ ID NO:120;
   (b) an isoleucine at the position corresponding to position 36 of SEQ ID NO:120;
   (c) an alanine at the position corresponding to position 56 of SEQ ID NO:120; and
   (d) an asparagine at the position corresponding to position 126 of SEQ ID NO:120.

4. The isolated protein of claim 3, wherein the protein comprises a glycine at the position corresponding to position 10 of SEQ ID NO:120, an isoleucine at the position corresponding to position 36 of SEQ ID NO:120, an alanine at the position corresponding to position 56 of SEQ ID NO:120, and an asparagine at the position corresponding to position 126 of SEQ ID NO:120.

5. The isolated protein of claim 1, wherein the amino acid sequence is identical to SEQ ID NO:120 or SEQ ID NO:125.

6. The isolated protein of claim 1, wherein the protein is a recombinant protein.

7. The isolated protein of claim 1, wherein said proteinic a fusion protein.

8. An isolated protein encoded by a recombinant nucleic acid molecule comprising a nucleic acid sequence at least 95% identical to SEQ ID NO:124, wherein the nucleic acid sequence comprises at least one codon selected from the group consisting of:
   (a) a codon encoding an isoleucine at the position corresponding to nucleotides 55-57 of SEQ ID NO:124;
   (b) a codon encoding an alanine at the position corresponding to nucleotides 115-117 of SEQ ID NO:124; and
   (c) a codon encoding an asparagine at the position corresponding to nucleotides 325-327 of SEQ ID NO:124;
   wherein the isolated protein is able to stimulate the proliferation of granulocytes or macrophages.

9. The isolated protein of claim 8, wherein the nucleic acid sequence comprises a codon encoding an isoleucine at the position corresponding to nucleotides 55-57 of SEQ ID NO:124, a codon encoding an alanine at the position corresponding to nucleotides 115-117 of SEQ ID NO:124, and a codon encoding an asparagine at the position corresponding to nucleotides 325-327 of SEQ ID NO:124.

10. The isolated protein of claim 8, wherein nucleic acid sequence comprises at least one codon selected from the group consisting of:
    (a) a codon encoding a glycine at the position corresponding to nucleotides 37-39 of SEQ ID NO:119;
    (b) a codon encoding an isoleucine at the position corresponding to nucleotides 115-117 of SEQ ID NO:119;
    (c) a codon encoding an alanine at the position corresponding to nucleotides 175-177 of SEQ ID NO:119; and
    (d) a codon encoding an asparagine at the position corresponding to nucleotides 385-387 of SEQ ID NO:119.

11. The isolated protein of claim 8, wherein nucleic acid sequence comprises a codon encoding a glycine at the position corresponding to nucleotides 37-39 of SEQ ID NO:119, a codon encoding an isoleucine at the position corresponding to nucleotides 115-117 of SEQ ID NO:119, a codon encoding an alanine at the position corresponding to nucleotides 175-177 of SEQ ID NO:119, and a codon encoding an asparagine at the position corresponding to nucleotides 385-387 of SEQ ID NO:119.

12. The isolated protein of claim 8, wherein nucleic acid sequence is identical in sequence to SEQ ID NO:119 or SEQ ID NO:124.

13. The isolated protein of claim 8, wherein the protein is a fusion protein.

14. A method to produce a protein, the method comprising:
    (a) obtaining a recombinant cell comprising a recombinant nucleic acid molecule that comprises a nucleic acid sequence at least 95% identical to SEQ ID NO:124, wherein nucleic acid sequence comprises at least one codon selected from the group consisting of:
       (i) a codon encoding an isoleucine at the position corresponding to nucleotides 55-57 of SEQ ID NO:124;
       (ii) a codon encoding an alanine at the position corresponding to nucleotides 115-117 of SEQ ID NO:124; and
       (iii) a codon encoding an asparagine at the position corresponding to nucleotides 325-327 of SEQ ID NO:124; and
    (b) culturing the recombinant cell under conditions sufficient for production of the protein encoded by the nucleic acid sequence.

15. The method of claim 14, wherein the protein is able to stimulate the proliferation of granulocytes or macrophages.

16. The method of claim 14, wherein the nucleic acid sequence comprises at least one codon encoding an isoleucine at the position corresponding to nucleotides 55-57 of SEQ ID NO:124, a codon encoding an alanine at the position corresponding to nucleotides 115-117 of SEQ ID NO:124, and a codon encoding an asparagine at the position corresponding to nucleotides 325-327 of SEQ ID NO:124.

17. The method of claim 14, wherein nucleic acid sequence comprises at least one codon selected from the group consisting of:
    (a) a codon encoding a glycine at the position corresponding to nucleotides 37-39 of SEQ ID NO:119;
    (b) a codon encoding an isoleucine at the position corresponding to nucleotides 115-117 of SEQ ID NO:119;
    (c) a codon encoding an alanine at the position corresponding to nucleotides 175-177 of SEQ ID NO:124; and (d) a codon encoding an asparagine at the position corresponding to nucleotides 385-387 of SEQ ID NO:124.

18. method of claim 14, wherein nucleic acid sequence is identical in sequence to SEQ ID NO:119 or SEQ ID NO:124.

* * * * *

UNITED STATES PATENT AND TRADEMARK OFFICE
CERTIFICATE OF CORRECTION

| | | |
|---|---|---|
| PATENT NO. | : 8,263,559 B2 | Page 1 of 1 |
| APPLICATION NO. | : 12/819964 | |
| DATED | : September 11, 2012 | |
| INVENTOR(S) | : Ramani S. Wonderling | |

It is certified that error appears in the above-identified patent and that said Letters Patent is hereby corrected as shown below:

In column 211, claim 1, lines 13-14, delete "is able to stimulate the proliferation of granulocytes or macrophages" and insert -- has GM-CSF activity --.

In column 211, claim 7, line 44, delete "ic" and insert -- is --.

In column 211, claim 8, lines 57-58, delete "is able to stimulate the proliferation of granulocytes or macrophages" and insert -- has GM-CSF activity --.

In column 212, claim 14, line 26, delete "A" and insert -- An in vitro --.

In column 212, claim 15, lines 43-44, delete "is able to stimulate the proliferation of granulocytes or macrophages" and insert -- has GM-CSF activity --.

In column 212, claim 17, line 60, after "and" begin "(d)" on a new line.

In column 212, claim 18, line 63, insert -- The -- before "method of claim".

Signed and Sealed this
Eighth Day of January, 2013

David J. Kappos
*Director of the United States Patent and Trademark Office*

SEQUENCE LISTING

```
<160> NUMBER OF SEQ ID NOS: 154

<210> SEQ ID NO 1
<211> LENGTH: 549
<212> TYPE: DNA
<213> ORGANISM: Canis familiaris
<220> FEATURE:
<221> NAME/KEY: CDS
<222> LOCATION: (43)..(438)

<400> SEQUENCE: 1
ggcacgaggt ctgctattgt cactgcaaat agagatctat ta atg ggt ctc acc      54
                                                 Met Gly Leu Thr
                                                   1
```

```
tcc caa ctg att cca act ctg gtc tgc tta cta gca ctc acc agc acc      102
Ser Gln Leu Ile Pro Thr Leu Val Cys Leu Leu Ala Leu Thr Ser Thr
  5              10                  15                  20 ttt gtc cac gga cat aac ttc aat att act att aaa gag atc atc aaa      150
Phe Val His Gly His Asn Phe Asn Ile Thr Ile Lys Glu Ile Ile Lys
                 25                  30                  35 atg ttg aac atc ctc aca gcg aga aac gac tcg tgc atg gag ctg act      198
Met Leu Asn Ile Leu Thr Ala Arg Asn Asp Ser Cys Met Glu Leu Thr
             40                  45                  50 gtc aag gac gtc ttc act gct cca aag aac aca agc gat aag gaa atc      246
Val Lys Asp Val Phe Thr Ala Pro Lys Asn Thr Ser Asp Lys Glu Ile
         55                  60                  65 ttc tgc aga gct gct act gta ctg cgg cag atc tat aca cac aac tgc      294
Phe Cys Arg Ala Ala Thr Val Leu Arg Gln Ile Tyr Thr His Asn Cys
 70                  75                  80 tcc aac aga tat ctc aga gga ctc tac agg aac ctc agc agc atg gca      342
Ser Asn Arg Tyr Leu Arg Gly Leu Tyr Arg Asn Leu Ser Ser Met Ala
 85                  90                  95                 100 aac aag acc tgt tct atg aat gaa atc aag aag agt aca ctg aaa gac      390
Asn Lys Thr Cys Ser Met Asn Glu Ile Lys Lys Ser Thr Leu Lys Asp
                105                 110                 115 ttc ttg gaa agg cta aaa gtg atc atg cag aag aaa tac tac agg cat      438
Phe Leu Glu Arg Leu Lys Val Ile Met Gln Lys Lys Tyr Tyr Arg His
            120                 125                 130 tgaagctgaa tattttaatt tatgagtttt taaatagctt tattttaaaa atatttatat    498
atttataaca taataaaata aaatatatat agaaaaaaaa aaaaaaaaa a              549

<210> SEQ ID NO 2
<211> LENGTH: 132
<212> TYPE: PRT
<213> ORGANISM: Canis familiaris

<400> SEQUENCE: 2

Met Gly Leu Thr Ser Gln Leu Ile Pro Thr Leu Val Cys Leu Leu Ala
  1               5                  10                  15

Leu Thr Ser Thr Phe Val His Gly His Asn Phe Asn Ile Thr Ile Lys
                 20                  25                  30

Glu Ile Ile Lys Met Leu Asn Ile Leu Thr Ala Arg Asn Asp Ser Cys
             35                  40                  45

Met Glu Leu Thr Val Lys Asp Val Phe Thr Ala Pro Lys Asn Thr Ser
 50                  55                  60

Asp Lys Glu Ile Phe Cys Arg Ala Ala Thr Val Leu Arg Gln Ile Tyr
 65                  70                  75                  80

Thr His Asn Cys Ser Asn Arg Tyr Leu Arg Gly Leu Tyr Arg Asn Leu
                 85                  90                  95

Ser Ser Met Ala Asn Lys Thr Cys Ser Met Asn Glu Ile Lys Lys Ser
            100                 105                 110

Thr Leu Lys Asp Phe Leu Glu Arg Leu Lys Val Ile Met Gln Lys Lys
        115                 120                 125

Tyr Tyr Arg His
        130

<210> SEQ ID NO 3
<211> LENGTH: 549
<212> TYPE: DNA
<213> ORGANISM: Canis familiaris

<400> SEQUENCE: 3
tttttttttt ttttttttc tatatatatt ttattttatt atgttataaa tatataaata     60
```

```
tttttaaaat aaagctattt aaaaactcat aaattaaaat attcagcttc aatgcctgta    120
gtatttcttc tgcatgatca cttttagcct ttccaagaag tctttcagtg tactcttctt    180
gatttcattc atagaacagg tcttgtttgc catgctgctg aggttcctgt agagtcctct    240
gagatatctg ttggagcagt tgtgtgtata gatctgccgc agtacagtag cagctctgca    300
gaagatttcc ttatcgcttg tgttctttgg agcagtgaag acgtccttga cagtcagctc    360
catgcacgag tcgtttctcg ctgtgaggat gttcaacatt tgatgatct ctttaatagt    420 aatattgaag ttatgtccgt ggacaaaggt gctggtgagt gctagtaagc agaccagagt    480
tggaatcagt tgggaggtga gacccattaa tagatctcta tttgcagtga caatagcaga    540
cctcgtgcc                                                           549

<210> SEQ ID NO 4
<211> LENGTH: 396
<212> TYPE: DNA
<213> ORGANISM: Canis familiaris

<400> SEQUENCE: 4
atgggtctca cctcccaact gattccaact ctggtctgct tactagcact caccagcacc     60
tttgtccacg gacataactt caatattact attaaagaga tcatcaaaat gttgaacatc    120
ctcacagcga gaaacgactc gtgcatggag ctgactgtca aggacgtctt cactgctcca    180
aagaacacaa gcgataagga atcttctgc agagctgcta ctgtactgcg gcagatctat    240
acacacaact gctccaacag atatctcaga ggactctaca ggaaccctcag cagcatggca    300 aacaagacct gttctatgaa tgaaatcaag aagagtacac tgaaagactt cttggaaagg    360
ctaaaagtga tcatgcagaa gaaatactac aggcat                              396

<210> SEQ ID NO 5
<211> LENGTH: 396
<212> TYPE: DNA
<213> ORGANISM: Canis familiaris

<400> SEQUENCE: 5
atgcctgtag tatttcttct gcatgatcac ttttagcctt ccaagaagt ctttcagtgt      60 actcttcttg atttcattca tagaacaggt cttgtttgcc atgctgctga ggttcctgta    120
gagtcctctg agatatctgt tggagcagtt gtgtgtatag atctgccgca gtacagtagc    180
agctctgcag aagatttcct tatcgcttgt gttctttgga gcagtgaaga cgtccttgac    240
agtcagctcc atgcacgagt cgtttctcgc tgtgaggatg ttcaacattt tgatgatctc    300
tttaatagta atattgaagt tatgtccgtg gacaaaggtg ctggtgagtg ctagtaagca    360
gaccagagtt ggaatcagtt gggaggtgag acccat                              396

<210> SEQ ID NO 6
<211> LENGTH: 1013
<212> TYPE: DNA
<213> ORGANISM: Canis familiaris
<220> FEATURE:
<221> NAME/KEY: CDS
<222> LOCATION: (35)..(916)

<400> SEQUENCE: 6
atctgaccat aggcatgagg ggcctccggc cgag atg ata gtg ctg gcg cca gcc     55
                                    Met Ile Val Leu Ala Pro Ala
                                     1               5 tgg agc cca act gcc tcc ctg ttg ctg ctg ctg ctc agc ccc ggc          103
Trp Ser Pro Thr Ala Ser Leu Leu Leu Leu Leu Leu Ser Pro Gly
```

```
                    10                  15                  20
ctc cgc ggg acc ccc gac tgc tcc ttc agc cac agc ccc atc tcc tcc            151
Leu Arg Gly Thr Pro Asp Cys Ser Phe Ser His Ser Pro Ile Ser Ser
 25                  30                  35 acc ttc gcg gtc acc atc cgc aag ctg tct gat tac ctg ctt cag gac            199
Thr Phe Ala Val Thr Ile Arg Lys Leu Ser Asp Tyr Leu Leu Gln Asp
 40                  45                  50                  55 tat cca gtc act gtc gcc tcc aac ctg cag gac gac gag ctc tgc ggg            247
Tyr Pro Val Thr Val Ala Ser Asn Leu Gln Asp Asp Glu Leu Cys Gly
                 60                  65                  70 gcg ttc tgg cgc ctg gtc ctg gcc cag cgc tgg atg gtg cgg ctc cag            295
Ala Phe Trp Arg Leu Val Leu Ala Gln Arg Trp Met Val Arg Leu Gln
             75                  80                  85 gct gtg gct gga tcc caa atg caa atc ctg ctg gag gct gtc aac acg            343
Ala Val Ala Gly Ser Gln Met Gln Ile Leu Leu Glu Ala Val Asn Thr
         90                  95                 100 gag ata cac ttt gtc acc ttc tgt gcc ttc cag ccc ctc ccc agc tgt            391
Glu Ile His Phe Val Thr Phe Cys Ala Phe Gln Pro Leu Pro Ser Cys
    105                 110                 115 ctt cgc ttc gtc cag acc aac atc tcc cac ctc ctg cag gac acc tcc            439
Leu Arg Phe Val Gln Thr Asn Ile Ser His Leu Leu Gln Asp Thr Ser
120                 125                 130                 135 cag cag ctg gcc gcc ctg aag ccc tgg atc acc cgc agg aat ttc tcc            487
Gln Gln Leu Ala Ala Leu Lys Pro Trp Ile Thr Arg Arg Asn Phe Ser
                140                 145                 150 ggg tgc ctg gag ctg cag tgt cag ccc gac tcc tct aca ttg gtg ccc            535
Gly Cys Leu Glu Leu Gln Cys Gln Pro Asp Ser Ser Thr Leu Val Pro
            155                 160                 165 cca agg agc ccc ggg gcc ctg gag gcc act gcc ttg cca gcc cct cag            583
Pro Arg Ser Pro Gly Ala Leu Glu Ala Thr Ala Leu Pro Ala Pro Gln
        170                 175                 180 gca cct cgg ctg ctc ctc ctg ctg ctg ccc gtg gct ctc ctg ctg            631
Ala Pro Arg Leu Leu Leu Leu Leu Leu Leu Pro Val Ala Leu Leu Leu
    185                 190                 195 atg tcc act gcc tgg tgc ctg cat tgg cga agg agg cgg cgg agg            679
Met Ser Thr Ala Trp Cys Leu His Trp Arg Arg Arg Arg Arg Arg
200                 205                 210                 215 tca ccc tac cct ggg gag cag agg aca ctg agg ccc agc gag cgg agc            727
Ser Pro Tyr Pro Gly Glu Gln Arg Thr Leu Arg Pro Ser Glu Arg Ser
                220                 225                 230 cat ctg ccc gag gac aca gag ctg gga cct gga ggg agt cag cta gag            775
His Leu Pro Glu Asp Thr Glu Leu Gly Pro Gly Gly Ser Gln Leu Glu
            235                 240                 245 act ggt ccc ttc ctc gac cac gca gcc ccg ctc gct ccc tcc cca gga            823
Thr Gly Pro Phe Leu Asp His Ala Ala Pro Leu Ala Pro Ser Pro Gly
        250                 255                 260 tca agg caa cgc ccg ccc cca acg ccc cca aag cca gcc cca gcc cca            871
Ser Arg Gln Arg Pro Pro Pro Thr Pro Pro Lys Pro Ala Pro Ala Pro
265                 270                 275 cct ctc ccc ctc tgt aca aag tcc ttg ccc cca aga aat tgt ata            916
Pro Leu Pro Leu Cys Thr Lys Ser Leu Pro Pro Arg Asn Cys Ile
280                 285                 290 taaatcatcc ttttctacca aaaaaaaaaa aaaaaaaaaa aaaaaaaaaa aaaaaaaaaa        976
aaaaaaaaaa aaaaaaaaaa aaaaaaaaaa aaaaaaa                                 1013

<210> SEQ ID NO 7
<211> LENGTH: 294
<212> TYPE: PRT
<213> ORGANISM: Canis familiaris
```

<400> SEQUENCE: 7

```
Met Ile Val Leu Ala Pro Ala Trp Ser Pro Thr Ala Ser Leu Leu Leu
 1               5                  10                  15
Leu Leu Leu Leu Ser Pro Gly Leu Arg Gly Thr Pro Asp Cys Ser Phe
            20                  25                  30
Ser His Ser Pro Ile Ser Ser Thr Phe Ala Val Thr Ile Arg Lys Leu
        35                  40                  45
Ser Asp Tyr Leu Leu Gln Asp Tyr Pro Val Thr Val Ala Ser Asn Leu
 50                  55                  60
Gln Asp Asp Glu Leu Cys Gly Ala Phe Trp Arg Leu Val Leu Ala Gln
 65                  70                  75                  80
Arg Trp Met Val Arg Leu Gln Ala Val Ala Gly Ser Gln Met Gln Ile
                85                  90                  95
Leu Leu Glu Ala Val Asn Thr Glu Ile His Phe Val Thr Phe Cys Ala
            100                 105                 110
Phe Gln Pro Leu Pro Ser Cys Leu Arg Phe Val Gln Thr Asn Ile Ser
        115                 120                 125
His Leu Leu Gln Asp Thr Ser Gln Gln Leu Ala Ala Leu Lys Pro Trp
130                 135                 140
Ile Thr Arg Arg Asn Phe Ser Gly Cys Leu Glu Leu Gln Cys Gln Pro
145                 150                 155                 160
Asp Ser Ser Thr Leu Val Pro Pro Arg Ser Pro Gly Ala Leu Glu Ala
                165                 170                 175
Thr Ala Leu Pro Ala Pro Gln Ala Pro Arg Leu Leu Leu Leu Leu Leu
            180                 185                 190
Leu Pro Val Ala Leu Leu Met Ser Thr Ala Trp Cys Leu His Trp
        195                 200                 205
Arg Arg Arg Arg Arg Arg Ser Pro Tyr Pro Gly Glu Gln Arg Thr
210                 215                 220
Leu Arg Pro Ser Glu Arg Ser His Leu Pro Glu Asp Thr Glu Leu Gly
225                 230                 235                 240
Pro Gly Gly Ser Gln Leu Glu Thr Gly Pro Phe Leu Asp His Ala Ala
                245                 250                 255
Pro Leu Ala Pro Ser Pro Gly Ser Arg Gln Arg Pro Pro Thr Pro
            260                 265                 270
Pro Lys Pro Ala Pro Ala Pro Pro Leu Pro Leu Cys Thr Lys Ser Leu
        275                 280                 285
Pro Pro Arg Asn Cys Ile
        290
```

<210> SEQ ID NO 8
<211> LENGTH: 1013
<212> TYPE: DNA
<213> ORGANISM: Canis familiaris

<400> SEQUENCE: 8

```
tttttttttt tttttttttt tttttttttt tttttttttt tttttttttt tttttttttt    60
tttttttttt ttttttttgg tagaaaagga tgatttatat acaatttctt ggggggcaagg   120
actttgtaca gagggggaga ggtggggctg gggctggctt tggggggcgtt ggggggcgggc   180
gttgccttga tcctggggag ggagcgagcg gggctgcgtg gtcgaggaag gaccagtct    240
ctagctgact ccctccaggt cccagctctg tgtcctcggg cagatggctc cgctcgctgg   300
gcctcagtgt cctctgctcc ccagggtagg gtgacctccg ccgccgcctc cttcgccaat   360
gcaggcacca ggcagtggac atcagcagga gagccacggg cagcagcagc aggaggagca   420
```

```
gccgaggtgc ctgaggggct ggcaaggcag tggcctccag ggccccgggg ctccttgggg      480
gcaccaatgt agaggagtcg ggctgacact gcagctccag gcacccggag aaattcctgc      540
gggtgatcca gggcttcagg gcggccagct gctgggaggt gtcctgcagg aggtgggaga      600
tgttggtctg gacgaagcga agacagctgg ggaggggctg gaaggcacag aaggtgacaa      660
agtgtatctc cgtgttgaca gcctccagca ggatttgcat ttgggatcca gccacagcct      720
ggagccgcac catccagcgc tgggccagga ccaggcgcca gaacgccccg cagagctcgt      780
cgtcctgcag gttggaggcg acagtgactg gatagtcctg aagcaggtaa tcagacagct      840
tgcggatggt gaccgcgaag gtggaggaga tggggctgtg gctgaaggag cagtcggggg      900
tcccgcggag gccggggctg agcagcagca gcagcaacag ggaggcagtt gggctccagg      960
ctggcgccag cactatcatc tcggccggag gcccctcatg cctatggtca gat           1013

<210> SEQ ID NO 9
<211> LENGTH: 882
<212> TYPE: DNA
<213> ORGANISM: Canis familiaris

<400> SEQUENCE: 9
atgatagtgc tggcgccagc ctggagccca actgcctccc tgttgctgct gctgctgctc       60
agccccggcc tccgcgggac ccccgactgc tccttcagcc acagccccat ctcctccacc      120
ttcgcggtca ccatccgcaa gctgtctgat tacctgcttc aggactatcc agtcactgtc      180
gcctccaacc tgcaggacga cgagctctgc ggggcgttct ggcgcctggt cctggcccag      240
cgctggatgg tgcggctcca ggctgtggct ggatcccaaa tgcaaatcct gctggaggct      300
gtcaacacgg agatacactt tgtcaccttc tgtgccttcc agcccctccc cagctgtctt      360
cgcttcgtcc agaccaacat ctcccacctc ctgcaggaca cctcccagca gctggccgcc      420
ctgaagccct ggatcacccg caggaatttc tccgggtgcc tggagctgca gtgtcagccc      480
gactcctcta cattggtgcc cccaaggagc cccggggccc tggaggccac tgccttgcca      540
gcccctcagg cacctcggct gctcctcctg ctgctgctgc ccgtggctct cctgctgatg      600
tccactgcct ggtgcctgca ttggcgaagg aggcggcggc ggaggtcacc ctaccctggg      660
gagcagagga cactgaggcc cagcgagcgg agccatctgc ccgaggacac agagctggga      720
cctggaggga gtcagctaga gactggtccc ttcctcgacc acgcagcccc gctcgctccc      780
tccccaggat caaggcaacg cccgccccca acgcccccaa agccagcccc agccccacct      840
ctccccctct gtacaaagtc cttgccccca agaaattgta ta                        882

<210> SEQ ID NO 10
<211> LENGTH: 882
<212> TYPE: DNA
<213> ORGANISM: Canis familiaris

<400> SEQUENCE: 10
tatacaattt cttgggggca aggactttgt acagagggg agaggtgggg ctggggctgg         60
cttttggggc gttgggggcg gcgttgcct tgatcctggg gagggagcga gcggggctgc        120
gtggtcgagg aagggaccag tctctagctg actccctcca ggtcccagct ctgtgtcctc      180
gggcagatgc ctccgctcgc tgggcctcag tgtcctctgc tccccagggt agggtgacct      240
ccgccgccgc ctccttcgcc aatgcaggca ccaggcagtg gacatcagca ggagagccac      300
gggcagcagc agcaggagga gcagccgagg tgcctgaggg gctggcaagg cagtggcctc      360
cagggccccg gggctccttg ggggcaccaa tgtagaggag tcgggctgac actgcagctc      420
```

```
caggcacccg gagaaattcc tgcgggtgat ccagggcttc agggcggcca gctgctggga    480
ggtgtcctgc aggaggtggg agatgttggt ctggacgaag cgaagacagc tggggagggg    540
ctggaaggca cagaaggtga caaagtgtat ctccgtgttg acagcctcca gcaggatttg    600
catttgggat ccagccacag cctggagccg caccatccag cgctgggcca ggaccaggcg    660
ccagaacgcc ccgcagagct cgtcgtcctg caggttggag cgacagtga ctggatagtc     720 ctgaagcagg taatcagaca gcttgcggat ggtgaccgcg aaggtggagg agatggggct    780
gtggctgaag gagcagtcgg gggtcccgcg gaggccgggg ctgagcagca gcagcagcaa    840
cagggaggca gttgggctcc aggctggcgc cagcactatc at                       882
```

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11

```
ctattaatgg gtctcacctc ccaact                                          26
```

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12

```
tcaactcggt gcacagagtc ttgg                                            24
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13

```
ctggcgccag cctggagccc                                                 20
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14

```
gggagatgtt ggtctggacg                                                 20
```

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15

```
gaccaggcgc cagaacgc                                                    18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
cggtcaccat ccgcaagc                                                    18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
tggcaaggca gtggcctc                                                    18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
gccgagatga tagtgctggc                                                  20

<210> SEQ ID NO 19
<211> LENGTH: 324
<212> TYPE: DNA
<213> ORGANISM: Canis familiaris
<220> FEATURE:
<221> NAME/KEY: CDS
<222> LOCATION: (1)..(324)

<400> SEQUENCE: 19 cat aac ttc aat att act att aaa gag atc atc aaa atg ttg aac atc       48
His Asn Phe Asn Ile Thr Ile Lys Glu Ile Ile Lys Met Leu Asn Ile
1               5                   10                  15 ctc aca gcg aga aac gac tcg tgc atg gag ctg act gtc aag gac gtc       96
Leu Thr Ala Arg Asn Asp Ser Cys Met Glu Leu Thr Val Lys Asp Val
            20                  25                  30 ttc act gct cca aag aac aca agc gat aag gaa atc ttc tgc aga gct      144
Phe Thr Ala Pro Lys Asn Thr Ser Asp Lys Glu Ile Phe Cys Arg Ala
        35                  40                  45 gct act gta ctg cgg cag atc tat aca cac aac tgc tcc aac aga tat      192
Ala Thr Val Leu Arg Gln Ile Tyr Thr His Asn Cys Ser Asn Arg Tyr
    50                  55                  60 ctc aga gga ctc tac agg aac ctc agc agc atg gca aac aag acc tgt      240
Leu Arg Gly Leu Tyr Arg Asn Leu Ser Ser Met Ala Asn Lys Thr Cys
65                  70                  75                  80 tct atg aat gaa atc aag aag agt aca ctg aaa gac ttc ttg gaa agg      288
Ser Met Asn Glu Ile Lys Lys Ser Thr Leu Lys Asp Phe Leu Glu Arg
                85                  90                  95 cta aaa gtg atc atg cag aag aaa tac tac agg cat                      324
Leu Lys Val Ile Met Gln Lys Lys Tyr Tyr Arg His
            100                 105
```

<210> SEQ ID NO 20
<211> LENGTH: 108
<212> TYPE: PRT
<213> ORGANISM: Canis familiaris

<400> SEQUENCE: 20

His Asn Phe Asn Ile Thr Ile Lys Glu Ile Lys Met Leu Asn Ile
1               5                   10                  15

Leu Thr Ala Arg Asn Asp Ser Cys Met Glu Leu Thr Val Lys Asp Val
            20                  25                  30

Phe Thr Ala Pro Lys Asn Thr Ser Asp Lys Glu Ile Phe Cys Arg Ala
        35                  40                  45

Ala Thr Val Leu Arg Gln Ile Tyr Thr His Asn Cys Ser Asn Arg Tyr
    50                  55                  60

Leu Arg Gly Leu Tyr Arg Asn Leu Ser Ser Met Ala Asn Lys Thr Cys
65                  70                  75                  80

Ser Met Asn Glu Ile Lys Lys Ser Thr Leu Lys Asp Phe Leu Glu Arg
                85                  90                  95

Leu Lys Val Ile Met Gln Lys Lys Tyr Tyr Arg His
            100                 105

<210> SEQ ID NO 21
<211> LENGTH: 324
<212> TYPE: DNA
<213> ORGANISM: Canis familiaris

<400> SEQUENCE: 21
atgcctgtag tatttcttct gcatgatcac ttttagcctt tccaagaagt ctttcagtgt        60
actcttcttg atttcattca tagaacaggt cttgtttgcc atgctgctga ggttcctgta       120
gagtcctctg agatatctgt tggagcagtt gtgtgtatag atctgccgca gtacagtagc       180
agctctgcag aagatttcct tatcgcttgt gttctttgga gcagtgaaga cgtccttgac       240
agtcagctcc atgcacgagt cgtttctcgc tgtgaggatg ttcaacattt tgatgatctc       300
tttaatagta atattgaagt tatg                                             324

<210> SEQ ID NO 22
<211> LENGTH: 804
<212> TYPE: DNA
<213> ORGANISM: Canis familiaris
<220> FEATURE:
<221> NAME/KEY: CDS
<222> LOCATION: (1)..(804)

<400> SEQUENCE: 22 acc ccc gac tgc tcc ttc agc cac agc ccc atc tcc tcc acc ttc gcg        48
Thr Pro Asp Cys Ser Phe Ser His Ser Pro Ile Ser Ser Thr Phe Ala
1               5                   10                  15 gtc acc atc cgc aag ctg tct gat tac ctg ctt cag gac tat cca gtc        96
Val Thr Ile Arg Lys Leu Ser Asp Tyr Leu Leu Gln Asp Tyr Pro Val
            20                  25                  30 act gtc gcc tcc aac ctg cag gac gac gag ctc tgc ggg gcg ttc tgg       144
Thr Val Ala Ser Asn Leu Gln Asp Asp Glu Leu Cys Gly Ala Phe Trp
        35                  40                  45 cgc ctg gtc ctg gcc cag cgc tgg atg gtg cgg ctc cag gct gtg gct       192
Arg Leu Val Leu Ala Gln Arg Trp Met Val Arg Leu Gln Ala Val Ala
    50                  55                  60 gga tcc caa atg caa atc ctg ctg gag gct gtc aac acg gag ata cac       240
Gly Ser Gln Met Gln Ile Leu Leu Glu Ala Val Asn Thr Glu Ile His
65                  70                  75                  80

-continued

| | | |
|---|---|---|
| ttt gtc acc ttc tgt gcc ttc cag ccc ctc ccc agc tgt ctt cgc ttc<br>Phe Val Thr Phe Cys Ala Phe Gln Pro Leu Pro Ser Cys Leu Arg Phe<br>                      85                                  90                              95 | 288 |
| gtc cag acc aac atc tcc cac ctc ctg cag gac acc tcc cag cag ctg<br>Val Gln Thr Asn Ile Ser His Leu Leu Gln Asp Thr Ser Gln Gln Leu<br>100                          105                            110 | 336 |
| gcc gcc ctg aag ccc tgg atc acc cgc agg aat ttc tcc ggg tgc ctg<br>Ala Ala Leu Lys Pro Trp Ile Thr Arg Arg Asn Phe Ser Gly Cys Leu<br>          115                        120                          125 | 384 |
| gag ctg cag tgt cag ccc gac tcc tct aca ttg gtg ccc cca agg agc<br>Glu Leu Gln Cys Gln Pro Asp Ser Ser Thr Leu Val Pro Pro Arg Ser<br>130                          135                            140 | 432 |
| ccc ggg gcc ctg gag gcc act gcc ttg cca gcc cct cag gca cct cgg<br>Pro Gly Ala Leu Glu Ala Thr Ala Leu Pro Ala Pro Gln Ala Pro Arg<br>145                        150                          155                        160 | 480 |
| ctg ctc ctc ctg ctg ctg ctg ccc gtg gct ctc ctg atg tcc act<br>Leu Leu Leu Leu Leu Leu Leu Pro Val Ala Leu Leu Met Ser Thr<br>                    165                            170                          175 | 528 |
| gcc tgg tgc ctg cat tgg cga agg agg cgg cgg agg tca ccc tac<br>Ala Trp Cys Leu His Trp Arg Arg Arg Arg Arg Arg Ser Pro Tyr<br>                180                            185                          190 | 576 |
| cct ggg gag cag agg aca ctg agg ccc agc gag cgg agc cat ctg ccc<br>Pro Gly Glu Gln Arg Thr Leu Arg Pro Ser Glu Arg Ser His Leu Pro<br>          195                        200                          205 | 624 |
| gag gac aca gag ctg gga cct gga ggg agt cag cta gag act ggt ccc<br>Glu Asp Thr Glu Leu Gly Pro Gly Gly Ser Gln Leu Glu Thr Gly Pro<br>210                          215                            220 | 672 |
| ttc ctc gac cac gca gcc ccg ctc gct ccc tcc cca gga tca agg caa<br>Phe Leu Asp His Ala Ala Pro Leu Ala Pro Ser Pro Gly Ser Arg Gln<br>225                        230                          235                        240 | 720 |
| cgc ccg ccc cca acg ccc cca aag cca gcc cca gcc cca cct ctc ccc<br>Arg Pro Pro Pro Thr Pro Pro Lys Pro Ala Pro Ala Pro Pro Leu Pro<br>                    245                            250                          255 | 768 |
| ctc tgt aca aag tcc ttg ccc cca aga aat tgt ata<br>Leu Cys Thr Lys Ser Leu Pro Pro Arg Asn Cys Ile<br>260                          265 | 804 |

<210> SEQ ID NO 23
<211> LENGTH: 268
<212> TYPE: PRT
<213> ORGANISM: Canis familiaris

<400> SEQUENCE: 23

Thr Pro Asp Cys Ser Phe Ser His Ser Pro Ile Ser Ser Thr Phe Ala
1               5                   10                  15

Val Thr Ile Arg Lys Leu Ser Asp Tyr Leu Leu Gln Asp Tyr Pro Val
            20                  25                  30

Thr Val Ala Ser Asn Leu Gln Asp Asp Glu Leu Cys Gly Ala Phe Trp
        35                  40                  45

Arg Leu Val Leu Ala Gln Arg Trp Met Val Arg Leu Gln Ala Val Ala
    50                  55                  60

Gly Ser Gln Met Gln Ile Leu Leu Glu Ala Val Asn Thr Glu Ile His
65                  70                  75                  80

Phe Val Thr Phe Cys Ala Phe Gln Pro Leu Pro Ser Cys Leu Arg Phe
                85                  90                  95

Val Gln Thr Asn Ile Ser His Leu Leu Gln Asp Thr Ser Gln Gln Leu
            100                 105                 110

Ala Ala Leu Lys Pro Trp Ile Thr Arg Arg Asn Phe Ser Gly Cys Leu
        115                 120                 125

```
Glu Leu Gln Cys Gln Pro Asp Ser Ser Thr Leu Val Pro Pro Arg Ser
        130                 135                 140

Pro Gly Ala Leu Glu Ala Thr Ala Leu Pro Ala Pro Gln Ala Pro Arg
145                 150                 155                 160

Leu Leu Leu Leu Leu Leu Leu Pro Val Ala Leu Leu Met Ser Thr
                165                 170                 175

Ala Trp Cys Leu His Trp Arg Arg Arg Arg Arg Arg Ser Pro Tyr
                180                 185                 190

Pro Gly Glu Gln Arg Thr Leu Arg Pro Ser Glu Arg Ser His Leu Pro
                195                 200                 205

Glu Asp Thr Glu Leu Gly Pro Gly Gly Ser Gln Leu Glu Thr Gly Pro
        210                 215                 220

Phe Leu Asp His Ala Ala Pro Leu Ala Pro Ser Pro Gly Ser Arg Gln
225                 230                 235                 240

Arg Pro Pro Pro Thr Pro Pro Lys Pro Ala Pro Ala Pro Pro Leu Pro
                245                 250                 255

Leu Cys Thr Lys Ser Leu Pro Pro Arg Asn Cys Ile
                260                 265
```

```
<210> SEQ ID NO 24
<211> LENGTH: 804
<212> TYPE: DNA
<213> ORGANISM: Canis familiaris

<400> SEQUENCE: 24
tatacaattt cttgggggca aggactttgt acagaggggg agaggtgggg ctggggctgg      60
ctttgggggc gttggggggcg ggcgttgcct tgatcctggg gagggagcga gcggggctgc    120
gtggtcgagg aagggaccag tctctagctg actccctcca ggtcccagct ctgtgtcctc    180
gggcagatgg ctccgctcgc tgggcctcag tgtcctctgc tccccagggt agggtgacct    240
ccgccgccgc ctccttcgcc aatgcaggca ccaggcagtg acatcagca ggagagccac     300 gggcagcagc agcaggagga gcagccgagg tgcctgaggg gctggcaagg cagtggcctc    360
cagggccccg gggctccttg ggggcaccaa tgtagaggag tcgggctgac actgcagctc    420
caggcacccg gagaaattcc tgcgggtgat ccagggcttc agggcggcca gctgctggga    480
ggtgtcctgc aggaggtggg agatgttggt ctggacgaag cgaagacagc tggggagggg    540
ctggaaggca cagaaggtga caaagtgtat ctccgtgttg acagcctcca gcaggatttg    600
catttgggat ccagccacag cctggagccg caccatccag cgctgggcca ggaccaggcg    660
ccagaacgcc ccgcagagct cgtcgtcctg caggttggag gcgacagtga ctggatagtc    720
ctgaagcagg taatcagaca gcttgcggat ggtgaccgcg aaggtggagg agatggggct    780
gtggctgaag gagcagtcgg gggt                                          804

<210> SEQ ID NO 25
<211> LENGTH: 985
<212> TYPE: DNA
<213> ORGANISM: Canis familiaris
<220> FEATURE:
<221> NAME/KEY: CDS
<222> LOCATION: (74)..(901)

<400> SEQUENCE: 25
ccggcctggc cccttccacg cccagctggg gcaagcctga tctgaccata ggcatgaggg      60
gcctccggcc gag atg ata gtg ctg gcg cca gcc tgg agc cca act gcc       109
                Met Ile Val Leu Ala Pro Ala Trp Ser Pro Thr Ala
                 1               5                  10
```

| | | |
|---|---|---|
| tcc ctg ttg ctg ctg ctg ctc agc ccc ggc ctc cgc ggg acc ccc<br>Ser Leu Leu Leu Leu Leu Leu Ser Pro Gly Leu Arg Gly Thr Pro<br>        15                    20                  25 | | 157 |
| gac tgc tcc ttc agc cac agc ccc atc tcc tcc acc ttc gcg gtc acc<br>Asp Cys Ser Phe Ser His Ser Pro Ile Ser Ser Thr Phe Ala Val Thr<br>    30                      35                    40 | | 205 |
| atc cgc aag ctg tct gat tac ctg ctt cag gac tat cca gtc act gtc<br>Ile Arg Lys Leu Ser Asp Tyr Leu Leu Gln Asp Tyr Pro Val Thr Val<br>45                    50                    55                    60 | | 253 |
| gcc tcc aac ctg cag gac gac gag ctc tgc ggg gcg ttc tgg cgc ctg<br>Ala Ser Asn Leu Gln Asp Asp Glu Leu Cys Gly Ala Phe Trp Arg Leu<br>                65                    70                    75 | | 301 |
| gtc ctg gcc cag cgc tgg atg gtg cgg ctc cag gct gtg gct gga tcc<br>Val Leu Ala Gln Arg Trp Met Val Arg Leu Gln Ala Val Ala Gly Ser<br>        80                    85                    90 | | 349 |
| caa atg caa atc ctg ctg gag gct gtc aac acg gag ata cac ttt gtc<br>Gln Met Gln Ile Leu Leu Glu Ala Val Asn Thr Glu Ile His Phe Val<br>            95                    100                 105 | | 397 |
| acc ttc tgt gcc ttc cag gac acc tcc cag cag ctg gcc gcc ctg aag<br>Thr Phe Cys Ala Phe Gln Asp Thr Ser Gln Gln Leu Ala Ala Leu Lys<br>      110                    115                 120 | | 445 |
| ccc tgg atc acc cgc agg aat ttc tcc ggg tgc ctg gag ctg cag tgt<br>Pro Trp Ile Thr Arg Arg Asn Phe Ser Gly Cys Leu Glu Leu Gln Cys<br>125                    130                    135                 140 | | 493 |
| cag ccc gac tcc tct aca ttg gtg ccc cca agg agc ccc ggg gcc ctg<br>Gln Pro Asp Ser Ser Thr Leu Val Pro Pro Arg Ser Pro Gly Ala Leu<br>                    145                    150                 155 | | 541 |
| gag gcc act gcc ttg cca gcc cct cag gca cct cgg ctg ctc ctc ctg<br>Glu Ala Thr Ala Leu Pro Ala Pro Gln Ala Pro Arg Leu Leu Leu Leu<br>        160                    165                 170 | | 589 |
| ctg ctg ctg ccc gtg gct ctc ctg atg tcc act gcc tgg tgc ctg<br>Leu Leu Leu Pro Val Ala Leu Leu Met Ser Thr Ala Trp Cys Leu<br>              175                    180                 185 | | 637 |
| cat tgg cga agg agg cgg cgg cgg agg tca ccc tac cct ggg gag cag<br>His Trp Arg Arg Arg Arg Arg Arg Ser Pro Tyr Pro Gly Glu Gln<br>      190                    195                 200 | | 685 |
| agg aca ctg agg ccc agc gag cgg agc cat ctg ccc gag gac aca gag<br>Arg Thr Leu Arg Pro Ser Glu Arg Ser His Leu Pro Glu Asp Thr Glu<br>205                    210                    215                 220 | | 733 |
| ctg gga cct ggg ggg agt cag cta gag act ggt ccc ttc ctc gac cac<br>Leu Gly Pro Gly Gly Ser Gln Leu Glu Thr Gly Pro Phe Leu Asp His<br>                    225                    230                 235 | | 781 |
| gca gcc ccg ctc gct ccc tcc cca gga tca agg caa cgc ccg ccc cca<br>Ala Ala Pro Leu Ala Pro Ser Pro Gly Ser Arg Gln Arg Pro Pro Pro<br>        240                    245                 250 | | 829 |
| acg ccc cca aag cca gcc cca gcc cca cct ctc ccc ctc tgt aca aag<br>Thr Pro Pro Lys Pro Ala Pro Ala Pro Pro Leu Pro Leu Cys Thr Lys<br>              255                    260                 265 | | 877 |
| tcc ttg ccc cca aga aat tgt ata taaatcatcc ttttctacca gcaaaaaaa<br>Ser Leu Pro Pro Arg Asn Cys Ile<br>       270                  275 | | 931 |
| aaaaaaaaaa aaaaaaaaaa aaaaaaaaaa aaaaaaaaaa aaaaaaaaaa aaaa | | 985 |

<210> SEQ ID NO 26
<211> LENGTH: 276
<212> TYPE: PRT
<213> ORGANISM: Canis familiaris

<400> SEQUENCE: 26

Met Ile Val Leu Ala Pro Ala Trp Ser Pro Thr Ala Ser Leu Leu Leu
1                    5                        10                        15

```
Leu Leu Leu Leu Ser Pro Gly Leu Arg Gly Thr Pro Asp Cys Ser Phe
             20                  25                  30

Ser His Ser Pro Ile Ser Ser Thr Phe Ala Val Thr Ile Arg Lys Leu
         35                  40                  45

Ser Asp Tyr Leu Leu Gln Asp Tyr Pro Val Thr Val Ala Ser Asn Leu
     50                  55                  60

Gln Asp Asp Glu Leu Cys Gly Ala Phe Trp Arg Leu Val Leu Ala Gln
65                  70                  75                  80

Arg Trp Met Val Arg Leu Gln Ala Val Ala Gly Ser Gln Met Gln Ile
                 85                  90                  95

Leu Leu Glu Ala Val Asn Thr Glu Ile His Phe Val Thr Phe Cys Ala
            100                 105                 110

Phe Gln Asp Thr Ser Gln Gln Leu Ala Ala Leu Lys Pro Trp Ile Thr
        115                 120                 125

Arg Arg Asn Phe Ser Gly Cys Leu Glu Leu Gln Cys Gln Pro Asp Ser
    130                 135                 140

Ser Thr Leu Val Pro Pro Arg Ser Pro Gly Ala Leu Glu Ala Thr Ala
145                 150                 155                 160

Leu Pro Ala Pro Gln Ala Pro Arg Leu Leu Leu Leu Leu Leu Leu Pro
                165                 170                 175

Val Ala Leu Leu Leu Met Ser Thr Ala Trp Cys Leu His Trp Arg Arg
            180                 185                 190

Arg Arg Arg Arg Ser Pro Tyr Pro Gly Glu Gln Arg Thr Leu Arg
        195                 200                 205

Pro Ser Glu Arg Ser His Leu Pro Glu Asp Thr Glu Leu Gly Pro Gly
210                 215                 220

Gly Ser Gln Leu Glu Thr Gly Pro Phe Leu Asp His Ala Ala Pro Leu
225                 230                 235                 240

Ala Pro Ser Pro Gly Ser Arg Gln Arg Pro Pro Thr Pro Pro Lys
                245                 250                 255

Pro Ala Pro Ala Pro Pro Leu Pro Leu Cys Thr Lys Ser Leu Pro Pro
                260                 265                 270

Arg Asn Cys Ile
        275

<210> SEQ ID NO 27
<211> LENGTH: 985
<212> TYPE: DNA
<213> ORGANISM: Canis familiaris

<400> SEQUENCE: 27
tttttttttt tttttttttt tttttttttt tttttttttt tttttttttt tttttttttt    60
ttgctggtag aaaaggatga tttatataca atttcttggg ggcaaggact tgtacagag    120 ggggagaggt ggggctgggg ctggctttgg gggcgttggg ggcgggcgtt gccttgatcc    180
tggggaggga gcgagcgggg ctgcgtggtc gaggaaggga ccagtctcta gctgactccc    240
tccaggtccc agctctgtgt cctcgggcag atggctccgc tcgctgggcc tcagtgtcct    300
ctgctcccca gggtagggtg acctccgccg ccgcctcctt cgccaatgca ggcaccaggc    360
agtggacatc agcaggagag ccacgggcag cagcagcagg aggagcagcc gaggtgcctg    420
aggggctggc aaggcagtgg cctccagggc cccggggctc cttgggggca ccaatgtaga    480
ggagtcgggc tgacactgca gctccaggca cccggagaaa ttcctgcggg tgatccaggg    540
cttcagggcg gccagctgct gggaggtgtc ctggaaggca cagaaggtga caaagtgtat    600
```

```
ctccgtgttg acagcctcca gcaggatttg catttgggat ccagccacag cctggagccg      660
caccatccag cgctgggcca ggaccaggcg ccagaacgcc ccgcagagct cgtcgtcctg      720
caggttggag gcgacagtga ctggatagtc ctgaagcagg taatcagaca gcttgcggat      780
ggtgaccgcg aaggtggagg agatggggct gtggctgaag gagcagtcgg gggtcccgcg      840
gaggccgggg ctgagcagca gcagcagcaa cagggaggca gttgggctcc aggctggcgc      900
cagcactatc atctcggccg gaggcccctc atgcctatgg tcagatcagg cttgccccag      960
ctgggcgtgg aagggccag gccgg                                            985

<210> SEQ ID NO 28
<211> LENGTH: 828
<212> TYPE: DNA
<213> ORGANISM: Canis familiaris

<400> SEQUENCE: 28
atgatagtgc tggcgccagc ctggagccca actgcctccc tgttgctgct gctgctgctc       60
agccccggcc tccgcgggac ccccgactgc tccttcagcc acagcccat ctcctccacc      120 ttcgcggtca ccatccgcaa gctgtctgat tacctgcttc aggactatcc agtcactgtc      180
gcctccaacc tgcaggacga cgagctctgc ggggcgttct ggcgcctggt cctggcccag      240
cgctggatgg tgcggctcca ggctgtggct ggatcccaaa tgcaaatcct gctgaaggct      300
gtcaacacgg agatacactt tgtcaccttc tgtgccttcc aggacacctc ccagcagctg      360
gccgccctga gccctggat cacccgcagg aatttctccg ggtgcctgga gctgcagtgt      420
cagcccgact cctctacatt ggtgccccca aggagccccg ggccctgga ggccactgcc      480 ttgccagccc ctcaggcacc tcggctgctc ctcctgctgc tgctgcccgt ggctctcctg      540
ctgatgtcca ctgcctggtg cctgcattgg cgaaggaggc ggcggcggag gtcaccctac      600
cctggggagc agaggacact gaggcccagc gagcggagcc atctgcccga ggacacagag      660
ctgggacctg gagggagtca gctagagact ggtcccttcc tcgaccacgc agccccgctc      720
gctccctccc caggatcaag gcaacgcccg ccccaacgc cccaaagcc agccccagcc      780 ccacctctcc ccctctgtac aaagtccttg cccccaagaa attgtata                  828

<210> SEQ ID NO 29
<211> LENGTH: 828
<212> TYPE: DNA
<213> ORGANISM: Canis familiaris

<400> SEQUENCE: 29
tatacaattt cttgggggca aggactttgt acagaggggg agaggtgggg ctggggctgg       60 ctttggggc gttggggcg gcgttgcct tgatcctggg gagggagcga gcggggctgc        120
gtggtcgagg aagggaccag tctctagctg actccctcca ggtcccagct ctgtgtcctc      180
gggcagatgg ctccgctcgc tgggcctcag tgtcctctgc tccccagggt agggtgacct      240
ccgccgccgc ctccttcgcc aatgcaggca ccaggcagtg acatcagca ggagagccac      300 gggcagcagc agcaggagga gcagccgagg tgcctgaggg gctggcaagg cagtggcctc      360
cagggccccg gggctccttg ggggcaccaa tgtagaggag tcgggctgac actgcagctc      420
caggcacccg gagaaattcc tgcgggtgat ccagggcttc agggcggcca gctgctggga      480
ggtgtcctgg aaggcacaga aggtgacaaa gtgtatctcc gtgttgacag cctccagcag      540
gatttgcatt tgggatccag ccacagcctg gagccgcacc atccagcgct gggcaggac      600 caggcgccag aacgccccgc agagctcgtc gtcctgcagg ttggaggcga cagtgactgg      660
```

```
atagtcctga agcaggtaat cagacagctt gcggatggtg accgcgaagg tggaggagat        720
ggggctgtgg ctgaaggagc agtcgggggt cccgcggagg ccggggctga gcagcagcag        780
cagcaacagg gaggcagttg ggctccaggc tggcgccagc actatcat                      828

<210> SEQ ID NO 30
<211> LENGTH: 750
<212> TYPE: DNA
<213> ORGANISM: Canis familiaris
<220> FEATURE:
<221> NAME/KEY: CDS
<222> LOCATION: (1)..(750)

<400> SEQUENCE: 30 acc ccc gac tgc tcc ttc agc cac agc ccc atc tcc tcc acc ttc gcg         48
Thr Pro Asp Cys Ser Phe Ser His Ser Pro Ile Ser Ser Thr Phe Ala
1               5                   10                  15 gtc acc atc cgc aag ctg tct gat tac ctg ctt cag gac tat cca gtc         96
Val Thr Ile Arg Lys Leu Ser Asp Tyr Leu Leu Gln Asp Tyr Pro Val
            20                  25                  30 act gtc gcc tcc aac ctg cag gac gac gag ctc tgc ggg gcg ttc tgg        144
Thr Val Ala Ser Asn Leu Gln Asp Asp Glu Leu Cys Gly Ala Phe Trp
        35                  40                  45 cgc ctg gtc ctg gcc cag cgc tgg atg gtg cgg ctc cag gct gtg gct        192
Arg Leu Val Leu Ala Gln Arg Trp Met Val Arg Leu Gln Ala Val Ala
    50                  55                  60 gga tcc caa atg caa atc ctg ctg gag gct gtc aac acg gag ata cac        240
Gly Ser Gln Met Gln Ile Leu Leu Glu Ala Val Asn Thr Glu Ile His
65                  70                  75                  80 ttt gtc acc ttc tgt gcc ttc cag gac acc tcc cag cag ctg gcc gcc        288
Phe Val Thr Phe Cys Ala Phe Gln Asp Thr Ser Gln Gln Leu Ala Ala
                85                  90                  95 ctg aag ccc tgg atc acc cgc agg aat ttc tcc ggg tgc ctg gag ctg        336
Leu Lys Pro Trp Ile Thr Arg Arg Asn Phe Ser Gly Cys Leu Glu Leu
            100                 105                 110 cag tgt cag ccc gac tcc tct aca ttg gtg ccc cca agg agc ccc ggg        384
Gln Cys Gln Pro Asp Ser Ser Thr Leu Val Pro Pro Arg Ser Pro Gly
        115                 120                 125 gcc ctg gag gcc act gcc ttg cca gcc cct cag gca cct cgg ctg ctc        432
Ala Leu Glu Ala Thr Ala Leu Pro Ala Pro Gln Ala Pro Arg Leu Leu
    130                 135                 140 ctc ctg ctg ctg ctg ccc gtg gct ctc ctg ctg atg tcc act gcc tgg        480
Leu Leu Leu Leu Leu Pro Val Ala Leu Leu Leu Met Ser Thr Ala Trp
145                 150                 155                 160 tgc ctg cat tgg cga agg agg cgg cgg agg tca ccc tac cct ggg             528
Cys Leu His Trp Arg Arg Arg Arg Arg Arg Ser Pro Tyr Pro Gly
                165                 170                 175 gag cag agg aca ctg agg ccc agc gag cgg agc cat ctg ccc gag gac        576
Glu Gln Arg Thr Leu Arg Pro Ser Glu Arg Ser His Leu Pro Glu Asp
            180                 185                 190 aca gag ctg gga cct gga ggg agt cag cta gag act ggt ccc ttc ctc        624
Thr Glu Leu Gly Pro Gly Gly Ser Gln Leu Glu Thr Gly Pro Phe Leu
        195                 200                 205 gac cac gca gcc ccg ctc gct ccc tcc cca gga tca agg caa cgc ccg        672
Asp His Ala Ala Pro Leu Ala Pro Ser Pro Gly Ser Arg Gln Arg Pro
    210                 215                 220 ccc cca acg ccc cca aag cca gcc cca gcc cct ctc ccc ctc tgt             720
Pro Pro Thr Pro Pro Lys Pro Ala Pro Ala Pro Leu Pro Leu Cys
225                 230                 235                 240 aca aag tcc ttg ccc cca aga aat tgt ata                                 750
Thr Lys Ser Leu Pro Pro Arg Asn Cys Ile
                245                 250
```

<210> SEQ ID NO 31
<211> LENGTH: 250
<212> TYPE: PRT
<213> ORGANISM: Canis familiaris

<400> SEQUENCE: 31

```
Thr Pro Asp Cys Ser Phe Ser His Ser Pro Ile Ser Ser Thr Phe Ala
1               5                   10                  15

Val Thr Ile Arg Lys Leu Ser Asp Tyr Leu Leu Gln Asp Tyr Pro Val
            20                  25                  30

Thr Val Ala Ser Asn Leu Gln Asp Asp Glu Leu Cys Gly Ala Phe Trp
        35                  40                  45

Arg Leu Val Leu Ala Gln Arg Trp Met Val Arg Leu Gln Ala Val Ala
    50                  55                  60

Gly Ser Gln Met Gln Ile Leu Leu Glu Ala Val Asn Thr Glu Ile His
65                  70                  75                  80

Phe Val Thr Phe Cys Ala Phe Gln Asp Thr Ser Gln Gln Leu Ala Ala
                85                  90                  95

Leu Lys Pro Trp Ile Thr Arg Arg Asn Phe Ser Gly Cys Leu Glu Leu
            100                 105                 110

Gln Cys Gln Pro Asp Ser Ser Thr Leu Val Pro Pro Arg Ser Pro Gly
        115                 120                 125

Ala Leu Glu Ala Thr Ala Leu Pro Ala Pro Gln Ala Pro Arg Leu Leu
    130                 135                 140

Leu Leu Leu Leu Leu Pro Val Ala Leu Leu Leu Met Ser Thr Ala Trp
145                 150                 155                 160

Cys Leu His Trp Arg Arg Arg Arg Arg Arg Ser Pro Tyr Pro Gly
                165                 170                 175

Glu Gln Arg Thr Leu Arg Pro Ser Glu Arg Ser His Leu Pro Glu Asp
            180                 185                 190

Thr Glu Leu Gly Pro Gly Gly Ser Gln Leu Glu Thr Gly Pro Phe Leu
        195                 200                 205

Asp His Ala Ala Pro Leu Ala Pro Ser Pro Gly Ser Arg Gln Arg Pro
    210                 215                 220

Pro Pro Thr Pro Pro Lys Pro Ala Pro Ala Pro Pro Leu Pro Leu Cys
225                 230                 235                 240

Thr Lys Ser Leu Pro Pro Arg Asn Cys Ile
                245                 250
```

<210> SEQ ID NO 32
<211> LENGTH: 750
<212> TYPE: DNA
<213> ORGANISM: Canis familiaris

<400> SEQUENCE: 32

```
tatacaattt cttgggggca aggactttgt acagagggg agaggtgggg ctggggctgg      60 ctttggggc gttgggggcg ggcgttgcct tgatcctggg gagggagcga gcggggctgc     120
gtggtcgagg aagggaccag tctctagctg actccctcca ggtcccagct ctgtgtcctc    180
gggcagatgg ctccgctcgc tgggcctcag tgtcctctgc tccccagggt agggtgacct    240
ccgccgccgc ctccttcgcc aatgcaggca ccaggcagtg acatcagca ggagagccac     300 gggcagcagc agcaggagga gcagccgagg tgcctgaggg gctggcaagg cagtggcctc    360
cagggccccg gggctccttg ggggcaccaa tgtagaggag tcgggctgac actgcagctc    420
caggcacccg gagaaattcc tgcgggtgat ccagggcttc agggcggcca gctgctggga    480
```

```
ggtgtcctgg aaggcacaga aggtgacaaa gtgtatctcc gtgttgacag cctccagcag      540
gatttgcatt tgggatccag ccacagcctg agccgcacc  atccagcgct gggccaggac      600
caggcgccag aacgccccgc agagctcgtc gtcctgcagg ttggaggcga cagtgactgg      660
atagtcctga agcaggtaat cagacagctt gcggatggtg accgcgaagg tggaggagat      720
ggggctgtgg ctgaaggagc agtcgggggt                                       750

<210> SEQ ID NO 33
<211> LENGTH: 1019
<212> TYPE: DNA
<213> ORGANISM: Canis familiaris
<220> FEATURE:
<221> NAME/KEY: CDS
<222> LOCATION: (74)..(166)

<400> SEQUENCE: 33
ccggcctggc ccttccacg cccagctggg gcaagcctga tctgaccata ggcatgaggg        60
gcctccggcc gag atg ata gtg ctg gcg cca gcc tgg agc cca act gtg        109
            Met Ile Val Leu Ala Pro Ala Trp Ser Pro Thr Val
              1               5                  10 cgt ata ccc ggg gga caa ggc ggg gga cag gca gag cgc tac cga gct       157
Arg Ile Pro Gly Gly Gln Gly Gly Gly Gln Ala Glu Arg Tyr Arg Ala
         15                  20                  25 ggg cag agc tgagagagca gacggacaga ggcctccctg ttgctgctgc                206
Gly Gln Ser
         30 tgctgctcag ccccggcctc cgcgggaccc ccgactgctc cttcagccac agccccatct      266 cctccacctt cgcggtcacc atccgcaagc tgtctgatta cctgcttcag gactatccag      326 tcactgtcgc ctccaacctg caggacgacg agctctgcgg ggcgttctgg cgcctggtcc      386 tggcccagcg ctggatggtg cggctccagg ctgtggctgg atcccaaatg caaatcctgc      446 tggaggctgt caacacggag atacactttg tcaccttctg tgccttccag gacacctccc      506 agcagctggc cgccctgaag ccctggatca cccgcaggaa tttctccggg tgcctggagc      566 tgcagtgtca gcccgactcc tctacattgg tgccccaag gagcccggg gccctggagg       626 ccactgcctt gccagcccct caggcacctc ggctgctcct cctgctgctg ctgcccgtgg      686 ctctcctgct gatgtccact gcctggtgcc tgcattggcg aaggaggcgg cggcggaggt      746 caccctaccc tggggagcag aggacactga ggcccagcga gcggagccat ctgcccgagg      806 acacagagct gggacctgga gggagtcagc tagagactgg tcccttcctc gaccacgcag      866 ccccgctcgc tccctcccca ggatcaaggc aacgcccgcc ccaacgcccc caaagccag      926 ccccagcccc acctctcccc ctctgtacaa agtccttgcc cccaagaaat tgtatataaa      986 tcatccttt ctaccaaaaa aaaaaaaaaa aaa                                   1019

<210> SEQ ID NO 34
<211> LENGTH: 31
<212> TYPE: PRT
<213> ORGANISM: Canis familiaris

<400> SEQUENCE: 34

Met Ile Val Leu Ala Pro Ala Trp Ser Pro Thr Val Arg Ile Pro Gly
  1               5                  10                  15

Gly Gln Gly Gly Gly Gln Ala Glu Arg Tyr Arg Ala Gly Gln Ser
             20                  25                  30

<210> SEQ ID NO 35
```

```
<211> LENGTH: 1019
<212> TYPE: DNA
<213> ORGANISM: Canis familiaris

<400> SEQUENCE: 35 ttttttttttt ttttttttgg tagaaaagga tgatttatat acaatttctt gggggcaagg      60
actttgtaca gagggggaga ggtggggctg gggctggctt tgggggcgtt gggggcgggc     120
gttgccttga tcctggggag ggagcgagcg gggctgcgtg gtcgaggaag ggaccagtct     180
ctagctgact ccctccaggt cccagctctg tgtcctcggg cagatggctc cgctcgctgg     240
gcctcagtgt cctctgctcc cagggtaggg gtgacctccg ccgccgcctc cttcgccaat     300
gcaggcacca ggcagtggac atcagcagga gagccacggg cagcagcagc aggaggagca     360
gccgaggtgc ctgaggggct ggcaaggcag tggcctccag gccccgggg ctccttgggg      420 gcaccaatgt agaggagtcg ggctgacact gcagctccag gcacccggag aaattcctgc     480
gggtgatcca gggcttcagg gcggccagct gctgggaggt gtcctggaag gcacagaagg     540
tgacaaagtg tatctccgtg ttgacagcct ccagcaggat ttgcatttgg gatccagcca     600
cagcctggag ccgcaccatc cagcgctggg ccaggaccag gcgccagaac gccccgcaga     660
gctcgtcgtc ctgcaggttg gaggcgacag tgactggata gtcctgaagc aggtaatcag     720
acagcttgcg gatggtgacc gcgaaggtgg aggagatggg gctgtggctg aaggagcagt     780
cgggggtccc gcggaggccg gggctgagca gcagcagcag caacagggag gcctctgtcc     840
gtctgctctc tcagctctgc ccagctcggt agcgctctgc ctgtccccg ccttgtcccc      900 cgggtatacg cacagttggg ctccaggctg gcgccagcac tatcatctcg gccggaggcc     960
cctcatgcct atggtcagat caggcttgcc ccagctgggc gtggaagggg ccaggccgg    1019

<210> SEQ ID NO 36
<211> LENGTH: 93
<212> TYPE: DNA
<213> ORGANISM: Canis familiaris

<400> SEQUENCE: 36
atgatagtgc tggcgccagc ctggagccca actgtgcgta tacccggggg acaaggcggg      60
ggacaggcag agcgctaccg agctgggcag agc                                   93

<210> SEQ ID NO 37
<211> LENGTH: 93
<212> TYPE: DNA
<213> ORGANISM: Canis familiaris

<400> SEQUENCE: 37
gctctgccca gctcggtagc gctctgcctg tcccccgcct tgtccccgg gtatacgcac       60 agttgggctc caggctggcg ccagcactat cat                                   93

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
tgaattcgga cataacttca atattac                                          27

<210> SEQ ID NO 39
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
tctcgagatt cagcttcaat gcctgta                                        27

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
cccaagctta tgggtctcac ctcccaac                                       28

<210> SEQ ID NO 41
<211> LENGTH: 395
<212> TYPE: DNA
<213> ORGANISM: Felis catus

<400> SEQUENCE: 41
ggccataggc atgaagggcc tccggccgag atgatagtgc tggcgccagc ctggagccca     60
actacctccc tgctgctgct gctactgctc agccctggcc tccgcgggtc ccccgactgt    120
tccttcagcc acagcccat ctcctccacc ttcaaggtca ccatccgaaa gctgtctgat    180
tacctgcttc aggattaccc agtcaccgtc gcctccaacc tacaggacga cgagctctgt    240
gggccattct ggcacctggt cctggcccag cgctggatgg gtcggctcaa ggctgtggct    300
gggtcccaga tgcaaagcct gctggaggcg gtcaacaccg agatacattt tgtcaccttg    360
tgtgccttcc agcccctccc cagctgtctt cgatt                                395

<210> SEQ ID NO 42
<211> LENGTH: 793
<212> TYPE: DNA
<213> ORGANISM: Felis catus

<400> SEQUENCE: 42
cttcaaggtc accatccgaa agctgtctga ttacctgctt caggattacc cagtcaccgt     60
cgcctccaac ctacaggacg acgagctctg tgggccattc tggcacctgg tcctggccca    120
gcgctggatg ggtcggctca aggctgtggc tgggtcccag atgcaaagcc tgctggaggc    180
ggtcaacacc gagatacatt ttgtcacctt gtgtgccttc agcccctccc cagctgtctc    240
tcgattcgtc cagaccaaca tctcccacct cctgcaggac acctccgagc agctggcggc    300
cttgaagccc tggatcaccc gcaggaattt ctcggggtgc ctggagctac agtgtcagcc    360
cgactcctcc accccactgc ccccaaggag ccccagggcc ttggaggcca cagccctgcc    420 agccccctcag gcccctctgc tgctcctcct gctgctgttg cctgtggctc tcttgctgat    480
gtccgccgcc tggtgcctgc actggcgaag aaggagatgg agaacgccct accccaggga    540
gcagaggaag acactgaggc ccagagagag gaatcacctg cccgaggaca cagagccggg    600
actcggagaa agtcagctag agactggttc cttcctcgac cacgctgccc cgctcactct    660
cccccgggga tggaggcaac gccagccccc aacgccagcc ccagacccac ctatcccct    720 ctgtacaaag tccttgtcct caggaaattg tatataaatc atcctttcct accaaaaaaa    780
aaaaaaaaaa aaa                                                         793
```

<210> SEQ ID NO 43
<211> LENGTH: 942
<212> TYPE: DNA
<213> ORGANISM: Felis catus
<220> FEATURE:
<221> NAME/KEY: CDS
<222> LOCATION: (31)..(903)

<400> SEQUENCE: 43

```
ggccataggc atgaagggcc tccggccgag atg ata gtg ctg gcg cca gcc tgg        54
                                 Met Ile Val Leu Ala Pro Ala Trp
                                  1               5 agc cca act acc tcc ctg ctg ctg cta ctg ctc agc cct ggc ctc            102
Ser Pro Thr Thr Ser Leu Leu Leu Leu Leu Leu Ser Pro Gly Leu
         10                  15                  20 cgc ggg tcc ccc gac tgt tcc ttc agc cac agc ccc atc tcc tcc acc        150
Arg Gly Ser Pro Asp Cys Ser Phe Ser His Ser Pro Ile Ser Ser Thr
 25                  30                  35                  40 ttc aag gtc acc atc cga aag ctg tct gat tac ctg ctt cag gat tac        198
Phe Lys Val Thr Ile Arg Lys Leu Ser Asp Tyr Leu Leu Gln Asp Tyr
                 45                  50                  55 cca gtc acc gtc gcc tcc aac cta cag gac gac gag ctc tgt ggg cca        246
Pro Val Thr Val Ala Ser Asn Leu Gln Asp Asp Glu Leu Cys Gly Pro
             60                  65                  70 ttc tgg cac ctg gtc ctg gcc cag cgc tgg atg ggt cgg ctc aag gct        294
Phe Trp His Leu Val Leu Ala Gln Arg Trp Met Gly Arg Leu Lys Ala
         75                  80                  85 gtg gct ggg tcc cag atg caa agc ctg ctg gag gcg gtc aac acc gag        342
Val Ala Gly Ser Gln Met Gln Ser Leu Leu Glu Ala Val Asn Thr Glu
 90                  95                 100 ata cat ttt gtc acc ttg tgt gcc ttc cag ccc ctc ccc agc tgt ctt        390
Ile His Phe Val Thr Leu Cys Ala Phe Gln Pro Leu Pro Ser Cys Leu
105                 110                 115                 120 cga ttc gtc cag acc aac atc tcc cac ctc ctg cag gac acc tcc gag        438
Arg Phe Val Gln Thr Asn Ile Ser His Leu Leu Gln Asp Thr Ser Glu
                125                 130                 135 cag ctg gcg gcc ttg aag ccc tgg atc acc cgc agg aat ttc tcg ggg        486
Gln Leu Ala Ala Leu Lys Pro Trp Ile Thr Arg Arg Asn Phe Ser Gly
            140                 145                 150 tgc ctg gag cta cag tgt cag ccc gac tcc tcc acc cca ctg ccc cca        534
Cys Leu Glu Leu Gln Cys Gln Pro Asp Ser Ser Thr Pro Leu Pro Pro
        155                 160                 165 agg agc ccc agg gcc ttg gag gcc aca gcc ctg cca gcc cct cag gcc        582
Arg Ser Pro Arg Ala Leu Glu Ala Thr Ala Leu Pro Ala Pro Gln Ala
170                 175                 180 cct ctg ctg ctc ctg ctg ctg ttg cct gtg gct ctc ttg ctg atg            630
Pro Leu Leu Leu Leu Leu Leu Leu Pro Val Ala Leu Leu Leu Met
185                 190                 195                 200 tcc gcc gcc tgg tgc ctg cac tgg cga aga agg aga tgg aga acg ccc        678
Ser Ala Ala Trp Cys Leu His Trp Arg Arg Arg Arg Trp Arg Thr Pro
                205                 210                 215 tac ccc agg gag cag agg aag aca ctg agg ccc aga gag agg aat cac        726
Tyr Pro Arg Glu Gln Arg Lys Thr Leu Arg Pro Arg Glu Arg Asn His
            220                 225                 230 ctg ccc gag gac aca gag ccg gga ctg gga gaa agt cag cta gag act        774
Leu Pro Glu Asp Thr Glu Pro Gly Leu Gly Glu Ser Gln Leu Glu Thr
        235                 240                 245 ggt tcc ttc ctc gac cac gct gcc ccg ctc act ctc ccc ccg gga tgg        822
Gly Ser Phe Leu Asp His Ala Ala Pro Leu Thr Leu Pro Pro Gly Trp
250                 255                 260
```

```
agg caa cgc cag ccc cca acg cca gcc cca gac cca cct atc ccc ctc    870
Arg Gln Arg Gln Pro Pro Thr Pro Ala Pro Asp Pro Pro Ile Pro Leu
265                 270                 275                 280 tgt aca aag tcc ttg tcc tca gga aat tgt ata taaatcatcc ttttctacca  923
Cys Thr Lys Ser Leu Ser Ser Gly Asn Cys Ile
                285                 290 aaaaaaaaaa aaaaaaaaa                                               942
```

<210> SEQ ID NO 44
<211> LENGTH: 291
<212> TYPE: PRT
<213> ORGANISM: Felis catus

<400> SEQUENCE: 44

Met Ile Val Leu Ala Pro Ala Trp Ser Pro Thr Thr Ser Leu Leu Leu
1               5                   10                  15

Leu Leu Leu Leu Ser Pro Gly Leu Arg Gly Ser Pro Asp Cys Ser Phe
            20                  25                  30

Ser His Ser Pro Ile Ser Ser Thr Phe Lys Val Thr Ile Arg Lys Leu
        35                  40                  45

Ser Asp Tyr Leu Leu Gln Asp Tyr Pro Val Thr Val Ala Ser Asn Leu
    50                  55                  60

Gln Asp Asp Glu Leu Cys Gly Pro Phe Trp His Leu Val Leu Ala Gln
65                  70                  75                  80

Arg Trp Met Gly Arg Leu Lys Ala Val Ala Gly Ser Gln Met Gln Ser
                85                  90                  95

Leu Leu Glu Ala Val Asn Thr Glu Ile His Phe Val Thr Leu Cys Ala
            100                 105                 110

Phe Gln Pro Leu Pro Ser Cys Leu Arg Phe Val Gln Thr Asn Ile Ser
        115                 120                 125

His Leu Leu Gln Asp Thr Ser Glu Gln Leu Ala Ala Leu Lys Pro Trp
    130                 135                 140

Ile Thr Arg Arg Asn Phe Ser Gly Cys Leu Glu Leu Gln Cys Gln Pro
145                 150                 155                 160

Asp Ser Ser Thr Pro Leu Pro Pro Arg Ser Pro Arg Ala Leu Glu Ala
                165                 170                 175

Thr Ala Leu Pro Ala Pro Gln Ala Pro Leu Leu Leu Leu Leu Leu Leu
            180                 185                 190

Leu Pro Val Ala Leu Leu Met Ser Ala Ala Trp Cys Leu His Trp
        195                 200                 205

Arg Arg Arg Arg Trp Arg Thr Pro Tyr Pro Arg Glu Gln Arg Lys Thr
210                 215                 220

Leu Arg Pro Arg Glu Arg Asn His Leu Pro Glu Asp Thr Glu Pro Gly
225                 230                 235                 240

Leu Gly Glu Ser Gln Leu Glu Thr Gly Ser Phe Leu Asp His Ala Ala
                245                 250                 255

Pro Leu Thr Leu Pro Pro Gly Trp Arg Gln Arg Gln Pro Pro Thr Pro
            260                 265                 270

Ala Pro Asp Pro Pro Ile Pro Leu Cys Thr Lys Ser Leu Ser Ser Gly
        275                 280                 285

Asn Cys Ile
    290

<210> SEQ ID NO 45
<211> LENGTH: 942
<212> TYPE: DNA
<213> ORGANISM: Felis catus

<400> SEQUENCE: 45

```
tttttttttt tttttttttt ggtagaaaag gatgatttat atacaattc ctgaggacaa        60
ggactttgta cagagggga taggtgggtc tggggctggc gttggggct ggcgttgcct        120
ccatcccggg gggagagtga gcggggcagc gtggtcgagg aaggaaccag tctctagctg      180
actttctccg agtcccggct ctgtgtcctc gggcaggtga ttcctctctc tgggcctcag     240
tgtcttcctc tgctccctgg ggtagggcgt tctccatctc cttcttcgcc agtgcaggca     300
ccaggcggcg gacatcagca agagagccac aggcaacagc agcaggagga gcagcagagg    360
ggcctgaggg gctggcaggg ctgtggcctc caaggccctg gggctccttg ggggcagtgg    420
ggtggaggag tcgggctgac actgtagctc caggcacccc gagaaattcc tgcgggtgat     480
ccagggcttc aaggccgcca gctgctcgga ggtgtcctgc aggaggtggg agatgttggt   540
ctggacgaat cgaagacagc tggggagggg ctggaaggca cacaaggtga caaaatgtat     600
ctcggtgttg accgcctcca gcaggctttg catctgggac ccagccacag ccttgagccg   660
acccatccag cgctgggcca ggaccaggtg ccagaatggc ccacagagct cgtcgtcctg   720
taggttggag gcgacggtga ctgggtaatc ctgaagcagg taatcagaca gctttcggat   780
ggtgaccttg aaggtggagg agatggggct gtggctgaag gaacagtcgg gggacccgcg    840
gaggccaggc ctgagcagta gcagcagcag caggaggta gttgggctcc aggctggcgc    900
cagcactatc atctcggccg gaggcccttc atgcctatgg cc                        942
```

<210> SEQ ID NO 46
<211> LENGTH: 873
<212> TYPE: DNA
<213> ORGANISM: Felis catus

<400> SEQUENCE: 46

```
atgatagtgc tggcgccagc ctggagccca actacctccc tgctgctgct gctactgctc    60
agccctggcc tccgcgggtc ccccgactgt tccttcagcc acagccccat ctcctccacc    120
ttcaaggtca ccatccgaaa gctgtctgat tacctgcttc aggattaccc agtcaccgtc   180
gcctccaacc tacaggacga cgagctctgt gggccattct ggcacctggt cctggcccag   240
cgctggatgg gtcggctcaa ggctgtggct gggtccagga tgcaaagcct gctggaggcg   300
gtcaacaccg agatacattt tgtcaccttg tgtgccttcc agcccctccc cagctgtctt   360
cgattcgtcc agaccaacat ctcccacctc ctgcaggaca cctccgagca gctggcggcc   420
ttgaagccct ggatcacccg caggaatttc tcggggtgcc tggagctaca gtgtcagccc  480
gactcctcca ccccactgcc cccaaggagc cccagggcct tggaggccac agccctgcca   540
gcccctcagg cccctctgct gctcctcctg ctgctgttgc ctgtggctct cttgctgatg   600
tccgccgcct ggtgcctgca ctggcgaaga aggagatgga gaacgcccta ccccagggag    660
cagaggaaga cactgaggcc cagagagagg aatcacctgc ccgaggacac agagccggga   720
ctcggagaaa gtcagctaga gactggttcc ttcctcgacc acgctgcccc gctcactctc    780
cccccggat ggaggcaacg ccagccccca acgccagccc cagacccacc tatccccctc    840
tgtacaaagt ccttgtcctc aggaaaattgt ata                                 873
```

<210> SEQ ID NO 47
<211> LENGTH: 873
<212> TYPE: DNA
<213> ORGANISM: Felis catus

<400> SEQUENCE: 47

-continued

```
tatacaattt cctgaggaca aggactttgt acagaggggg ataggtgggt ctggggctgg      60 cgttggggc tggcgttgcc tccatcccgg ggggagagtg agcggggcag cgtggtcgag      120
gaaggaacca gtctctagct gactttctcc gagtcccggc tctgtgtcct cgggcaggtg     180
attcctctct ctgggcctca gtgtcttcct ctgctccctg gggtagggcg ttctccatct     240
ccttcttcgc cagtgcaggc accaggcggc ggacatcagc aagagagcca caggcaacag     300
cagcaggagg agcagcagag gggcctgagg ggctggcagg gctgtggcct ccaaggccct     360
ggggctcctt gggggcagtg gggtggagga gtcgggctga cactgtagct ccaggcaccc     420
cgagaaattc ctgcgggtga tccagggctt caaggccgcc agctgctcgg aggtgtcctg     480
caggaggtgg gagatgttgg tctggacgaa tcgaagacag ctggggaggg gctggaaggc     540
acacaaggtg acaaaatgta tctcggtgtt gaccgcctcc agcaggcttt gcatctggga     600
cccagccaca gccttgagcc gacccatcca gcgctgggcc aggaccaggt gccagaatgg     660
cccacagagc tcgtcgtcct gtaggttgga ggcgacggtg actgggtaat cctgaagcag     720
gtaatcagac agctttcgga tggtgacctt gaaggtggag gagatggggc tgtggctgaa     780
ggaacagtcg ggggacccgc ggaggccagg gctgagcagt agcagcagca gcagggaggt     840
agttgggctc caggctggcg ccagcactat cat                                  873
```

<210> SEQ ID NO 48
<211> LENGTH: 795
<212> TYPE: DNA
<213> ORGANISM: Felis catus
<220> FEATURE:
<221> NAME/KEY: CDS
<222> LOCATION: (1)..(795)

<400> SEQUENCE: 48

```
tcc ccc gac tgt tcc ttc agc cac agc ccc atc tcc tcc acc ttc aag       48
Ser Pro Asp Cys Ser Phe Ser His Ser Pro Ile Ser Ser Thr Phe Lys
1               5                   10                  15 gtc acc atc cga aag ctg tct gat tac ctg ctt cag gat tac cca gtc       96
Val Thr Ile Arg Lys Leu Ser Asp Tyr Leu Leu Gln Asp Tyr Pro Val
            20                  25                  30 acc gtc gcc tcc aac cta cag gac gac gag ctc tgt ggg cca ttc tgg      144
Thr Val Ala Ser Asn Leu Gln Asp Asp Glu Leu Cys Gly Pro Phe Trp
        35                  40                  45 cac ctg gtc ctg gcc cag cgc tgg atg ggt cgg ctc aag gct gtg gct      192
His Leu Val Leu Ala Gln Arg Trp Met Gly Arg Leu Lys Ala Val Ala
    50                  55                  60 ggg tcc cag atg caa agc ctg ctg gag gcg gtc aac acc gag ata cat      240
Gly Ser Gln Met Gln Ser Leu Leu Glu Ala Val Asn Thr Glu Ile His
65                  70                  75                  80 ttt gtc acc ttg tgt gcc ttc cag ccc ctc ccc agc tgt ctt cga ttc      288
Phe Val Thr Leu Cys Ala Phe Gln Pro Leu Pro Ser Cys Leu Arg Phe
                85                  90                  95 gtc cag acc aac atc tcc cac ctc ctg cag gac acc tcc gag cag ctg      336
Val Gln Thr Asn Ile Ser His Leu Leu Gln Asp Thr Ser Glu Gln Leu
            100                 105                 110 gcg gcc ttg aag ccc tgg atc acc cgc agg aat ttc tcg ggg tgc ctg      384
Ala Ala Leu Lys Pro Trp Ile Thr Arg Arg Asn Phe Ser Gly Cys Leu
        115                 120                 125 gag cta cag tgt cag ccc gac tcc tcc acc cca ctg ccc cca agg agc      432
Glu Leu Gln Cys Gln Pro Asp Ser Ser Thr Pro Leu Pro Pro Arg Ser
    130                 135                 140 ccc agg gcc ttg gag gcc aca gcc ctg cca gcc cct cag gcc cct ctg      480
Pro Arg Ala Leu Glu Ala Thr Ala Leu Pro Ala Pro Gln Ala Pro Leu
```

```
                145                 150                 155                 160
ctg ctc ctc ctg ctg ctg ttg cct gtg gct ctc ttg ctg atg tcc gcc            528
Leu Leu Leu Leu Leu Leu Leu Pro Val Ala Leu Leu Leu Met Ser Ala
                    165                 170                 175 gcc tgg tgc ctg cac tgg cga aga agg aga tgg aga acg ccc tac ccc            576
Ala Trp Cys Leu His Trp Arg Arg Arg Arg Trp Arg Thr Pro Tyr Pro
                180                 185                 190 agg gag cag agg aag aca ctg agg ccc aga gag agg aat cac ctg ccc            624
Arg Glu Gln Arg Lys Thr Leu Arg Pro Arg Glu Arg Asn His Leu Pro
            195                 200                 205 gag gac aca gag ccg gga ctc gga gaa agt cag cta gag act ggt tcc            672
Glu Asp Thr Glu Pro Gly Leu Gly Glu Ser Gln Leu Glu Thr Gly Ser
210                 215                 220 ttc ctc gac cac gct gcc ccg ctc act ctc ccc ccg gga tgg agg caa            720
Phe Leu Asp His Ala Ala Pro Leu Thr Leu Pro Pro Gly Trp Arg Gln
225                 230                 235                 240 cgc cag ccc cca acg cca gcc cca gac cca cct atc ccc ctc tgt aca            768
Arg Gln Pro Pro Thr Pro Ala Pro Asp Pro Pro Ile Pro Leu Cys Thr
                245                 250                 255 aag tcc ttg tcc tca gga aat tgt ata                                        795
Lys Ser Leu Ser Ser Gly Asn Cys Ile
            260                 265

<210> SEQ ID NO 49
<211> LENGTH: 265
<212> TYPE: PRT
<213> ORGANISM: Felis catus

<400> SEQUENCE: 49

Ser Pro Asp Cys Ser Phe Ser His Ser Pro Ile Ser Ser Thr Phe Lys
1               5                   10                  15

Val Thr Ile Arg Lys Leu Ser Asp Tyr Leu Leu Gln Asp Tyr Pro Val
                20                  25                  30

Thr Val Ala Ser Asn Leu Gln Asp Asp Glu Leu Cys Gly Pro Phe Trp
            35                  40                  45

His Leu Val Leu Ala Gln Arg Trp Met Gly Arg Leu Lys Ala Val Ala
        50                  55                  60

Gly Ser Gln Met Gln Ser Leu Leu Glu Ala Val Asn Thr Glu Ile His
65                  70                  75                  80

Phe Val Thr Leu Cys Ala Phe Gln Pro Leu Pro Ser Cys Leu Arg Phe
                85                  90                  95

Val Gln Thr Asn Ile Ser His Leu Leu Gln Asp Thr Ser Glu Gln Leu
                100                 105                 110

Ala Ala Leu Lys Pro Trp Ile Thr Arg Arg Asn Phe Ser Gly Cys Leu
            115                 120                 125

Glu Leu Gln Cys Gln Pro Asp Ser Ser Thr Pro Leu Pro Pro Arg Ser
        130                 135                 140

Pro Arg Ala Leu Glu Ala Thr Ala Leu Pro Ala Pro Gln Ala Pro Leu
145                 150                 155                 160

Leu Leu Leu Leu Leu Leu Leu Pro Val Ala Leu Leu Leu Met Ser Ala
                165                 170                 175

Ala Trp Cys Leu His Trp Arg Arg Arg Arg Trp Arg Thr Pro Tyr Pro
            180                 185                 190

Arg Glu Gln Arg Lys Thr Leu Arg Pro Arg Glu Arg Asn His Leu Pro
        195                 200                 205

Glu Asp Thr Glu Pro Gly Leu Gly Glu Ser Gln Leu Glu Thr Gly Ser
    210                 215                 220
```

-continued

```
Phe Leu Asp His Ala Ala Pro Leu Thr Leu Pro Pro Gly Trp Arg Gln
225                 230                 235                 240

Arg Gln Pro Pro Thr Pro Ala Pro Asp Pro Pro Ile Pro Leu Cys Thr
            245                 250                 255

Lys Ser Leu Ser Ser Gly Asn Cys Ile
        260                 265
```

<210> SEQ ID NO 50
<211> LENGTH: 795
<212> TYPE: DNA
<213> ORGANISM: Felis catus

<400> SEQUENCE: 50

```
tatacaattt cctgaggaca aggactttgt acagaggggg ataggtgggt ctggggctgg    60
cgttggggc tggcgttgcc tccatcccgg ggggagagtg agcggggcag cgtggtcgag    120
gaaggaacca gtctctagct gactttctcc gagtcccggc tctgtgtcct cgggcaggtg    180
attcctctct ctgggcctca gtgtcttcct ctgctccctg gggtagggcg ttctccatct    240
ccttcttcgc cagtgcaggc accaggcggc ggacatcagc aagagagcca caggcaacag    300
cagcaggagg agcagcagag gggcctgagg ggctggcagg gctgtggcct ccaaggccct    360
ggggctcctt gggggcagtg gggtggagga gtcgggctga cactgtagct ccaggcaccc    420
cgagaaattc ctgcgggtga tccagggctt caaggccgcc agctgctcgg aggtgtcctg    480
caggaggtgg gagatgttgg tctggacgaa tcgaagacag ctggggaggg gctggaaggc    540
acacaaggtg acaaaatgta tctcggtgtt gaccgcctcc agcaggcttt gcatctggga    600
cccagccaca gccttgagcc gacccatcca gcgctgggcc aggaccaggt gccagaatgg    660
cccacagagc tcgtcgtcct gtaggttgga ggcgacggtg actgggtaat cctgaagcag    720
gtaatcagac agctttcgga tggtgacctt gaaggtggag gagatgggc tgtggctgaa    780
ggaacagtcg gggga                                                      795
```

<210> SEQ ID NO 51
<211> LENGTH: 321
<212> TYPE: DNA
<213> ORGANISM: Canis familiaris

<400> SEQUENCE: 51

```
aatgtgtctt ctgctttgga aaagtgtcac ccttggacaa gctgtgaaac caaaggcctg    60
gtgaaggttc aggcgggaac taacaagact gatgttatct gtggtcccca gcctcggtta    120
agagccctag tggtggtccc catcattatg gggatcctgc ttgttgtcct gttggtgtct    180
gcctgcatcc gaaaggtggt caagaagcca gagaataagg ttatgtatca ggaccctgtg    240
gaggacttgg aggaatttcc tatgccccccg cactccattg ctccggtgca agagaccta    300
catgggtgcc agcccgtcac c                                               321
```

<210> SEQ ID NO 52
<211> LENGTH: 1425
<212> TYPE: DNA
<213> ORGANISM: Canis familiaris
<220> FEATURE:
<221> NAME/KEY: CDS
<222> LOCATION: (196)..(1017)

<400> SEQUENCE: 52

```
tagactcccg ggaatattca ggggaactcc cggcgctaag ggtctccagg agctccgccc    60
tgcccaacga agccggccac gattggtccc cgaagacccc gccatctcc tgggcggggc    120
```

```
gggcgggggc aagggctggg gagttactaa agacatcccc gcgccctac tccgctgcct         180 gctattcacc tcgcc atg gtt ctc ctg cct ctg cgc tgt ctc ttc tgg ggc         231
             Met Val Leu Leu Pro Leu Arg Cys Leu Phe Trp Gly
              1               5                  10 tcc ttg ttg acc acc gtc tac cca gaa cca cgc act gca tgc aga gaa         279
Ser Leu Leu Thr Thr Val Tyr Pro Glu Pro Arg Thr Ala Cys Arg Glu
         15                  20                  25 aag caa tac cta gta gac agt cag tgc tgt aat atg tgc cca cca gga         327
Lys Gln Tyr Leu Val Asp Ser Gln Cys Cys Asn Met Cys Pro Pro Gly
         30                  35                  40 gag aaa ctg gtg aat gac tgc cta cat acc att gac acg gaa tgc act         375
Glu Lys Leu Val Asn Asp Cys Leu His Thr Ile Asp Thr Glu Cys Thr
 45              50                  55                  60 cgt tgc caa aca ggc gaa ttc cta gac act tgg aac gca gag aga cac         423
Arg Cys Gln Thr Gly Glu Phe Leu Asp Thr Trp Asn Ala Glu Arg His
             65                  70                  75 tgt cac cag cac aaa tac tgc gac ccc aac cta ggg ctc cat gtc gag         471
Cys His Gln His Lys Tyr Cys Asp Pro Asn Leu Gly Leu His Val Glu
             80                  85                  90 aag gag ggc acg tca gaa aca gac acc act tgc aca tgc gat gaa ggt         519
Lys Glu Gly Thr Ser Glu Thr Asp Thr Thr Cys Thr Cys Asp Glu Gly
             95                 100                 105 ctg cat tgt acc aac gct gcc tgt gag agc tgc acc atg cac agc ctg         567
Leu His Cys Thr Asn Ala Ala Cys Glu Ser Cys Thr Met His Ser Leu
    110                 115                 120 tgc ccc cct ggc ctg gga gtc aaa cag atc gct aca ggg att tct gat         615
Cys Pro Pro Gly Leu Gly Val Lys Gln Ile Ala Thr Gly Ile Ser Asp
125             130                 135                 140 acc atc tgc gat ccc tgc ccc atc ggc ttc ttc tcc aat gtg tct tct         663
Thr Ile Cys Asp Pro Cys Pro Ile Gly Phe Phe Ser Asn Val Ser Ser
                145                 150                 155 gct ttg gaa aag tgt cac cct tgg aca agc tgt gaa acc aaa ggc ctg         711
Ala Leu Glu Lys Cys His Pro Trp Thr Ser Cys Glu Thr Lys Gly Leu
                160                 165                 170 gtg aag gtt cag gcg gga act aac aag act gat gtt atc tgt ggt ccc         759
Val Lys Val Gln Ala Gly Thr Asn Lys Thr Asp Val Ile Cys Gly Pro
        175                 180                 185 cag cct cgg tta aga gcc cta gtg gtg tcc ccc atc att atg ggg atc         807
Gln Pro Arg Leu Arg Ala Leu Val Val Val Pro Ile Ile Met Gly Ile
    190                 195                 200 ctg ctt gtt gtc ctg ttg gtg tct gcc tgc atc cga aag gtg gtc aag         855
Leu Leu Val Val Leu Leu Val Ser Ala Cys Ile Arg Lys Val Val Lys
205                 210                 215                 220 aag cca gag aat aag gtt atg tat cag gac cct gtg gag gac ttg gag         903
Lys Pro Glu Asn Lys Val Met Tyr Gln Asp Pro Val Glu Asp Leu Glu
                225                 230                 235 gaa ttt cct atg ccc ccg cac tcc att gct ccg gtg caa gag acc tta         951
Glu Phe Pro Met Pro Pro His Ser Ile Ala Pro Val Gln Glu Thr Leu
                240                 245                 250 cat ggg tgc cag ccc gtc acc cag gag gac ggc aaa gag agc cgc atc         999
His Gly Cys Gln Pro Val Thr Gln Glu Asp Gly Lys Glu Ser Arg Ile
        255                 260                 265 tcc gtg cag gag aga gtg tgaggcagcg tgtgcccagg agtgtgacag                1047
Ser Val Gln Glu Arg Val
270 cgtgggagag tgggcgcgtg gctggagagc ctggagctgc tggaggggca tgaaggggcg       1107 gtgctcccct gcctgcaccc ctgtgctgca gaaacagaga accttccacc ccaccctgg       1167 agcccattcc acctcccaac ttgcttttaa agatggagat gaaactttg gggggccaga       1227
```

```
tagtaatatc caccaaccca gcatttcagg gccctgaggt gtatatcacg gtggtttcta    1287
cgagcccagg aagacccacg aagagccatt gtggcattgt ttgtgacagt ggacaactgg    1347
aggccactta gctgttcagc agcagggac tggctaaata aaatttgtaa tatatttata    1407
aaaaaaaaaa aaaaaaaa                                                   1425
```

<210> SEQ ID NO 53
<211> LENGTH: 274
<212> TYPE: PRT
<213> ORGANISM: Canis familiaris

<400> SEQUENCE: 53

```
Met Val Leu Leu Pro Leu Arg Cys Leu Phe Trp Gly Ser Leu Leu Thr
1               5                   10                  15

Thr Val Tyr Pro Glu Pro Arg Thr Ala Cys Arg Glu Lys Gln Tyr Leu
            20                  25                  30

Val Asp Ser Gln Cys Cys Asn Met Cys Pro Pro Gly Glu Lys Leu Val
        35                  40                  45

Asn Asp Cys Leu His Thr Ile Asp Thr Glu Cys Thr Arg Cys Gln Thr
    50                  55                  60

Gly Glu Phe Leu Asp Thr Trp Asn Ala Glu Arg His Cys His Gln His
65                  70                  75                  80

Lys Tyr Cys Asp Pro Asn Leu Gly Leu His Val Glu Lys Glu Gly Thr
                85                  90                  95

Ser Glu Thr Asp Thr Thr Cys Thr Cys Asp Glu Gly Leu His Cys Thr
            100                 105                 110

Asn Ala Ala Cys Glu Ser Cys Thr Met His Ser Leu Cys Pro Pro Gly
        115                 120                 125

Leu Gly Val Lys Gln Ile Ala Thr Gly Ile Ser Asp Thr Ile Cys Asp
    130                 135                 140

Pro Cys Pro Ile Gly Phe Phe Ser Asn Val Ser Ser Ala Leu Glu Lys
145                 150                 155                 160

Cys His Pro Trp Thr Ser Cys Glu Thr Lys Gly Leu Val Lys Val Gln
                165                 170                 175

Ala Gly Thr Asn Lys Thr Asp Val Ile Cys Gly Pro Gln Pro Arg Leu
            180                 185                 190

Arg Ala Leu Val Val Val Pro Ile Ile Met Gly Ile Leu Leu Val Val
        195                 200                 205

Leu Leu Val Ser Ala Cys Ile Arg Lys Val Val Lys Lys Pro Glu Asn
    210                 215                 220

Lys Val Met Tyr Gln Asp Pro Val Glu Asp Leu Glu Glu Phe Pro Met
225                 230                 235                 240

Pro Pro His Ser Ile Ala Pro Val Gln Glu Thr Leu His Gly Cys Gln
                245                 250                 255

Pro Val Thr Gln Glu Asp Gly Lys Glu Ser Arg Ile Ser Val Gln Glu
            260                 265                 270

Arg Val
```

<210> SEQ ID NO 54
<211> LENGTH: 1425
<212> TYPE: DNA
<213> ORGANISM: Canis familiaris

<400> SEQUENCE: 54

```
tttttttttt tttttttta taaatatatt acaaatttta tttagccagt cccctgctgc      60
tgaacagcta agtggcctcc agttgtccac tgtcacaaac aatgccacaa tggctcttcg    120
```

```
tgggtcttcc tgggctcgta gaaaccaccg tgatatacac ctcagggccc tgaaatgctg    180
ggttggtgga tattactatc tggccccca aaagtttcat ctccatcttt aaaagcaagt     240
tgggaggtgg aatgggctcc aggggtgggg tggaaggttc tctgtttctg cagcacaggg    300
gtgcaggcag gggagcaccg ccccttcatg cccctccagc agctccaggc tctccagcca    360
cgcgcccact ctcccacgct gtcacactcc tgggcacacg ctgcctcaca ctctctcctg    420
cacggagatg cggctctctt tgccgtcctc ctgggtgacg ggctggcacc catgtaaggt    480
ctcttgcacc ggagcaatgg agtgcggggg cataggaaat tcctccaagt cctccacagg    540
gtcctgatac ataaccttat tctctggctt cttgaccacc tttcggatgc aggcagacac    600
caacaggaca acaagcagga tccccataat gatgggggacc accactaggg ctcttaaccg   660
aggctgggga ccacagataa catcagtctt gttagttccc gcctgaacct tcaccaggcc    720
tttggtttca cagcttgtcc aagggtgaca cttttccaaa gcagaagaca cattggagaa    780
gaagccgatg gggcagggat cgcagatggt atcagaaatc cctgtagcga tctgtttgac    840
tcccaggcca ggggggcaca ggctgtgcat ggtgcagctc tcacaggcag cgttggtaca    900
atgcagacct tcatcgcatg tgcaagtggt gtctgtttct gacgtgccct ccttctcgac    960
atggagccct aggttggggt cgcagtattt gtgctggtga cagtgtctct ctgcgttcca    1020
agtgtctagg aattcgcctg tttggcaacg agtgcattcc gtgtcaatgg tatgtaggca    1080
gtcattcacc agtttctctc ctggtgggca catattacag cactgactgt ctactaggta    1140
ttgcttttct ctgcatgcag tgcgtggttc tgggtagacg tggtcaaca aggagcccca     1200 gaagagacag cgcagaggca ggagaaccat ggcgaggtga atagcaggca gcggagtagg    1260
ggcgcgggga tgtctttagt aactcccag cccttgcccc cgcccgcccc gcccaggaga     1320 tgggcgggt cttcggggac caatcgtggc cggcttcgtt gggcagggcg gagctcctgg     1380
agacccttag cgccgggagt tcccctgaat attcccggga gtcta                    1425
```

<210> SEQ ID NO 55  
<211> LENGTH: 822  
<212> TYPE: DNA  
<213> ORGANISM: Canis familiaris

<400> SEQUENCE: 55

```
atggttctcc tgcctctgcg ctgtctcttc tggggctcct tgttgaccac cgtctaccca    60
gaaccacgca ctgcatgcag agaaaagcaa tacctagtag acagtcagtg ctgtaatatg    120
tgcccaccag gagagaaact ggtgaatgac tgcctacata ccattgacac ggaatgcact    180
cgttgccaaa caggcgaatt cctagacact tggaacgcag agagacactg tcaccagcac    240
aaatactgcg accccaacct agggctccat gtcgagaagg agggcacgtc agaaacagac    300
accacttgca catgcgatga aggtctgcat tgtaccaacg ctgcctgtga gagctgcacc    360
atgcacagcc tgtgccccc tggcctggga gtcaaacaga tcgctacagg gatttctgat    420
accatctgcg atccctgccc catcggcttc ttctccaatg tgtcttctgc tttggaaaag    480 tgtcacccctt ggacaagctg tgaaaccaaa ggcctggtga aggttcaggc gggaactaac    540
aagactgatg ttatctgtgg tccccagcct cggttaagag ccctagtggt ggtccccatc    600
attatgggga tcctgcttgt tgtcctgttg gtgtctgcct gcatccgaaa ggtggtcaag    660
aagccagaga ataaggttat gtatcaggac cctgtggagg acttggagga atttcctatg    720
cccccgcact ccattgctcc ggtgcaagag accttacatg ggtgccagcc cgtcacccag    780
gaggacggca aagagagccg catctccgtg caggagagag tg                       822
```

<210> SEQ ID NO 56
<211> LENGTH: 822
<212> TYPE: DNA
<213> ORGANISM: Canis familiaris

<400> SEQUENCE: 56

```
cactctctcc tgcacggaga tgcggctctc tttgccgtcc tcctgggtga cgggctggca      60
cccatgtaag gtctcttgca ccggagcaat ggagtgcggg ggcataggaa attcctccaa     120
gtcctccaca gggtcctgat acataacctt attctctggc ttcttgacca cctttcggat     180
gcaggcagac accaacagga caacaagcag gatccccata atgatgggga ccaccactag     240
ggctcttaac cgaggctggg gaccacagat aacatcagtc ttgttagttc ccgcctgaac     300
cttcaccagg cctttggttt cacagcttgt ccaagggtga cacttttcca aagcagaaga     360
cacattggag aagaagccga tggggcaggg atcgcagatg gtatcagaaa tccctgtagc     420
gatctgtttg actcccaggc caggggggca caggctgtgc atggtgcagc tctcacaggc     480
agcgttggta caatgcagac cttcatcgca tgtgcaagtg gtgtctgttt ctgacgtgcc     540
ctccttctcg acatggagcc ctaggttggg gtcgcagtat ttgtgctggt gacagtgtct     600
ctctgcgttc caagtgtcta ggaattcgcc tgtttggcaa cgagtgcatt ccgtgtcaat     660
ggtatgtagg cagtcattca ccagtttctc tcctggtggg cacatattac agcactgact     720
gtctactagg tattgctttt ctctgcatgc agtgcgtggt tctgggtaga cggtggtcaa     780
caaggagccc cagaagagac agcgcagagg caggagaacc at                        822
```

<210> SEQ ID NO 57
<211> LENGTH: 765
<212> TYPE: DNA
<213> ORGANISM: Canis familiaris
<220> FEATURE:
<221> NAME/KEY: CDS
<222> LOCATION: (1)..(765)

<400> SEQUENCE: 57

```
cca gaa cca cgc act gca tgc aga gaa aag caa tac cta gta gac agt       48
Pro Glu Pro Arg Thr Ala Cys Arg Glu Lys Gln Tyr Leu Val Asp Ser
1               5                  10                  15 cag tgc tgt aat atg tgc cca cca gga gag aaa ctg gtg aat gac tgc       96
Gln Cys Cys Asn Met Cys Pro Pro Gly Glu Lys Leu Val Asn Asp Cys
            20                  25                  30 cta cat acc att gac acg gaa tgc act cgt tgc caa aca ggc gaa ttc      144
Leu His Thr Ile Asp Thr Glu Cys Thr Arg Cys Gln Thr Gly Glu Phe
        35                  40                  45 cta gac act tgg aac gca gag aga cac tgt cac cag cac aaa tac tgc      192
Leu Asp Thr Trp Asn Ala Glu Arg His Cys His Gln His Lys Tyr Cys
    50                  55                  60 gac ccc aac cta ggg ctc cat gtc gag aag gag ggc acg tca gaa aca      240
Asp Pro Asn Leu Gly Leu His Val Glu Lys Glu Gly Thr Ser Glu Thr
65                  70                  75                  80 gac acc act tgc aca tgc gat gaa ggt ctg cat tgt acc aac gct gcc      288
Asp Thr Thr Cys Thr Cys Asp Glu Gly Leu His Cys Thr Asn Ala Ala
                85                  90                  95 tgt gag agc tgc acc atg cac agc ctg tgc ccc cct ggc ctg gga gtc      336
Cys Glu Ser Cys Thr Met His Ser Leu Cys Pro Pro Gly Leu Gly Val
            100                 105                 110 aaa cag atc gct aca ggg att tct gat acc atc tgc gat ccc tgc ccc      384
Lys Gln Ile Ala Thr Gly Ile Ser Asp Thr Ile Cys Asp Pro Cys Pro
        115                 120                 125
```

```
atc ggc ttc ttc tcc aat gtg tct tct gct ttg gaa aag tgt cac cct      432
Ile Gly Phe Phe Ser Asn Val Ser Ser Ala Leu Glu Lys Cys His Pro
130                 135                 140 tgg aca agc tgt gaa acc aaa ggc ctg gtg aag gtt cag gcg gga act      480
Trp Thr Ser Cys Glu Thr Lys Gly Leu Val Lys Val Gln Ala Gly Thr
145                 150                 155                 160 aac aag act gat gtt atc tgt ggt ccc cag cct cgg tta aga gcc cta      528
Asn Lys Thr Asp Val Ile Cys Gly Pro Gln Pro Arg Leu Arg Ala Leu
                165                 170                 175 gtg gtg gtc ccc atc att atg ggg atc ctg ctt gtt gtc ctg ttg gtg      576
Val Val Val Pro Ile Ile Met Gly Ile Leu Leu Val Val Leu Leu Val
                180                 185                 190 tct gcc tgc atc cga aag gtg gtc aag aag cca gag aat aag gtt atg      624
Ser Ala Cys Ile Arg Lys Val Val Lys Lys Pro Glu Asn Lys Val Met
            195                 200                 205 tat cag gac cct gtg gag gac ttg gag gaa ttt cct atg ccc ccg cac      672
Tyr Gln Asp Pro Val Glu Asp Leu Glu Glu Phe Pro Met Pro Pro His
210                 215                 220 tcc att gct ccg gtg caa gag acc tta cat ggg tgc cag ccc gtc acc      720
Ser Ile Ala Pro Val Gln Glu Thr Leu His Gly Cys Gln Pro Val Thr
225                 230                 235                 240 cag gag gac ggc aaa gag agc cgc atc tcc gtg cag gag aga gtg          765
Gln Glu Asp Gly Lys Glu Ser Arg Ile Ser Val Gln Glu Arg Val
                245                 250                 255

<210> SEQ ID NO 58
<211> LENGTH: 255
<212> TYPE: PRT
<213> ORGANISM: Canis familiaris

<400> SEQUENCE: 58

Pro Glu Pro Arg Thr Ala Cys Arg Glu Lys Gln Tyr Leu Val Asp Ser
1               5                   10                  15

Gln Cys Cys Asn Met Cys Pro Pro Gly Glu Lys Leu Val Asn Asp Cys
                20                  25                  30

Leu His Thr Ile Asp Thr Glu Cys Thr Arg Cys Gln Thr Gly Glu Phe
            35                  40                  45

Leu Asp Thr Trp Asn Ala Glu Arg His Cys His Gln His Lys Tyr Cys
50                  55                  60

Asp Pro Asn Leu Gly Leu His Val Glu Lys Glu Gly Thr Ser Glu Thr
65                  70                  75                  80

Asp Thr Thr Cys Thr Cys Asp Glu Gly Leu His Cys Thr Asn Ala Ala
                85                  90                  95

Cys Glu Ser Cys Thr Met His Ser Leu Cys Pro Pro Gly Leu Gly Val
            100                 105                 110

Lys Gln Ile Ala Thr Gly Ile Ser Asp Thr Ile Cys Asp Pro Cys Pro
        115                 120                 125

Ile Gly Phe Phe Ser Asn Val Ser Ser Ala Leu Glu Lys Cys His Pro
130                 135                 140

Trp Thr Ser Cys Glu Thr Lys Gly Leu Val Lys Val Gln Ala Gly Thr
145                 150                 155                 160

Asn Lys Thr Asp Val Ile Cys Gly Pro Gln Pro Arg Leu Arg Ala Leu
                165                 170                 175

Val Val Val Pro Ile Ile Met Gly Ile Leu Leu Val Val Leu Leu Val
                180                 185                 190

Ser Ala Cys Ile Arg Lys Val Val Lys Lys Pro Glu Asn Lys Val Met
            195                 200                 205

Tyr Gln Asp Pro Val Glu Asp Leu Glu Glu Phe Pro Met Pro Pro His
```

```
                            210                 215                 220
Ser Ile Ala Pro Val Gln Glu Thr Leu His Gly Cys Gln Pro Val Thr
225                 230                 235                 240

Gln Glu Asp Gly Lys Glu Ser Arg Ile Ser Val Gln Glu Arg Val
                245                 250                 255

<210> SEQ ID NO 59
<211> LENGTH: 765
<212> TYPE: DNA
<213> ORGANISM: Canis familiaris

<400> SEQUENCE: 59
cactctctcc tgcacggaga tgcggctctc tttgccgtcc tcctgggtga cgggctggca      60
cccatgtaag gtctcttgca ccggagcaat ggagtgcggg ggcataggaa attcctccaa     120
gtcctccaca gggtcctgat acataacctt attctctggc ttcttgacca cctttcggat     180
gcaggcagac accaacagga caacaagcag gatccccata atgatgggga ccaccactag     240
ggctcttaac cgaggctggg gaccacagat aacatcagtc ttgttagttc ccgcctgaac     300
cttcaccagg cctttggttt cacagcttgt ccaagggtga cacttttcca agcagaaga     360 cacattggag aagaagccga tggggcaggg atcgcagatg gtatcagaaa tccctgtagc     420
gatctgtttg actcccaggc cagggggggca caggctgtgc atggtgcagc tctcacaggc     480
agcgttggta caatgcagac cttcatcgca tgtgcaagtg gtgtctgttt ctgacgtgcc     540
ctccttctcg acatggagcc ctaggttggg gtcgcagtat ttgtgctggt gacagtgtct     600
ctctgcgttc caagtgtcta ggaattcgcc tgtttggcaa cgagtgcatt ccgtgtcaat     660
ggtatgtagg cagtcattca ccagtttctc tcctggtggg cacatattac agcactgact     720
gtctactagg tattgctttt ctctgcatgc agtgcgtggt tctgg                    765

<210> SEQ ID NO 60
<211> LENGTH: 336
<212> TYPE: DNA
<213> ORGANISM: Felis catus
<220> FEATURE:
<221> NAME/KEY: CDS
<222> LOCATION: (1)..(336)

<400> SEQUENCE: 60 aat gtg tca tct gct tcg gaa aag tgt cac cct tgg acg agg tgt gag       48
Asn Val Ser Ser Ala Ser Glu Lys Cys His Pro Trp Thr Arg Cys Glu
1                5                  10                  15 acc aaa ggc ctg gtg gag ctt cag gcg ggg acc aac aag acg gat gcc       96
Thr Lys Gly Leu Val Glu Leu Gln Ala Gly Thr Asn Lys Thr Asp Ala
            20                  25                  30 gtc tgc ggt ttc cag gat cgg ata aga gcc ctg gtg gtg atc ccc atc      144
Val Cys Gly Phe Gln Asp Arg Ile Arg Ala Leu Val Val Ile Pro Ile
        35                  40                  45 acg atg gtg gtc ctg ctt gct gtc ttg ttg gtg tct gcg tat atc aga      192
Thr Met Val Val Leu Leu Ala Val Leu Leu Val Ser Ala Tyr Ile Arg
    50                  55                  60 aag gtg acc aag aag cca gag aat aag gtc ctc cag cct aag gct gtg      240
Lys Val Thr Lys Lys Pro Glu Asn Lys Val Leu Gln Pro Lys Ala Val
65                  70                  75                  80 tcg cag gac cct gtg gag gac ttg gag gtc ctt cct gtc ccc ctc cac      288
Ser Gln Asp Pro Val Glu Asp Leu Glu Val Leu Pro Val Pro Leu His
                85                  90                  95 ccc att gct ccg gtg cag gag acc tta cac ggg tgc cag ccg gtc acc      336
Pro Ile Ala Pro Val Gln Glu Thr Leu His Gly Cys Gln Pro Val Thr
            100                 105                 110
```

<210> SEQ ID NO 61
<211> LENGTH: 112
<212> TYPE: PRT
<213> ORGANISM: Felis catus

<400> SEQUENCE: 61

Asn Val Ser Ser Ala Ser Glu Lys Cys His Pro Trp Thr Arg Cys Glu
1               5                   10                  15

Thr Lys Gly Leu Val Glu Leu Gln Ala Gly Thr Asn Lys Thr Asp Ala
            20                  25                  30

Val Cys Gly Phe Gln Asp Arg Ile Arg Ala Leu Val Val Ile Pro Ile
        35                  40                  45

Thr Met Val Val Leu Leu Ala Val Leu Leu Val Ser Ala Tyr Ile Arg
    50                  55                  60

Lys Val Thr Lys Lys Pro Glu Asn Lys Val Leu Gln Pro Lys Ala Val
65                  70                  75                  80

Ser Gln Asp Pro Val Glu Asp Leu Glu Val Leu Pro Val Pro Leu His
                85                  90                  95

Pro Ile Ala Pro Val Gln Glu Thr Leu His Gly Cys Gln Pro Val Thr
            100                 105                 110

<210> SEQ ID NO 62
<211> LENGTH: 336
<212> TYPE: DNA
<213> ORGANISM: Felis catus

<400> SEQUENCE: 62
ggtgaccggc tggcacccgt gtaaggtctc ctgcaccgga gcaatggggt ggaggggggac      60 aggaaggacc tccaagtcct ccacagggtc ctgcgacaca gccttaggct ggaggacctt     120
attctctggc ttcttggtca cctttctgat atacgcagac accaacaaga cagcaagcag     180
gaccaccatc gtgatgggga tcaccaccag ggctcttatc cgatcctgga aaccgcagac     240
ggcatccgtc ttgttggtcc ccgcctgaag ctccaccagg cctttggtct cacacctcgt     300
ccaagggtga cacttttccg aagcagatga cacatt                              336

<210> SEQ ID NO 63
<211> LENGTH: 390
<212> TYPE: DNA
<213> ORGANISM: Canis familiaris

<400> SEQUENCE: 63
ataagtgagg ctagtagtaa cccagcgtcc gttctgcggt gggcgccaaa agggtactac      60
accataagca gcaacctggt gagcctcgag aatgggaaac agttggccgt gaaaagacaa     120
ggactctatt acgtctatgc ccaagtcacc ttctgctcca atcgggcagc ttcgagtcaa     180
gctccgttcg tcgccagcct atgcctccat tccccgagtg aacggagag agtcttactc     240 cgcgccgcga gctcccgcgg ctcgtccaaa ccttgcggcc aacagtccat ccacttggga     300
ggagtatttg aattgcatcc aggtgcttcg gtgttcgtca acgtgactga tccaagccaa     360
gtgagccacg ggaccggctt cacgtctttt                                      390

<210> SEQ ID NO 64
<211> LENGTH: 1878
<212> TYPE: DNA
<213> ORGANISM: Canis familiaris
<220> FEATURE:
<221> NAME/KEY: CDS
<222> LOCATION: (284)..(1063)

-continued

```
<400> SEQUENCE: 64
aatgtatgga agaagaaact tgtttcttct ttactaacaa aagggaaagc ctggaagtga      60
atgatatggg tataattaaa aaaaaaaaaa aaaaaaaaaa aaaacccttta cgtaactttt    120 tttgctggga gagaagacta cgaagcacat tttccaggaa gtgtgggctg caacgattgt    180
gcgctcttaa ctaatcctga gtaaggtggc cactttgaca gtgttttcat gctgcctctg    240
ccaccttctc ggtctgaaga tatcatttca actctaacac agc atg atc gaa aca      295
                                              Met Ile Glu Thr
                                                1 tat agc caa act gct ccc cga tct gtg gcc act gga cca ccc gtc agt      343
Tyr Ser Gln Thr Ala Pro Arg Ser Val Ala Thr Gly Pro Pro Val Ser
 5              10                  15                  20 atg aaa att ttt atg tat ttg ctt act gtt ttt ctc atc acc cag atg      391
Met Lys Ile Phe Met Tyr Leu Leu Thr Val Phe Leu Ile Thr Gln Met
             25                  30                  35 att gga tcg gca ctc ttt gct gta tat ctt cac aga aga ttg gac aag      439
Ile Gly Ser Ala Leu Phe Ala Val Tyr Leu His Arg Arg Leu Asp Lys
         40                  45                  50 ata gaa gat gaa agg aat ctt tat gaa gat ttt gtg ttc atg aaa acg      487
Ile Glu Asp Glu Arg Asn Leu Tyr Glu Asp Phe Val Phe Met Lys Thr
     55                  60                  65 tta cag aaa tgc aac aaa ggg gag ggg tcc ttg tcc tta ctg aac tgt      535
Leu Gln Lys Cys Asn Lys Gly Glu Gly Ser Leu Ser Leu Leu Asn Cys
 70                  75                  80 gag gaa att aaa agc caa ttt gaa gcc ttt ctc aag gag ata atg cta      583
Glu Glu Ile Lys Ser Gln Phe Glu Ala Phe Leu Lys Glu Ile Met Leu
85                  90                  95                 100 aac aac gaa atg aag aaa gaa gaa aac att gca atg caa aaa ggt gat      631
Asn Asn Glu Met Lys Lys Glu Glu Asn Ile Ala Met Gln Lys Gly Asp
                105                 110                 115 cag gat cct cga att gca gcc cat gtc ata agt gag gct agt agt aac      679
Gln Asp Pro Arg Ile Ala Ala His Val Ile Ser Glu Ala Ser Ser Asn
            120                 125                 130 cca gcg tcc gtt ctg cgg tgg gcg cca aaa ggg tac tac acc ata agc      727
Pro Ala Ser Val Leu Arg Trp Ala Pro Lys Gly Tyr Tyr Thr Ile Ser
        135                 140                 145 agc aac ctg gtg agc ctc gag aat ggg aaa cag ttg gcc gtg aaa aga      775
Ser Asn Leu Val Ser Leu Glu Asn Gly Lys Gln Leu Ala Val Lys Arg
    150                 155                 160 caa gga ctc tat tac gtc tat gcc caa gtc acc ttc tgc tcc aat cgg      823
Gln Gly Leu Tyr Tyr Val Tyr Ala Gln Val Thr Phe Cys Ser Asn Arg
165                 170                 175                 180 gca gct tcg agt caa gct ccg ttc gtc gcc agc cta tgc ctc cat tcc      871
Ala Ala Ser Ser Gln Ala Pro Phe Val Ala Ser Leu Cys Leu His Ser
                185                 190                 195 ccg agt gga acg gag aga gtc tta ctc cgc gcc gcg agc tcc cgc ggc      919
Pro Ser Gly Thr Glu Arg Val Leu Leu Arg Ala Ala Ser Ser Arg Gly
            200                 205                 210 tcg tcc aaa cct tgc ggc caa cag tcc atc cac ttg gga gga gta ttt      967
Ser Ser Lys Pro Cys Gly Gln Gln Ser Ile His Leu Gly Gly Val Phe
        215                 220                 225 gaa ttg cat cca ggt gct tcg gtg ttc gtc aac gtg act gat cca agc     1015
Glu Leu His Pro Gly Ala Ser Val Phe Val Asn Val Thr Asp Pro Ser
    230                 235                 240 caa gtg agc cac ggg acc ggc ttc acg tct ttt ggc tta ctc aaa ctc     1063
Gln Val Ser His Gly Thr Gly Phe Thr Ser Phe Gly Leu Leu Lys Leu
245                 250                 255                 260 tgagtgctgg cacctcacag gctgcagctc agctcctgtt ggtggtcttc gtaatacggc   1123
```

```
cgagcagtta agaccaccac ccctgttgaa ctgcctattt ataaccctag gatcctcctc    1183
gtggagaact atttattata cacccccagg cgtggagggc tgcaagaagg gaatgacagg    1243 gcggggcag cgccaacagg ccccggtcgg taagagttga tattctggaa gcagccgccc     1303
cactgatgca gacatccaga gagtcccatg aaaaagacga gactattatg cacagattga    1363
atcctcagta aacggcagat aattagtcca gtttcgtttt gtttctttgc atgcagtgtc    1423
tttcactgga gaatgtactc gatttccccg cgaagatgct gaagggcaac agggagcctc    1483
agctcacagt cagttacggt tgacccgggg tccccggggc cccgatggag gggacaggct    1543
ccagaaagtc tgatggcgcg gagaactgga aaaccctgcc cccaccagcc accctgacac    1603
tcattctctc cctcctccgc ccccctcccc cacagtcag gctgttgcta atcggttatc     1663
ttatttcaac cctgttgcct ctccaccagt gtaggcggga ggagagagca gaggctgccc    1723
actcctcctc ctgaaatgac tgtatttaaa ggaaatctct cctacctacc tgcagtctcc    1783
attgtttcca gagtgaactt gtgattatct tgttatttat ttttgaata ataaagcgcc     1843 cttaacgtta aaaaaaaaaa aaaaaaaaa aaaaa                                1878

<210> SEQ ID NO 65
<211> LENGTH: 260
<212> TYPE: PRT
<213> ORGANISM: Canis familiaris

<400> SEQUENCE: 65

Met Ile Glu Thr Tyr Ser Gln Thr Ala Pro Arg Ser Val Ala Thr Gly
1               5                   10                  15

Pro Pro Val Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu Tyr Glu Asp Phe Val
        50                  55                  60

Phe Met Lys Thr Leu Gln Lys Cys Asn Lys Gly Glu Gly Ser Leu Ser
65                  70                  75                  80

Leu Leu Asn Cys Glu Glu Ile Lys Ser Gln Phe Glu Ala Phe Leu Lys
                85                  90                  95

Glu Ile Met Leu Asn Asn Glu Met Lys Lys Glu Asn Ile Ala Met
                100                 105                 110

Gln Lys Gly Asp Gln Asp Pro Arg Ile Ala Ala His Val Ile Ser Glu
        115                 120                 125

Ala Ser Ser Asn Pro Ala Ser Val Leu Arg Trp Ala Pro Lys Gly Tyr
    130                 135                 140

Tyr Thr Ile Ser Ser Asn Leu Val Ser Leu Glu Asn Gly Lys Gln Leu
145                 150                 155                 160

Ala Val Lys Arg Gln Gly Leu Tyr Tyr Val Tyr Ala Gln Val Thr Phe
                165                 170                 175

Cys Ser Asn Arg Ala Ala Ser Ser Gln Ala Pro Phe Val Ala Ser Leu
            180                 185                 190

Cys Leu His Ser Pro Ser Gly Thr Glu Arg Val Leu Leu Arg Ala Ala
        195                 200                 205

Ser Ser Arg Gly Ser Ser Lys Pro Cys Gly Gln Gln Ser Ile His Leu
    210                 215                 220

Gly Gly Val Phe Glu Leu His Pro Gly Ala Ser Val Phe Val Asn Val
225                 230                 235                 240
```

```
Thr Asp Pro Ser Gln Val Ser His Gly Thr Gly Phe Thr Ser Phe Gly
            245                 250                 255
Leu Leu Lys Leu
        260
```

<210> SEQ ID NO 66
<211> LENGTH: 1878
<212> TYPE: DNA
<213> ORGANISM: Canis familiaris

<400> SEQUENCE: 66

```
ttttttttttt tttttttttt tttttttaacg ttaagggcgc tttattattc aaaaaataaa      60
taacaagata atcacaagtt cactctggaa acaatggaga ctgcaggtag gtaggagaga     120
tttcctttaa atacagtcat ttcaggagga ggagtgggca gcctctgctc tctcctcccg     180
cctacactgg tggagaggca cagggttga  aataagataa ccgattagca acagcctgac     240
tgtgggggga gggggggcgga ggaggggagag aatgagtgtc agggtggctg gtgggggcag     300
ggttttccag ttctccgcgc catcagactt tctggagcct gtcccctcca tcggggcccc     360
ggggaccccg ggtcaaccgt aactgactgt gagctgaggc tccctgttgc ccttcagcat     420
cttcgcgggg aaatcgagta cattctccag tgaaagacac tgcatgcaaa gaaacaaaac     480
gaaactggac taattatctg ccgtttactg aggattcaat ctgtgcataa tagtctcgtc     540
tttttcatgg gactctctgg atgtctgcat cagtggggcg gctgcttcca gaatatcaac     600
tcttaccgac cggggcctgt tggcgctgcc ccgccctgt cattcccttc ttgcagccct     660
ccacgcctgg gggtgtataa taaatagttc tccacgagga ggatcctagg gttataaata     720
ggcagttcaa caggggtggt ggtcttaact gctcggccgt attacgaaga ccaccaacag     780
gagctgagct gcagcctgtg aggtgccagc actcagagtt tgagtaagcc aaaagacgtg     840
aagccggtcc cgtggctcac ttggcttgga tcagtcacgt tgacgaacac cgaagcacct     900
ggatgcaatt caaatactcc tcccaagtgg atggactgtt ggccgcaagg tttggacgag     960
ccgcggggagc tcgcgcgcg gagtaagact ctctccgttc cactcgggga atggaggcat    1020
aggctggcga cgaacggagc ttgactcgaa gctgcccgat tggagcagaa ggtgacttgg    1080
gcatagacgt aatagagtcc ttgtcttttc acggccaact gtttcccatt ctcgaggctc    1140
accaggttgc tgcttatggt gtagtaccct tttggcgccc accgcagaac ggacgctggg    1200
ttactactag cctcacttat gacatgggct gcaattcgag gatcctgatc accttttttgc    1260
attgcaatgt tttcttcttt ttcatttcg ttgtttagca ttatctcctt gagaaaggct    1320
tcaaattggc ttttaatttc ctcacagttc agtaaggaca aggacccctc cccctttgttg    1380
catttctgta acgttttcat gaacacaaaa tcttcataaa gattcctttc atcttctatc    1440
ttgtccaatc ttctgtgaag atatacagca aagagtgccg atccaatcat ctgggtgatg    1500
agaaaaacag taagcaaata cataaaaatt ttcatactga cgggtggtcc agtggccaca    1560
gatcggggag cagtttggct atatgtttcg atcatgctgt gttagagttg aaatgatatc    1620
ttcagaccga gaaggtggca gaggcagcat gaaaacactg tcaaagtggc caccttactc    1680
aggattagtt aagagcgcac aatcgttgca gcccacactt cctggaaaat gtgcttcgta    1740
gtcttctctc ccagcaaaaa aagttacgta aaggttttt tttttttttt tttttttttt    1800
taattatacc catatcattc acttccaggc tttcccttt gttagtaaag aagaaacaag    1860
tttcttcttc catacatt                                                 1878
```

<210> SEQ ID NO 67

```
<211> LENGTH: 780
<212> TYPE: DNA
<213> ORGANISM: Canis familiaris

<400> SEQUENCE: 67
atgatcgaaa catatagcca aactgctccc cgatctgtgg ccactggacc acccgtcagt        60
atgaaaattt ttatgtattt gcttactgtt tttctcatca cccagatgat tggatcggca       120
ctctttgctg tatatcttca cagaagattg acaagatag aagatgaaag gaatctttat        180
gaagattttg tgttcatgaa acgttacag aaatgcaaca aaggggaggg gtccttgtcc        240
ttactgaact gtgaggaaat taaaagccaa tttgaagcct ttctcaagga gataatgcta       300
aacaacgaaa tgaagaaaga agaaaacatt gcaatgcaaa aaggtgatca ggatcctcga       360
attgcagccc atgtcataag tgaggctagt agtaacccag cgtccgttct gcggtgggcg       420
ccaaaagggt actacaccat aagcagcaac ctggtgagcc tcgagaatgg gaaacagttg       480
gccgtgaaaa gacaaggact ctattacgtc tatgcccaag tcaccttctg ctccaatcgg       540
gcagcttcga gtcaagctcc gttcgtcgcc agcctatgcc tccattcccc gagtggaacg       600
gagagagtct tactccgcgc cgcgagctcc cgcggctcgt ccaaaccttg cggccaacag       660
tccatccact tgggaggagt atttgaattg catccaggtg cttcggtgtt cgtcaacgtg       720
actgatccaa gccaagtgag ccacgggacc ggcttcacgt cttttggctt actcaaactc       780

<210> SEQ ID NO 68
<211> LENGTH: 780
<212> TYPE: DNA
<213> ORGANISM: Canis familiaris

<400> SEQUENCE: 68
gagtttgagt aagccaaaag acgtgaagcc ggtcccgtgg ctcacttggc ttggatcagt        60
cacgttgacg aacaccgaag cacctggatg caattcaaat actcctccca agtggatgga       120
ctgttggccg caaggtttgg acgagccgcg ggagctcgcg gcgcggagta agactctctc       180
cgttccactc ggggaatgga ggcataggct ggcgacgaac ggagcttgac tcgaagctgc       240
ccgattggag cagaaggtga cttgggcata gacgtaatag agtccttgtc ttttcacggc       300
caactgtttc ccattctcga ggctcaccag gttgctgctt atggtgtagt accctttggg       360
cgcccaccgc agaacggacg ctgggttact actagcctca cttatgacat gggctgcaat       420
tcgaggatcc tgatcaccct tttgcattgc aatgttttct tctttcttca tttcgttgtt       480
tagcattatc tccttgagaa aggcttcaaa ttggctttta atttcctcac agttcagtaa       540
ggacaaggac ccctcccctt tgttgcattt ctgtaacgtt ttcatgaaca caaaatcttc       600
ataaagattc ctttcatctt ctatcttgtc caatcttctg tgaagatata cagcaaagag       660
tgccgatcca atcatctggg tgatgagaaa aacagtaagc aaatacataa aaattttcat       720
actgacgggt ggtccagtgg ccacagatcg gggagcagtt tggctatatg tttcgatcat       780

<210> SEQ ID NO 69
<211> LENGTH: 633
<212> TYPE: DNA
<213> ORGANISM: Canis familiaris
<220> FEATURE:
<221> NAME/KEY: CDS
<222> LOCATION: (1)..(633)

<400> SEQUENCE: 69 ttg gac aag ata gaa gat gaa agg aat ctt tat gaa gat ttt gtg ttc         48
Leu Asp Lys Ile Glu Asp Glu Arg Asn Leu Tyr Glu Asp Phe Val Phe
1               5                   10                  15
```

```
atg aaa acg tta cag aaa tgc aac aaa ggg gag ggg tcc ttg tcc tta      96
Met Lys Thr Leu Gln Lys Cys Asn Lys Gly Glu Gly Ser Leu Ser Leu
         20                  25                  30 ctg aac tgt gag gaa att aaa agc caa ttt gaa gcc ttt ctc aag gag     144
Leu Asn Cys Glu Glu Ile Lys Ser Gln Phe Glu Ala Phe Leu Lys Glu
             35                  40                  45 ata atg cta aac aac gaa atg aag aaa gaa gaa aac att gca atg caa     192
Ile Met Leu Asn Asn Glu Met Lys Lys Glu Glu Asn Ile Ala Met Gln
 50                  55                  60 aaa ggt gat cag gat cct cga att gca gcc cat gtc ata agt gag gct     240
Lys Gly Asp Gln Asp Pro Arg Ile Ala Ala His Val Ile Ser Glu Ala
 65                  70                  75                  80 agt agt aac cca gcg tcc gtt ctg cgg tgg gcg cca aaa ggg tac tac     288
Ser Ser Asn Pro Ala Ser Val Leu Arg Trp Ala Pro Lys Gly Tyr Tyr
                 85                  90                  95 acc ata agc agc aac ctg gtg agc ctc gag aat ggg aaa cag ttg gcc     336
Thr Ile Ser Ser Asn Leu Val Ser Leu Glu Asn Gly Lys Gln Leu Ala
                100                 105                 110 gtg aaa aga caa gga ctc tat tac gtc tat gcc caa gtc acc ttc tgc     384
Val Lys Arg Gln Gly Leu Tyr Tyr Val Tyr Ala Gln Val Thr Phe Cys
            115                 120                 125 tcc aat cgg gca gct tcg agt caa gct ccg ttc gtc gcc agc cta tgc     432
Ser Asn Arg Ala Ala Ser Ser Gln Ala Pro Phe Val Ala Ser Leu Cys
130                 135                 140 ctc cat tcc ccg agt gga acg gag aga gtc tta ctc cgc gcc gcg agc     480
Leu His Ser Pro Ser Gly Thr Glu Arg Val Leu Leu Arg Ala Ala Ser
145                 150                 155                 160 tcc cgc ggc tcg tcc aaa cct tgc ggc caa cag tcc atc cac ttg gga     528
Ser Arg Gly Ser Ser Lys Pro Cys Gly Gln Gln Ser Ile His Leu Gly
                165                 170                 175 gga gta ttt gaa ttg cat cca ggt gct tcg gtg ttc gtc aac gtg act     576
Gly Val Phe Glu Leu His Pro Gly Ala Ser Val Phe Val Asn Val Thr
            180                 185                 190 gat cca agc caa gtg agc cac ggg acc ggc ttc acg tct ttt ggc tta     624
Asp Pro Ser Gln Val Ser His Gly Thr Gly Phe Thr Ser Phe Gly Leu
        195                 200                 205 ctc aaa ctc                                                          633
Leu Lys Leu
    210
```

<210> SEQ ID NO 70
<211> LENGTH: 211
<212> TYPE: PRT
<213> ORGANISM: Canis familiaris

<400> SEQUENCE: 70

```
Leu Asp Lys Ile Glu Asp Glu Arg Asn Leu Tyr Glu Asp Phe Val Phe
1               5                   10                  15

Met Lys Thr Leu Gln Lys Cys Asn Lys Gly Glu Gly Ser Leu Ser Leu
            20                  25                  30

Leu Asn Cys Glu Glu Ile Lys Ser Gln Phe Glu Ala Phe Leu Lys Glu
        35                  40                  45

Ile Met Leu Asn Asn Glu Met Lys Lys Glu Glu Asn Ile Ala Met Gln
    50                  55                  60

Lys Gly Asp Gln Asp Pro Arg Ile Ala Ala His Val Ile Ser Glu Ala
65                  70                  75                  80

Ser Ser Asn Pro Ala Ser Val Leu Arg Trp Ala Pro Lys Gly Tyr Tyr
                85                  90                  95

Thr Ile Ser Ser Asn Leu Val Ser Leu Glu Asn Gly Lys Gln Leu Ala
```

```
                        100                 105                 110
        Val Lys Arg Gln Gly Leu Tyr Tyr Val Tyr Ala Gln Val Thr Phe Cys
                    115                 120                 125

Ser Asn Arg Ala Ala Ser Ser Gln Ala Pro Phe Val Ala Ser Leu Cys
                130                 135                 140

Leu His Ser Pro Ser Gly Thr Glu Arg Val Leu Leu Arg Ala Ala Ser
        145                 150                 155                 160

Ser Arg Gly Ser Ser Lys Pro Cys Gly Gln Gln Ser Ile His Leu Gly
                        165                 170                 175

Gly Val Phe Glu Leu His Pro Gly Ala Ser Val Phe Val Asn Val Thr
                    180                 185                 190

Asp Pro Ser Gln Val Ser His Gly Thr Gly Phe Thr Ser Phe Gly Leu
                    195                 200                 205

Leu Lys Leu
            210

<210> SEQ ID NO 71
<211> LENGTH: 633
<212> TYPE: DNA
<213> ORGANISM: Canis familiaris

<400> SEQUENCE: 71
gagtttgagt aagccaaaag acgtgaagcc ggtcccgtgg ctcacttggc ttggatcagt      60
cacgttgacg aacaccgaag cacctggatg caattcaaat actcctccca gtggatgga     120 ctgttggccg caaggtttgg acgagccgcg ggagctcgcg gcgcggagta agactctctc    180
cgttccactc ggggaatgga ggcataggct ggcgacgaac ggagcttgac tcgaagctgc    240
ccgattggag cagaaggtga cttgggcata gacgtaatag agtccttgtc ttttcacggc    300
caactgtttc ccattctcga ggctcaccag gttgctgctt atggtgtagt accctttttgg   360 cgcccaccgc agaacggacg ctgggttact actagcctca cttatgacat gggctgcaat    420
tcgaggatcc tgatcacctt tttgcattgc aatgttttct tctttcttca tttcgttgtt    480
tagcattatc tccttgagaa aggcttcaaa ttggctttta atttcctcac agttcagtaa    540
ggacaaggac ccctccccctt tgttgcattt ctgtaacgtt ttcatgaaca caaaatcttc   600
ataaagattc ctttcatctt ctatcttgtc caa                                  633

<210> SEQ ID NO 72
<211> LENGTH: 885
<212> TYPE: DNA
<213> ORGANISM: Felis catus
<220> FEATURE:
<221> NAME/KEY: CDS
<222> LOCATION: (29)..(808)

<400> SEQUENCE: 72
gaagatacca tttcaacttt aacacagc atg atc gaa aca tat agc caa act          52
                              Met Ile Glu Thr Tyr Ser Gln Thr
                                1               5 gct ccc cgc tcc gtg gcc cct gga cca ccc gtc agt atg aaa att ttt       100
Ala Pro Arg Ser Val Ala Pro Gly Pro Pro Val Ser Met Lys Ile Phe
    10                  15                  20 atg tat tta ctt act gtg ttt ctc atc acc cag atg att ggg tca gca       148
Met Tyr Leu Leu Thr Val Phe Leu Ile Thr Gln Met Ile Gly Ser Ala
25                  30                  35                  40 ctc ttt gct gtg tat ctt cac aga aga ctg gac aag ata gaa gat gaa       196
Leu Phe Ala Val Tyr Leu His Arg Arg Leu Asp Lys Ile Glu Asp Glu
                45                  50                  55
```

| | | |
|---|---|---|
| agg aat ctt tat gaa gat ttt gtg ttc atg aaa aca tta cag aaa tgc<br>Arg Asn Leu Tyr Glu Asp Phe Val Phe Met Lys Thr Leu Gln Lys Cys<br>        60                      65                  70 | | 244 |
| aac aaa gga gag ggg gcc tta tcc tta ctg aac tgt gag gaa att aaa<br>Asn Lys Gly Glu Gly Ala Leu Ser Leu Leu Asn Cys Glu Glu Ile Lys<br>        75                      80                  85 | | 292 |
| agc cgg ttt gaa gcc ttt ctc aag gag ata atg cta aac aaa gaa acg<br>Ser Arg Phe Glu Ala Phe Leu Lys Glu Ile Met Leu Asn Lys Glu Thr<br>    90                      95                  100 | | 340 |
| aag aaa gaa aaa aat gtt gca atg caa aaa ggc gac cag gat cct cga<br>Lys Lys Glu Lys Asn Val Ala Met Gln Lys Gly Asp Gln Asp Pro Arg<br>105                      110                  115                  120 | | 388 |
| gtt gca gca cat gtc ata agt gag gcc agc agt agc aca gcg tct gtt<br>Val Ala Ala His Val Ile Ser Glu Ala Ser Ser Ser Thr Ala Ser Val<br>                      125                  130                  135 | | 436 |
| ctc cag tgg gcc ccc aaa ggc tac tac acc ata agc agc aac ttg gtg<br>Leu Gln Trp Ala Pro Lys Gly Tyr Tyr Thr Ile Ser Ser Asn Leu Val<br>              140                  145                  150 | | 484 |
| acc ctc gag aac ggg aag cag ctg gcc gtt aaa aga caa gga ctc tat<br>Thr Leu Glu Asn Gly Lys Gln Leu Ala Val Lys Arg Gln Gly Leu Tyr<br>            155                  160                  165 | | 532 |
| tat atc tac gcc caa gtc acc ttc tgt tcc aat cgg gaa gct tcg agt<br>Tyr Ile Tyr Ala Gln Val Thr Phe Cys Ser Asn Arg Glu Ala Ser Ser<br>170                      175                  180 | | 580 |
| caa gct ccg ttc ata gcc agc ctc tgc ctg cat tcc ccg agt gga tcc<br>Gln Ala Pro Phe Ile Ala Ser Leu Cys Leu His Ser Pro Ser Gly Ser<br>185                      190                  195                  200 | | 628 |
| gag aga gtc tta ctc aga gct gca aat gcc cgc agt tcc tcc aaa ccc<br>Glu Arg Val Leu Leu Arg Ala Ala Asn Ala Arg Ser Ser Ser Lys Pro<br>                      205                  210                  215 | | 676 |
| tgt ggg cag caa tcc att cac ttg gga gga gtc ttc gaa ctg cat cca<br>Cys Gly Gln Gln Ser Ile His Leu Gly Gly Val Phe Glu Leu His Pro<br>            220                  225                  230 | | 724 |
| ggt gct tcg gtg ttc gtg aac gtg act gat ccg agc caa gtg agc cac<br>Gly Ala Ser Val Phe Val Asn Val Thr Asp Pro Ser Gln Val Ser His<br>              235                  240                  245 | | 772 |
| ggg acg ggc ttc acg tct ttt ggc ttg ctc aaa ctc tgaacactgg<br>Gly Thr Gly Phe Thr Ser Phe Gly Leu Leu Lys Leu<br>        250                      255                  260 | | 818 |
| cacctcgcag gccgcgaggc ctgcaggccg cggctgagct cacgctggga gtcttcacaa | | 878 |
| tacagca | | 885 |

```
<210> SEQ ID NO 73
<211> LENGTH: 260
<212> TYPE: PRT
<213> ORGANISM: Felis catus

<400> SEQUENCE: 73
```

Met Ile Glu Thr Tyr Ser Gln Thr Ala Pro Arg Ser Val Ala Pro Gly
1               5                   10                  15

Pro Pro Val Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu Tyr Glu Asp Phe Val
        50                  55                  60

Phe Met Lys Thr Leu Gln Lys Cys Asn Lys Gly Glu Gly Ala Leu Ser
65                  70                  75                  80

Leu Leu Asn Cys Glu Glu Ile Lys Ser Arg Phe Glu Ala Phe Leu Lys

```
                    85                  90                  95
Glu Ile Met Leu Asn Lys Glu Thr Lys Glu Lys Asn Val Ala Met
                100                 105                 110

Gln Lys Gly Asp Gln Asp Pro Arg Val Ala Ala His Val Ile Ser Glu
            115                 120                 125

Ala Ser Ser Thr Ala Ser Val Leu Gln Trp Ala Pro Lys Gly Tyr
    130                 135                 140

Tyr Thr Ile Ser Ser Asn Leu Val Thr Leu Glu Asn Gly Lys Gln Leu
145                 150                 155                 160

Ala Val Lys Arg Gln Gly Leu Tyr Tyr Ile Tyr Ala Gln Val Thr Phe
                165                 170                 175

Cys Ser Asn Arg Glu Ala Ser Ser Gln Ala Pro Phe Ile Ala Ser Leu
            180                 185                 190

Cys Leu His Ser Pro Gly Ser Glu Arg Val Leu Leu Arg Ala Ala
        195                 200                 205

Asn Ala Arg Ser Ser Ser Lys Pro Cys Gly Gln Gln Ser Ile His Leu
        210                 215                 220

Gly Gly Val Phe Glu Leu His Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260

<210> SEQ ID NO 74
<211> LENGTH: 885
<212> TYPE: DNA
<213> ORGANISM: Felis catus

<400> SEQUENCE: 74
tgctgtatta tgaagactcc cagcgtgagc tcagccgcgg cctgcaggcc tcgcggcctg      60
cgaggtgcca gtgttcagag tttgagcaag ccaaaagacg tgaagcccgt cccgtggctc     120
acttggctcg gatcagtcac gttcacgaac accgaagcac ctggatgcag ttcgaagact     180
cctcccaagt gaatggattg ctgcccacag ggtttggagg aactgcgggc atttgcagct     240
ctgagtaaga ctctctcgga tccactcggg gaatgcaggc agaggctggc tatgaacgga     300
gcttgactcg aagcttcccg attggaacag aaggtgactt gggcgtagat ataatagagt     360
ccttgtcttt taacggccag ctgcttcccg ttctcgaggg tcaccaagtt gctgcttatg     420
gtgtagtagc ctttgggggc ccactggaga acagacgctg tgctactgct ggcctcactt     480
atgacatgtg ctgcaactcg aggatcctgg tcgcctttt gcattgcaac atttttttct      540
ttcttcgttt ctttgtttag cattatctcc ttgagaaagg cttcaaaccg gcttttaatt     600
tcctcacagt tcagtaagga taaggccccc tctcctttgt tgcatttctg taatgttttc     660
atgaacacaa atcttcata aagattcctt tcatcttcta tcttgtccag tcttctgtga      720
agatacacag caaagagtgc tgacccaatc atctgggtga tgagaaacac agtaagtaaa     780
tacataaaaa ttttcatact gacgggtggt ccagggccca cggagcgggg agcagtttgg     840
ctatatgttt cgatcatgct gtgttaaagt tgaaatggta tcttc                    885

<210> SEQ ID NO 75
<211> LENGTH: 780
<212> TYPE: DNA
<213> ORGANISM: Felis catus

<400> SEQUENCE: 75
```

```
atgatcgaaa catatagcca aactgctccc cgctccgtgg ccctggacc accgtcagt        60 atgaaaattt ttatgtattt acttactgtg tttctcatca cccagatgat tgggtcagca      120
ctctttgctg tgtatcttca cagaagactg acaagataga agatgaaag gaatctttat       180 gaagattttg tgttcatgaa acattacag aaatgcaaca aggagagggg ggccttatcc       240
ttactgaact gtgaggaaat taaaagccgg tttgaagcct ttctcaagga gataatgcta     300
aacaaagaaa cgaagaaaga aaaaatgtt gcaatgcaaa aaggcgacca ggatcctcga      360
gttgcagcac atgtcataag tgaggccagc agtagcacag cgtctgttct ccagtgggcc     420
cccaaaggct actacaccat aagcagcaac ttggtgaccc tcgagaacgg gaagcagctg    480
gccgttaaaa gacaaggact ctattatatc tacgcccaag tcaccttctg ttccaatcgg    540
gaagcttcga gtcaagctcc gttcatagcc agcctctgcc tgcattcccc gagtggatcc    600
gagagagtct tactcagagc tgcaaatgcc cgcagttcct ccaaaccctg tgggcagcaa    660
tccattcact tgggaggagt cttcgaactg catccaggtg cttcggtgtt cgtgaacgtg    720
actgatccga gccaagtgag ccacgggacg ggcttcacgt cttttggctt gctcaaactc   780
```

<210> SEQ ID NO 76
<211> LENGTH: 780
<212> TYPE: DNA
<213> ORGANISM: Felis catus
<400> SEQUENCE: 76

```
gagtttgagc aagccaaaag acgtgaagcc cgtcccgtgg ctcacttggc tcggatcagt      60
cacgttcacg aacaccgaag cacctggatg cagttcgaag actcctccca agtgaatgga    120
ttgctgccca cagggtttgg aggaactgcg ggcatttgca gctctgagta agactctctc    180
ggatccactc ggggaatgca ggcagaggct ggctatgaac ggagcttgac tcgaagcttc   240
ccgattggaa cagaaggtga cttgggcgta gatataatag agtccttgtc ttttaacggc   300
cagctgcttc ccgttctcga gggtcaccaa gttgctgctt atggtgtagt agcctttggg   360
ggcccactgg agaacagacg ctgtgctact gctggcctca cttatgacat gtgctgcaac   420
tcgaggatcc tggtcgcctt tttgcattgc aacatttttt tctttcttcg tttctttgtt   480
tagcattatc tccttgagaa aggcttcaaa ccggcttta atttcctcac agttcagtaa    540
ggataaggcc ccctctcctt tgttgcattt ctgtaatgtt ttcatgaaca caaaatcttc    600
ataaagattc ctttcatctt ctatcttgtc cagtcttctg tgaagataca cagcaaagag   660
tgctgaccca atcatctggg tgatgagaaa cacagtaagt aaatacataa aaatttcat    720 actgacgggt ggtccagggg ccacggagcg gggagcagtt tggctatatg tttcgatcat   780
```

<210> SEQ ID NO 77
<211> LENGTH: 633
<212> TYPE: DNA
<213> ORGANISM: Felis catus
<220> FEATURE:
<221> NAME/KEY: CDS
<222> LOCATION: (1)..(633)

<400> SEQUENCE: 77

```
ctg gac aag ata gaa gat gaa agg aat ctt tat gaa gat ttt gtg ttc        48
Leu Asp Lys Ile Glu Asp Glu Arg Asn Leu Tyr Glu Asp Phe Val Phe
1               5                   10                  15 atg aaa aca tta cag aaa tgc aac aaa gga gag ggg gcc tta tcc tta       96
Met Lys Thr Leu Gln Lys Cys Asn Lys Gly Glu Gly Ala Leu Ser Leu
            20                  25                  30
```

| | | |
|---|---|---|
| ctg aac tgt gag gaa att aaa agc cgg ttt gaa gcc ttt ctc aag gag<br>Leu Asn Cys Glu Glu Ile Lys Ser Arg Phe Glu Ala Phe Leu Lys Glu<br>35              40                  45 | | 144 |
| ata atg cta aac aaa gaa acg aag aaa gaa aaa aat gtt gca atg caa<br>Ile Met Leu Asn Lys Glu Thr Lys Lys Glu Lys Asn Val Ala Met Gln<br>50              55                  60 | | 192 |
| aaa ggc gac cag gat cct cga gtt gca gca cat gtc ata agt gag gcc<br>Lys Gly Asp Gln Asp Pro Arg Val Ala Ala His Val Ile Ser Glu Ala<br>65              70                  75              80 | | 240 |
| agc agt agc aca gcg tct gtt ctc cag tgg gcc ccc aaa ggc tac tac<br>Ser Ser Ser Thr Ala Ser Val Leu Gln Trp Ala Pro Lys Gly Tyr Tyr<br>85              90                  95 | | 288 |
| acc ata agc agc aac ttg gtg acc ctc gag aac ggg aag cag ctg gcc<br>Thr Ile Ser Ser Asn Leu Val Thr Leu Glu Asn Gly Lys Gln Leu Ala<br>100             105                 110 | | 336 |
| gtt aaa aga caa gga ctc tat tat atc tac gcc caa gtc acc ttc tgt<br>Val Lys Arg Gln Gly Leu Tyr Tyr Ile Tyr Ala Gln Val Thr Phe Cys<br>115             120                 125 | | 384 |
| tcc aat cgg gaa gct tcg agt caa gct ccg ttc ata gcc agc ctc tgc<br>Ser Asn Arg Glu Ala Ser Ser Gln Ala Pro Phe Ile Ala Ser Leu Cys<br>130             135                 140 | | 432 |
| ctg cat tcc ccg agt gga tcc gag aga gtc tta ctc aga gct gca aat<br>Leu His Ser Pro Ser Gly Ser Glu Arg Val Leu Leu Arg Ala Ala Asn<br>145             150                 155             160 | | 480 |
| gcc cgc agt tcc tcc aaa ccc tgt ggg cag caa tcc att cac ttg gga<br>Ala Arg Ser Ser Ser Lys Pro Cys Gly Gln Gln Ser Ile His Leu Gly<br>165                 170                 175 | | 528 |
| gga gtc ttc gaa ctg cat cca ggt gct tcg gtg ttc gtg aac gtg act<br>Gly Val Phe Glu Leu His Pro Gly Ala Ser Val Phe Val Asn Val Thr<br>180             185                 190 | | 576 |
| gat ccg agc caa gtg agc cac ggg acg ggc ttc acg tct ttt ggc ttg<br>Asp Pro Ser Gln Val Ser His Gly Thr Gly Phe Thr Ser Phe Gly Leu<br>195             200                 205 | | 624 |
| ctc aaa ctc<br>Leu Lys Leu<br>210 | | 633 |

```
<210> SEQ ID NO 78
<211> LENGTH: 211
<212> TYPE: PRT
<213> ORGANISM: Felis catus

<400> SEQUENCE: 78

Leu Asp Lys Ile Glu Asp Glu Arg Asn Leu Tyr Glu Asp Phe Val Phe
1               5                   10                  15

Met Lys Thr Leu Gln Lys Cys Asn Lys Gly Glu Gly Ala Leu Ser Leu
                20                  25                  30

Leu Asn Cys Glu Glu Ile Lys Ser Arg Phe Glu Ala Phe Leu Lys Glu
            35                  40                  45

Ile Met Leu Asn Lys Glu Thr Lys Lys Glu Lys Asn Val Ala Met Gln
        50                  55                  60

Lys Gly Asp Gln Asp Pro Arg Val Ala Ala His Val Ile Ser Glu Ala
65                  70                  75                  80

Ser Ser Ser Thr Ala Ser Val Leu Gln Trp Ala Pro Lys Gly Tyr Tyr
                85                  90                  95

Thr Ile Ser Ser Asn Leu Val Thr Leu Glu Asn Gly Lys Gln Leu Ala
            100                 105                 110

Val Lys Arg Gln Gly Leu Tyr Tyr Ile Tyr Ala Gln Val Thr Phe Cys
        115                 120                 125
```

```
Ser Asn Arg Glu Ala Ser Ser Gln Ala Pro Phe Ile Ala Ser Leu Cys
    130                 135                 140
Leu His Ser Pro Ser Gly Ser Glu Arg Val Leu Leu Arg Ala Ala Asn
145                 150                 155                 160
Ala Arg Ser Ser Lys Pro Cys Gly Gln Gln Ser Ile His Leu Gly
                165                 170                 175
Gly Val Phe Glu Leu His Pro Gly Ala Ser Val Phe Val Asn Val Thr
            180                 185                 190
Asp Pro Ser Gln Val Ser His Gly Thr Gly Phe Thr Ser Phe Gly Leu
        195                 200                 205
Leu Lys Leu
    210

<210> SEQ ID NO 79
<211> LENGTH: 633
<212> TYPE: DNA
<213> ORGANISM: Felis catus

<400> SEQUENCE: 79
gagtttgagc aagccaaaag acgtgaagcc cgtcccgtgg ctcacttggc tcggatcagt      60
cacgttcacg aacaccgaag cacctggatg cagttcgaag actcctccca agtgaatgga     120
ttgctgccca cagggtttgg aggaactgcg ggcatttgca gctctgagta agactctctc     180
ggatccactc ggggaatgca ggcagaggct ggctatgaac ggagcttgac tcgaagcttc     240
ccgattggaa cagaaggtga cttgggcgta gatataatag agtccttgtc ttttaacggc     300
cagctgcttc ccgttctcga gggtcaccaa gttgctgctt atggtgtagt agcctttggg     360
ggcccactgg agaacagacg ctgtgctact gctggcctca cttatgacat gtgctgcaac     420
tcgaggatcc tggtcgcctt tttgcattgc aacatttttt tctttcttcg tttctttgtt     480
tagcattatc tccttgagaa aggcttcaaa ccggctttta atttcctcac agttcagtaa     540
ggataaggcc ccctctcctt tgttgcattt ctgtaatgtt tcatgaaca caaaatcttc      600 ataaagattc ctttcatctt ctatcttgtc cag                                 633

<210> SEQ ID NO 80
<211> LENGTH: 610
<212> TYPE: DNA
<213> ORGANISM: Canis familiaris
<220> FEATURE:
<221> NAME/KEY: CDS
<222> LOCATION: (29)..(430)

<400> SEQUENCE: 80
caaggcaaac actgaacatt tcagagct atg aga atg ctt ctg aat ttg agt        52
                             Met Arg Met Leu Leu Asn Leu Ser
                               1               5 ttg cta gct ctt ggg gct gcc tat gtt tct gcc ttt gct gta gaa aat       100
Leu Leu Ala Leu Gly Ala Ala Tyr Val Ser Ala Phe Ala Val Glu Asn
        10                  15                  20 ccc atg aat aga ctg gtg gca gag acc ttg aca ctg ctc tcc act cat      148
Pro Met Asn Arg Leu Val Ala Glu Thr Leu Thr Leu Leu Ser Thr His
25                  30                  35                  40 cga act tgg ctg ata ggc gat ggg aac ctg atg att cct act cct gaa      196
Arg Thr Trp Leu Ile Gly Asp Gly Asn Leu Met Ile Pro Thr Pro Glu
                45                  50                  55 aat aaa aat cac caa ctg tgc att aaa gaa gtt ttt cag ggt ata gac      244
Asn Lys Asn His Gln Leu Cys Ile Lys Glu Val Phe Gln Gly Ile Asp
            60                  65                  70 aca ttg aag aac caa act gcc cac ggg gag gct gtg gat aaa cta ttc      292
```

```
         Thr Leu Lys Asn Gln Thr Ala His Gly Glu Ala Val Asp Lys Leu Phe
                  75                  80                  85 caa aac ttg tct tta ata aaa gaa cac ata gag cgc caa aaa aaa agg          340
Gln Asn Leu Ser Leu Ile Lys Glu His Ile Glu Arg Gln Lys Lys Arg
         90                  95                 100 tgt gca gga gaa aga tgg aga gtg aca aag ttc cta gac tac ctg caa          388
Cys Ala Gly Glu Arg Trp Arg Val Thr Lys Phe Leu Asp Tyr Leu Gln
105                 110                 115                 120 gta ttt ctt ggt gta ata aac acc gag tgg aca ccg gaa agt                  430
Val Phe Leu Gly Val Ile Asn Thr Glu Trp Thr Pro Glu Ser
                125                 130 tgagaacaaa ccggcttatt gtagtggaag attttggaga agaatggttt tttggcgatg        490
agaatgaggg ccaaccaaca gtagggactt aatggccagt ataactaagc ttcagagaca        550
aagtaaatat ttcaggcatc ctactacttt atcacttcac acagatgaaa tatatttgag        610

<210> SEQ ID NO 81
<211> LENGTH: 134
<212> TYPE: PRT
<213> ORGANISM: Canis familiaris

<400> SEQUENCE: 81

Met Arg Met Leu Leu Asn Leu Ser Leu Leu Ala Leu Gly Ala Ala Tyr
1               5                   10                  15

Val Ser Ala Phe Ala Val Glu Asn Pro Met Asn Arg Leu Val Ala Glu
            20                  25                  30

Thr Leu Thr Leu Leu Ser Thr His Arg Thr Trp Leu Ile Gly Asp Gly
        35                  40                  45

Asn Leu Met Ile Pro Thr Pro Glu Asn Lys Asn His Gln Leu Cys Ile
    50                  55                  60

Lys Glu Val Phe Gln Gly Ile Asp Thr Leu Lys Asn Gln Thr Ala His
65                  70                  75                  80

Gly Glu Ala Val Asp Lys Leu Phe Gln Asn Leu Ser Leu Ile Lys Glu
                85                  90                  95

His Ile Glu Arg Gln Lys Lys Arg Cys Ala Gly Glu Arg Trp Arg Val
            100                 105                 110

Thr Lys Phe Leu Asp Tyr Leu Gln Val Phe Leu Gly Val Ile Asn Thr
        115                 120                 125

Glu Trp Thr Pro Glu Ser
    130

<210> SEQ ID NO 82
<211> LENGTH: 610
<212> TYPE: DNA
<213> ORGANISM: Canis familiaris

<400> SEQUENCE: 82
ctcaaatata tttcatctgt gtgaagtgat aaagtagtag gatgcctgaa atatttactt         60
tgtctctgaa gcttagttat actggccatt aagtccctac tgttggttgg ccctcattct        120
catcgccaaa aaaccattct tctccaaaat cttccactac aataagccgg tttgttctca        180
actttccggt gtccactcgg tgtttattac accaagaaat acttgcaggt agtctaggaa        240
ctttgtcact ctccatcttt ctcctgcaca cctttttttt tggcgctcta tgtgttcttt        300
tattaaagac aagttttgga atagtttatc cacagcctcc ccgtgggcag tttggttctt        360
caatgtgtct atacccctgaa aaacttcttt aatgcacagt tggtgatttt tattttcagg       420
agtaggaatc atcaggttcc catcgcctat cagccaagtt cgatgagtgg agagcagtgt        480
```

```
caaggtctct gccaccagtc tattcatggg attttctaca gcaaaggcag aaacataggc      540
agccccaaga gctagcaaac tcaaattcag aagcattctc atagctctga atgttcagt      600 gtttgccttg                                                             610
```

<210> SEQ ID NO 83
<211> LENGTH: 402
<212> TYPE: DNA
<213> ORGANISM: Canis familiaris

<400> SEQUENCE: 83

```
atgagaatgc ttctgaattt gagtttgcta gctcttgggg ctgcctatgt ttctgccttt       60
gctgtagaaa atcccatgaa tagactggtg gcagagacct tgacactgct ctccactcat      120
cgaacttggc tgataggcga tgggaacctg atgattccta ctcctgaaaa taaaaatcac      180
caactgtgca ttaaagaagt ttttcagggt atagacacat tgaagaacca aactgcccac      240
ggggaggctg tggataaact attccaaaac ttgtctttaa taaaagaaca catagagcgc      300
caaaaaaaaa ggtgtgcagg agaaagatgg agagtgacaa agttcctaga ctacctgcaa      360
gtatttcttg gtgtaataaa caccgagtgg acaccggaaa gt                         402
```

<210> SEQ ID NO 84
<211> LENGTH: 402
<212> TYPE: DNA
<213> ORGANISM: Canis familiaris

<400> SEQUENCE: 84

```
actttccggt gtccactcgg tgtttattac accaagaaat acttgcaggt agtctaggaa       60
ctttgtcact ctccatcttt ctcctgcaca cctttttttt tggcgctcta tgtgttcttt      120
tattaaagac aagttttgga atagtttatc cacagcctcc ccgtgggcag tttggttctt      180
caatgtgtct atacccctgaa aaacttcttt aatgcacagt tggtgatttt tattttcagg     240
agtaggaatc atcaggttcc catcgcctat cagccaagtt cgatgagtgg agagcagtgt      300
caaggtctct gccaccagtc tattcatggg attttctaca gcaaaggcag aaacataggc      360
agccccaaga gctagcaaac tcaaattcag aagcattctc at                         402
```

<210> SEQ ID NO 85
<211> LENGTH: 345
<212> TYPE: DNA
<213> ORGANISM: Canis familiaris
<220> FEATURE:
<221> NAME/KEY: CDS
<222> LOCATION: (1)..(345)

<400> SEQUENCE: 85

```
ttt gct gta gaa aat ccc atg aat aga ctg gtg gca gag acc ttg aca        48
Phe Ala Val Glu Asn Pro Met Asn Arg Leu Val Ala Glu Thr Leu Thr
1               5                   10                  15 ctg ctc tcc act cat cga act tgg ctg ata ggc gat ggg aac ctg atg        96
Leu Leu Ser Thr His Arg Thr Trp Leu Ile Gly Asp Gly Asn Leu Met
            20                  25                  30 att cct act cct gaa aat aaa aat cac caa ctg tgc att aaa gaa gtt       144
Ile Pro Thr Pro Glu Asn Lys Asn His Gln Leu Cys Ile Lys Glu Val
        35                  40                  45 ttt cag ggt ata gac aca ttg aag aac caa act gcc cac ggg gag gct       192
Phe Gln Gly Ile Asp Thr Leu Lys Asn Gln Thr Ala His Gly Glu Ala
    50                  55                  60 gtg gat aaa cta ttc caa aac ttg tct tta ata aaa gaa cac ata gag       240
Val Asp Lys Leu Phe Gln Asn Leu Ser Leu Ile Lys Glu His Ile Glu
65                  70                  75                  80
```

```
cgc caa aaa aaa agg tgt gca gga gaa aga tgg aga gtg aca aag ttc    288
Arg Gln Lys Lys Arg Cys Ala Gly Glu Arg Trp Arg Val Thr Lys Phe
             85                  90                  95 cta gac tac ctg caa gta ttt ctt ggt gta ata aac acc gag tgg aca    336
Leu Asp Tyr Leu Gln Val Phe Leu Gly Val Ile Asn Thr Glu Trp Thr
            100                 105                 110 ccg gaa agt                                                        345
Pro Glu Ser
        115

<210> SEQ ID NO 86
<211> LENGTH: 115
<212> TYPE: PRT
<213> ORGANISM: Canis familiaris

<400> SEQUENCE: 86

Phe Ala Val Glu Asn Pro Met Asn Arg Leu Val Ala Glu Thr Leu Thr
1               5                   10                  15

Leu Leu Ser Thr His Arg Thr Trp Leu Ile Gly Asp Gly Asn Leu Met
            20                  25                  30

Ile Pro Thr Pro Glu Asn Lys Asn His Gln Leu Cys Ile Lys Glu Val
            35                  40                  45

Phe Gln Gly Ile Asp Thr Leu Lys Asn Gln Thr Ala His Gly Glu Ala
        50                  55                  60

Val Asp Lys Leu Phe Gln Asn Leu Ser Leu Ile Lys Glu His Ile Glu
65                  70                  75                  80

Arg Gln Lys Lys Arg Cys Ala Gly Glu Arg Trp Arg Val Thr Lys Phe
                85                  90                  95

Leu Asp Tyr Leu Gln Val Phe Leu Gly Val Ile Asn Thr Glu Trp Thr
            100                 105                 110

Pro Glu Ser
        115

<210> SEQ ID NO 87
<211> LENGTH: 345
<212> TYPE: DNA
<213> ORGANISM: Canis familiaris

<400> SEQUENCE: 87
actttccggt gtccactcgg tgtttattac accaagaaat acttgcaggt agtctaggaa     60
ctttgtcact ctccatcttt ctcctgcaca ccttttttt tggcgctcta tgtgttcttt    120
tattaaagac aagttttgga atagtttatc cacagcctcc ccgtgggcag tttggttctt    180
caatgtgtct ataccctgaa aaacttcttt aatgcacagt tggtgatttt tattttcagg    240
agtaggaatc atcaggttcc catcgcctat cagccaagtt cgatgagtgg agagcagtgt    300
caaggtctct gccaccagtc tattcatggg attttctaca gcaaa                   345

<210> SEQ ID NO 88
<211> LENGTH: 166
<212> TYPE: DNA
<213> ORGANISM: Canis familiaris

<400> SEQUENCE: 88
ctcagcttag gccagcctac gacctgcctg ctcttccctc gctcctcctg cattggctct     60
gggctccatg gcgctctggt tgactgtggt cattgctctc acctgcctcg gtggccttgc    120
ctccccgagc cctgtgactc cctcccccaac cctcaaggag ctcatt                  166
```

<210> SEQ ID NO 89
<211> LENGTH: 272
<212> TYPE: DNA
<213> ORGANISM: Canis familiaris

<400> SEQUENCE: 89

```
tggccttgcc tccccgagcc ctgtgactcc ctccccaacc ctcaaggagc tcattgagga      60
gctggtcaac atcacccaga atcaggcatc cctctgcaac ggcagcatgg tgtggagcgt     120
caacctgacc gccggcatgt actgcgcagc tctagaatct ctgatcaatg tctccgactg     180
cagcgccatc caaaggaccc agaggatgct gaaagcactg tgctctcaaa agcccgcggc     240
agggcagatt tccagtgaac gcagccgaga ca                                   272
```

<210> SEQ ID NO 90
<211> LENGTH: 278
<212> TYPE: DNA
<213> ORGANISM: Canis familiaris

<400> SEQUENCE: 90

```
atggcgctct ggttgactgt ggtcattgct ctcacctgcc tcggtggcct tgcctccccg      60
agccctgtga ctccctcccc aaccctcaag gagctcattg aggagctggt caacatcacc     120
cagaatcagg catccctctg caacggcagc atggtgtgga gcgtcaacct gaccgccggc     180
atgtactgcg cagctctaga atctctgatc aatgtctccg actgcagcgc catccaaagg     240
acccagagga tgctgaaagc actgtgctct caaaagcc                             278
```

<210> SEQ ID NO 91
<211> LENGTH: 1302
<212> TYPE: DNA
<213> ORGANISM: Canis familiaris
<220> FEATURE:
<221> NAME/KEY: CDS
<222> LOCATION: (52)..(444)

<400> SEQUENCE: 91

```
ctacgacctg cctgctcttc cctcgctcct cctgcattgg ctctgggctc c atg gcg        57
                                                        Met Ala
                                                          1 ctc tgg ttg act gtg gtc att gct ctc acc tgc ctc ggt ggc ctt gcc       105
Leu Trp Leu Thr Val Val Ile Ala Leu Thr Cys Leu Gly Gly Leu Ala
        5                  10                  15 tcc ccg agc cct gtg act ccc tcc cca acc ctc aag gag ctc att gag       153
Ser Pro Ser Pro Val Thr Pro Ser Pro Thr Leu Lys Glu Leu Ile Glu
 20                  25                  30 gag ctg gtc aac atc acc cag aat cag gca tcc ctc tgc aac ggc agc       201
Glu Leu Val Asn Ile Thr Gln Asn Gln Ala Ser Leu Cys Asn Gly Ser
 35                  40                  45                  50 atg gtg tgg agc gtc aac ctg acc gcc ggc atg tac tgc gca gct cta       249
Met Val Trp Ser Val Asn Leu Thr Ala Gly Met Tyr Cys Ala Ala Leu
                 55                  60                  65 gaa tct ctg atc aat gtc tcc gac tgc agc gcc atc caa agg acc cag       297
Glu Ser Leu Ile Asn Val Ser Asp Cys Ser Ala Ile Gln Arg Thr Gln
             70                  75                  80 agg atg ctg aaa gca ctg tgc tct caa aag ccc gcg gca ggg cag att       345
Arg Met Leu Lys Ala Leu Cys Ser Gln Lys Pro Ala Ala Gly Gln Ile
         85                  90                  95 tcc agt gaa cgc agc cga gac acc aaa att gaa gtg atc cag ttg gtg       393
Ser Ser Glu Arg Ser Arg Asp Thr Lys Ile Glu Val Ile Gln Leu Val
    100                 105                 110 aaa aac ctg ctc acc tat gta agg gga gtt tat cgc cat gga aat ttc       441
Lys Asn Leu Leu Thr Tyr Val Arg Gly Val Tyr Arg His Gly Asn Phe
```

```
                 115                 120                 125                 130 aga tgaagcatga aaacttagca tccttatctg tagacccaga cctgaccact           494
Arg taagttccag attcattttt ctttccgacg tcacaaattt cttagggagg tggggggggg    554
ggagaaccat ttcctcagct gggacctcag cctgcaccgc ctgcctccat ggagctgagc    614
ccagccaccc ctgccttggt gcatggggcc cagccgggtg ccctcctcc gtctgcactt     674 catcaacgct gagggaaagc actgcatccc atgactgtcc cctcctcaga gcaaagtgca    734
gcattacagt ggaggcagat atgtgtggga ggggtcttg ctgtacctgg gagtggcaca     794
gacatgtttc ttcttagcct tatttattat tgtgtgttat ttaaacaagt gtctttgttt    854
gtgctgggga cagggagtgg cttggagctg ggggcccagt gactcgggtt tagagagtcc    914
ctgggaataa gcactgtgtg taaaattctg ctacctcact gggatcctgg ggccgacaca    974
ggggacagga gaagggtca gagatgctgc tcttgtctgc cactcagcag ctggccctca    1034
gccaagcagt aatttattgt ttttccttgt atttaaagtt aagaaataaa atatgttatc   1094
aaagagttaa taatatatag aagagtagcc taaaaggctg catttggtgt gtgtggccag   1154
gccggggcgg gtggggggga gggtgttgtc actgaatgtg ctctttcact gactttgtca   1214
aactggaagc cagaaataaa gatggtgaca agagaaaaaa aaaaaaaaaa aaaaaaaaa    1274 aaaaaaaaaa aaaaaaaaaa aaaaaaaa                                     1302

<210> SEQ ID NO 92
<211> LENGTH: 131
<212> TYPE: PRT
<213> ORGANISM: Canis familiaris

<400> SEQUENCE: 92

Met Ala Leu Trp Leu Thr Val Val Ile Ala Leu Thr Cys Leu Gly Gly
 1               5                  10                  15

Leu Ala Ser Pro Ser Pro Val Thr Pro Ser Pro Thr Leu Lys Glu Leu
             20                  25                  30

Ile Glu Glu Leu Val Asn Ile Thr Gln Asn Gln Ala Ser Leu Cys Asn
         35                  40                  45

Gly Ser Met Val Trp Ser Val Asn Leu Thr Ala Gly Met Tyr Cys Ala
     50                  55                  60

Ala Leu Glu Ser Leu Ile Asn Val Ser Asp Cys Ser Ala Ile Gln Arg
 65                  70                  75                  80

Thr Gln Arg Met Leu Lys Ala Leu Cys Ser Gln Lys Pro Ala Ala Gly
                 85                  90                  95

Gln Ile Ser Ser Glu Arg Ser Arg Asp Thr Lys Ile Glu Val Ile Gln
            100                 105                 110

Leu Val Lys Asn Leu Leu Thr Tyr Val Arg Gly Val Tyr Arg His Gly
        115                 120                 125

Asn Phe Arg
    130

<210> SEQ ID NO 93
<211> LENGTH: 1302
<212> TYPE: DNA
<213> ORGANISM: Canis familiaris

<400> SEQUENCE: 93
tttttttttt tttttttttt tttttttttt tttttttttt tttttttttt ttttctcttg     60
tcaccatctt tatttctggc ttccagtttg acaaagtcag tgaaagagca cattcagtga    120
```

```
caacaccctc ccccccaccc gccccggcct ggccacacac accaaatgca gccttttagg      180
ctactcttct atatattatt aactctttga taacatattt tatttcttaa ctttaaatac      240
aaggaaaaac aataaattac tgcttggctg agggccagct gctgagtggc agacaagagc      300
agcatctctg accctttctc ctgtcccctg tgtcggcccc aggatcccag tgaggtagca      360
gaattttaca cacagtgctt attcccaggg actctctaaa cccgagtcac tgggccccca      420
gctccaagcc actccctgtc cccagcacaa acaaagacac ttgtttaaat aacacacaat      480
aataaataag gctaagaaga aacatgtctg tgccactccc aggtacagca agacccctc       540
ccacacatat ctgcctccac tgtaatgctg cactttgctc tgaggagggg acagtcatgg      600
gatgcagtgc tttccctcag cgttgatgaa gtgcagacgg aggagggcca cccggctggg      660
ccccatgcac caaggcaggg gtggctgggc tcagctccat ggaggcaggc ggtgcaggct      720
gaggtcccag ctgaggaaat ggttctcccc cccccccacc tccctaagaa atttgtgacg      780
tcggaaagaa aaatgaatct ggaacttaag tggtcaggtc tgggtctaca gataaggatg      840
ctaagttttc atgcttcatc tgaaatttcc atggcgataa actccccta  cataggtgag      900
caggtttttc accaactgga tcacttcaat tttggtgtct cggctgcgtt cactggaaat      960
ctgccctgcc gcgggctttt gagagcacag tgctttcagc atcctctggg tcctttggat     1020
ggcgctgcag tcggagacat tgatcagaga ttctagagct cgcagtaca tgccggcgt      1080
caggttgacg ctccacacca tgctgccgtt gcagagggat gcctgattct gggtgatgtt     1140
gaccagctcc tcaatgagct ccttgagggt tggggaggga gtcacagggc tcggggaggc     1200
aaggccaccg aggcaggtga gagcaatgac cacagtcaac cagagcgcca tggagcccag     1260
agccaatgca ggaggagcga gggaagagca ggcaggtcgt ag                         1302

<210> SEQ ID NO 94
<211> LENGTH: 393
<212> TYPE: DNA
<213> ORGANISM: Canis familiaris

<400> SEQUENCE: 94
atggcgctct ggttgactgt ggtcattgct ctcacctgcc tcggtggcct tgcctccccg       60
agccctgtga ctccctcccc aaccctcaag agctcattg aggagctggt caacatcacc       120
cagaatcagg catccctctg caacggcagc atggtgtgga cgtcaacct gaccgccggc       180
atgtactgcg cagctctaga atctctgatc aatgtctccg actgcagcgc catccaaagg      240
acccagagga tgctgaaagc actgtgctct caaaagcccg cggcagggca gatttccagt      300
gaacgcagcc gagacaccaa aattgaagtg atccagttgg tgaaaaacct gctcacctat      360
gtaaggggag tttatcgcca tggaaatttc aga                                   393

<210> SEQ ID NO 95
<211> LENGTH: 393
<212> TYPE: DNA
<213> ORGANISM: Canis familiaris

<400> SEQUENCE: 95
tctgaaattt ccatggcgat aaactcccct tacataggtg agcaggtttt tcaccaactg       60
gatcacttca ttttggtgt ctcggctgcg ttcactggaa atctgccctg ccgcgggctt      120
ttgagagcac agtgctttca gcatcctctg gtcctttgg atggcgctgc agtcggagac      180
attgatcaga gattctagag ctgcgcagta catgccggcg tcaggttga cgctccacac      240
catgctgccg ttgcagaggg atgcctgatt ctgggtgatg ttgaccagct cctcaatgag      300
```

```
ctccttgagg gttggggagg gagtcacagg gctcggggag gcaaggccac cgaggcaggt    360
gagagcaatg accacagtca accagagcgc cat                                 393

<210> SEQ ID NO 96
<211> LENGTH: 333
<212> TYPE: DNA
<213> ORGANISM: Canis familiaris
<220> FEATURE:
<221> NAME/KEY: CDS
<222> LOCATION: (1)..(333)

<400> SEQUENCE: 96 agc cct gtg act ccc tcc cca acc ctc aag gag ctc att gag gag ctg     48
Ser Pro Val Thr Pro Ser Pro Thr Leu Lys Glu Leu Ile Glu Glu Leu
1               5                   10                  15 gtc aac atc acc cag aat cag gca tcc ctc tgc aac ggc agc atg gtg     96
Val Asn Ile Thr Gln Asn Gln Ala Ser Leu Cys Asn Gly Ser Met Val
            20                  25                  30 tgg agc gtc aac ctg acc gcc ggc atg tac tgc gca gct cta gaa tct    144
Trp Ser Val Asn Leu Thr Ala Gly Met Tyr Cys Ala Ala Leu Glu Ser
        35                  40                  45 ctg atc aat gtc tcc gac tgc agc gcc atc caa agg acc cag agg atg    192
Leu Ile Asn Val Ser Asp Cys Ser Ala Ile Gln Arg Thr Gln Arg Met
    50                  55                  60 ctg aaa gca ctg tgc tct caa aag ccc gcg gca ggg cag att tcc agt    240
Leu Lys Ala Leu Cys Ser Gln Lys Pro Ala Ala Gly Gln Ile Ser Ser
65                  70                  75                  80 gaa cgc agc cga gac acc aaa att gaa gtg atc cag ttg gtg aaa aac    288
Glu Arg Ser Arg Asp Thr Lys Ile Glu Val Ile Gln Leu Val Lys Asn
                85                  90                  95 ctg ctc acc tat gta agg gga gtt tat cgc cat gga aat ttc aga        333
Leu Leu Thr Tyr Val Arg Gly Val Tyr Arg His Gly Asn Phe Arg
            100                 105                 110

<210> SEQ ID NO 97
<211> LENGTH: 111
<212> TYPE: PRT
<213> ORGANISM: Canis familiaris

<400> SEQUENCE: 97

Ser Pro Val Thr Pro Ser Pro Thr Leu Lys Glu Leu Ile Glu Glu Leu
1               5                   10                  15

Val Asn Ile Thr Gln Asn Gln Ala Ser Leu Cys Asn Gly Ser Met Val
            20                  25                  30

Trp Ser Val Asn Leu Thr Ala Gly Met Tyr Cys Ala Ala Leu Glu Ser
        35                  40                  45

Leu Ile Asn Val Ser Asp Cys Ser Ala Ile Gln Arg Thr Gln Arg Met
    50                  55                  60

Leu Lys Ala Leu Cys Ser Gln Lys Pro Ala Ala Gly Gln Ile Ser Ser
65                  70                  75                  80

Glu Arg Ser Arg Asp Thr Lys Ile Glu Val Ile Gln Leu Val Lys Asn
                85                  90                  95

Leu Leu Thr Tyr Val Arg Gly Val Tyr Arg His Gly Asn Phe Arg
            100                 105                 110

<210> SEQ ID NO 98
<211> LENGTH: 333
<212> TYPE: DNA
<213> ORGANISM: Canis familiaris

<400> SEQUENCE: 98
```

```
tctgaaattt ccatggcgat aaactcccct tacataggtg agcaggtttt tcaccaactg    60
gatcacttca attttggtgt ctcggctgcg ttcactggaa atctgccctg ccgcgggctt   120
ttgagagcac agtgctttca gcatcctctg ggtcctttgg atggcgctgc agtcggagac   180
attgatcaga gattctagag ctgcgcagta catgccggcg gtcaggttga cgctccacac   240
catgctgccg ttgcagaggg atgcctgatt ctgggtgatg ttgaccagct cctcaatgag   300
ctccttgagg gttggggagg gagtcacagg gct                                333
```

<210> SEQ ID NO 99
<211> LENGTH: 1269
<212> TYPE: DNA
<213> ORGANISM: Canis familiaris
<220> FEATURE:
<221> NAME/KEY: CDS
<222> LOCATION: (57)..(446)

<400> SEQUENCE: 99

```
ccagcctacg acctgcctgc tcttccctcg ctcctcctgc attggctctg gctcc atg     59
                                                              Met
                                                              1 gcg ctc tgg ttg act gtg gtc att gct ctc acc tgc ctc ggt ggc ctt    107
Ala Leu Trp Leu Thr Val Val Ile Ala Leu Thr Cys Leu Gly Gly Leu
            5                  10                  15 gcc tcc ccg agc cct gtg act ccc tcc cca acc ctc aag gag ctc att    155
Ala Ser Pro Ser Pro Val Thr Pro Ser Pro Thr Leu Lys Glu Leu Ile
         20                  25                  30 gag gag ctg gtc aac atc acc cag aat cag gca tcc ctc tgc aac ggc    203
Glu Glu Leu Val Asn Ile Thr Gln Asn Gln Ala Ser Leu Cys Asn Gly
     35                  40                  45 agc atg gtg tgg agc gtc aac ctg acc gcc ggc atg tac tgc gca gct    251
Ser Met Val Trp Ser Val Asn Leu Thr Ala Gly Met Tyr Cys Ala Ala
 50                  55                  60                  65 cta gaa tct ctg atc aat gtc tcc gac tgc agc gcc atc caa agg acc    299
Leu Glu Ser Leu Ile Asn Val Ser Asp Cys Ser Ala Ile Gln Arg Thr
                 70                  75                  80 cag agg atg ctg aaa gca ctg tgc tct caa aag ccc gcg gca ggg att    347
Gln Arg Met Leu Lys Ala Leu Cys Ser Gln Lys Pro Ala Ala Gly Ile
             85                  90                  95 tcc agt gaa cgc agc cga gac acc aaa att gaa gtg atc cag ttg gtg    395
Ser Ser Glu Arg Ser Arg Asp Thr Lys Ile Glu Val Ile Gln Leu Val
        100                 105                 110 aaa aac ctg ctc acc tat gta agg gga gtt tat cgc cat gga aat ttc    443
Lys Asn Leu Leu Thr Tyr Val Arg Gly Val Tyr Arg His Gly Asn Phe
    115                 120                 125 aga tgaagcatga aaacttagca tccttatctg tagacccaga cctgaccact          496
Arg
130 taagttccag attcattttt ctttccgacg tcacaaattt cttagggagg tggggggggg   556 ggagaaccat ttcctcagct gggacctcag cctgcaccgc ctgcctccat ggagctgagc   616 ccagccaccc ctgccttggt gcatggggcc cagccgggtg gccctcctcc gtctgcactt   676 catcaacgct gagggaaagc actgcatccc atgactgtcc cctcctcaga gcaaagtgca   736 gcattacagt ggaggcagat atgtgtggga gggggtcttg ctgtacctgg gagtggcaca   796 gacatgtttc ttcttagcct tatttattat tgtgtgttat ttaaacaagt gtctttgttt   856 gtgctgggga cagggagtgg cttggagctg ggggcccagt gactcgggtt tagagagtcc   916 ctgggaataa gcactgtgtg taaaattctg ctacctcact gggatcctgg ggccgacaca   976 ggggacagga gaaagggtca gagatgctgc tcttgtctgc cactcagcag ctggccctca  1036
```

```
gccaagcagt aatttattgt ttttccttgt atttaaagtt aagaaataaa atatgttatc    1096
aaagagttaa taatatatag aagagtagcc taaaaggctg catttggtgt gtgtggccag    1156 gccgggcgg gtgggggga gggtgttgtc actgaatgtg ctctttcact gactttgtca     1216
aactggaagc cagaaataaa gatggtgaca agagaaaaaa aaaaaaaaaa aaa           1269
```

<210> SEQ ID NO 100
<211> LENGTH: 130
<212> TYPE: PRT
<213> ORGANISM: Canis familiaris

<400> SEQUENCE: 100

```
Met Ala Leu Trp Leu Thr Val Val Ile Ala Leu Thr Cys Leu Gly Gly
1               5                   10                  15

Leu Ala Ser Pro Ser Pro Val Thr Pro Ser Pro Thr Leu Lys Glu Leu
            20                  25                  30

Ile Glu Glu Leu Val Asn Ile Thr Gln Asn Gln Ala Ser Leu Cys Asn
        35                  40                  45

Gly Ser Met Val Trp Ser Val Asn Leu Thr Ala Gly Met Tyr Cys Ala
    50                  55                  60

Ala Leu Glu Ser Leu Ile Asn Val Ser Asp Cys Ser Ala Ile Gln Arg
65                  70                  75                  80

Thr Gln Arg Met Leu Lys Ala Leu Cys Ser Gln Lys Pro Ala Ala Gly
                85                  90                  95

Ile Ser Ser Glu Arg Ser Arg Asp Thr Lys Ile Glu Val Ile Gln Leu
            100                 105                 110

Val Lys Asn Leu Leu Thr Tyr Val Arg Gly Val Tyr Arg His Gly Asn
        115                 120                 125

Phe Arg
    130
```

<210> SEQ ID NO 101
<211> LENGTH: 1269
<212> TYPE: DNA
<213> ORGANISM: Canis familiaris

<400> SEQUENCE: 101

```
tttttttttt ttttttttc tcttgtcacc atctttattt ctggcttcca gtttgacaaa     60
gtcagtgaaa gagcacattc agtgacaaca ccctcccccc cacccgcccc ggcctggcca   120
cacacaccaa atgcagcctt ttaggctact cttctatata ttattaactc tttgataaca   180
tattttattt cttaacttta aatacaagga aaaacaataa attactgctt ggctgagggc   240
cagctgctga gtggcagaca agagcagcat ctctgaccct ttctcctgtc ccctgtgtcg   300
gccccaggat cccagtgagg tagcagaatt ttacacacag tgcttattcc cagggactct   360
ctaaacccga gtcactgggc cccagctcc aagccactcc ctgtcccag cacaaacaaa     420 gacacttgtt taaataacac acaataataa ataaggctaa gaagaaacat gtctgtgcca   480
ctcccaggta cagcaagacc ccctcccaca catatctgcc tccactgtaa tgctgcactt   540
tgctctgagg aggggacagt catgggatgc agtgctttcc ctcagcgttg atgaagtgca   600
gacggaggag ggccacccgg ctgggcccca tgcaccaagg caggggtggc tgggctcagc   660
tccatggagg caggcggtgc aggctgaggt cccagctgag gaaatggttc tccccccccc   720
ccacctccct aagaaatttg tgacgtcgga agaaaaatg aatctggaac ttaagtggtc    780
aggtctgggt ctacagataa ggatgctaag ttttcatgct tcatctgaaa tttccatggc   840
```

-continued

```
gataaactcc ccttacatag gtgagcaggt ttttcaccaa ctggatcact tcaattttgg      900
tgtctcggct gcgttcactg gaaatccctg ccgcgggctt ttgagagcac agtgctttca      960
gcatcctctg gtcctttgg atggcgctgc agtcggagac attgatcaga gattctagag      1020
ctgcgcagta catgccggcg gtcaggttga cgctccacac catgctgccg ttgcagaggg      1080
atgcctgatt ctgggtgatg ttgaccagct cctcaatgag ctccttgagg gttggggagg      1140
gagtcacagg gctcggggag gcaaggccac cgaggcaggt gagagcaatg accacagtca      1200
accagagcgc catggagccc agagccaatg caggaggagc gagggaagag caggcaggtc      1260
gtaggctgg                                                             1269
```

<210> SEQ ID NO 102
<211> LENGTH: 390
<212> TYPE: DNA
<213> ORGANISM: Canis familiaris

<400> SEQUENCE: 102

```
atggcgctct ggttgactgt ggtcattgct ctcacctgcc tcggtggcct tgcctccccg      60
agccctgtga ctccctcccc aaccctcaag gagctcattg aggagctggt caacatcacc      120
cagaatcagg catccctctg caacggcagc atggtgtgga gcgtcaacct gaccgccggc      180
atgtactgcg cagctctaga atctctgatc aatgtctccg actgcagcgc catccaaagg      240
acccagagga tgctgaaagc actgtgctct caaaagcccg cggcagggat ttccagtgaa      300
cgcagccgag acaccaaaat tgaagtgatc cagttggtga aaaacctgct cacctatgta      360
aggggagttt atcgccatgg aaatttcaga                                      390
```

<210> SEQ ID NO 103
<211> LENGTH: 390
<212> TYPE: DNA
<213> ORGANISM: Canis familiaris

<400> SEQUENCE: 103

```
tctgaaattt ccatggcgat aaactcccct tacataggtg agcaggtttt caccaactg      60 gatcacttca attttggtgt ctcggctgcg ttcactggaa atccctgccg cgggcttttg      120
agagcacagt gctttcagca tcctctgggt cctttggatg gcgctgcagt cggagacatt      180
gatcagagat tctagagctg cgcagtacat gccggcggtc aggttgacgc tccacaccat      240
gctgccgttg cagagggatg cctgattctg ggtgatgttg accagctcct caatgagctc      300
cttgagggtt ggggagggag tcacagggct cggggaggca aggccaccga ggcaggtgag      360
agcaatgacc acagtcaacc agagcgccat                                      390
```

<210> SEQ ID NO 104
<211> LENGTH: 330
<212> TYPE: DNA
<213> ORGANISM: Canis familiaris
<220> FEATURE:
<221> NAME/KEY: CDS
<222> LOCATION: (1)..(330)

<400> SEQUENCE: 104

```
agc cct gtg act ccc tcc cca acc ctc aag gag ctc att gag gag ctg      48
Ser Pro Val Thr Pro Ser Pro Thr Leu Lys Glu Leu Ile Glu Glu Leu
1               5                   10                  15 gtc aac atc acc cag aat cag gca tcc ctc tgc aac ggc agc atg gtg      96
Val Asn Ile Thr Gln Asn Gln Ala Ser Leu Cys Asn Gly Ser Met Val
            20                  25                  30 tgg agc gtc aac ctg acc gcc ggc atg tac tgc gca gct cta gaa tct     144
Trp Ser Val Asn Leu Thr Ala Gly Met Tyr Cys Ala Ala Leu Glu Ser
```

```
ctg atc aat gtc tcc gac tgc agc gcc atc caa agg acc cag agg atg     192
Leu Ile Asn Val Ser Asp Cys Ser Ala Ile Gln Arg Thr Gln Arg Met
     50                  55                  60 ctg aaa gca ctg tgc tct caa aag ccc gcg gca ggg att tcc agt gaa     240
Leu Lys Ala Leu Cys Ser Gln Lys Pro Ala Ala Gly Ile Ser Ser Glu
 65                  70                  75                  80 cgc agc cga gac acc aaa att gaa gtg atc cag ttg gtg aaa aac ctg     288
Arg Ser Arg Asp Thr Lys Ile Glu Val Ile Gln Leu Val Lys Asn Leu
                 85                  90                  95 ctc acc tat gta agg gga gtt tat cgc cat gga aat ttc aga             330
Leu Thr Tyr Val Arg Gly Val Tyr Arg His Gly Asn Phe Arg
                100                 105                 110
```

Trp Ser Val Asn Leu Thr Ala Gly Met Tyr Cys Ala Ala Leu Glu Ser
         35                  40                  45

<210> SEQ ID NO 105
<211> LENGTH: 110
<212> TYPE: PRT
<213> ORGANISM: Canis familiaris

<400> SEQUENCE: 105

Ser Pro Val Thr Pro Ser Pro Thr Leu Lys Glu Leu Ile Glu Leu
 1               5                  10                  15

Val Asn Ile Thr Gln Asn Gln Ala Ser Leu Cys Asn Gly Ser Met Val
             20                  25                  30

Trp Ser Val Asn Leu Thr Ala Gly Met Tyr Cys Ala Ala Leu Glu Ser
         35                  40                  45

Leu Ile Asn Val Ser Asp Cys Ser Ala Ile Gln Arg Thr Gln Arg Met
     50                  55                  60

Leu Lys Ala Leu Cys Ser Gln Lys Pro Ala Ala Gly Ile Ser Ser Glu
 65                  70                  75                  80

Arg Ser Arg Asp Thr Lys Ile Glu Val Ile Gln Leu Val Lys Asn Leu
                 85                  90                  95

Leu Thr Tyr Val Arg Gly Val Tyr Arg His Gly Asn Phe Arg
                100                 105                 110

<210> SEQ ID NO 106
<211> LENGTH: 330
<212> TYPE: DNA
<213> ORGANISM: Canis familiaris

<400> SEQUENCE: 106
tctgaaattt ccatggcgat aaactcccct tacataggtg agcaggtttt tcaccaactg     60
gatcacttca attttggtgt ctcggctgcg ttcactggaa atccctgccg cgggcttttg    120
agagcacagt gctttcagca tcctctgggt cctttggatg gcgctgcagt cggagacatt    180
gatcagagat tctagagctg cgcagtacat gccggcggtc aggttgacgc tccacaccat    240
gctgccgttg cagagggatg cctgattctg ggtgatgttg accagctcct caatgagctc    300
cttgagggtt ggggagggag tcacagggct                                     330

<210> SEQ ID NO 107
<211> LENGTH: 567
<212> TYPE: DNA
<213> ORGANISM: Felis catus
<220> FEATURE:
<221> NAME/KEY: CDS
<222> LOCATION: (1)..(567)

<400> SEQUENCE: 107

```
atg gcg ctg ccc tct tcc ttc ttg gtg gcc ctg gtg gcg ctg ggc tgc      48
```

```
Met Ala Leu Pro Ser Ser Phe Leu Val Ala Leu Val Ala Leu Gly Cys
1               5                   10                  15 aac tcc gtc tgc tct ctg ggc tgt gac ctg cct cag acc cac ggc ctg    96
Asn Ser Val Cys Ser Leu Gly Cys Asp Leu Pro Gln Thr His Gly Leu
                20                  25                  30 ctg aac agg agg gcc ttg acg ctc ctg gga caa atg agg aga ctc cct   144
Leu Asn Arg Arg Ala Leu Thr Leu Leu Gly Gln Met Arg Arg Leu Pro
            35                  40                  45 gcc agc tcc tgt cag aag gac aga aat gac ttc gcc ttc ccc cag gac   192
Ala Ser Ser Cys Gln Lys Asp Arg Asn Asp Phe Ala Phe Pro Gln Asp
        50                  55                  60 gtg ttt ggt gga gac cag tcc cac aag gcc caa gcc ctc tcg gtg gtg   240
Val Phe Gly Gly Asp Gln Ser His Lys Ala Gln Ala Leu Ser Val Val
65                  70                  75                  80 cac gtg acg aac cag aag atc ttc cac ttc ttc tgc aca gag gcg tcc   288
His Val Thr Asn Gln Lys Ile Phe His Phe Phe Cys Thr Glu Ala Ser
                85                  90                  95 tcg tct gct gct tgg aac acc acc ctc ctg gag gaa ttc tgc acg gga   336
Ser Ser Ala Ala Trp Asn Thr Thr Leu Leu Glu Glu Phe Cys Thr Gly
                100                 105                 110 ctt gat tgg cag ctg acc cgc ctg gaa gcc tgt gtc atg cag gag gtg   384
Leu Asp Trp Gln Leu Thr Arg Leu Glu Ala Cys Val Met Gln Glu Val
            115                 120                 125 ggg gag gga gag gct ccc ctc acg aac gag gac tcc atc ctg agg aac   432
Gly Glu Gly Glu Ala Pro Leu Thr Asn Glu Asp Ser Ile Leu Arg Asn
        130                 135                 140 tac ttc caa aga ctc tcc ctc tac ctg caa gag aag aaa tac agc cct   480
Tyr Phe Gln Arg Leu Ser Leu Tyr Leu Gln Glu Lys Lys Tyr Ser Pro
145                 150                 155                 160 tgt gcc tgg gag atc gtc aga gca gaa atc atg aga tcc ttg tat tat   528
Cys Ala Trp Glu Ile Val Arg Ala Glu Ile Met Arg Ser Leu Tyr Tyr
                165                 170                 175 tca tca aca gcc ttg cag aaa aga tta agg agc gag aaa               567
Ser Ser Thr Ala Leu Gln Lys Arg Leu Arg Ser Glu Lys
                180                 185

<210> SEQ ID NO 108
<211> LENGTH: 189
<212> TYPE: PRT
<213> ORGANISM: Felis catus

<400> SEQUENCE: 108

Met Ala Leu Pro Ser Ser Phe Leu Val Ala Leu Val Ala Leu Gly Cys
1               5                   10                  15

Asn Ser Val Cys Ser Leu Gly Cys Asp Leu Pro Gln Thr His Gly Leu
                20                  25                  30

Leu Asn Arg Arg Ala Leu Thr Leu Leu Gly Gln Met Arg Arg Leu Pro
            35                  40                  45

Ala Ser Ser Cys Gln Lys Asp Arg Asn Asp Phe Ala Phe Pro Gln Asp
        50                  55                  60

Val Phe Gly Gly Asp Gln Ser His Lys Ala Gln Ala Leu Ser Val Val
65                  70                  75                  80

His Val Thr Asn Gln Lys Ile Phe His Phe Phe Cys Thr Glu Ala Ser
                85                  90                  95

Ser Ser Ala Ala Trp Asn Thr Thr Leu Leu Glu Glu Phe Cys Thr Gly
                100                 105                 110

Leu Asp Trp Gln Leu Thr Arg Leu Glu Ala Cys Val Met Gln Glu Val
            115                 120                 125

Gly Glu Gly Glu Ala Pro Leu Thr Asn Glu Asp Ser Ile Leu Arg Asn
```

```
                  130                 135                 140
Tyr Phe Gln Arg Leu Ser Leu Tyr Leu Gln Glu Lys Lys Tyr Ser Pro
145                 150                 155                 160

Cys Ala Trp Glu Ile Val Arg Ala Glu Ile Met Arg Ser Leu Tyr Tyr
                165                 170                 175

Ser Ser Thr Ala Leu Gln Lys Arg Leu Arg Ser Glu Lys
                180                 185

<210> SEQ ID NO 109
<211> LENGTH: 567
<212> TYPE: DNA
<213> ORGANISM: Felis catus

<400> SEQUENCE: 109
tttctcgctc cttaatcttt tctgcaaggc tgttgatgaa taatacaagg atctcatgat     60
ttctgctctg acgatctccc aggcacaagg gctgtatttc ttctcttgca ggtagaggga    120
gagtctttgg aagtagttcc tcaggatgga gtcctcgttc gtgagggag cctctccctc    180 ccccacctcc tgcatgacac aggcttccag gcgggtcagc tgccaatcaa gtcccgtgca    240
gaattcctcc aggagggtgg tgttccaagc agcagacgag gacgcctctg tgcagaagaa    300
gtggaagatc ttctggttcg tcacgtgcac caccgagagg gcttgggcct tgtgggactg    360
gtctccacca aacacgtcct gggggaaggc gaagtcattt ctgtccttct gacaggagct    420
ggcagggagt ctcctcattt gtcccaggag cgtcaaggcc ctcctgttca gcaggccgtg    480
ggtctgaggc aggtcacagc ccagagagca gacggagttg cagcccagcg ccaccagggc    540
caccaagaag gaagagggca gcgccat                                       567

<210> SEQ ID NO 110
<211> LENGTH: 567
<212> TYPE: DNA
<213> ORGANISM: Felis catus
<220> FEATURE:
<221> NAME/KEY: CDS
<222> LOCATION: (1)..(567)

<400> SEQUENCE: 110 atg gcg ctg ccc tct tcc ttc ttg gtg gcc ctg gtg gcg ctg ggc tgc     48
Met Ala Leu Pro Ser Ser Phe Leu Val Ala Leu Val Ala Leu Gly Cys
1               5                   10                  15 aac tcc gtc tgc tct ctg ggc tgt gac ctg cct cag acc cac ggc ctg     96
Asn Ser Val Cys Ser Leu Gly Cys Asp Leu Pro Gln Thr His Gly Leu
                20                  25                  30 ctg aac agg agg gcc ttg acg ctc ctg gga caa atg agg aga ctc cct    144
Leu Asn Arg Arg Ala Leu Thr Leu Leu Gly Gln Met Arg Arg Leu Pro
            35                  40                  45 gcc agc tcc tgt cag aag gac agg aat gac ttc gcc ttc ccc cag gac    192
Ala Ser Ser Cys Gln Lys Asp Arg Asn Asp Phe Ala Phe Pro Gln Asp
        50                  55                  60 gtg ttc ggt gga gac cag tcc cac aag gct caa gcc ctc tcg gtg gtg    240
Val Phe Gly Gly Asp Gln Ser His Lys Ala Gln Ala Leu Ser Val Val
65                  70                  75                  80 cac gtg acg aac cag gag atc ttc cac ttc ttc tgc aca gag gcg tcc    288
His Val Thr Asn Gln Glu Ile Phe His Phe Phe Cys Thr Glu Ala Ser
                85                  90                  95 tcg tct gct gct tgg aac acc acc ctc ctg gag gaa ttc tgc acg gga    336
Ser Ser Ala Ala Trp Asn Thr Thr Leu Leu Glu Glu Phe Cys Thr Gly
            100                 105                 110 ctt gat cgg cag ctg acc cgc ctg gaa gcc tgt gtc gtg cag gag gtg    384
Leu Asp Arg Gln Leu Thr Arg Leu Glu Ala Cys Val Val Gln Glu Val
```

```
                  115                 120                 125
ggg gag gga gag gct ccc ctc acg aac gag gac tcc ctc ctg agg aac        432
Gly Glu Gly Glu Ala Pro Leu Thr Asn Glu Asp Ser Leu Leu Arg Asn
        130                 135                 140 tac ttc caa aga ctc tcc ctc tac ctg caa gag aag aaa tac agc cct        480
Tyr Phe Gln Arg Leu Ser Leu Tyr Leu Gln Glu Lys Lys Tyr Ser Pro
145                 150                 155                 160 tgt gcc tgg gag atc gtc aga gca gaa atc atg aga tcc ttg tat tat        528
Cys Ala Trp Glu Ile Val Arg Ala Glu Ile Met Arg Ser Leu Tyr Tyr
                165                 170                 175 tca tca aca gcc ttg caa aaa aga tta agg agc gag aaa                    567
Ser Ser Thr Ala Leu Gln Lys Arg Leu Arg Ser Glu Lys
            180                 185

<210> SEQ ID NO 111
<211> LENGTH: 189
<212> TYPE: PRT
<213> ORGANISM: Felis catus

<400> SEQUENCE: 111

Met Ala Leu Pro Ser Ser Phe Leu Val Ala Leu Val Ala Leu Gly Cys
1               5                   10                  15

Asn Ser Val Cys Ser Leu Gly Cys Asp Leu Pro Gln Thr His Gly Leu
            20                  25                  30

Leu Asn Arg Arg Ala Leu Thr Leu Leu Gly Gln Met Arg Arg Leu Pro
        35                  40                  45

Ala Ser Ser Cys Gln Lys Asp Arg Asn Asp Phe Ala Phe Pro Gln Asp
    50                  55                  60

Val Phe Gly Gly Asp Gln Ser His Lys Ala Gln Ala Leu Ser Val Val
65                  70                  75                  80

His Val Thr Asn Gln Glu Ile Phe His Phe Cys Thr Glu Ala Ser
                85                  90                  95

Ser Ser Ala Ala Trp Asn Thr Thr Leu Leu Glu Glu Phe Cys Thr Gly
            100                 105                 110

Leu Asp Arg Gln Leu Thr Arg Leu Glu Ala Cys Val Val Gln Glu Val
        115                 120                 125

Gly Glu Gly Glu Ala Pro Leu Thr Asn Glu Asp Ser Leu Leu Arg Asn
    130                 135                 140

Tyr Phe Gln Arg Leu Ser Leu Tyr Leu Gln Glu Lys Lys Tyr Ser Pro
145                 150                 155                 160

Cys Ala Trp Glu Ile Val Arg Ala Glu Ile Met Arg Ser Leu Tyr Tyr
                165                 170                 175

Ser Ser Thr Ala Leu Gln Lys Arg Leu Arg Ser Glu Lys
            180                 185

<210> SEQ ID NO 112
<211> LENGTH: 567
<212> TYPE: DNA
<213> ORGANISM: Felis catus

<400> SEQUENCE: 112
tttctcgctc cttaatcttt tttgcaaggc tgttgatgaa taatacaagg atctcatgat        60
ttctgctctg acgatctccc aggcacaagg gctgtatttc ttctcttgca ggtagaggga      120
gagtctttgg aagtagttcc tcaggaggga gtcctcgttc gtgagggggag cctctccctc     180 ccccacctcc tgcacgacac aggcttccag gcgggtcagc tgccgatcaa gtcccgtgca      240
gaattcctcc aggagggtgg tgttccaagc agcagacgag gacgcctctg tgcagaagaa      300
```

```
gtggaagatc tcctggttcg tcacgtgcac caccgagagg gcttgagcct tgtgggactg      360
gtctccaccg aacacgtcct gggggaaggc gaagtcattc ctgtccttct gacaggagct      420
ggcagggagt ctcctcattt gtcccaggag cgtcaaggcc ctcctgttca gcaggccgtg      480
ggtctgaggc aggtcacagc ccagagagca gacggagttg cagcccagcg ccaccagggc      540
caccaagaag gaagagggca gcgccat                                          567
```

```
<210> SEQ ID NO 113
<211> LENGTH: 498
<212> TYPE: DNA
<213> ORGANISM: Felis catus
<220> FEATURE:
<221> NAME/KEY: CDS
<222> LOCATION: (1)..(498)

<400> SEQUENCE: 113 tgt gac ctg cct cag acc cac ggc ctg ctg aac agg agg gcc ttg acg       48
Cys Asp Leu Pro Gln Thr His Gly Leu Leu Asn Arg Arg Ala Leu Thr
1               5                   10                  15 ctc ctg gga caa atg agg aga ctc cct gcc agc tcc tgt cag aag gac       96
Leu Leu Gly Gln Met Arg Arg Leu Pro Ala Ser Ser Cys Gln Lys Asp
            20                  25                  30 aga aat gac ttc gcc ttc ccc cag gac gtg ttt ggt gga gac cag tcc      144
Arg Asn Asp Phe Ala Phe Pro Gln Asp Val Phe Gly Gly Asp Gln Ser
        35                  40                  45 cac aag gcc caa gcc ctc tcg gtg gtg cac gtg acg aac cag aag atc      192
His Lys Ala Gln Ala Leu Ser Val Val His Val Thr Asn Gln Lys Ile
    50                  55                  60 ttc cac ttc ttc tgc aca gag gcg tcc tcg tct gct gct tgg aac acc      240
Phe His Phe Phe Cys Thr Glu Ala Ser Ser Ser Ala Ala Trp Asn Thr
65                  70                  75                  80 acc ctc ctg gag gaa ttc tgc acg gga ctt gat tgg cag ctg acc cgc      288
Thr Leu Leu Glu Glu Phe Cys Thr Gly Leu Asp Trp Gln Leu Thr Arg
                85                  90                  95 ctg gaa gcc tgt gtc atg cag gag gtg ggg gag gga gag gct ccc ctc      336
Leu Glu Ala Cys Val Met Gln Glu Val Gly Glu Gly Glu Ala Pro Leu
            100                 105                 110 acg aac gag gac tcc atc ctg agg aac tac ttc caa aga ctc tcc ctc      384
Thr Asn Glu Asp Ser Ile Leu Arg Asn Tyr Phe Gln Arg Leu Ser Leu
        115                 120                 125 tac ctg caa gag aag aaa tac agc cct tgt gcc tgg gag atc gtc aga      432
Tyr Leu Gln Glu Lys Lys Tyr Ser Pro Cys Ala Trp Glu Ile Val Arg
    130                 135                 140 gca gaa atc atg aga tcc ttg tat tat tca tca aca gcc ttg cag aaa      480
Ala Glu Ile Met Arg Ser Leu Tyr Tyr Ser Ser Thr Ala Leu Gln Lys
145                 150                 155                 160 aga tta agg agc gag aaa                                              498
Arg Leu Arg Ser Glu Lys
                165

<210> SEQ ID NO 114
<211> LENGTH: 166
<212> TYPE: PRT
<213> ORGANISM: Felis catus

<400> SEQUENCE: 114

Cys Asp Leu Pro Gln Thr His Gly Leu Leu Asn Arg Arg Ala Leu Thr
1               5                   10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
```

```
                    35                  40                  45
His Lys Ala Gln Ala Leu Ser Val Val His Val Thr Asn Gln Lys Ile
    50                  55                  60

Phe His Phe Phe Cys Thr Glu Ala Ser Ser Ala Ala Trp Asn Thr
65                  70                  75                  80

Thr Leu Leu Glu Glu Phe Cys Thr Gly Leu Asp Trp Gln Leu Thr Arg
                    85                  90                  95

Leu Glu Ala Cys Val Met Gln Glu Val Gly Glu Gly Glu Ala Pro Leu
                100                 105                 110

Thr Asn Glu Asp Ser Ile Leu Arg Asn Tyr Phe Gln Arg Leu Ser Leu
                115                 120                 125

Tyr Leu Gln Glu Lys Lys Tyr Ser Pro Cys Ala Trp Glu Ile Val Arg
            130                 135                 140

Ala Glu Ile Met Arg Ser Leu Tyr Tyr Ser Ser Thr Ala Leu Gln Lys
145                 150                 155                 160

Arg Leu Arg Ser Glu Lys
                165

<210> SEQ ID NO 115
<211> LENGTH: 498
<212> TYPE: DNA
<213> ORGANISM: Felis catus

<400> SEQUENCE: 115
tttctcgctc cttaatcttt tctgcaaggc tgttgatgaa taatacaagg atctcatgat    60
ttctgctctg acgatctccc aggcacaagg gctgtatttc ttctcttgca ggtagaggga   120
gagtctttgg aagtagttcc tcaggatgga gtcctcgttc gtgagggag cctctcccctc   180 ccccacctcc tgcatgacac aggcttccag gcgggtcagc tgccaatcaa gtcccgtgca   240
gaattcctcc aggagggtgg tgttccaagc agcagacgag gacgcctctg tgcagaagaa   300
gtggaagatc ttctggttcg tcacgtgcac caccgagagg gcttgggcct tgtgggactg   360
gtctccacca aacacgtcct ggggaaggc gaagtcattt ctgtccttct gacaggagct   420
ggcagggagt ctcctcattt gtcccaggag cgtcaaggcc tcctgttca gcaggccgtg    480 ggtctgaggc aggtcaca                                                  498

<210> SEQ ID NO 116
<211> LENGTH: 498
<212> TYPE: DNA
<213> ORGANISM: Felis catus
<220> FEATURE:
<221> NAME/KEY: CDS
<222> LOCATION: (1)..(498)

<400> SEQUENCE: 116 tgt gac ctg cct cag acc cac ggc ctg ctg aac agg agg gcc ttg acg     48
Cys Asp Leu Pro Gln Thr His Gly Leu Leu Asn Arg Arg Ala Leu Thr
1               5                   10                  15 ctc ctg gga caa atg agg aga ctc cct gcc agc tcc tgt cag aag gac     96
Leu Leu Gly Gln Met Arg Arg Leu Pro Ala Ser Ser Cys Gln Lys Asp
            20                  25                  30 agg aat gac ttc gcc ttc ccc cag gac gtg ttc ggt gga gac cag tcc    144
Arg Asn Asp Phe Ala Phe Pro Gln Asp Val Phe Gly Gly Asp Gln Ser
        35                  40                  45 cac aag gct caa gcc ctc tcg gtg gtg cac gtg acg aac cag gag atc    192
His Lys Ala Gln Ala Leu Ser Val Val His Val Thr Asn Gln Glu Ile
    50                  55                  60 ttc cac ttc ttc tgc aca gag gcg tcc tcg tct gct gct tgg aac acc    240
```

```
                Phe His Phe Phe Cys Thr Glu Ala Ser Ser Ala Ala Trp Asn Thr
                 65              70                  75                  80 acc ctc ctg gag gaa ttc tgc acg gga ctt gat cgg cag ctg acc cgc        288
Thr Leu Leu Glu Glu Phe Cys Thr Gly Leu Asp Arg Gln Leu Thr Arg
                 85                  90                  95 ctg gaa gcc tgt gtc gtg cag gag gtg ggg gag gga gag gct ccc ctc        336
Leu Glu Ala Cys Val Val Gln Glu Val Gly Glu Gly Glu Ala Pro Leu
                100                 105                 110 acg aac gag gac tcc ctc ctg agg aac tac ttc caa aga ctc tcc ctc        384
Thr Asn Glu Asp Ser Leu Leu Arg Asn Tyr Phe Gln Arg Leu Ser Leu
                115                 120                 125 tac ctg caa gag aag aaa tac agc cct tgt gcc tgg gag atc gtc aga        432
Tyr Leu Gln Glu Lys Lys Tyr Ser Pro Cys Ala Trp Glu Ile Val Arg
    130                 135                 140 gca gaa atc atg aga tcc ttg tat tat tca tca aca gcc ttg caa aaa        480
Ala Glu Ile Met Arg Ser Leu Tyr Tyr Ser Ser Thr Ala Leu Gln Lys
145                 150                 155                 160 aga tta agg agc gag aaa                                                498
Arg Leu Arg Ser Glu Lys
                165

<210> SEQ ID NO 117
<211> LENGTH: 166
<212> TYPE: PRT
<213> ORGANISM: Felis catus

<400> SEQUENCE: 117

Cys Asp Leu Pro Gln Thr His Gly Leu Leu Asn Arg Arg Ala Leu Thr
 1               5                  10                  15

Leu Leu Gly Gln Met Arg Arg Leu Pro Ala Ser Ser Cys Gln Lys Asp
                20                  25                  30

Arg Asn Asp Phe Ala Phe Pro Gln Asp Val Phe Gly Gly Asp Gln Ser
            35                  40                  45

His Lys Ala Gln Ala Leu Ser Val Val His Val Thr Asn Gln Glu Ile
        50                  55                  60

Phe His Phe Phe Cys Thr Glu Ala Ser Ser Ala Ala Trp Asn Thr
 65              70                  75                  80

Thr Leu Leu Glu Glu Phe Cys Thr Gly Leu Asp Arg Gln Leu Thr Arg
                85                  90                  95

Leu Glu Ala Cys Val Val Gln Glu Val Gly Glu Gly Glu Ala Pro Leu
               100                 105                 110

Thr Asn Glu Asp Ser Leu Leu Arg Asn Tyr Phe Gln Arg Leu Ser Leu
               115                 120                 125

Tyr Leu Gln Glu Lys Lys Tyr Ser Pro Cys Ala Trp Glu Ile Val Arg
    130                 135                 140

Ala Glu Ile Met Arg Ser Leu Tyr Tyr Ser Ser Thr Ala Leu Gln Lys
145                 150                 155                 160

Arg Leu Arg Ser Glu Lys
                165

<210> SEQ ID NO 118
<211> LENGTH: 498
<212> TYPE: DNA
<213> ORGANISM: Felis catus

<400> SEQUENCE: 118
tttctcgctc cttaatcttt tttgcaaggc tgttgatgaa taatacaagg atctcatgat     60
ttctgctctg acgatctccc aggcacaagg gctgtatttc ttctcttgca ggtagaggga    120
```

```
gagtctttgg aagtagttcc tcaggaggga gtcctcgttc gtgagggag cctctccctc    180 ccccacctcc tgcacgacac aggcttccag gcgggtcagc tgccgatcaa gtcccgtgca    240
gaattcctcc aggagggtgg tgttccaagc agcagacgag gacgcctctg tgcagaagaa    300
gtggaagatc tcctggttcg tcacgtgcac caccgagagg gcttgagcct tgtgggactg    360
gtctccaccg aacacgtcct gggggaaggc gaagtcattc ctgtccttct gacaggagct    420
ggcagggagt ctcctcattt gtcccaggag cgtcaaggcc tcctgttca gcaggccgtg    480 ggtctgaggc aggtcaca                                                  498

<210> SEQ ID NO 119
<211> LENGTH: 444
<212> TYPE: DNA
<213> ORGANISM: Felis catus
<220> FEATURE:
<221> NAME/KEY: CDS
<222> LOCATION: (10)..(441)

<400> SEQUENCE: 119 ggatccacc atg tgg ctg cag aac ctg ctt ttc ctg ggc act gtg gtc tgc     51
          Met Trp Leu Gln Asn Leu Leu Phe Leu Gly Thr Val Val Cys
            1               5                  10 agc atc tct gca ccc acc agt tca ccc agc tct gtc act cgg ccc tgg      99
Ser Ile Ser Ala Pro Thr Ser Ser Pro Ser Ser Val Thr Arg Pro Trp
 15              20                  25                  30 caa cac gtg gat gcc atc aag gag gcc ctg agc ctt ctg aac aac agt     147
Gln His Val Asp Ala Ile Lys Glu Ala Leu Ser Leu Leu Asn Asn Ser
                 35                  40                  45 agt gaa ata act gct gtg atg aat gaa gca gta gaa gtc gtc tct gaa     195
Ser Glu Ile Thr Ala Val Met Asn Glu Ala Val Glu Val Val Ser Glu
             50                  55                  60 atg ttt gac cct gag gag ccg aaa tgc ctg cag act cac cta aag ctg     243
Met Phe Asp Pro Glu Glu Pro Lys Cys Leu Gln Thr His Leu Lys Leu
         65                  70                  75 tac gag cag ggc cta cgg ggc agc ctc atc agc ctc aag gag cct ctg     291
Tyr Glu Gln Gly Leu Arg Gly Ser Leu Ile Ser Leu Lys Glu Pro Leu
     80                  85                  90 aga atg atg gcc aac cat tac aag cag cac tgc ccc ctt act ccg gaa     339
Arg Met Met Ala Asn His Tyr Lys Gln His Cys Pro Leu Thr Pro Glu
 95                 100                 105                 110 acg ccc tgt gaa acc cag act atc acc ttc aaa aat ttc aaa gag aat     387
Thr Pro Cys Glu Thr Gln Thr Ile Thr Phe Lys Asn Phe Lys Glu Asn
                115                 120                 125 ctg aag gat ttt ctg ttt aac aac ccc ttt gac tgc tgg gga cca gac     435
Leu Lys Asp Phe Leu Phe Asn Asn Pro Phe Asp Cys Trp Gly Pro Asp
            130                 135                 140 cag aag taa                                                          444
Gln Lys <210> SEQ ID NO 120
<211> LENGTH: 144
<212> TYPE: PRT
<213> ORGANISM: Felis catus

<400> SEQUENCE: 120

Met Trp Leu Gln Asn Leu Leu Phe Leu Gly Thr Val Val Cys Ser Ile
  1               5                  10                  15

Ser Ala Pro Thr Ser Ser Pro Ser Ser Val Thr Arg Pro Trp Gln His
             20                  25                  30

Val Asp Ala Ile Lys Glu Ala Leu Ser Leu Leu Asn Asn Ser Ser Glu
         35                  40                  45
```

```
Ile Thr Ala Val Met Asn Glu Ala Val Glu Val Val Ser Glu Met Phe
    50                  55                  60

Asp Pro Glu Glu Pro Lys Cys Leu Gln Thr His Leu Lys Leu Tyr Glu
 65              70                  75                  80

Gln Gly Leu Arg Gly Ser Leu Ile Ser Leu Lys Glu Pro Leu Arg Met
                 85                  90                  95

Met Ala Asn His Tyr Lys Gln His Cys Pro Leu Thr Pro Glu Thr Pro
                100                 105                 110

Cys Glu Thr Gln Thr Ile Thr Phe Lys Asn Phe Lys Glu Asn Leu Lys
            115                 120                 125

Asp Phe Leu Phe Asn Asn Pro Phe Asp Cys Trp Gly Pro Asp Gln Lys
130                 135                 140

<210> SEQ ID NO 121
<211> LENGTH: 444
<212> TYPE: DNA
<213> ORGANISM: Felis catus

<400> SEQUENCE: 121
ttacttctgg tctggtcccc agcagtcaaa ggggttgtta acagaaaat ccttcagatt      60 ctctttgaaa ttttgaagg tgatagtctg ggtttcacag ggcgtttccg gagtaagggg    120
gcagtgctgc ttgtaatggt tggccatcat tctcagaggc tccttgaggc tgatgaggct    180
gccccgtagg ccctgctcgt acagctttag gtgagtctgc aggcatttcg gctcctcagg    240
gtcaaacatt tcagagacga cttctactgc ttcattcatc acagcagtta tttcactact    300
gttgttcaga aggctcaggg cctccttgat ggcatccacg tgttgccagg ccgagtgac    360 agagctgggt gaactggtgg gtgcagagat gctgcagacc acagtgccca ggaaaagcag    420
gttctgcagc cacatggtgg atcc                                          444

<210> SEQ ID NO 122
<211> LENGTH: 432
<212> TYPE: DNA
<213> ORGANISM: Felis catus

<400> SEQUENCE: 122
atgtggctgc agaacctgct tttcctgggc actgtggtct gcagcatctc tgcacccacc     60 agttcacccca gctctgtcac tcggccctgg caacacgtgg atgccatcaa ggaggccctg   120
agccttctga caacagtag tgaaataact gctgtgatga atgaagcagt agaagtcgtc    180
tctgaaatgt ttgaccctga ggagccgaaa tgcctgcaga ctcacctaaa gctgtacgag    240
cagggcctac ggggcagcct catcagcctc aaggagcctc tgagaatgat ggccaaccat    300
tacaagcagc actgccccct tactccggaa acgccctgtg aaacccagac tatcaccttc    360
aaaaatttca agagaatctg aaggattttt ctgtttaaca ccccttttga ctgctgggga    420
ccagaccaga ag                                                        432

<210> SEQ ID NO 123
<211> LENGTH: 432
<212> TYPE: DNA
<213> ORGANISM: Felis catus

<400> SEQUENCE: 123
cttctggtct ggtccccagc agtcaaaggg gttgttaaac agaaaatcct tcagattctc     60
tttgaaattt tgaaggtga tagtctgggt tcacagggc gtttccgag taagggggca    120 gtgctgcttg taatggttgg ccatcattct cagaggctcc ttgaggctga tgaggctgcc   180
```

```
ccgtaggccc tgctcgtaca gctttaggtg agtctgcagg catttcggct cctcagggtc    240
aaacatttca gagacgactt ctactgcttc attcatcaca gcagttattt cactactgtt    300
gttcagaagg ctcagggcct ccttgatggc atccacgtgt tgccaggcc gagtgacaga    360 gctgggtgaa ctggtgggtg cagagatgct gcagaccaca gtgcccagga aaagcaggtt    420
ctgcagccac at                                                         432
```

```
<210> SEQ ID NO 124
<211> LENGTH: 381
<212> TYPE: DNA
<213> ORGANISM: Felis catus
<220> FEATURE:
<221> NAME/KEY: CDS
<222> LOCATION: (1)..(381)

<400> SEQUENCE: 124
```

| gca | ccc | acc | agt | tca | ccc | agc | tct | gtc | act | cgg | ccc | tgg | caa | cac | gtg |  48 |
|-----|-----|-----|-----|-----|-----|-----|-----|-----|-----|-----|-----|-----|-----|-----|-----|-----|
| Ala | Pro | Thr | Ser | Ser | Pro | Ser | Ser | Val | Thr | Arg | Pro | Trp | Gln | His | Val | |
| 1 | | | | 5 | | | | | 10 | | | | | 15 | | |

| gat | gcc | atc | aag | gag | gcc | ctg | agc | ctt | ctg | aac | aac | agt | agt | gaa | ata |  96 |
|-----|-----|-----|-----|-----|-----|-----|-----|-----|-----|-----|-----|-----|-----|-----|-----|-----|
| Asp | Ala | Ile | Lys | Glu | Ala | Leu | Ser | Leu | Leu | Asn | Asn | Ser | Ser | Glu | Ile | |
| | | | 20 | | | | | 25 | | | | | 30 | | | |

| act | gct | gtg | atg | aat | gaa | gca | gta | gaa | gtc | gtc | tct | gaa | atg | ttt | gac | 144 |
|-----|-----|-----|-----|-----|-----|-----|-----|-----|-----|-----|-----|-----|-----|-----|-----|-----|
| Thr | Ala | Val | Met | Asn | Glu | Ala | Val | Glu | Val | Val | Ser | Glu | Met | Phe | Asp | |
| | | 35 | | | | | 40 | | | | | 45 | | | | |

| cct | gag | gag | ccg | aaa | tgc | ctg | cag | act | cac | cta | aag | ctg | tac | gag | cag | 192 |
|-----|-----|-----|-----|-----|-----|-----|-----|-----|-----|-----|-----|-----|-----|-----|-----|-----|
| Pro | Glu | Glu | Pro | Lys | Cys | Leu | Gln | Thr | His | Leu | Lys | Leu | Tyr | Glu | Gln | |
| 50 | | | | | 55 | | | | | 60 | | | | | | |

| ggc | cta | cgg | ggc | agc | ctc | atc | agc | ctc | aag | gag | cct | ctg | aga | atg | atg | 240 |
|-----|-----|-----|-----|-----|-----|-----|-----|-----|-----|-----|-----|-----|-----|-----|-----|-----|
| Gly | Leu | Arg | Gly | Ser | Leu | Ile | Ser | Leu | Lys | Glu | Pro | Leu | Arg | Met | Met | |
| 65 | | | | | 70 | | | | | 75 | | | | | 80 | |

| gcc | aac | cat | tac | aag | cag | cac | tgc | ccc | ctt | act | ccg | gaa | acg | ccc | tgt | 288 |
|-----|-----|-----|-----|-----|-----|-----|-----|-----|-----|-----|-----|-----|-----|-----|-----|-----|
| Ala | Asn | His | Tyr | Lys | Gln | His | Cys | Pro | Leu | Thr | Pro | Glu | Thr | Pro | Cys | |
| | | | | 85 | | | | | 90 | | | | | 95 | | |

| gaa | acc | cag | act | atc | acc | ttc | aaa | aat | ttc | aaa | gag | aat | ctg | aag | gat | 336 |
|-----|-----|-----|-----|-----|-----|-----|-----|-----|-----|-----|-----|-----|-----|-----|-----|-----|
| Glu | Thr | Gln | Thr | Ile | Thr | Phe | Lys | Asn | Phe | Lys | Glu | Asn | Leu | Lys | Asp | |
| | | | 100 | | | | | 105 | | | | | 110 | | | |

| ttt | ctg | ttt | aac | aac | ccc | ttt | gac | tgc | tgg | gga | cca | gac | cag | aag | | 381 |
|-----|-----|-----|-----|-----|-----|-----|-----|-----|-----|-----|-----|-----|-----|-----|-----|-----|
| Phe | Leu | Phe | Asn | Asn | Pro | Phe | Asp | Cys | Trp | Gly | Pro | Asp | Gln | Lys | | |
| | | 115 | | | | | 120 | | | | | 125 | | | | |

```
<210> SEQ ID NO 125
<211> LENGTH: 127
<212> TYPE: PRT
<213> ORGANISM: Felis catus

<400> SEQUENCE: 125
```

Ala Pro Thr Ser Ser Pro Ser Ser Val Thr Arg Pro Trp Gln His Val
1               5                   10                  15

Asp Ala Ile Lys Glu Ala Leu Ser Leu Leu Asn Asn Ser Ser Glu Ile
            20                  25                  30

Thr Ala Val Met Asn Glu Ala Val Glu Val Val Ser Glu Met Phe Asp
        35                  40                  45

Pro Glu Glu Pro Lys Cys Leu Gln Thr His Leu Lys Leu Tyr Glu Gln
50                  55                  60

Gly Leu Arg Gly Ser Leu Ile Ser Leu Lys Glu Pro Leu Arg Met Met
65                  70                  75                  80

Ala Asn His Tyr Lys Gln His Cys Pro Leu Thr Pro Glu Thr Pro Cys
                85                  90                  95

```
Glu Thr Gln Thr Ile Thr Phe Lys Asn Phe Lys Glu Asn Leu Lys Asp
            100                 105                 110

Phe Leu Phe Asn Asn Pro Phe Asp Cys Trp Gly Pro Asp Gln Lys
        115                 120                 125
```

<210> SEQ ID NO 126
<211> LENGTH: 381
<212> TYPE: DNA
<213> ORGANISM: Felis catus

<400> SEQUENCE: 126

| | | | | | |
|---|---|---|---|---|---|
| cttctggtct | ggtccccagc | agtcaaaggg | gttgttaaac | agaaaatcct | tcagattctc | 60 |
| tttgaaattt | ttgaaggtga | tagtctgggt | ttcacagggc | gtttccggag | taaggggggca | 120 |
| gtgctgcttg | taatggttgg | ccatcattct | cagaggctcc | ttgaggctga | tgaggctgcc | 180 |
| ccgtaggccc | tgctcgtaca | gctttaggtg | agtctgcagg | catttcggct | cctcagggtc | 240 |
| aaacatttca | gagacgactt | ctactgcttc | attcatcaca | gcagttattt | cactactgtt | 300 |
| gttcagaagg | ctcagggcct | ccttgatggc | atccacgtgt | tgccagggcc | gagtgacaga | 360 |
| gctgggtgaa | ctggtgggtg | c | | | | 381 |

<210> SEQ ID NO 127
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 127
cctcgagatt cagctttcaa tgcctgta                                    28

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 128
tgcccrstcg gcttcttctc c                                           21

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 129
cgactctctt trccrtcctc ctg                                         23

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 130
cctcaaattg cggcacatgt c                                           21

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 131
ctgttcagag tttgagtaag cc                                              22

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 132
gaagatacca tttcaacttt aacacagc                                        28

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 133
tgctgtattg tgaagactcc cagc                                            24

<210> SEQ ID NO 134
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 134
atgcactttc tttgcc                                                     16

<210> SEQ ID NO 135
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 135
ctggaggaaa akacttcrat gattctgata tctgaaatat at                        42

<210> SEQ ID NO 136
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 136
ctgacycttk sttggscctc attctca                                         27

<210> SEQ ID NO 137

```
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 137
gggctcgaga aaagatttgc tgtagaaaat cccatg                              36

<210> SEQ ID NO 138
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 138
cccgcggccg ctcaactttc cggtgtccac tc                                  32

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 139
gtcmtggctc tyrcttgcct tgg                                            23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 140
aaastgggcy acytcgattt tgg                                            23

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 141
gtgatgttgm ycagctcctc                                                20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 142
aattaaccct cactaaaggg                                                20

<210> SEQ ID NO 143
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 143
atggcgctct ggttgactgt                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 144
ggcttttgag agcacagtgc                                              20

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 145
ccccatatga gccctgtgac tccctcccc                                    29

<210> SEQ ID NO 146
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 146
ggggaattct catctgaaat ttccatggcg                                   30

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 147
atggcgctgc cctcttcctt cttg                                         24

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 148
tcatttctcg ctccttaatc ttttctgc                                     28

<210> SEQ ID NO 149
<211> LENGTH: 37
<212> TYPE: DNA
<213> ORGANISM: Artificial Sequence
<220> FEATURE:
```

```
<223> OTHER INFORMATION: Description of Artificial Sequence: Synthetic
      Primer

<400> SEQUENCE: 149
cagggatcca ccatgtggct gcagaacctg cttttcc                              37

<210> SEQ ID NO 150
<211> LENGTH: 50
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 150
ttacttctgg tctggtcccc agcagtcaaa ggggttgtta aacagaaaat                50

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 151
cacagyccca tctcctcc                                                   18

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 152
gtaatacgac tcactatagg gc                                              22

<210> SEQ ID NO 153
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 153
acggaattcg agatgatagt gctggc                                          26

<210> SEQ ID NO 154
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 154
gtgtctagat ttggtagaaa aggatgat                                        28
```